US009328335B2

(12) United States Patent
Durrett et al.

(10) Patent No.: US 9,328,335 B2
(45) Date of Patent: May 3, 2016

(54) METHOD TO PRODUCE ACETYLDIACYLGLYCEROLS (AC-TAGS) BY EXPRESSION OF AN ACETYLTRANSFERASE GENE ISOLATED FROM EUONYMUS ALATUS (BURNING BUSH)

(75) Inventors: Timothy Durrett, Manhattan, KS (US); John Ohlrogge, Okemos, MI (US); Michael Pollard, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 768 days.

(21) Appl. No.: 13/519,660

(22) PCT Filed: Dec. 29, 2010

(86) PCT No.: PCT/US2010/062407
§ 371 (c)(1),
(2), (4) Date: Jan. 16, 2013

(87) PCT Pub. No.: WO2011/082253
PCT Pub. Date: Jul. 7, 2011

(65) Prior Publication Data
US 2013/0116462 A1 May 9, 2013

Related U.S. Application Data

(60) Provisional application No. 61/291,290, filed on Dec. 30, 2009, provisional application No. 61/334,838, filed on May 14, 2010.

(51) Int. Cl.
*C12N 9/10* (2006.01)
*C12N 15/82* (2006.01)
*C12P 7/64* (2006.01)

(52) U.S. Cl.
CPC .......... *C12N 9/1029* (2013.01); *C12N 15/8247* (2013.01); *C12P 7/6463* (2013.01); *Y02T 50/678* (2013.01)

(58) Field of Classification Search
None
See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis |
| 4,695,411 | A | 9/1987 | Stern et al. |
| 4,940,838 | A | 7/1990 | Schilperoort et al. |
| 4,945,050 | A | 7/1990 | Sanford et al. |
| 4,965,188 | A | 10/1990 | Mullis et al. |
| 4,981,785 | A | 1/1991 | Nayak |
| 5,057,422 | A | 10/1991 | Bol et al. |
| 5,173,410 | A | 12/1992 | Ahlquist |
| 5,187,267 | A | 2/1993 | Comai et al. |
| 5,352,605 | A | 10/1994 | Fraley et al. |
| 5,358,691 | A | 10/1994 | Clark et al. |
| 5,451,513 | A | 9/1995 | Maliga et al. |
| 5,500,360 | A | 3/1996 | Ahlquist et al. |
| 5,501,967 | A | 3/1996 | Offringa et al. |
| 5,538,848 | A | 7/1996 | Livak et al. |
| 5,545,817 | A | 8/1996 | McBride et al. |
| 5,545,818 | A | 8/1996 | McBride et al. |
| 5,584,807 | A | 12/1996 | McCabe |
| 5,599,677 | A | 2/1997 | Dowell et al. |
| 5,639,606 | A | 6/1997 | Willey |
| 5,643,765 | A | 7/1997 | Willey |
| 5,672,480 | A | 9/1997 | Dowell et al. |
| 5,824,877 | A | 10/1998 | Hinchee et al. |
| 5,846,717 | A | 12/1998 | Brow et al. |
| 5,846,795 | A | 12/1998 | Ahlquist et al. |
| 5,866,330 | A | 2/1999 | Kinzler et al. |
| 5,866,785 | A | 2/1999 | Donson et al. |

(Continued)

FOREIGN PATENT DOCUMENTS

| DE | 4317414 C1 | 4/1994 |
|---|---|---|
| EP | 0292435 A1 | 11/1988 |

(Continued)

OTHER PUBLICATIONS

Bouvier-Nave et al. Expression in yeast and tobacco of plant cDNAs encoding acyl CoA:diacylglycerol acyltransferase. Eur. J. Biochem. 267, 85-96, 2000.*

(Continued)

*Primary Examiner* — Medina A Ibrahim
*Assistant Examiner* — Wayne Zhong
(74) *Attorney, Agent, or Firm* — Schwegman Lundberg & Woessner, P.A.

(57) ABSTRACT

The present invention relates to novel diacylglycerol acyltransferase genes and proteins, and methods of their use. In particular, the invention describes genes encoding proteins having diacylglycerol acetyltransferase activity, specifically for transferring an acetyl group to a diacylglycerol substrate to form acetyl-Triacylglycerols (ac-TAGS), for example, a 3-acetyl-1,2-diacyl-sn-glycerol. The present invention encompasses both native and recombinant wild-type forms of the transferase, as well as mutants and variant forms. The present invention also relates to methods of using novel diacylglycerol acyltransferase genes and proteins, including their expression in transgenic organisms at commercially viable levels, for increasing production of 3-acetyl-1,2-diacyl-sn-glycerols in plant oils and altering the composition of oils produced by microorganisms, such as yeast, by increasing ac-TAG production. Additionally, oils produced by methods of the present inventions comprising genes and proteins are contemplated for use as biodiesel fuel, in polymer production and as naturally produced food oils with reduced calories.

30 Claims, 17 Drawing Sheets

(56) References Cited

U.S. PATENT DOCUMENTS

| | | | |
|---|---|---|---|
| 5,876,978 A | 3/1999 | Willey et al. |
| 5,885,530 A | 3/1999 | Babson et al. |
| 5,965,794 A | 10/1999 | Turpen |
| 5,977,438 A | 11/1999 | Turpen et al. |
| 5,981,839 A | 11/1999 | Knauf et al. |
| 5,981,840 A | 11/1999 | Zhao et al. |
| 5,985,557 A | 11/1999 | Prudent et al. |
| 5,994,069 A | 11/1999 | Hall et al. |
| 6,001,567 A | 12/1999 | Brow et al. |
| 6,051,757 A | 4/2000 | Barton et al. |
| 6,090,543 A | 7/2000 | Prudent et al. |
| 6,159,750 A | 12/2000 | Edmonds |
| 7,122,367 B2 | 10/2006 | Milcamps et al. |
| 7,429,473 B2 | 9/2008 | Milcamps et al. |
| 7,511,189 B2 | 3/2009 | Zou et al. |
| 8,362,318 B2 | 1/2013 | Benning |
| 9,062,331 B2 | 6/2015 | Benning et al. |
| 2007/0028329 A1 | 2/2007 | Milcamps et al. |
| 2007/0204370 A1 | 8/2007 | Mietkiewska et al. |
| 2007/0231819 A1 | 10/2007 | Lawrence et al. |
| 2010/0317073 A1 | 12/2010 | Sayre et al. |
| 2011/0061130 A1 | 3/2011 | Zou et al. |
| 2013/0212736 A1 | 8/2013 | Benning et al. |
| 2015/0203861 A1 | 7/2015 | Benning et al. |

FOREIGN PATENT DOCUMENTS

| | | |
|---|---|---|
| EP | 0332581 A2 | 9/1989 |
| WO | WO-93/07278 A1 | 4/1993 |
| WO | WO-93/18176 A1 | 9/1993 |
| WO | WO-94/13822 A2 | 6/1994 |
| WO | WO-95/14098 A1 | 5/1995 |
| WO | WO-95/16783 A1 | 6/1995 |
| WO | WO-2011/082253 A2 | 7/2011 |

OTHER PUBLICATIONS

Friedberg (Automated protein function prediction—the genomic challenge. Brief. Bioinformatics. 7:225-242, 2006).*

Hill et al (Functional analysis of conserved histidines in ADP-glucose pyrophosphorylase from *Escherichia coli*. Biochem. Biophys. Res. Comm. 244:573-577, 1998).*

Guo et al (Protein tolerance to random amino acid change, Proc. Natl. Acad. Sci. USA 101:9205-9210, 2004).*

"U.S. Appl. No. 13/719,868, Non Final Office Action mailed Sep. 25, 2014", 7 pgs.

"U.S. Appl. No. 13/719,868, Preliminary Amendment filed Dec. 19, 2012", 3 pgs.

"U.S. Appl. No. 13/719,868, Response filed Dec. 16, 2014 to Non Final Office Action mailed Sep. 25, 2014", 6 pgs.

"U.S. Appl. No. 13/719,868, Supplemental Preliminary Amendment filed May 1, 2013", 3 pgs.

"U.S. Appl. No. 12/639,304, Interview Summary mailed Sep. 18, 2012", 1 pg.

"U.S. Appl. No. 12/639,304, Non-Final Office Action mailed Mar. 15, 2012", 15 pgs.

"U.S. Appl. No. 12/639,304, Notice of Allowance mailed Sep. 18, 2012", 8 pgs.

"U.S. Appl. No. 12/639,304, Response filed Jan. 31, 2012 to Restriction Requirement mailed Jan. 3, 2012", 4 pgs.

"U.S. Appl. No. 12/639,304, Response filed Jun. 5, 2012 to Non-Final Office Action mailed Mar. 15, 2012", 13 pgs.

"U.S. Appl. No. 12/639,304, Restriction Requirement mailed Jan. 3, 2012", 6 pgs.

"U.S. Appl. No. 13/719,868, Preliminary Amendment filed Apr. 30, 2013", 7 pgs.

"International Application Serial No. PCT/US2010/062407, International Preliminary Report on Patentability dated Jul. 4, 2012", 7 pgs.

"International Application Serial No. PCT/US2010/062407, International Search Report mailed Aug. 2, 2011", 5 pgs.

"International Application Serial No. PCT/US2010/062407, Invitation to pay additional fees mailed Jun. 6, 2011", 2 pgs.

"International Application Serial No. PCT/US2010/062407, Written Opinion mailed Aug. 2, 2011", 6 pgs.

"UniProt Direct Submission. B9SSQ4_RICCO", [online]. © 2002-2012 UniProt Consortium [retrieved on Jun. 27, 2012]. Retrieved from the Internet: <URL: http://www.uniprot.org/uniproVB9SSQ4>, (Apr. 18, 2012), 3 pgs.

"UniProt Direct Submission. D6NSS8_EUOAL", [online]. © 2002-2012 UniProt Consortium [retrieved on Jun. 27, 2012]. Retrieved from the Internet: <URL: http://www.uniprot.org/uniproVD6NSS8>, (Nov. 16, 2011), 3 pgs.

Adams, M. D., et al., "Rapid cDNA sequencing (expressed sequence tags) from a directionally cloned human infant brain cDNA library", *Nat. Genet.*, 4(4), (1993), 373-380.

Ballas, N., et al., "Efficient functioning of plant promoters and poly(A) sites in *Xenopus* oocytes.", *Nucleic Acids Res.*, 17(19), (1989), 7891-7903.

Baud, S., et al., "An integrated overview of seed development in Arabidopsis thaliana ecotype WS", *Plant Physiol. Biochem.*, 40(2), (2002), 151-160.

Bauer, D., et al., "Identification of differentially expressed mRNA species by an Improved display technique (DDRT-PCR)", *Nucleic Acids Res.*, 21(18), (1993), 4272-4280.

Beachy, R. N., et al., "Accumulation and assembly of soybean β-conglycinin in seeds of transformed petunia plants", *EMBO J.*, 4(12), (1985), 3047-3053.

Bertioli, D. J., et al., "An analysis of differential display shows a strong bias towards high copy number mRNAs", *Nucleic Acids Res.* 23(21), (1995), 4520-4523.

Bevan, M., et al., "A chimaeric antibiotic resistance gene as a selectable marker for plant cell transformation", *Nature*, 304, (1983), 184-187.

Bligh, E. G., et al., "A Rapid Method of Total Lipid Extraction and Purification", Canadian *Journal of Biochemistry and Physiology.*, 37(8), (1959), 911-917.

Blochlinger, K., et al., "Hygromycin B Phosphotransferase as a Selectable Marker for DNA Transfer Experiments with Higher Eucaryotic Cells", *Mol. Cell. Biol.*, 4(12), (1984), 2929-2931.

Bourouis, M., et al., "Vectors containing a prokaryotic dihydrofolate reductase gene transform *Drosophila* cells to methotrexate-resistance", *The EMBO Journal*, 2(7), (1983), 1099-1104.

Bouvier-Nave, P., et al., "Expression in Yeast and Tobacco of Plant cDNAs Encoding Acyl CoA Diacylglycerol Acyltransferase", *Eur. J. Biochem.* 267(1), (2000), 85-96.

Burgal, J., et al., "Metabolic engineering of hydroxy fatty acid production in plants: RcDGAT2 drives dramatic increases in ricinoleate levels in seed oil", *Plant Biotechnology Journal*, 6(8), (2008), 819-831.

Callis, J., et al., "Introns Increase Gene Expression in Cultured Maize Cells", *Genes and Development*, 1(10), (1987), 1183-1200.

Casas, A. M., et al., "Transgenic sorghum plants via microprojectile bombardment", *Proc. Natl. Acad. Sci. USA*, 90(23), (1993), 11212-11216.

Chamberlin, M., et al., "New RNA polymerase from *Escherichia coli* infected with Bacteriophage T7", *Nature*, 228(5268), (1970), 227-23139.

Chao, W. S., et al,. "Leucine Aminopeptidase RNAs, Proteins, and Activities Increase in Response to Water Deficit, Salinity, and the Wound Signals Systemin, Methyl Jasmonate, and Abscisic Acid.", *Plant Physiol*, 120(4), (1999), 979-992.

Chen, Q., "Biosynthesis of Phytosterol Esters: Identification of a Sterol O-Acyltransferase in Arabidopsis", *Plant Physiol.*, 145, (2007), 974-984.

Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Nature Biotechnology*, 9, (1991), 957-962.

Christou, P., et al., "Stable Transformation of Soybean Callus by DNA-Coated Gold Particles", *Plant Physiol.*, 87(3), (1988), 671-67444.

(56) References Cited

OTHER PUBLICATIONS

Crossway, A., et al., "Integration of foreign DNA following microinjection of tobacco mesophyll protoplasts", *Mol. Gen. Genet.*, 202(2), (1986), 179-185.

Crossway, A., et al., "Micromanipulation Techniques in Plant Biotechnology", *BioTechniques*, 4(4), (1986), 320-334.

Dahlqvist, A., et al., "Phospholipid diacylglycerol acyltransferase: An enzyme that catalyzes the acyl-CoA-independent formation of triacylglycerol in yeast and plants", *Proc. Natl. Acad. Sci. USA.* 97(12). (2000), 6487-6492.

Datta, S. K., et al., "Genetically Engineered Fertile Indica-Rice Recovered from Protoplasts", *Nat. Biotechnol.* 8(8), (1990), 736-740.

Dehesh, K., et al., "Production of high levels of 8:0 and 10:0 fatty acids in transgenic canola by overexpression of Ch FatB2, a thioesterase cDNA from *Cuphea hookeriana*", *The Plant Journal*, 9(2), (1996), 167-172.

Dehesh, K., et al., "Two Novel Thioesterases are Key Determinants of Bimodal Distribution of Acyl Chain Length of *Cuphea palustris* Seed Oil", *Plant Physiology*, 110(1), (1996), 203-210.

Derisi, J., et al., "Use of a cDNA microarray to analyse gene expression patters in human cancer", *Nature Genetics*, vol. 14, (Dec. 1996), 457-460.

Durrett, T. P, et al., "A distinct DGAT with sn-3 acetyltransferase activity that synthesizes unusual, reduced-viscosity oils in *Euonymus* and transgenic seeds", *Proc. Natl. Acad. Sci. USA,*. 107(20), (May 18, 2010), 9464-9469.

Durrett, T. P., et al., "Plant triacylglycerols as feedstocks for the production of biofuels", *The Plant Journal*, 54(4), (2008), 593-607.

Dyer, J. D., et al., "Development and potential of genetically engineered oilseeds", *Seed Sci. Res.*, 15, (2005), 255-267.

Fraley, R. T., et al., "Liposome-mediated delivery of tobacco mosaic virus RNA into tobacco protoplasts: A sensitive assay for monitoring lipolipo-some-protoplast interactions", *Proc. Natl. Acad. Sci., USA*, 79, (1982), 1859-1863.

Fromm, M. E., et al., "Expression of genes transferred into monocot and dicot plant cells by electroporation", *Proc. Nat. Acad. Sci. USA*, 82, (1985), 5824-5828.

Fromm, M. E., et al., "Inheritance and Expression of Chimeric Genes in the Progeny of Transgenic Maize Plants", *Nature Biotechnology*, 8(9), (1990), 833-839.

Garbarino, J. E., et al., "Isolation of a ubiquitin-ribosomai protein gene (ubi3) from potato and expression of its promoter in transgenic plants.", *Plant Mol. Biol.*, 24(1), (1994), 119-127.

Gordon-Kamm, W. J., et al., "Transformation of Maize Cells and Regeneration of Fertile Transgenic Plants", *The Plant Cell*, 2(7), (1990), 603-61860.

Guerineau, F., et al., "Effect of deletions in the cauliflower mosaic virus polyadenylation sequence on the choice of the polyadenylation sites in tobacco protoplasts", *Mol. Gen. Genet.*, 262(1-2), (1991), 141-144.

Habu, Y., et al., "Amplified Restriction Fragment Length Polymorphism-based mRNA Fingerprinting Using a Single Restriction Enzyme That Recognizes a 4-bp Sequence", *Biochem Biophys Res Commun.*, 234(2), (1997), 516-521.

Hayashimoto, A., et al., "A Polyethylene Glycol-Mediated Protoplast Transformation System for Production of Fertile Transgenic Rice Plants.", *Plant Physiol.*, 93(3), (1990), 857-863.

He, X., et al., "Cloning and Characterization of a cDNA Encoding Diacylglycerol Acyltransferase from Castor Bean", *Lipids*, 39(4), (2004), 311-318.

He, X., et al., "Regulation of Diacylglycerol Acyltransferase in Developing Seeds of Castor", *Lipids*, 39(9), (2004), 865-871.

Hedrick, S. M., et al "Sequence Relationships Between Putative T-cell Receptor Polypeptides and Immunoglobulins", *Nature*, 308(5955), (1984), 153-158.

Hill, M., et al., "Biolistic introduction of a synthetic Bt gene into elite maize", *Euphytica*,85(1-3), (1995), 119-123.

Hinchee, M. A., et al., "Production of Transgenic Soybean Plants Using *Agrobacterium*-Mediated DNA Transfer", *Nature Biotechnology*. 6, (1988), 915-922.

Hobbs, D. H. et al, "Cloning of a cDNA encoding diacylglycerol acyltransferase from *Arabidopsis thaliana* and its functional expression", *FEBS Lett.*, 452(3), (1999), 145-149.

Ichihara, K., et al., "Diacylglycerol Acyltransferase in Maturing Safflower Seeds: Its Influences on the Fatty Acid Composition of Triacylglycerol and on the Rate of Triacylglycerol Synthesis", *Biochem Biophys. Acta*. 958(1), (1988), 125-129.

Ishida, Y., et al., "High efficiency transformation of maize (*Zea mays* L.) mediated by *Agrobacterium tumefaciens*", *Nature Biotechnology*, 14(6), (1996), 745-750.

Ito, T., et al., "Fluorescent Differential Display Arbitrarily Primed RT-PCR Fingerprinting on an Automated DNA Sequencer", *FEBS Lett.*, 351(2), (1994), 231-236.

J. Sambrook, et al., *Molecular Cloning: A Laboratory Manual*, 2nd Ed., Cold Spring Harbor Laboratory Press, NY, (1989), pp. 16.6-16.8.

J. Sambrook, et al., *Molecular Cloning: A Laboratory Manual*, Cold Spring Harbor Press, NY, (1989), pp. 9.31-9.58.

J. Sambrook, et al., *Molecular Cloning: A Laboratory Manual*, Cold Spring Harbor Press, NY, (1989), pp. 7.39-7.52.

Jahne, A., et al., "Regeneration of Transgenic, Microspore-Derived, Fertile Barley", *Theor. Appl. Genet.*, 89(4), (1994), 525-533.

Jako, C, et al., "Seed-Specific Over-Expression of an Arabidopsis CDNA Encoding a Diacylglycerol Acyltransferase Enhances Seed Oil Content and Seed Weight", *Plant Physiology*, 126(2), (2001), 861-874.

Jaworski, J., et al., "Industrial Oils from Transgenic Plants", *Curr. Opin. Plant Biol.*, 6(2). (2003), 178-184.

Joshi, C. P., et al., "Putative polyadenylation signals in nuclear genes of higher plants: a compilation and analysis", *Nucleic Acid Res.*, 15(23), (1987), 9627-9640.

Kacian, D. L., et al., "A Replicating RNA Molecule Suitable for a Detailed Analysis of Extracellular Evolution and Replication", *Proc. Natl. Acad. Sci. USA*, 69(10), (1972), 3038-3042.

Kalscheuer, R., et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1*", *J. Biol. Chem.*, 278(10), (2003), 8075-8082.

Katavic, V., et al., "Alteration of Seed Fatty Acid Composition by an Ethyl Methanesulfonate-lnduced Mutation in Arabidopsis Thaliana Affecting Diacylglycerol Acyltransferase Activity", *Plant Physiol.*, 108(1), (1995), 399-409.

Kennedy, E. P., "Biosynthesis of Complex Lipids", *Federation Proceedings*, 20, (1961), 934-940.

King, A., "Cuticular wax biosynthesis in petunia petals: cloning and characterization of an alcohol-acyltransferase that synthesizes wax-esters", *Planta*, 226(2), (2007), 381-394.

Klaus, D., et al., "Increased fatty acid production in potato by engineering of acetyl-CoA carboxylase", *Planta*. 219, (2004), 389-396.

Klein, T. M., et al., "Factors Influencing Gene Delivery into *Zea mays* Cells by High Velocity Microprojectiles", *Nature Biotechnology*, 6(5), (1988), 559-563.

Klein, T. M., et al., "Genetic Transformation of Maize Cells by Particle Bombardment", *Plant Physiology*, 91(1), (1989), 440-444.

Klein, T. M., et al., "Transfer of Foreign Genes into Intact Maize Cells with High-Velocity Microprojectiles", *Proc. Nat. Acad. Sci. USA*, 85, (1988), 4305-4309.

Knothe, G., et al., "Kinematic viscosity of biodiesel fuel components and related compounds. Influence of compound structure and comparison to petrodiesel fuel components", *Fuel*, 84(9), (Jun. 2005), 1059-1065.

Knudsen, S., et al., "Transformation of the developing barley endosperm by particle bombardment", *Planta*. 185, (1991), 330-336.

Koziel, M. G., et al., "Field Performance of Elite Transgenic Maize Plants Expressing as Insecticidal Protein Derived from *Bacillus thuringiensis*", *Nature Biotechnology*, 11, (1993), 194-200.

Koziel, M. G., et al., "Transgenic Maize for the Control of European Corn Borer and Other Maize Insect Pests", *Ann. N Y Acad. Sci.* 792(1), (1996), 164-171.

Krens, F. A., et al., "In Vitro transformation of plant protoplasts with Ti-plasmid DNA.", *Nature*, 296, (1982), 72-74.

Kroon, J. T., et al., "Identification and functional expression of a type 2 acyl-CoA:diacylglycerol acyltransferase (DGAT2) in developing

(56) References Cited

OTHER PUBLICATIONS castor bean seeds which has high homology to the major triglyceride biosynthetic enzyme of fungi and animals", *Phytochemsitry*, 67(23), (2006), 2541-2549.

Kunst, L., et al., "Fatty acid elongation in developing seeds of *Arabidopsis thaliana*", *Plant Physiol. Biochem.*, 30(4), (1992), 425-434.

Lardizabal, K. D., et al., "DGAT1 is a new Diacylglycerol Acyltransferase Gene Family—Purification, Cloning and Expression in Insect Cells of two Polypeptides from *Mortierella Ramanniana* with Diacylglycerol Acyltransferase Activity", *J. Biol. Chem.*, 276(42), (2001), 38862-38869.

Lardizabal, K. D., et al., "Purification of a Jojoba Embryo Wax Synthase, Cloning of its cDNA, and Production of High Levels of Wax in Seeds of Transgenic Arabidopsis", *Plant Physiol.*, 122(3). (2000), 645-655.

Li, F., et al., "Identification of the Wax Ester Synthase/Acyl-Coenzyme A:Diacylglycerol Acyltransferase WSD1 Required for Stem Wax Ester Biosynthesis in Arabidopsis", *Plant Physiology*, 148(1), (2008), 97-107.

Liang, P., et al., "Differential Display of Eukaryotic Messenger RNA by Means of the Polymerase Chain Reaction", *Science*, 257(5072), (1992), 967-971.

Liang, P., et al., "Distribution and cloning of eukaryotic mRNAs by means of differential display: refinements and optimization", *Nucleic Acids Research*, 21(14), (1993), 3269-3275.

Maniatis, T., et al., "Regulation of Inducible and Tissue-Specific Gene Expression", *Science*, 236(4806), (1987), 1237-1245.

McCabe, D. E., et al., "Stable Transformation of Soybean (*Glycine max*) by Particle Acceleration", *Nature Biotechnology*, 6, (Aug. 1988), 923-926.

Mietiewska, E., et al., "Seed-Specific Heterologous Expression of a Nasturtium FAE Gene in Arabidopsis Results in a DramaticIncrease in the Proportion of Erucic Acid", *Plant Physiol.*, 136(1), (2004), 2665-2675.

Milcamps, A., et al., "Isolation of a Gene-Encoding a1,2 Diacylglycerol-sn-Acetyl-CoA Acetyltransferase from Developing Seeds of *Euonymus alatus*", *J. Biol. Chem.* 280(7), (2005). 5370-5377.

Millar, A. A., et al., "Very-long-chain fatty acid biosynthesis is controlled through the expression and specificity of the condensing enzyme", *Plant J.*, 12(1), (1997), 121-131.

Mogen, B. D., et al., "Upstream sequences other than AAUAAA are required for efficient messenger RNA 3'-end formation in plants.", *The Plant Cell*, 2(12), (1990), 1261-1272.

Munroe, D., et al., "Tales of poly(A): a review", *Gene*, 91(2), (1990), 151-158.

Murphy, D. J., "Production of novel oils in plants", *Curr Opin Biotechnol.*, 10, (1999), 175-180.

Nehra, N. S., et al., "Self-fertile transgenic wheat plants regenerated from isolated scutellar tissues following microprojectile bombardment with two distinct gene constructs", *The Plant Journal*, 5(2), (1994), 285-297.

Nykiforuk, C. L., et al., "Characterization of cDNAs Encoding Diacylglycerol Acyltransferase from Cultures of *Brassica Napus* and Sucrose-Mediated Induction of Enzyme Biosynthesis", *Biochem. Biophys Acta*, 1580(2-3), (2002), 95-109.

Odell, J., et al., "Identification of DNA Sequences Required for Activity of the Cauliflower Mosaic Virus 35S Promoter", *Nature*. 313, (1985), 810-812.

Ohlrogge, J., et al., "Lipid Biosynthesis", *The Plant Cell*, 7(7), (1995), 957-970.

Okubo, K., et al., "Large Scale cDNA Sequencing for Analysis of Quantitative and Qualitiative Aspects of Gene Expression", *Nat. Genet.*, 2(3), (1992), 173-179.

Paszkowski, J., et al., "Direct Gene Transfer to Plants", *The EMBO Journal*, 3(12), (1984), 2717-2722.

Pillai, M. G., et al., "Biosynthesis of Triacylglycerol Molecular Species in an Oleaginous Fungus, *Mortierella ramanniana* var. *angulispora*", *J. Biochem*, 132(1), (2002), 121-126.

Proudfoot, N. J., "Poly(A) signals", *Cell*, 64. (1991), 671-674.

Riggs, C. D., et al., "Stable transformation of tobacco by electroporation: evidence for plasmid concatenation", *Proc. Natl. Acad. Sci. USA*, 83(15), (1986), 5602-5606.

Rosenberg, A. H., et al., "Vectors for selective expression of cloned DNAs by T7 RNA Polymerase", *Gene*, 56(1), (1987), 125-135.

Routaboul, C, et al., "Proposal for a new UVA protection factor: use of an in vitro model of immediate pigment darkening.", *European Journal of Dermatology*, 12(5), (Sep.-Oct. 2002), 439-44.

Routaboul, J. M., et al., "The TAG1 locus of *Arabidopsis* encodes for a diacylglycerol acyltransferase", *Plant Physiol. Bioch.*, 37(11), (1999), 831-840.

Saha, S., et al., "Cytosolic Triacylglycerol Biosynthetic Pathway in Oilseeds. Molecular Cloning and Expression of Peanut Cytosolic Diacylglycerol Acyltransferase", *Plant Physiology*, 141(4), (2006), 1533-1543.

Sandager, L., et al., "Storage Lipid Synthesis Is Non-essential in Yeast*". *J. of Biological Chem.*, 277, (2002), 6478-6482.

Sanfaçon, H., et al., "A dissection of the cauliflower mosaic virus polyadenylation signal", *Genes Dev.*, 5, (1991), 141-149.

Sanford, J. C., et al., "Delivery of Substances into Cells and Tissues Using a Particle Bombardment Process", *Particulate Sci. Technol.*, 5, (1987), 27-37.

Schell, J., "Transgenic Plants as Tools to Study the Molecular Organization of Plant Genes", *Science*, 237(4819), (1987), 1176-1183.

Schena, M., "Quantitative Monitoring of Gene Expression Patterns with a Complementary DNA Microarray", *Science*, 270(5235), (1995), 467-470.

Shanklin, J., et al., "Desaturation and Related Modifications of Fatty Acids", *Annual Review Plant Physiol. Plant Mol. Biol.*, 49, (1998), 611-641.

Shimamoto, K., et al., "Fertile transgenic rice plants regenerated from transformed protoplasts", *Nature*, 338. (1989), 274-276.

Shimkets, R. A., et al., "Gene Expression Analysis by Transcript Profiling Coupled to a Gene Database Query", *Nat.Biotechnol*. 17(8), (1999), 798-303.

Shockey, J. M., et al., "Tung Tree DGAT1 and DGAT2 Have Nonredundant Functions in Triacylglycerol Biosynthesis and are Localized to Different Subdomains of the Endoplasmic Reticulum", *The Plant Cell*, 18(9), (2006), 2294-2313.

Singh, S. P., et al., "Metabolic Engineering of New Fatty Acids in Plants", *Curr Opin. Plant Biol.*, 8(2), (2005), 197-203.

Smith, S. J., "Obesity resistance and multiple mechanisms of triglyceride synthesis in mice lacking Dgat", *Nat. Genet.*, 25(1), (2000), 87-90.

Somers, D. A., et al., "Fertile, Transgenic Oat Plants.", *Nature Biotechnology*, 10, (1992), 1589-1594.

Song, K., et al., "A Method for Examining Expression of Homologous Genes in Plant Polyploids", *Plant Mol Biol.* 26(4), (1994), 1065-1071.

Spencer, T. M., et al., "Bialaphos selection of stable tranformants from maize cell culture", *Theoretical and Applied Genetics* 79(5), (1990), 625-631.

Stahl, U., et al., "Cloning and Functional Characterization of a Phospholipid Diacylglycerol Acyltransferase from Arabidopsis", *Plant Physiol.*, 135, (2004), 1324-1335.

Staub, J. M., et al., "Accumulation of D1 polypeptide in tobacco plastids is regulated via the untranslated region of the psbA mRNA.", *EMBO J.*, 12(2), (1993), 601-606.

Staub, J. M., et al., "Long Regions of Homologous DNA are Incorporated into the Tobacco Plastid Genome by Transformation.", *The Plant Cell*, 4(1), (1992), 4-39.

Stone, B., et al., "Targeted RNA fingerprinting: the cloning of differentially-expressed cDNA fragments enriched for members of the zinc finger gene family", *Nucleic Acids Res*. 22(13), (1994), 2612-2618.

Stone, S. J., "Lipopenia and Skin Barrier Abnormalities in DGAT2-deficient Mice", *J. Biol. Chem.*, 279(12), (2004), 11767-11776.

Svab, Z., et al., "High-frequency plastid transformation in tobacco by selection for a chimeric aadA gene", *Proc. Natl. Acad. Sci. USA*,. 90(3), (1993), 913-917.

Svab, Z., et al., "Stable transformation of plastids in higher plants", *Proc. Natl. Acad. Sci. USA.*, 87, (1990), 8526-8530.

(56) References Cited

OTHER PUBLICATIONS

Thelen, J. J., et al., "Metabolic Engineering of Fatty Acid Biosynthesis in Plants.", *Metabolic Engineering*, 4(1), (2002), 12-21.

Torbert, K. A., et al., "Use of paromomycin as a selective agent for oat transformation", *Plant Cell Reports*, 14, (1995), 635-640.

Umbeck, P., et al., "Genetically transformed cotton (*Gossypium hirsutum* L.) plants", *Nature Biotechnology*, 5, (1987), 263-266.

Vasil, V., et al., "Rapid Production of Transgenic Wheat Plants by Direct Bombardment of Cultured immature Embryos", *Nature Biotechnology*, 11, (1993), 1553-1558.

Velculescu, V. E., et al., "Serial Analysis of Gene Expression", *Science*, 270(5235), (1995), 484-487.

Vieira, J., et al., "The pUC plasmids, an M13mp7-derived system for insertion mutagenesis and sequencing with synthetic universal primers", *Gene* 19(3), (1982), 259-268.

Vogel, G., et al., "Cholinephosphotransferase and Diacylglycerol Acyltransferase—Substrate Specificities at a Key Branchpoint in Seed Lipid Metabolism", *Plant Physiol.* 110, (1996), 923-931.

Voss, S. D., et al., "The Role of Enhancers in the Regulation of Cell-Type-Specific Transcriptional Control", *Trends Biochem. Sci.*, 11, (1986), 287-289.

Wan, Y., et al., "Generation of Large Numbers of Independently Transformed Fertile Barley Plants", *Plant Physiol.*, 104, (1994), 37-48.

Wang, N., et al., "Assessment of FAE1 polymorphisms in three Brassica species using EcoTILLING and their association with differences in seed erucic acid contents", *BMC Plant Biology*, 10: 137, (2010), 1-11.

Wang, X., et al., "Direct Sequencing of DNA Isolated from mRNA Differential Display", *Biotechniques* 18(3), (1995), 448-453.

Weeks, J. T., et al., "Rapid Production of Multiple Independent Lines of Fertile Transgenic Wheat (*Triticum aestivum*)", *Plant Physiol.*, 102, (1993), 1077-1084.

Weising, K., et al., "Foreign Genes in Plants: Transfer, Structure, Expression and Applications", *Annu. Rev. Genet.* 22, (1988), 421-477.

White, J., et al., "A cassette containing the bar gene of *Streptomyces hygroscopicus*: a selectable marker for plant transformation", *Nucleic Acids Research*, 18(4), (1990), 1062.

Wu, D. Y., et al., "The Ligation Amplification Reaction (LAR)—Amplification of Specific DNA Sequences Using Sequential Rounds of Template-Dependent Ligation", *Genomics*.4(4), (1989), 560-569.

Yen, C.-L. E., et al., "Thematic Review Series: Glycerolipids. DGAT enzymes and triacylglycerol biosynthesis", *J. Lipid Res.*, 49, (2008), 2283-2301.

Zhang, L., et al., "Gene Expression Profiles in Normal and Cancer Cells", *Science* 276, (1997), 560-569.

Zhang, M., et al., "DGAT1 and PDAT1 Acyltransferases Have Overlapping Functions in *Arabidopsis* Triacylglycerol Biosynthesis and Are Essential for Normal Pollen and Seed Development", *Plant Cell*, 21(12), (2009), 3885-3901.

Zou, J., et al., "Modification of Seed Oil Content and Acyl Composition in the Brassicaceae by Expression of a Yeast sn-2 Acyltransferase Gene", *Plant Cell*, 9(6), (1997), 909-923.

Zou, J. et al., "The *Arabidopsis thaliana* TAG1 mutant has a mutation in a diacylglycerol acyltransferase gene", *Plant J.* 19(6), (1999), 645-653.

"U.S. Appl. No. 13/719,868, Notice of Allowance mailed Feb. 17, 2015", 5 pgs.

\* cited by examiner

FIG. 5

>EaDACT SEQ ID NO:10
ATGATGGATGCTCATCAAGAGATCAAGAACTTCATCAAGGATTTGGGTACAAGCCATGGTATGTCTATTCTTACGCTTACTACTCTCCCTCAAGACTTCCAAAAGGACTCTCAAGGTTAC
TCTCTTTACTTCCTGTCCTTTATCCTCTTAATTAATCCCTATTAATCGCTTCCCTTGAACATCTCTTCTTCATTCTTCATCAATCACCCGCTTCTTCCTTGCTTGGCTAACACATTCAAGGTCATCTC
TTTGCCTTTGATCAAGGCCCTTTGTATCCACTCCCACAAAACCCTCTACATTCATCTCATCTAAAGTCTGTTCCATTGGGTCATTGGTCATCTCCACCAATACAAAAAGTACATGGATCCAA
ACAAACCCATCTCCAATTTCACATCTTTTGAAAAAGGCATTCATGTCATTCATTGGATATCTCACTCCTCTCTATGTGGAACATAATTGTCAAGTGTCCACGTCTCGACTGTCTAAGTTCCTTTGTGCCCAACTAGAAACATTGTTCATATCTAATT
AGTGGTCTTAGTGATCATTGTTGTCATCGTGTACGTTATGTGGATATCTGCACCCAGTGGAATCCTTTGTGGGTTTGATGTTGAACCACAATTCAAAGA
GCCTTACCTTGCTACTTCACTACAAGACTTTTGGGCCCGTAGGTGGAACATAATTGTGTCAAGTGTCCTACGTCGACTGTCTACGCCCACTAGAACATTGTTCATATCTAATT
GGGTCTAGATGGGCTTATTTTCCAGCTATAATTGCAACATTTGTCGTATCAGGAGTTATGCATGATGTAGTACATATGTACAATGATATCCCAACTGGATATGACAG
GGCACTTCGTCCTACATGGGATTTGTGAGGTGGAGATGAAGTGTAAGAGATCAAGGAGTGGCGCGGCATCCAGCTGTCCATTGGGTAATGGTGATGGGGTT
TGTGATGGGGACTAGTGTTTCCTTACTCTTTGTGCCACTATTAAGGGATAATGTGACCAAATTGTAGCAGAAGAGTACTCAATTTTGTTTAATTTTGTGAGGGAGAAGATTGTCATG
CTTGGAACACAAGGTTTGTGTGTGGAAATTGA

>17392_F SEQ ID NO:11
CAC CAT GAT GGA TGC TCA TCA AGA G
>17329_R2 SEQ ID NO:12
ATT TAT TTC ATC GTC ATC ATC AAT TTC C

>Ea39113 SEQ ID NO:13
attacggccgggacattataatcaataataaaataggattgagtctcgagatgaaggacttgaattccaagccaccgagtccgctgagcacgacggcgcacatccaaggacga
tcggcccctcctcaagcccgaggcagtccggtgctcctcaatggaagcctccaggacatgcagcgcatgctatcgcaacgacgtgtacggcgccccacgggacgcggcgag
ttgccgttggcggagaaggtcctgctgctggctgtgtgacgcgcagatggctgcgtgattgtctgcggtggttgtttctccagagtcatgtcttcgtgtt
tctctcgtccgcagaatccgtgacgggagcaggaggattacgcgacatggaggagctgaagtcgaggactggtgagaggacaaagaccaatccaaagatccagaagaccgcg
tgggtttactggattaacgagaccatatggattccagaagcttcacagacaagcttcagagcgcgttctgtgcttggtgctaactcctatctgttggtctcatcatgca
gcgattgtatctaatcacgtatcatatttggatcatgtcagaggggagcctaagtcatcgacttcaccatatctgacttccattcaccacgtcaaaatggctgccgctatat
agtgcctgttgttgtttatgttcagagggcacaacacaatggagacactacaaatgtgagacactacaaatggagacactccctcaggaaacctcatcaaaatggctcgccgctattac
gatgcttttccagagggcacaacactacaggagggcacgcactgatcctgccaataattcattaatcacgagggcacatgttacctgctcaaaccacatcgaagaga
ttcagtcctgcctggactcaattatccgggcacgcatgataatgttcgaaggttgatgctcagagagggcaattgataatgccgatatcggatcagcagaggacatctatcatgtgctctcaatgg
aagataatccaaactctatgctgtgtgcatcagaaagcgatctaatttcatggcctgctccgcctccagtgggtttcttagtgtacattgtacattttgcttatacatg
taataatagcctgcctagtgtattgcatccagaaagcgatctaatttcatggcctgctccgcctccagtgggtttcttagtgtacattgtacattttgcttatacatg
cacaactaagggaggtacccttcctcccacattctaccctcaaaagatgttgttcgtttgctgagtcctgtaattttag >39113_F SEQ ID NO:14
CAC CAT GGA GTC TGA GAT GAA GGA C
>39113_R SEQ ID NO:15
TCA ATC GTC TTT CTG ATG CAA TAC ACT AG

FIG. 6

>EaDAcT SEQ ID NO:01
MMDAHQEIKNFIKVWVQAMVCLSYAYYFSSRLPKGLLRLLSLLPVLYLLLIAPLNISSFILSSITGFFLAWLITFKVISFAFDQGPLYPLPQN
LLHFISIACLPITIKRNPSPKLKSTTNPSPISHLLKKAFMSFPSKVLFHWVIAHLYQYKKYMDPNVLVIYCCHVYVMLDISLSLCATLAEFL
CGFDVEPQFKEPYLATSLQDFWGRRWNIIVSSVLRSTVYAPTRNIASYLIGSRWAYFPAIIATFVVSGVMHDVVYYVMHMYPKWDMTGHFV
LHGICEALEVEMKCKRSRSDKWRRHPAVDWVMVMGFVMGTSVSLLFVPLLRDNVDQIVAERYSILFNFVREKIVMLGTRPVCGN

Table 3. Context of EaDAcT polypeptide with other plant polypeptides.

| Polypeptide | Identities = No. aa/aa (percent) | SEQ ID NO:XX |
|---|---|---|
| EaDAcT [Euonymus alatus] | 363/363 (100%) | SEQ ID NO:01 |
| unnamed protein product [Vitis vinifera]ACCESSION CAO38873 | 164/342 (47%) * | SEQ ID NO:02 |
| hypothetical protein [Vitis vinifera]ACCESSION CAN61366 | 159/339 (46%) * | SEQ ID NO:03 |
| hypothetical protein [Vitis vinifera][wine grape] ACCESSION XP_002276902 | 171/368 (46%) * | SEQ ID NO:04 |
| hypothetical protein [Vitis vinifera] ACCESSION CAN61368 | 157/350 (44%) * | SEQ ID NO:05 |
| wax synthase isoform 3 [Vitis vinifera] ACCESSION AAO18666 | 156/350 (44%) * | SEQ ID NO:06 |
| predicted protein [Populus trichocarpa]ACCESSION XP_002314065 | 150/339 (44%) * | SEQ ID NO:07 |
| acyltransferase, putative [Ricinus communis] [castor bean] ACCESSION EEF33334 | 157/362 (43%) * | SEQ ID NO:08 |
| 1,2-diacyl-sn-glycerol:acyl-CoA acyltransferase [Euonymus alatus]. DGAT1: 507 aa total; ACCESSION AAV31083*** | 34/121 (28%) ** | SEQ ID NO:09 |

* - Nearest Identities from BLAST of EaDAcT; (National Center for Biotechnology Information (NCBI), Bethesda, Maryland at //blast.ncbi.nlm.nih.gov/Blast.cgi.)
** - Align two sequences, NCBI.
*** - Milcamps, et al., J. Biol. Chem. 280 (7), 5370-5377 (2005), U.S. Patent Nos. 7,122,367 and 7,429,473, all of which are herein incorporated by reference in their entirety.

BaDAcT expressed under control of strong seed specific 2S seed storage protein promoter
Neutral lipids isolated from T3 seeds, analysed using ESI-MS Expression of EaDAcT in WT Arabidopsis Results in Accumulation of High Levels of AcTAGs Expression of EaDAcT in Arabidopsis plants containing mutations in enzymes necessary for endogenous TAG synthesis results in enhanced levels of acTAG accumulation FIG. 16
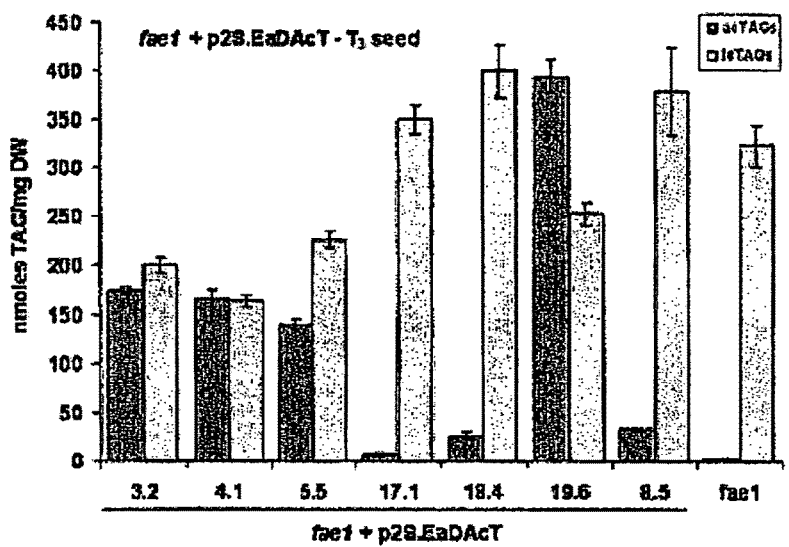
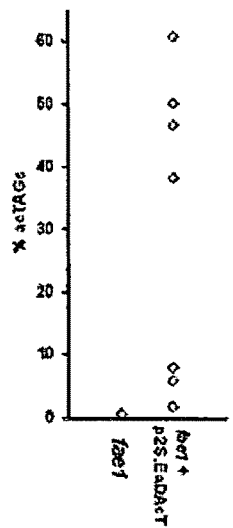

SEQUENCE LISTING

```
<160> NUMBER OF SEQ ID NOS: 20

<210> SEQ ID NO 1
<211> LENGTH: 363
<212> TYPE: PRT
<213> ORGANISM: Euonymus alatus

<400> SEQUENCE: 1

Met Met Asp Ala His Gln Glu Ile Lys Asn Phe Ile Lys Val Trp Val
1               5                   10                  15

Gln Ala Met Val Cys Leu Ser Tyr Ala Tyr Tyr Phe Ser Ser Arg Leu
            20                  25                  30

Pro Lys Gly Leu Leu Arg Leu Leu Ser Leu Leu Pro Val Leu Tyr Leu
        35                  40                  45

Leu Leu Ile Ala Pro Leu Asn Ile Ser Ser Phe Ile Leu Ser Ser Ile
    50                  55                  60
```

```
Thr Gly Phe Phe Leu Ala Trp Leu Thr Thr Phe Lys Val Ile Ser Phe
 65                  70                  75                  80

Ala Phe Asp Gln Gly Pro Leu Tyr Pro Leu Pro Gln Asn Leu Leu His
                 85                  90                  95

Phe Ile Ser Ile Ala Cys Leu Pro Ile Thr Ile Lys Arg Asn Pro Ser
            100                 105                 110

Pro Lys Leu Lys Ser Thr Thr Asn Pro Ser Pro Ile Ser His Leu Leu
        115                 120                 125

Lys Lys Ala Phe Met Ser Phe Pro Ser Lys Val Leu Phe His Trp Val
    130                 135                 140

Ile Ala His Leu Tyr Gln Tyr Lys Lys Tyr Met Asp Pro Asn Val Val
145                 150                 155                 160

Leu Val Ile Tyr Cys Cys His Val Tyr Val Met Leu Asp Ile Ser Leu
                165                 170                 175

Ser Leu Cys Ala Thr Leu Ala Glu Phe Leu Cys Gly Phe Asp Val Glu
            180                 185                 190

Pro Gln Phe Lys Glu Pro Tyr Leu Ala Thr Ser Leu Gln Asp Phe Trp
        195                 200                 205

Gly Arg Arg Trp Asn Ile Ile Val Ser Ser Val Leu Arg Ser Thr Val
    210                 215                 220

Tyr Ala Pro Thr Arg Asn Ile Ala Ser Tyr Leu Ile Gly Ser Arg Trp
225                 230                 235                 240

Ala Tyr Phe Pro Ala Ile Ile Ala Thr Phe Val Val Ser Gly Val Met
                245                 250                 255

His Asp Val Val Tyr Tyr Val Tyr Met Met His Met Tyr Pro Lys Trp
            260                 265                 270

Asp Met Thr Gly His Phe Val Leu His Gly Ile Cys Glu Ala Leu Glu
        275                 280                 285

Val Glu Met Lys Cys Lys Arg Ser Arg Ser Asp Lys Trp Arg Arg His
    290                 295                 300

Pro Ala Val Asp Trp Val Met Val Met Gly Phe Val Met Gly Thr Ser
305                 310                 315                 320

Val Ser Leu Leu Phe Val Pro Leu Leu Arg Asp Asn Val Asp Gln Ile
                325                 330                 335

Val Ala Glu Glu Tyr Ser Ile Leu Phe Asn Phe Val Arg Glu Lys Ile
            340                 345                 350

Val Met Leu Gly Thr Arg Phe Val Cys Gly Asn
        355                 360

<210> SEQ ID NO 2
<211> LENGTH: 415
<212> TYPE: PRT
<213> ORGANISM: Vitis vinifera

<400> SEQUENCE: 2

Met Asp Gly Glu Ile Lys Ser Leu Ile Lys Val Trp Ile Ser Ala Ile
  1               5                  10                  15

Ser Ser Ile Cys Tyr Cys Tyr Phe Phe Val Val Arg Leu Pro Val Gly
             20                  25                  30

Leu Phe Arg Leu Leu Phe Leu Leu Pro Met Phe Tyr Leu Phe Ile Ile
         35                  40                  45

Leu Pro Leu Asn Leu Ser Ser Ala His Leu Val Gly Thr Thr Ala Phe
     50                  55                  60

Tyr Leu Ala Trp Leu Ala Asn Phe Lys Phe Ile Leu Phe Ser Phe Gly
 65                  70                  75                  80
```

His Gly Pro Leu Ser Phe Pro Ser His Pro Pro Lys Ser Val Leu Arg
                85                  90                  95

Phe Ile Ser Ile Ala Cys Leu Pro Ile Lys Ile Lys Thr Val Pro Ser
            100                 105                 110

Pro Lys Ser His Ser Lys Val Ala Phe Leu Ile Lys Ala Leu Ala Leu
        115                 120                 125

Ala Ala Leu Leu Lys Val Tyr Lys Tyr Arg Gln Phe Leu His Pro Asn
    130                 135                 140

Val Ile Leu Ala Leu Tyr Cys Cys His Val Tyr Leu Ala Ala Glu Leu
145                 150                 155                 160

Ile Leu Ala Leu Ala Ala Pro Ala Arg Ala Ile Gly Leu Glu Leu
                165                 170                 175

Glu Pro Gln Phe Asn Glu Pro Tyr Leu Ala Thr Ser Leu Gln Asp Phe
            180                 185                 190

Trp Gly Arg Arg Trp Asn Leu Met Val Ser Ser Ile Leu Arg Pro Thr
            195                 200                 205

Ile Tyr Phe Pro Ile Leu Met Ser Glu Arg Trp Ser Pro Leu Pro Ala
    210                 215                 220

Val Val Ala Thr Phe Leu Val Ser Gly Leu Met His Glu Leu Leu Phe
225                 230                 235                 240

Tyr Tyr Val Asn Arg Val Ser Pro Ser Trp Glu Met Thr Ser Phe Phe
                245                 250                 255

Val Leu His Gly Val Cys Leu Val Val Glu Val Gly Val Lys Ser Val
            260                 265                 270

Phe Ser Gly Arg Trp Arg Leu His Trp Ala Ala Ser Val Pro Leu Thr
        275                 280                 285

Val Gly Phe Val Val Ala Thr Ser Phe Trp Leu Phe Phe Pro Pro Leu
    290                 295                 300

Ile Arg Ala Gly Ala Asp Met Arg Val Met Glu Glu Ala His Ser Ile
305                 310                 315                 320

Val Lys Lys Glu Asp Leu Ile Glu Tyr Arg Gly Val Lys Glu Phe Lys
                325                 330                 335

Pro Lys Tyr Gln Met Lys Val Asp Arg Phe Phe Phe Ile Pro Glu Glu
            340                 345                 350

Val His Ile Leu Pro Gly Ser Ala Ser Ile Met Val Arg Asn Asn Ser
        355                 360                 365

Ile Ile Gly Val Asp Thr Arg Ile Thr Leu Asn Thr Arg Ser Arg Val
    370                 375                 380

Ser Gly Leu Val Arg Val Glu Arg Lys Lys Arg Ile Glu Leu Lys
385                 390                 395                 400

Ile Phe Ser Gly Asp Ile Gln Phe Pro Gly Asp Met Cys Ile Ala
                405                 410                 415

<210> SEQ ID NO 3
<211> LENGTH: 2238
<212> TYPE: PRT
<213> ORGANISM: Vitis vinifera

<400> SEQUENCE: 3

Met Val Ile Trp Asp Ser Trp Trp Gly Tyr Lys Glu Leu Pro His Gln
1               5                   10                  15

His Arg Met Thr Val Cys Gly Gly Asn Leu Gly Gly Asp Trp Val Ser
            20                  25                  30

Leu His Ser Thr Ala Ala Lys Met Ser Ser Phe Val Gly Val Leu Val

```
                35                  40                  45
Ser Asp Gln Trp Leu Gln Ser Gln Phe Thr Gln Val Glu Leu Arg Ser
 50                  55                  60

Leu Lys Ser Lys Phe Met Ala Val Arg Asn Gln Asn Gly Lys Val Thr
 65                  70                  75                  80

Val Gly Asp Leu Pro Ala Leu Met Val Lys Leu Lys Ala Phe Ser Asp
                 85                  90                  95

Met Phe Lys Glu Glu Ile Arg Gly Ile Leu Gly Ser Gly Ala
                100                 105                 110

Asp Met Asn Asp Glu Val Asp Phe Glu Ala Phe Leu Arg Ala Tyr Leu
                115                 120                 125

Asn Leu Gln Gly Arg Gly Thr Glu Lys Leu Gly Gly Ser Asn His Ser
130                 135                 140

Ser Ser Phe Leu Lys Ala Thr Thr Thr Leu Leu His Thr Ile Ile
145                 150                 155                 160

Glu Ser Glu Lys Ala Ser Tyr Val Ala His Ile Asn Ser Tyr Leu Gly
                165                 170                 175

Asp Asp Pro Phe Leu Lys Gln Tyr Leu Pro Leu Asp Pro Ser Thr Asn
                180                 185                 190

Asp Leu Phe Asp Leu Val Lys Asp Gly Val Leu Leu Cys Lys Leu Ile
                195                 200                 205

Asn Val Ala Val Pro Gly Thr Ile Asp Glu Arg Ala Ile Asn Thr Lys
210                 215                 220

Arg Val Leu Asn Pro Trp Glu Arg Asn Glu Asn His Thr Leu Cys Leu
225                 230                 235                 240

Asn Ser Ala Lys Ala Ile Gly Cys Thr Val Val Asn Ile Gly Thr Gln
                245                 250                 255

Asp Leu Ile Glu Gly Arg Ile Gln Leu Leu Ala Asp Leu Asn Leu Lys
                260                 265                 270

Lys Thr Pro Gln Leu Val Glu Leu Val Asp Asp Gly Asn Asp Val Glu
                275                 280                 285

Glu Leu Met Gly Leu Ala Pro Glu Lys Val Leu Leu Lys Trp Met Asn
290                 295                 300

Phe His Leu Lys Lys Ala Gly Tyr Lys Lys Pro Ile Thr Asn Phe Ser
305                 310                 315                 320

Ser Asp Leu Lys Asp Gly Glu Ala Tyr Ala Tyr Leu Leu Asn Val Leu
                325                 330                 335

Ala Pro Glu His Cys Ser Pro Ala Thr Leu Asp Ala Lys Asp Pro Thr
                340                 345                 350

His Arg Ala Lys Leu Val Leu Asp His Ala Glu Arg Met Asp Cys Lys
                355                 360                 365

Arg Tyr Leu Ser Pro Lys Asp Ile Val Glu Gly Ser Pro Asn Leu Asn
                370                 375                 380

Leu Ala Phe Val Ala Gln Ile Phe His Gln Arg Ser Gly Leu Ser Ala
385                 390                 395                 400

Asp Cys Lys Asn Ile Ser Phe Ala Glu Met Met Thr Asp Asp Val Leu
                405                 410                 415

Ile Ser Arg Glu Glu Arg Cys Phe Arg Leu Trp Ile Asn Ser Leu Gly
                420                 425                 430

Ile Val Thr Tyr Val Asn Asn Leu Phe Glu Asp Val Arg Asn Gly Trp
                435                 440                 445

Ile Leu Leu Glu Val Leu Asp Lys Val Ser Pro Gly Ser Val Asn Trp
450                 455                 460
```

```
Lys Arg Ala Ser Lys Pro Pro Ile Lys Met Pro Phe Arg Lys Val Glu
465                 470                 475                 480

Asn Cys Asn Gln Val Ile Gly Ile Gly Lys Gln Leu Lys Phe Ser Leu
                485                 490                 495

Val Asn Val Ala Gly Glu Asp Ile Val Gln Gly Asn Lys Lys Leu Ile
                500                 505                 510

Leu Ala Phe Leu Trp Gln Leu Met Arg Tyr Asn Met Leu Gln Leu Leu
            515                 520                 525

Lys Asn Leu Arg Phe His Ser Gln Gly Lys Glu Met Thr Asp Ala Asp
530                 535                 540

Ile Leu Lys Trp Ala Asn Asn Lys Val Lys Arg Thr Gly Arg Thr Ser
545                 550                 555                 560

Gln Met Glu Ser Phe Lys Asp Lys Asn Leu Ser Asn Gly Ile Phe Phe
                565                 570                 575

Leu Asp Leu Leu Ser Ala Val Glu Pro Arg Val Val Asn Trp Asn Leu
            580                 585                 590

Val Thr Lys Gly Glu Ser Glu Glu Lys Lys Leu Asn Ala Thr Tyr
            595                 600                 605

Ile Ile Ser Val Ala Arg Lys Leu Gly Cys Ser Ile Phe Leu Leu Pro
610                 615                 620

Glu Asp Ile Met Glu Gly Ala Val Arg Lys Leu Leu Leu Gly Cys
625                 630                 635                 640

Leu Tyr Ser Asp Lys Arg Met Ala Ser Ser Asp Asp Glu Gly Glu Thr
                645                 650                 655

Leu Pro Gly Ser Val Ser Asn Tyr His Phe Val Asp Asp Lys Gly Glu
                660                 665                 670

Pro Ile Ser Phe Ser Val Leu Pro Ile Gln Trp Ser Lys Gly Asp Asn
            675                 680                 685

Leu Asp Ser Lys Lys Glu Pro Ile Phe Leu Asp Gly Asn Ala Asp Asn
            690                 695                 700

Gly Leu Gln Lys Ile Tyr Lys Gln Val Ile Ala Trp Lys Phe Asp Leu
705                 710                 715                 720

Ser Asp Val Asn Pro Glu Ile Ser Val Leu Ser Lys Glu Asn Asn Trp
                725                 730                 735

Ile Lys Leu Gln Lys Pro Arg Lys Ser Phe Glu Asp Ile Ile Arg Ser
                740                 745                 750

Ile Leu Ile Thr Val Trp Cys Leu His Ser Met Lys Lys Asn Pro Glu
            755                 760                 765

Thr Ser Gly Lys Ser Leu Trp Asp His Leu Ser Arg Val Phe Ser Leu
            770                 775                 780

Tyr Asp Val Arg Pro Ser Glu Asn Asp Leu Val Asp His Thr Thr Leu
785                 790                 795                 800

Ile Ser Glu Ala Val Lys Arg Asp Glu Gly Leu Ala Lys Ser Lys Phe
                805                 810                 815

Leu Leu Thr Phe Leu Glu Glu Lys Pro Arg Lys Arg Lys Ser Phe Glu
            820                 825                 830

Asp Val Pro Thr Thr Ser Lys Pro Gly Phe Ile Val Asp Tyr Met Asp
            835                 840                 845

Glu Asp Gly Ile Ser Glu Thr Gly Glu Val Gly Ser Asp Glu Glu Glu
            850                 855                 860

Asp Leu Phe Asp Ser Val Cys Ser Met Cys Asp Asn Gly Gly Asp Leu
865                 870                 875                 880
```

-continued

Leu Cys Cys Glu Gly Arg Cys Met Arg Ser Phe His Ala Thr Lys Glu
            885                 890                 895

Ala Gly Glu Glu Ser Leu Cys Ala Thr Leu Gly Met Ser Val Ala Gln
        900                 905                 910

Val Glu Ala Met Gln Asn Phe Tyr Cys Lys Asn Cys Lys Tyr Lys Gln
        915                 920                 925

His Gln Cys Phe Ser Cys Gly Lys Leu Gly Ser Ser Asp Lys Ser Ser
930                 935                 940

Gly Ala Glu Val Phe Leu Cys Ala Asn Ala Thr Cys Gly Arg Phe Tyr
945                 950                 955                 960

His Pro Gln Cys Val Ala Lys Leu Leu His Arg Glu Asp Glu Ala Ala
            965                 970                 975

Ala Glu Asp Leu Gln Lys Asn Ile Tyr Ala Gly Glu Leu Phe Ala Cys
        980                 985                 990

Pro Ile His Arg Cys His Val Cys Lys Gln Gly Glu Asp Lys Lys Asp
            995                 1000                1005

Leu Glu Leu Gln Phe Ala Ile Cys Arg Arg Cys Pro Lys Ser Tyr
    1010                1015                1020

His Arg Lys Cys Leu Pro Arg Lys Ile Ser Phe Glu Asp Leu Asp
    1025                1030                1035

Glu Glu Gly Ile Ile Gln Arg Ala Trp Asp Gly Leu Leu Pro Asn
    1040                1045                1050

Arg Ile Leu Ile Tyr Cys Leu Lys His Glu Ile Asp Glu Leu Leu
    1055                1060                1065

Gly Thr Pro Ile Arg Asp His Ile Lys Phe Pro Asn Asp Glu Glu
    1070                1075                1080

Lys Met Glu Lys Arg Arg Ser Glu Leu Phe Ser Ser Arg Lys Asp
    1085                1090                1095

Leu Asp Lys Val Val Ser Lys Lys Arg Ser Leu Val Ser Glu Asp
    1100                1105                1110

Ser Pro Arg Glu Arg Met Ala Val Lys Ala Thr Lys Gln Val Glu
    1115                1120                1125

Lys Leu Ser Ser Thr Val Lys Asp Gly Asp Ser Thr Lys Lys Ser
    1130                1135                1140

Glu Lys Arg Ser Ser Gly Pro Asp Pro Ser Lys Arg Leu Lys Val
    1145                1150                1155

Thr Gly Phe Ser Lys Lys Ser Leu Asp Asp Asn Val Lys Ser Ile
    1160                1165                1170

Ser Lys Lys Val Asp Lys Ser Ser Met Ala Asp Glu Asn Lys Thr
    1175                1180                1185

Ser Leu Gly Glu Gln Leu Tyr Ala Leu Ile Lys Asn Arg Ser Glu
    1190                1195                1200

Pro Arg Lys Glu Asp Thr Pro Asn Ser Glu Leu Glu Gln Lys Val
    1205                1210                1215

Val Thr Lys Lys Thr Ser Ser Leu Pro Ser Leu Asp Arg Asp
    1220                1225                1230

Ser Glu Asn Arg Ile Leu Ala Ile Ile Lys Glu Ser Lys Ser Leu
    1235                1240                1245

Ile Thr Leu Glu Asp Val Met Lys Lys His Lys Val Pro Ser Thr
    1250                1255                1260

His Ala Tyr Ser Ser Lys Asn Thr Val Asp Arg Thr Ile Thr Gln
    1265                1270                1275

Gly Lys Val Glu Gly Ser Ile Glu Ala Leu Arg Ala Ala Leu Lys

```
            1280               1285               1290
Lys Leu Glu Gly Gly Gly Ser Ile Glu Asp Ala Lys Ala Val Cys
    1295               1300              1305

Glu Pro Glu Val Leu Asn Gln Ile Val Lys Trp Lys Asn Lys Leu
    1310               1315              1320

Lys Val Tyr Leu Ala Pro Phe Leu His Gly Met Arg Tyr Thr Ser
    1325               1330              1335

Phe Gly Arg His Phe Thr Lys Val Asp Lys Leu Lys Glu Ile Val
    1340               1345              1350

Glu Lys Leu His Tyr Tyr Val Lys Asn Gly Asp Thr Ile Val Asp
    1355               1360              1365

Phe Cys Cys Gly Ala Asn Asp Phe Ser Cys Leu Met Lys Gln Lys
    1370               1375              1380

Leu Glu Glu Met Gly Lys Lys Cys Ser Tyr Lys Asn Tyr Asp Val
    1385               1390              1395

Ile Gln Pro Lys Asn Asp Phe Asn Phe Glu Lys Arg Asp Trp Met
    1400               1405              1410

Ser Val Lys Gln Lys Glu Leu Pro Thr Gly Ser Gln Leu Ile Met
    1415               1420              1425

Gly Leu Asn Pro Pro Phe Gly Val Lys Ala Ser Leu Ala Asn Met
    1430               1435              1440

Phe Ile Asn Lys Ala Leu Gln Phe Lys Pro Lys Leu Leu Ile Leu
    1445               1450              1455

Ile Val Pro Pro Glu Thr Glu Arg Leu Asp Lys Lys Arg Pro Pro
    1460               1465              1470

Tyr Asp Leu Ile Trp Glu Asp Asn Glu Leu Ser Gly Lys Ser
    1475               1480              1485

Phe Tyr Leu Pro Gly Ser Val Asp Val Asn Asp Lys Gln Ile Glu
    1490               1495              1500

Gln Trp Asn Val Asn Pro Pro Leu Leu Tyr Leu Trp Ser Arg Gln
    1505               1510              1515

Asp Trp Thr Thr Lys His Arg Ala Ile Ala Gln Lys Cys Gly His
    1520               1525              1530

Val Ser Arg Arg Arg Arg Val Ser His Leu Glu Lys Ile Gln Asn
    1535               1540              1545

Glu Glu Pro Val Leu Asp His Pro Met Ala Asp Gln Thr His Ser
    1550               1555              1560

Gly His Val Ser Met Met Leu Asp Glu His Ser Val Glu Asn His
    1565               1570              1575

Glu Leu Glu His Glu Glu Arg Arg Glu Ile Val Thr Ala Gly Arg
    1580               1585              1590

Val Glu Ser Ser Pro His Ser Gly Val Asp Arg Glu Asp His Gly
    1595               1600              1605

Lys Lys Leu Leu Asn Glu Asn Ser Lys Gln Arg His Gly Lys Gly
    1610               1615              1620

Lys His Glu Lys Arg Thr Glu Asn Ile Ser Asp Asp Lys Gln Ile
    1625               1630              1635

Met Thr Pro Val Ser Glu Met Cys Lys Gly Thr Ser Cys Thr Ser
    1640               1645              1650

Ser Pro Arg Ala Ser Asp Ala Arg Ser Thr Val Asp Ile His Gln
    1655               1660              1665

Pro Glu Ala Leu Lys Lys Ser Ser Pro Val Glu Val Gly Glu Glu
    1670               1675              1680
```

```
Val Tyr Pro His Phe Gln Pro Gly Val Pro Asp Ser Ser Leu Gln
1685                1690                1695

Arg Thr Gly Tyr Gly Gly Ser His Ala Ser Ile Pro Glu Asp Met
    1700            1705                1710

Ala Arg Arg Tyr Arg Leu Asp Ser Glu Glu Pro Phe Ser Ser Thr
1715                1720                1725

Ile His Arg Trp Ser Thr Gly Val Ser Pro Gly Leu Asp Tyr Gly
    1730            1735                1740

Ile Arg Asn Ser Glu Glu Pro Phe Thr Ser Tyr Met Arg Gly Ser
1745                1750                1755

Ile Asp Asn Leu Gly Tyr Arg His Ser Ile Arg Asp Arg Asp Glu
    1760            1765                1770

Tyr Gly Arg Asn Ala Asp Ile Arg Ser Gln Val Gln Ser Tyr Gly
1775                1780                1785

Leu His Asp Pro Ile Gly Met Ser Gln Arg Ser Asn Tyr Leu Ala
    1790            1795                1800

Gly Gln Asp Pro Arg Phe Gly Gln Met Gly Ser Phe Pro Ser Thr
1805                1810                1815

Tyr Gly His Pro Gly Ser Gly Ala Glu Ser Ser Tyr Ser Arg Met
    1820            1825                1830

Asn Thr Ser Ala Met Gln Arg Tyr Ala Pro Gln Leu Asp Glu Leu
1835                1840                1845

Asn His Thr Arg Met Asn Ser Phe Gly Tyr Glu Arg Pro Met Pro
    1850            1855                1860

Ile Arg Asn Asn Ile Tyr Asp Pro Leu Ala Pro Pro Arg Pro Gly
1865                1870                1875

Phe Gln Ala Asp Ser Met Gly Phe Ala Pro Gly Leu His His Pro
    1880            1885                1890

Phe Ser Lys Gln Asn Ser Ser Val Arg Leu Pro Val Gly Leu Phe
1895                1900                1905

Arg Leu Leu Phe Leu Leu Pro Met Phe Tyr Leu Phe Ile Ile Leu
    1910            1915                1920

Pro Leu Asn Leu Ser Ser Ala His Leu Val Gly Thr Thr Ala Phe
1925                1930                1935

Tyr Leu Ala Trp Leu Ala Asn Phe Lys Phe Ile Leu Phe Ser Phe
    1940            1945                1950

Gly His Gly Pro Leu Ser Phe Pro Ser His Pro Thr Lys Ser Leu
1955                1960                1965

Leu Arg Phe Ile Ser Ile Ala Cys Leu Pro Ile Lys Ile Lys Thr
    1970            1975                1980

Val Pro Ser Pro Lys Ser His Ser Val Ser Glu Asn Ser Thr Asp
1985                1990                1995

Pro Leu Ser Glu Ile Val Met Lys Leu Pro Arg Pro Leu Leu Leu
    2000            2005                2010

Ala Ile Lys Ala Leu Leu Phe Ala Ile Leu Ile Arg Ile Tyr Asn
2015                2020                2025

Tyr Lys Arg His Leu His Pro Asn Val Val Leu Phe Leu Tyr Cys
    2030            2035                2040

Cys His Met Tyr Leu Ala Leu Glu Ile Val Gln Ala Met Ala Ala
2045                2050                2055

Ile Pro Ala Arg Ala Ile Pro Gly Phe Glu Leu Glu Pro Gln Phe
    2060            2065                2070
```

```
Asn Glu Pro Tyr Leu Thr Thr Ser Leu Gln Asp Phe Trp Gly Arg
    2075                2080                2085

Arg Trp Asn Leu Ser Val Thr Asn Ile Leu Arg Pro Thr Val Tyr
    2090                2095                2100

Asp Pro Val Arg Ser Ile Cys Thr Arg Ile Leu Gly Lys Glu Trp
    2105                2110                2115

Ala Pro Val Pro Gly Val Leu Ala Ala Phe Leu Val Ser Gly Leu
    2120                2125                2130

Met His Glu Ser Leu Tyr Tyr Tyr Ile Thr Arg Val Ser Pro Thr
    2135                2140                2145

Trp Glu Val Thr Gly Phe Phe Val Leu Gln Gly Leu Cys Thr Val
    2150                2155                2160

Ser Glu Val Val Val Lys Lys Ala Leu Gly Gly Arg Trp Arg Leu
    2165                2170                2175

His Arg Ala Val Ser Gly Pro Leu Thr Ile Gly Phe Val Cys Val
    2180                2185                2190

Thr Ala Asp Trp Leu Phe Phe Pro Gln Leu Leu Arg Asn His Ile
    2195                2200                2205

Asp Glu Arg Ala Ile Arg Glu Tyr Ser Ile Leu Val Asp Phe Val
    2210                2215                2220

Lys Gln Lys Phe Leu Thr Leu Pro Pro Pro Phe Met Ala His Pro
    2225                2230                2235

<210> SEQ ID NO 4
<211> LENGTH: 364
<212> TYPE: PRT
<213> ORGANISM: Vitis vinifera

<400> SEQUENCE: 4

Met Asp Gly Glu Ile Lys Ser Leu Ile Lys Val Trp Ile Ser Ala Ile
1               5                   10                  15

Ser Ser Ile Cys Tyr Cys Tyr Phe Phe Val Val Arg Leu Pro Val Gly
            20                  25                  30

Leu Phe Arg Leu Leu Phe Leu Leu Pro Met Phe Tyr Leu Phe Ile Ile
            35                  40                  45

Leu Pro Leu Asn Leu Ser Ser Ala His Leu Val Gly Thr Thr Ala Phe
        50                  55                  60

Tyr Leu Ala Trp Leu Ala Asn Phe Lys Phe Ile Leu Phe Ser Phe Gly
65              70                  75                  80

His Gly Pro Leu Ser Phe Pro Ser His Pro Pro Lys Ser Val Leu Arg
                85                  90                  95

Phe Ile Ser Ile Ala Cys Leu Pro Ile Lys Ile Lys Thr Val Pro Ser
            100                 105                 110

Pro Lys Ser His Ser Val Ser Glu Asn Ser Thr Asp Pro Leu Ser Glu
        115                 120                 125

Ile Val Met Lys Leu Pro Arg Pro Leu Leu Leu Ala Ile Lys Ala Leu
    130                 135                 140

Leu Phe Ala Ile Leu Ile Arg Ile Tyr Asn Tyr Lys Arg His Leu His
145                 150                 155                 160

Pro Asn Val Val Leu Phe Leu Tyr Cys Cys His Met Tyr Leu Ala Leu
                165                 170                 175

Glu Ile Val Gln Ala Met Ala Ala Ile Pro Ala Arg Ala Ile Pro Gly
            180                 185                 190

Phe Glu Leu Glu Pro Gln Phe Asn Glu Pro Tyr Leu Thr Thr Ser Leu
        195                 200                 205
```

-continued

Gln Asp Phe Trp Gly Arg Arg Trp Asn Leu Ser Val Thr Asn Ile Leu
210                 215                 220

Arg Pro Thr Val Tyr Asp Pro Val Arg Ser Ile Cys Thr Arg Ile Leu
225                 230                 235                 240

Gly Lys Lys Trp Ala Pro Val Pro Gly Val Leu Ala Ala Phe Leu Val
            245                 250                 255

Ser Gly Leu Met His Glu Ser Leu Tyr Tyr Tyr Ile Thr Arg Val Ser
            260                 265                 270

Pro Thr Trp Glu Val Thr Gly Phe Phe Val Leu Gln Gly Leu Cys Thr
        275                 280                 285

Val Ser Glu Val Val Lys Lys Ala Leu Gly Gly Arg Trp Arg Leu
    290                 295                 300

His Arg Ala Val Ser Gly Pro Leu Thr Ile Gly Phe Val Cys Val Thr
305                 310                 315                 320

Ala Ala Trp Leu Phe Phe Pro Gln Leu Leu Arg Asn His Ile Asp Glu
                325                 330                 335

Arg Ala Ile Arg Glu Tyr Ser Ile Leu Val Asp Phe Val Lys Gln Lys
            340                 345                 350

Phe Leu Thr Leu Pro Pro Pro Phe Met Ala His Pro
            355                 360

<210> SEQ ID NO 5
<211> LENGTH: 364
<212> TYPE: PRT
<213> ORGANISM: Vitis vinifera

<400> SEQUENCE: 5

Met Gly Gly Glu Ile Lys Gly Leu Ile Lys Val Cys Leu Ser Val Leu
1               5                   10                  15

Ala Ser Leu Cys Tyr Ser Tyr Phe Ile Val Ser Lys Ile Pro Lys Gly
            20                  25                  30

Lys Phe Arg Leu Leu Ser Leu Leu Pro Ile Phe Ser Leu Phe Val Ala
        35                  40                  45

Leu Pro Leu Phe Leu Ser Thr Ala Ile Leu Ser Gly Ile Thr Ala Phe
50                  55                  60

Phe Ile Thr Trp Leu Ala Thr Phe Arg Leu Ala Leu Phe Ser Phe Asp
65                  70                  75                  80

Leu Gly Pro Leu Ser Thr Gly Ser Pro Lys Ser Leu Leu Val Phe Ile
                85                  90                  95

Ala Ile Ala Cys Leu Pro Ile Lys Ile Lys Pro Asn Gln Gln His Pro
            100                 105                 110

Ser Arg Gln Glu Pro His Lys Pro Pro Arg Leu Pro Leu Asn Phe Ala
        115                 120                 125

Val Lys Val Leu Ala Phe Gly Val Phe Ile Gly Phe Tyr Gln Tyr Lys
130                 135                 140

Glu Leu Val His Pro Lys Ile Phe Leu Gly Leu Cys Cys Gln Val
145                 150                 155                 160

Phe Leu Phe Leu Glu Val Leu Phe Ser Leu Cys Ser Ala Leu Val Arg
                165                 170                 175

Cys Thr Met Gly Leu Glu Val Glu Gln Pro Ser Asp Glu Pro Tyr Leu
            180                 185                 190

Ser Thr Ser Leu Gln Asp Phe Trp Gly Arg Arg Trp Asn Leu Met Val
        195                 200                 205

Thr Asn Leu Leu Arg His Thr Val Tyr Lys Pro Val Lys Ser Ala Ala

```
                210                 215                 220
Glu Thr Val Met Ser Glu Arg Trp Ser Pro Leu Pro Ala Val Val Ala
225                 230                 235                 240

Thr Phe Leu Val Ser Gly Leu Met His Glu Leu Leu Phe Tyr Tyr Val
                245                 250                 255

Asn Arg Val Ser Pro Ser Trp Glu Met Thr Ser Phe Phe Val Leu His
                260                 265                 270

Gly Val Cys Leu Val Val Glu Val Gly Val Lys Ser Val Phe Ser Gly
                275                 280                 285

Arg Trp Arg Leu His Trp Ala Ala Ser Val Pro Leu Thr Val Gly Phe
                290                 295                 300

Val Val Ala Thr Ser Phe Trp Leu Phe Phe Pro Pro Leu Ile Arg Ala
305                 310                 315                 320

Gly Ala Asp Met Arg Val Met Glu Glu Val Lys Val Leu Leu Glu Pro
                325                 330                 335

Met Arg Glu Lys Ile Pro Leu Leu Pro Leu Leu Asn Ser Thr Arg Glu
                340                 345                 350

Gln Leu Leu Leu Phe Asp Leu Ser Gly Arg His Lys
                355                 360

<210> SEQ ID NO 6
<211> LENGTH: 364
<212> TYPE: PRT
<213> ORGANISM: Vitis vinifera

<400> SEQUENCE: 6

Met Gly Gly Glu Ile Lys Gly Leu Ile Lys Val Cys Leu Ser Val Leu
1               5                   10                  15

Ala Ser Leu Cys Tyr Ser Tyr Phe Ile Val Ser Lys Ile Pro Lys Gly
                20                  25                  30

Lys Phe Arg Leu Leu Ser Leu Leu Pro Ile Phe Ser Leu Phe Val Ala
                35                  40                  45

Leu Pro Leu Phe Leu Ser Thr Ala Ile Leu Ser Gly Ile Thr Ala Phe
        50                  55                  60

Phe Ile Thr Trp Leu Ala Thr Phe Arg Leu Ala Leu Ser Phe Asp
65                  70                  75                  80

Leu Gly Pro Leu Ser Thr Gly Ser Pro Lys Ser Leu Leu Val Phe Ile
                85                  90                  95

Ala Ile Ala Cys Leu Pro Ile Lys Ile Lys Pro Asn Gln Gln His Pro
                100                 105                 110

Ser Arg Gln Asp Pro His Lys Pro Arg Leu Pro Leu Asn Phe Ala
                115                 120                 125

Val Lys Val Leu Ala Phe Gly Val Phe Ile Gly Phe Tyr Gln Tyr Lys
                130                 135                 140

Glu Leu Val His Pro Lys Ile Phe Leu Gly Leu Leu Cys Cys Gln Val
145                 150                 155                 160

Phe Leu Phe Leu Glu Val Leu Phe Ser Leu Cys Ser Ala Leu Val Arg
                165                 170                 175

Cys Thr Thr Gly Leu Glu Val Glu Gln Pro Ser Asp Glu Pro Tyr Leu
                180                 185                 190

Ser Thr Leu Leu Gln Asp Phe Trp Gly Arg Arg Trp Asn Leu Met Val
                195                 200                 205

Thr Asn Leu Leu Arg His Thr Val Tyr Lys Pro Val Lys Ser Ala Ala
                210                 215                 220
```

```
Glu Thr Val Met Ser Glu Arg Trp Ser Pro Leu Pro Ala Val Val Ala
225                 230                 235                 240

Thr Phe Leu Val Ser Gly Leu Met His Glu Leu Leu Phe Tyr Tyr Val
                245                 250                 255

Asn Arg Val Ser Pro Ser Trp Glu Met Thr Ser Phe Phe Val Leu His
                260                 265                 270

Gly Val Cys Leu Val Val Glu Val Gly Val Lys Ser Val Phe Ser Gly
            275                 280                 285

Arg Trp Arg Leu His Trp Ala Ser Val Pro Leu Thr Val Gly Phe
        290                 295                 300

Val Val Ala Thr Ser Phe Trp Leu Phe Phe Pro Pro Leu Ile Arg Ala
305                 310                 315                 320

Gly Ala Asp Met Arg Val Met Glu Glu Val Lys Val Leu Leu Glu Pro
                325                 330                 335

Met Arg Glu Lys Ile Pro Leu Leu Pro Leu Leu Asn Ser Thr Arg Glu
                340                 345                 350

Gln Leu Leu Leu Asp Leu Ser Gly Arg His Lys
                355                 360

<210> SEQ ID NO 7
<211> LENGTH: 347
<212> TYPE: PRT
<213> ORGANISM: Populus trichocarpa

<400> SEQUENCE: 7

Met Glu Gly Glu Ile Leu Asn Phe Ile Arg Val Trp Ile Ser Val Leu
1               5                   10                  15

Val Ser Leu Cys Phe Cys Tyr Ser Ile Arg Asn Ile Val Pro Lys Gly
                20                  25                  30

Thr Lys Arg Leu Leu Ser Val Leu Pro Val Val Cys Leu Phe Leu Tyr
            35                  40                  45

Leu Pro Leu Lys Ile Ser Ser Val His Leu Gly Gly Ser Thr Ala Phe
        50                  55                  60

Phe Ile Ala Trp Leu Ala Asn Phe Lys Val Leu Leu Phe Ala Phe Gly
65                  70                  75                  80

Lys Gly Pro Leu Ser Ser Asp Pro Ser Ile Ser Leu Pro Leu Phe Ile
                85                  90                  95

Ala Leu Ala Cys Leu Pro Ile Lys Ile Arg Gln Lys Glu Asn Pro Ala
                100                 105                 110

Pro Ser Arg Gly Lys Glu Gly Leu Arg Asn Tyr Ala Val Lys Gly Val
            115                 120                 125

Leu Leu Ala Met Leu Ile Arg Ala Tyr Asp Tyr Ser Asp Tyr Ile His
        130                 135                 140

Pro Asn Val Ile Leu Met Tyr Ser Phe His Val Tyr Phe Leu Leu
145                 150                 155                 160

Glu Ile Leu Leu Ala Val Gly Ala Val Leu Ala Arg Asn Phe Leu Gly
                165                 170                 175

Leu Glu Leu Glu Pro Gln Phe Asn Glu Pro Tyr Leu Ala Thr Ser Leu
            180                 185                 190

Gln Asp Phe Trp Gly Cys Arg Trp Asn Leu Val Val Thr Ser Ile Leu
        195                 200                 205

Arg Pro Thr Val Tyr Glu Pro Thr Arg Ala Ile Gly Ser His Leu Ile
    210                 215                 220

Gly Arg Lys Trp Ala Pro Leu Pro Ala Val Phe Ala Thr Phe Val Val
225                 230                 235                 240
```

-continued

```
Ser Ala Ile Met His Glu Ile Ile Phe Tyr Tyr Leu Gly Arg Val Arg
                245                 250                 255

Pro Asn Trp Glu Ile Ser Trp Phe Phe Leu Leu His Gly Phe Cys Leu
            260                 265                 270

Thr Ala Glu Ile Ala Leu Lys Lys Val Leu Asn Asp Arg Trp Arg Leu
        275                 280                 285

Pro Lys Met Ile Ser Thr Met Leu Thr Val Gly Phe Val Met Ser Thr
    290                 295                 300

Gly Phe Trp Leu Phe Phe Pro Lys Phe Val Glu Tyr Lys Val Asp Val
305                 310                 315                 320

Arg Ala Phe Glu Glu Tyr Ala Glu Ile Gly Ala Tyr Met Lys Asn Val
                325                 330                 335

Ser Gln Ser Ile Ala Arg Val Leu Pro Gly His
            340                 345

<210> SEQ ID NO 8
<211> LENGTH: 359
<212> TYPE: PRT
<213> ORGANISM: Ricinus communis

<400> SEQUENCE: 8

Met Glu Gly Glu Phe Lys Asn Phe Ile Lys Val Trp Ile Leu Ala Thr
1               5                   10                  15

Thr Cys Leu Cys Tyr Cys Tyr Tyr Val Ala Ser Lys Ile Pro Lys Gly
            20                  25                  30

Val Phe Arg Leu Ile Ser Leu Leu Pro Ile Phe Tyr Leu Phe Ile Ile
        35                  40                  45

Leu Pro Leu Val Leu Thr Ser Phe His Leu Gly Ala Pro Thr Thr Phe
    50                  55                  60

Phe Leu Ile Trp Leu Ala Asn Phe Lys Leu Leu Leu Phe Ser Phe Asp
65                  70                  75                  80

Gln Gly Pro Leu Ser Pro Ala Ser Leu Lys Leu Phe His Phe Ile Ser
                85                  90                  95

Leu Thr Tyr Leu Pro Ile Lys Leu Arg Gln Asn Asn Asp Pro Ser His
            100                 105                 110

Thr Gln Lys His Gln Thr Ala Tyr Thr Thr Ser Ala Pro Phe Leu Pro
        115                 120                 125

Arg Arg Val Val Leu Pro Leu Lys Val Leu Leu Val Ala Leu Leu Phe
    130                 135                 140

His Cys Tyr Ser Tyr Lys Gln Phe Leu His Pro Tyr Leu Ile Leu Ala
145                 150                 155                 160

Leu Tyr Cys Leu His Met Tyr Leu Glu Leu Glu Ile Ile Leu Ala Ile
                165                 170                 175

Ser Ala Thr Pro Ala Arg Val Leu Phe Gly Phe Glu Leu Glu Pro Gln
            180                 185                 190

Phe Asn Glu Pro Tyr Leu Ala Thr Ser Leu Gln Asp Phe Trp Gly Arg
        195                 200                 205

Arg Trp Asn Leu Met Val Thr Ser Ile Leu His Pro Thr Val Tyr Tyr
    210                 215                 220

Pro Val Arg Gln Phe Phe Met Gly Leu Ile Gly Gln Thr Trp Ala Ser
225                 230                 235                 240

Leu Pro Ala Phe Val Ala Thr Phe Val Val Ser Gly Leu Met His Glu
                245                 250                 255

Ile Ile Tyr Phe Tyr Val Thr Arg Val Ser Pro Thr Trp Glu Val Thr
```

```
            260                 265                 270
Trp Phe Phe Ile Val His Gly Val Cys Val Val Ile Glu Val Ala Leu
        275                 280                 285
Lys Lys Met Ala Lys Gly Arg Trp Glu Leu Asp Arg Ala Ile Ser Ile
    290                 295                 300
Pro Leu Thr Val Val Phe Val Gly Val Thr Ala Val Trp Leu Phe Phe
305                 310                 315                 320
Pro Gln Leu Thr Arg Asn Arg Ile Asp Asp Lys Ala Ile Gly Glu Tyr
                325                 330                 335
Ser Ile Phe Val Asn Leu Leu Lys Gln Glu Leu Met Cys Phe Leu Ser
            340                 345                 350
Tyr Phe Phe Asn Gly Ile Gln
        355

<210> SEQ ID NO 9
<211> LENGTH: 507
<212> TYPE: PRT
<213> ORGANISM: Euonymus alatus

<400> SEQUENCE: 9

Met Ala Ala Asn Leu Asn Glu Ala Ser Asp Leu Asn Phe Ser Leu Arg
1               5                   10                  15
Arg Arg Thr Gly Gly Ile Ser Ser Thr Thr Val Pro Asp Ser Ser Ser
            20                  25                  30
Glu Thr Ser Ser Ser Glu Ala Asp Tyr Leu Asp Gly Gly Lys Gly Ala
        35                  40                  45
Ala Asp Val Lys Asp Arg Gly Asp Gly Ala Val Glu Phe Gln Asn Ser
    50                  55                  60
Met Lys Asn Val Glu Arg Ile Glu Lys His Glu Ser Arg Val Gly Leu
65                  70                  75                  80
Asp Ser Arg Phe Thr Tyr Arg Pro Ser Val Pro Ala His Arg Thr Ile
                85                  90                  95
Lys Glu Ser Pro Leu Ser Ser Asp Ala Ile Phe Lys Gln Ser His Ala
            100                 105                 110
Gly Leu Phe Asn Leu Cys Ile Val Val Leu Val Ala Val Asn Ser Arg
        115                 120                 125
Leu Ile Ile Glu Asn Leu Met Lys Tyr Gly Trp Leu Ile Arg Ser Gly
    130                 135                 140
Phe Trp Phe Ser Ser Arg Ser Leu Arg Asp Trp Pro Leu Phe Met Cys
145                 150                 155                 160
Cys Leu Thr Leu Pro Val Phe Pro Leu Ala Ala Phe Leu Phe Glu Lys
                165                 170                 175
Leu Ala Gln Lys Asn Leu Ile Ser Glu Pro Val Val Val Leu Leu His
            180                 185                 190
Ile Val Asn Thr Thr Ala Ala Val Leu Tyr Pro Val Leu Val Ile Leu
        195                 200                 205
Arg Cys Asp Ser Ala Phe Met Ser Gly Val Thr Leu Met Leu Phe Ala
    210                 215                 220
Cys Ile Val Trp Leu Lys Leu Val Ser Tyr Ala His Thr Asn Tyr Asp
225                 230                 235                 240
Met Arg Ala Leu Thr Lys Ser Val Glu Lys Gly Asp Thr Pro Leu Ser
                245                 250                 255
Ser Gln Asn Met Asp Tyr Ser Phe Asp Val Asn Ile Lys Ser Leu Ala
            260                 265                 270
```

```
Tyr Phe Met Val Ala Pro Thr Leu Cys Tyr Gln Ile Ser Tyr Pro Arg
            275                 280                 285

Thr Pro Tyr Val Arg Lys Gly Trp Val Val Arg Gln Phe Val Lys Leu
        290                 295                 300

Ile Ile Phe Thr Gly Leu Met Gly Phe Ile Ile Glu Gln Tyr Ile Asn
305                 310                 315                 320

Pro Ile Val Gln Asn Ser Gln His Pro Leu Lys Gly Asn Phe Leu Tyr
                325                 330                 335

Ala Ile Glu Arg Val Leu Lys Leu Ser Val Pro Asn Leu Tyr Val Trp
            340                 345                 350

Leu Cys Met Phe Tyr Cys Leu Phe His Leu Trp Leu Asn Ile Leu Ala
        355                 360                 365

Glu Leu Leu Cys Phe Gly Asp Arg Glu Phe Tyr Lys Asp Trp Trp Asn
370                 375                 380

Ala Lys Thr Val Glu Glu Tyr Trp Arg Met Trp Asn Met Pro Val His
385                 390                 395                 400

Lys Trp Met Val Arg His Ile Tyr Phe Pro Cys Leu Arg Asn Gly Ile
            405                 410                 415

Pro Lys Gly Val Ala Phe Val Ile Ser Phe Leu Val Ser Ala Val Phe
        420                 425                 430

His Glu Leu Cys Ile Ala Val Pro Cys His Ile Phe Lys Leu Trp Ala
        435                 440                 445

Phe Phe Gly Ile Met Leu Gln Val Pro Leu Val Leu Ile Thr Ser Tyr
        450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Leu Tyr Tyr
                485                 490                 495

His Asp Leu Met Asn Arg Asn Gly Lys Met Glu
            500                 505
```

<210> SEQ ID NO 10
<211> LENGTH: 1084
<212> TYPE: DNA
<213> ORGANISM: Euonymus alatus

<400> SEQUENCE: 10

```
atgatggatg ctcatcaaga gatcaagaac ttcatcaagg tttgggtaca agccatggta      60
tgtctatctt acgcttacta cttctcctca agacttccaa aaggactctt aaggttactc    120
tcttactcc tgtcctttat ctcctattaa tcgctccctt gaacatctct tctttcattc     180
tttcatcaat caccggcttc ttccttgctt ggctaacaac attcaaggtc atctcttttg    240
cctttgatca aggcctttgt atccactccc acaaaacctc ctacatttca tctcaatagc    300
ttgtcttccc atcacaatca agcgaaaccc atcaccaaaa ttgaaatcca acaaaaccc     360
atctccaatt tcacatcttt taaaaaggca ttcatgtcat ttccatctaa agtcttgttc    420
cattgggtca ttgctcatct ctaccaatac aaaaagtaca tggatccaaa cgtggtctta    480
gtgatctatt gttgtcatgt gtacgttagt tggatatctc actctctcta tgtgcaaccc    540
tagctgaatt cctttgtggg tttgatgttg aaccacaatt caaagagcct taccttgcta    600
cttcactaca agactttggg ggccgtaggt ggaactaatt gtgtcaagtg tcctacgttc    660
gactgtctat gccccaacta gaaacattgc ttcatatcta attgggtcta gatgggctta    720
ttttccagct ataattgcaa catttgtcgt atcaggagtt atcatgatgt agtgtactat    780
```

```
gtgtacatga tgcatatgta tcccaagtgg gatatgacag ggcacttcgt cctacatggg      840
atttgtgaag ctttggaggt ggagatgaag tgtaagagat caaggagtgc aagtggcggc      900
ggcatccagc tgtcgattgg gtaatggtga tggggtttgt gatggggact agtgtttcct      960
tactctttgt gccactatta agggataatg tggaccaaat tgtagcagaa gagtaccaat     1020 tttgttaat tttgtgaggg agaagattgt catgcttgga acaaggtttg tgtgtggaaa      1080
ttga                                                                  1084

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
caccatgatg gatgctcatc aagag                                             25

<210> SEQ ID NO 12
<211> LENGTH: 28
<212> TYPE: DNA
<213> ORGANISM: Artificial Sequence
<220> FEATURE:
<223> OTHER INFORMATION: Synthetic

<400> SEQUENCE: 12
atttatttca tcgtcatcat caatttcc                                          28

<210> SEQ ID NO 13
<211> LENGTH: 1362
<212> TYPE: DNA
<213> ORGANISM: Artificial Sequence
<220> FEATURE:
<223> OTHER INFORMATION: Synthetic

<400> SEQUENCE: 13
attacggccg gggacattat aataattata ataaaatagg aatggagtct gagatgaagg        60
acttgaattc caagccaccg gagtccgctg agcacgacgg cgccacatcc aaggacgatc       120 ggccctctc aagcccgagg cagtcggtgt ctcaatggaa agcctccagg acatggagaa       180
gaaattcgca gcgtatgtac gcaacgacgt gtacggcccc acgggacgcg gcgagttgcc       240
gttggcggag aaggcctgct cgctgtggct tgtgtgacgc tggtgccgat aagagtgatt       300
cttgccgtga ttgtattggt tttctattac ttgatttgta ggatttgtac tctcttctcg       360
tcgccgaatc gtgacgggga gaggaggatt acgcgcacat ggaaggctgg aggagagccg       420
tgattgtctc gtgcgggagg ttttctcca gagtcatgct cttcgtgttt gggttttact       480
ggattaacga gacctatagg attccagagc ttcacaagac aagccctcct cgcctaatga       540
gcaaggaggg acaaagacca atccaaagat cctagaaaga cctgcggcga ttgtatctaa       600
tcacgtatca tatttggata ttttgtacca tatgtttctt cttttccgag ctttgttgct       660
aagagatcag tggctaaaact ctatcttgtt ggtctcatca gcaagtgcct tggttgtgtt       720
tatgttcaga gggagtctaa gtcatctgac ttcaagggtg ttcaggtgtt gtgactgaaa       780
gaatcaggga aactcatcaa aatgggtctg ccgctattat gatgcttttt ccagagggca       840
caactacaaa tggagactac atccttccat tcaagacagg tgcctttctg caagagctcc       900
cgtccgtcca gtgatactaa ggtatcctta ccagagattc agtcctgcct gggactcaat       960
atccggggca cgccatgtaa tattcctact ttgccaattc attaatcaca tggagggaca      1020
```

```
tggttacctg tctacaaccc atcacaggaa gagaaagata atccaaaact ctatgctgat    1080
aatgttcgaa ggttgatgtc tagagagggc aatttgataa tgtcggatat tggactagca    1140
gagagagaat ctatcatgct gctctcaatg gtaataatag cctgcctagt gtattgcatc    1200
agaaagacga ttgataattt catggcctcg ctccaaaatg atagtctcag ttgggtttct    1260
tagtgtacat gatatttgct tatacatgca caactaaggg gaggtacctt cttccacatt    1320
ttactctaaa agatgttggt ttgctgagtc ttgtaatttt ag                       1362
```

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14

```
caccatggag tctgagatga aggac                                          25
```

<210> SEQ ID NO 15
<211> LENGTH: 29
<212> TYPE: DNA
<213> ORGANISM: Artificial Sequence
<220> FEATURE:
<223> OTHER INFORMATION: Synthetic

<400> SEQUENCE: 15

```
tcaatcgtct ttctgatgca atacactag                                      29
```

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16

```
aaattcgagc tggtcacctc                                                20
```

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17

```
cataagcttc aagagtgtaa aacgtaccga tca                                 33
```

<210> SEQ ID NO 18
<211> LENGTH: 33
<212> TYPE: DNA
<213> ORGANISM: Artificial Sequence
<220> FEATURE:
<223> OTHER INFORMATION: Synthetic

<400> SEQUENCE: 18

```
gttctgcagg ttttgctatt tgtgtatgtt ttc                                 33
```

<210> SEQ ID NO 19
<211> LENGTH: 1148
<212> TYPE: DNA
<213> ORGANISM: Artificial Sequence
<220> FEATURE:

<223> OTHER INFORMATION: Synthetic

<400> SEQUENCE: 19

```
caagagtgta aaacgtaccg atcaaatgtc tttataaaaa aaacgtgttg atgttgttct      60
gtgaatacaa ttagttctgg ttaacagctg gtcgaccatt ttctgatgag aatttatgta     120
aggccattgc tctggtgttg agaaggttta gtttggttca agctaaccgt ggttagaaag     180
ttagaatata atgtgtttct tgatcagtga tatcgatcgg atttgtatta ttcatattgt     240
ttactctttg agtaattcat agtggtaact cttttttttt ttttttttt ttcatattgg      300
taactctttg aaatgaaaaa catagctaag aattgctagc tttgatttag tcgagacgta     360
cgaactctcg attttggttt ttgatttgtt ggtgtaaaac tctcgatatt cataactcgt     420
aagattttgt acgtatcatc ttcttattct cttcatcgct ctgttttcaa ttttatgtca     480
aaacatggtt ttggtaattt cttttactcc tacttcacgg tttgagttat aatttttttg     540
gtaaaccctt aaccacgagt tttgatgtat tttgacacct ctaattatgt gtgtatacgt     600
acacatataa ttcggtattt tcttaacata tatatccctc ataaaaattt cttacatgca     660
ttgttcgtga gtgacccgtt aatatatata ttgatagata ctcttataaa attatattct     720
aaatttcaga ttaagctggc acaactatat ttccaacatc actagctacc atcaaaagat     780
tgacttctca tcttactcga ttgaaaccaa attaacatag ggttttatt taaataaaag     840
tttaaccttc ttttaaaaa attgttcata gtgtcatgtc agaacaagag ctacaaatca     900
cacatagcat gcataagcgg agctatgatg agtggtattg ttttgttcgt cacttgtcac     960
tcttttccaa cacataatcc cgacaacaac gtaagagcat ctctctctct ccacacacac    1020
tcatgcatgc atgcattctt acacgtgatt gccatgcaaa tctcctttct cacctataaa    1080
tacaaaccaa cccttcacta cactcttcac tcaaaccaaa acaagaaaac atacacaaat    1140
agcaaaac                                                             1148
```

<210> SEQ ID NO 20
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (50)..(50)
<223> OTHER INFORMATION: n is a, c, g, or t

<400> SEQUENCE: 20

```
tagaggccga ggcggccgac atgttttgtt ttttttctt tttttttvn                50
```

METHOD TO PRODUCE ACETYLDIACYLGLYCEROLS (AC-TAGS) BY EXPRESSION OF AN ACETYLTRANSFERASE GENE ISOLATED FROM *EUONYMUS ALATUS* (BURNING BUSH)

PRIORITY CLAIM TO RELATED APPLICATIONS

This application is a U.S. National Stage Filing under 35 U.S.C. §371 of International Patent Application Serial No. PCT/US2010/062407, filed Dec. 29, 2010, and published on Jul. 7, 2011 as WO 2011/082253, which claims priority under 35 U.S.C. §119 to Provisional Application Ser. Nos. 61/291,290, filed Dec. 30, 2009 and 61/334,838, filed May 14, 2010, the disclosures of which applications are specifically incorporated herein by reference in their entireties.

GOVERNMENT INTERESTS

This invention was made with government support under DE-FC02-07ER64494 awarded by the U.S. Department of Energy and under 2005-35504-16195 awarded by the U.S. Department of Agriculture. The government has certain rights in the invention.

FIELD OF THE INVENTION

The present invention relates to novel diacylglycerol acyltransferase genes and proteins, and methods of their use. In particular, the invention describes genes encoding proteins having diacylglycerol acetyltransferase activity, specifically for transferring an acetyl group to a diacylglycerol substrate to form acetyl-Triacylglycerols (ac-TAGs), for example, a 3-acetyl-1,2-diacyl-sn-glycerol. The present invention encompasses both native and recombinant wild-type forms of the transferase, as well as mutants and variant forms. The present invention also relates to methods of using novel diacylglycerol acyltransferase genes and proteins, including their expression in transgenic organisms at commercially viable levels, for increasing production of 3-acetyl-1,2-diacyl-sn-glycerols in plant oils and altering the composition of oils produced by microorganisms, such as yeast, by increasing ac-TAG production. Additionally, oils produced by methods of the present inventions comprising genes and proteins are contemplated for use as biodiesel fuel, in polymer production and as naturally produced food oils with reduced calories.

BACKGROUND

Triacylglycerols (TAGs) produced by plants are one of the most energy-rich and abundant forms of reduced carbon (carbon bonds that store energy) available from nature. Conventional oils from crop plant species are a variety of lipids and fatty acids including triacylglycerols (TAGs) with 3 long acyl chains. TAGs show structural similarity and similar energy content compared to aliphatic acyclic components of diesel fuel molecules. Given their chemical structure similarities, plant oils represent a logical substitute as a renewable energy source for conventional petroleum (crude oil)-derived diesel, a non-renewable energy source, Durrett, Benning, Ohlrogge, Plant Journal. 2008, 54(4):593-607, herein incorporated by reference. Time estimates vary widely on when global peak production of nonrenewable conventional petroleum begins declining, some estimate reductions in production as early as 2025. Despite a range of estimates, there is universal agreement that there is a finite limit of crude petroleum and natural gas in the earth's crust available for profitable extraction.

Currently, plant oils are converted to fatty acid esters that are used as biofuel. The resulting fuel is commonly referred to as biodiesel, and offers many advantages over conventional diesel. Chief among these is that biodiesel is derived from renewable sources. In addition, the production and subsequent consumption of biodiesel results in arguably less greenhouse gas emission compared to conventional diesel. However, the widespread adoption of biodiesel faces a number of challenges. One major challenge is the limited supply of biodiesel feedstocks, i.e. plant TAGs. Thus, plant oil production in general needs to be greatly increased for biodiesel to replace a major proportion of the current and future fuel needs of the world.

Another major challenge is providing plant feedstocks that do not require the conversion of plant oils into fatty acid esters, i.e, transesterification (see, FIG. 1). This conversion is necessary because plant oils produced in sufficient quantity for commercial use, i.e. current biodiesel feedstocks including from feedstocks from oil seed crop plants, such as soybean seeds, rapeseeds, and sunflower seeds, are unsuitable for direct use as fuel in unmodified diesel engines. In particular, these plant oils are too viscous for use in modern diesel engines. High viscosity of plant TAGs results in a number of problems including poor atomization in engines, leading to incomplete combustion and subsequent problems, such as carbon deposition and coking. Further, during the high temperatures of combustion the acyl chains in TAGs polymerize leading to gum formation.

Transesterification of plant TAGs into useable fuel also results in a number of problems associated with efficient biofuel production. In particular, transesterification results in yield losses, such as losses due to triglyceride saponification and methyl ester dissolution in glycerol, as well as uncertainty over the glycerol credit itself to cover unit operation costs. Further, mixtures of unconverted monoglyceride, diglyceride and triglyceride impurities affect engine performance. Residual alcohol content in biodiesel attacks natural rubber seals and gaskets, i.e. unmodified for use with currently available biodiesel. Biodiesel also undergoes chemical and biological modification over time that affects its quality during long-term storage.

Thus, there is a need for an increase in production of biodiesel feedstock and a need of higher quality biofuel feedstock before biodiesel can replace a major proportion of current and future biodiesel needs globally and in the United States.

SUMMARY OF THE INVENTION

The present invention relates to novel diacylglycerol acyltransferase genes and proteins, and methods of their use. In particular, the invention describes genes encoding proteins having diacylglycerol acetyltransferase activity, specifically for transferring an acetyl group to a diacylglycerol substrate to form acetyl-Triacylglycerols (ac-TAGs), for example, a 3-acetyl-1,2-diacyl-sn-glycerol. The present invention encompasses both native and recombinant wild-type forms of the transferase, as well as mutants and variant forms. The present invention also relates to methods of using novel diacylglycerol acyltransferase genes and proteins, including their expression in transgenic organisms at commercially viable levels, for increasing production of 3-acetyl-1,2-diacyl-sn-glycerols in plant oils and altering the composition of oils produced by microorganisms, such as yeast, by increasing ac-TAG production. Additionally, oils produced by methods of the present inventions comprising genes and proteins are contemplated for use as biodiesel fuel, in polymer production and as naturally produced food oils with reduced calories.

The present invention relates to the efficient production of acetyl-TriAcylGlycerols (ac-TAGs) by biological organisms (bio-production) for use in biofuels. In particular, the present invention provides systems and methods for producing ac-TAGs with transgenic organisms expressing the diacylglycerol acyltransferase (DAcT) gene derived from *Euonymus alatus*. In one embodiment DAcT is expressed in yeast and oil-seed crop plants, such as soybean plants, rapeseed plants, *Jatropha* plants, etc. for use in providing biofuels. In other embodiments, DAcT is expressed in oil-seed crop plants, such as soybean plants and Canola-quality plants, etc., for use as commercial sources of oil used in food preparation. In further embodiments, DAcT is expressed in yeast and oil-seed crop plants for providing novel TAG monomers for use in commercial reactions to provide a more refined control of polymers and polymer properties for commercial applications.

The present invention provides an isolated nucleic acid sequence encoding a short chain acyl-CoA diacylglycerol acyltransferase plant protein. In some embodiments, said plant is selected from the group consisting of Celastraceae, Lardizabalaceae, Ranunculaceae, Rosaceae, and Vitaceae. In some embodiments, said plant is selected from the group consisting of *Euonymus, Maytenus, Akebia, Adonis, Sorbus* and *Vitis* species. In some embodiments, said plant is an *Euonymus alata* plant. In one embodiment, said isolated nucleic acid sequence is at least 85% identical to SEQ ID NO:10. Accordingly, in other embodiments, said isolated nucleic acid sequence is at least 70%, 75%, 80%, 85%, 90%, 95%, 98%, 99% (or more) identical to SEQ ID NO:10. In some embodiments, said isolated nucleic acid sequence encodes a protein at least 85% identical to SEQ ID NO:01. Accordingly, in other embodiments, said acetyl-CoA diacylglycerol acetyltransferase protein comprises a polypeptide at least 38%, 40%, 45%, 50%, 55%, 60%, 65%, 70%, 75%, 80%, 85%, 90%, 95%, 98%, 99% (or more) identical to SEQ ID NO:01. In some embodiments, said isolated nucleic acid sequence encodes a protein selected from the group consisting of SEQ ID NOs:01-08. In some embodiments, said protein is capable of acetylating a diacylglycerol substrate comprising a fatty acid to form an acetyltriacylglycerol. In some embodiments, said fatty acid is selected from the group consisting of butyrate, caproate, caprylate, caprate, laurate, myristate, palmitate, palmitoleate, stearate, oleate, linoleate, linolenate, arachidonate, eicosenoate, eicosadienoate, and erucate. In some embodiments, said diacylglycerol substrate is selected from the group consisting of 1,2-dipalmitoyl-glycerol, 1-palmitoyl-2-oleoyl-glycerol, 2-palmitoyl-1-oleoyl-glycerol, and 1,2-dioleoyl-glycerol. In some embodiments, said diacylglycerol acyltransferase protein is capable of acylating said diacylglycerol substrate with an acyl-coenzyme A substrate. In some embodiments, said acyl-coenzyme A substrate is selected from the group consisting of a two carbon acyl-coenzyme A, a three carbon acyl-coenzyme A, a short chain acyl-coenzyme A, and a medium chain acyl-coenzyme A. In some embodiments, said acyl-coenzyme A substrate is selected from the group consisting of an acetyl-coenzyme A, propionyl-coenzyme A, butyryl-coenzyme A, hexanoyl-coenzyme A, octanoyl-coenzyme A, and deconyl-coenzyme A.

The present invention further provides a vector comprising said isolated nucleic acid sequence. The present inventions are not limited to a particular vector. Indeed a variety of vectors are contemplated, including but not limited to an expression vector, a vector active in a plant cell, a vector active in a fungal cell, a vector active in a yeast cell, a vector active in an algal cell, etc. In some embodiments, a vector is adapted for use in an *Agrobacterium* mediated transfection. In some embodiments, a vector active in a plant is a p2S.GATEWAY vector. In some embodiments, a vector active in a yeast cell is a pYES-DEST52 vector. In one embodiment, said nucleic acid sequence is operably linked to a heterologous promoter. The present inventions are not limited to a particular promoter. Indeed a variety of promoters are contemplated, including but not limited to diacylglycerol acyltransferase promoters, promoters active in a plant cell, promoters active in a seed, promoters active in a fungal cell, promoters active in a yeast cell, promoters active in an algal cell, promoters from an *Euonymus alata* plant, promoters from a crop oil plant, et cetera. In some embodiments, said heterologous promoter is a tissue specific promoter. In some embodiments, said heterologous promoter is a seed specific promoter. The present inventions are not limited to a particular promoter active in a seed. Indeed a variety of promoters active in a seed are contemplated, including but not limited to a 2S promoter sequence, seed storage protein promoters, such as a phaseolin promoter, a napin promoter, an oleosin promoter, et cetera.

The present invention further provides a host cell comprising said vector. In some embodiments, said host cell is selected from the group consisting of a plant cell and a microorganism. In some embodiments, said plant cell is selected from the group consisting of an edible crop plant cell, an oil seed crop plant cell, a seed cell, a pollen cell, an ovule cell, mesenchymal cell, meristem cell, an endosperm cell, a male reproductive cell, a female reproductive cell, and an embryo cell. In some embodiments, said plant cell is selected from the group consisting of a *Jatropha* plant, an oil crop plant, a palm oil plant, and an alga. In some embodiments, said plant cell is selected from the group consisting of *Brassica* plants and Brassicaceae plants. In some embodiments, said plant cell is selected from the group consisting of *Arabidopsis* plants, *Camelina* plants, and *crambe* plants. In some embodiments, said microorganism is a fungus cell. In one embodiment, said fungus cell is a yeast cell. In some embodiments, said host cell has lower long chain-triacylglycerol production. In some embodiments, said host cell has low long chain-triacylglycerol production. In some embodiments, said host cell expresses a mutant fatty acid elongase 1 gene resulting in lower long chain-triacylglycerol production. In some embodiments, said host cell expresses a mutant fatty acid elongase 1 gene resulting in low long chain-triacylglycerol production. In some embodiments, said mutant fatty acid elongase 1 gene encodes a mutant FAE1 protein. In some embodiments, said mutant fatty acid elongase 1 gene has a stop codon resulting in a truncation mutant FAE1 protein. In some embodiments, said host cell comprises at least one silenced fatty acid elongase 1 gene, wherein said gene is silenced due to a mutation which results in lowered expression of said gene in the host cell. In some embodiments, said host cell comprises at least one silenced fatty acid elongase 1 gene, wherein said silencing results in low long chain-triacylglycerol production in the host cell. In some embodiments, said host cell comprises at least one silenced triacylglycerol synthesis gene, wherein said gene is silenced due to a mutation that results in lowered expression of said gene. In some embodiments, said host cell comprises at least one silenced triacylglycerol synthesis gene, wherein said gene is silenced due to iRNA for targeting said silenced gene. In some embodiments, said silenced triacylglycerol synthesis gene is selected from the group consisting of diacylglycerol acyltransferase 1, diacylglycerol acyltransferase 2, and phospholipid:diacylglycerol acyltransferase.

The present invention further provides an oil produced by said host cell comprising a triacylglycerol consisting of two acyl groups and an acetyl group. In some embodiments, said triacylglycerol comprises a 3-acetyl-1,2-diacyl-sn-glycerol. In some embodiments, said oil has lower caloric energy than an oil isolated from a nontransformed host cell. In one embodiment, said triacylglycerol ranges from 1%-99% (molar ratio) of total triacylglycerols in said isolated oil. In some embodiments, said triacylglycerol is at least 44% (molar ratio) of total triacylglycerols in said oil. In some embodiments, said triacylglycerol is at least 60% (molar ratio) of total triacylglycerols in said oil. In some embodiments, said oil has a Kinematic viscosity at 24° C. ranging from 8-40 cSt.

The present invention further provides a plant, wherein said plant comprises a heterologous plant nucleic acid sequence encoding an acetyl-CoA diacylglycerol acyltransferase protein. In some embodiments, said plant has low long chain-triacylglycerol production. In some embodiments, said plant further comprises a mutant gene, wherein said mutant gene is selected from the group consisting of a diacylglycerol acyltransferase 1, diacylglycerol acyltransferase 2, and phospholipid; diacylglycerol acyltransferase gene.

The present invention further provides a seed, wherein said seed comprises a heterologous plant nucleic acid sequence encoding an acetyl-CoA diacylglycerol acyltransferase protein.

The present invention provides compositions comprising an isolated nucleic acid sequence encoding a short chain acyl-CoA diacylglycerol acyltransferase plant protein. In some embodiments, said protein is capable of acetylating a diacylglycerol substrate comprising a fatty acid to form an acetyltriacylglycerol. In some embodiments, said fatty acid is selected from the group consisting of butyrate, caproate, caprylate, caprate, laurate, myristate, palmitate, palmitoleate, stearate, oleate, linoleate, linolenate, arachidonate, eicosenoate, eicosadienoate, and erucate. The present inventions are not limited to a particular diacylglycerol substrate. Indeed a variety of substrates are contemplated, including but not limited to 1,2-dipalmitoyl-glycerol, 1-palmitoyl-2 oleoyl-glycerol, 2-palmitoyl-1-oleoyl-glycerol, 1,2-dioleoyl-glycerol, and the like. In some embodiments, said diacylglycerol acyltransferase protein is capable of acylating said diacylglycerol substrate with an acyl-coenzyme A substrate. The present inventions are not limited to a particular acyl-coenzyme A substrate. Indeed a variety of acyl-coenzyme A substrates are contemplated, including but not limited to a two carbon acyl coenzyme A, a three carbon acyl-coenzyme A, a short chain acyl-coenzyme A, a medium chain acyl-coenzyme A, and the like. In some embodiments, said acyl-coenzyme A substrate is selected from the group consisting of an acetyl-coenzyme A, propionyl-coenzyme A, butyryl-coenzyme A, hexanoyl-coenzyme A, octanoyl-coenzyme A, and deconyl-coenzyme A. In some embodiments, said acetyl-CoA diacylglycerol acetyltransferase protein is at least 85% identical to SEQ ID NO:01. Accordingly, in other embodiments, said acetyl-CoA diacylglycerol acetyltransferase protein comprises a polypeptide at least 38%, 40%, 45%, 50%, 55%, 60%, 65%, 70%, 75%, 80%, 85%, 90%, 95%, 98%, 99% (or more) identical to SEQ ID NO:01. In some embodiments, said acetyl-CoA diacylglycerol acetyltransferase protein is selected from the group consisting of SEQ ID NOs:01-08. In some embodiments, said plant is selected from the group consisting of Celastraceae, Lardizabalaceae, Ranunculaceae, Rosaceae, and Vitaceae. In some embodiments, said plant is selected from the group consisting of *Euonymus, Maytenus, Akebia, Adonis, Sorbus,* and *Vitis* species. In some embodiments, said plant is an *Euonymus alata* plant. Moreover, the present invention provides compositions comprising an isolated nucleic acid sequence encoding a short chain acyl-CoA diacylglycerol acyltransferase plant protein operably linked to a heterologous promoter. The present inventions are not limited to a particular promoter. Indeed a variety of promoters are contemplated, including but not limited to diacylglycerol acyltransferase promoters, promoters active in a plant cell, promoters active in a seed, promoters active in a fungal cell, promoters active in a yeast cell, promoters active in an algal cell, promoters from an *Euonymus alata* plant, promoters from a crop oil plant, et cetera. In some embodiments, said heterologous promoter is a tissue specific promoter. In some embodiments, said heterologous promoter is a seed specific promoter. The present inventions are not limited to a particular promoter active in a seed. Indeed a variety of promoters active in a seed are contemplated, including but not limited to a 2S promoter sequence, seed storage protein promoters, such as a phaseolin promoter, a napin promoter, an oleosin promoter, etc.

Additionally, in some embodiments, the inventions provide compositions comprising a vector further comprising said nucleic acid sequence. The present inventions are not limited to a particular vector. Indeed a variety of vectors are contemplated, including but not limited to an expression vector, a vector active in a plant cell, a vector active in a fungal cell, a vector active in a yeast cell, a vector active in an algal cell, etc. In some embodiments, a vector is adapted for use in an *Agrobacterium* mediated transfection. In some embodiments, a vector active in a plant is a p2S.GATEWAY vector. In some embodiments, a vector active in a yeast cell is a pYES-DEST52 vector.

Additionally, in some embodiments, the inventions provide a host cell comprising said vector of the present inventions. In some embodiments, said host cell is selected from the group consisting of a plant cell and a microorganism. The present inventions are not limited to a particular plant cell. Indeed a variety of plant cells are contemplated, including but not limited to an edible crop plant cell and an oil crop plant cell. In some embodiments, said host cell is selected from the group consisting of a mesenchymal cell, meristem cell, an endosperm cell, a pollen cell, a seed cell, oil seed plant cell, a male reproductive cell, a female reproductive cell, and an embryo cell. In some embodiments, said plant cell includes but is not limited to a *Jatropha* plant cell, an oil crop plant cell, a palm oil plant cell, an alga cell, etc. In some embodiments, said plant cell includes but is not limited to a *Brassica* plant cell and Brassicaceae plant cell. In some embodiments, said plant cell includes but is not limited to an *Arabidopsis* plant cell, *Camelina* plant cell, *crambe* plant cell, etc. In some embodiments, said microorganism is a fungus cell. The present inventions are not limited to a particular fungus cell. Indeed a variety of fungus cells are contemplated, including but not limited to a yeast cell, an oleaginous fungal cell, an oleaginous yeast cell, etc. In yet further embodiments, said host cell has low long chain-triacylglycerol production. In one embodiment, low long chain-triacylglycerol production has altered substrate availability. In one embodiment, altered substrate availability is the result of reduced DAGAT gene expression. In one embodiment, altered substrate availability is the result of reduced DAGAT protein expression. In other embodiments, altered substrate availability is the result of changes in genes controlling fatty acid production, such as citrate lyase, fatty acid elongase gene 1 (fae1), and the like. In some embodiments, said host cell comprises at least one silenced fatty acid elongase gene 1 (fae1 gene). In some embodiments, said host cell comprises at least one mutant fatty acid elongase 1 (fae1) gene. In some embodiments, said host cell comprises at least one fatty acid elongase 1 (fae1) gene comprising a mutation for reducing expression of a functional FAE1 protein. In some embodiments, said host cell comprises at least one mutant fatty acid elongase 1 (fae1) protein which results in low amounts of long chain fatty acids in said cell. In an exemplary embodiment, said host cell is a CB25 *Arabidopsis* plant line cell. In some embodiments, said host cell comprises at least one silenced triacylglycerol synthesis gene, wherein said silenced gene has reduced expression when compared to the gene in a wild-type plant. It is not meant to limit the method of reduction in expression of said triacylglycerol synthesis gene. Indeed a variety of methods are contemplated including identifying a natural mutation in said gene, inducing a mutation in said gene, engineering the reduction in expression of said gene and the like. In some embodiments, said expression is reduced due to a mutation that results in lowered expression of said gene. In some embodiments, said expression is reduced due to expression of a truncation mutant, such as a fatty acid elongase 1 (fae1) gene comprising a stop codon within the coding region. In some embodiments, said expression is reduced due to expression of an RNAi molecule for silencing said gene. In some embodiments, said silenced triacylglycerol synthesis gene is selected from the group consisting of diacylglycerol acyltransferase 1, diacylglycerol acyltransferase 2, phospholipid: diacylglycerol acyltransferase, and the like.

The present invention provides a composition comprising a host cell, wherein said host cell comprises a heterologous plant nucleic acid sequence encoding an acetyl-CoA diacylglycerol acyltransferase protein. In some embodiments, said host cell is an oil seed plant cell, mesenchymal cell, meristem cell, an endosperm cell, a pollen cell, a seed cell, a male reproductive cell, a female reproductive cell, an ovule cell, and an embryo cell, etc. In some embodiments, said composition further comprises acetyltriacylglycerol. In some embodiments, said host cell further comprises acetyltriacylglycerol. In some embodiments, said acetyltriacylglycerol comprises a 3-acetyl-1,2-diacyl-sn-glycerol.

Additionally, in some embodiments, the inventions provide oil produced by said host cell of the present inventions comprising a triacylglycerol molecule consisting of two acyl groups and an acetyl group. In preferred embodiments, said triacylglycerol is an acetyltriacylglycerol. In some embodiments, said triacylglycerol comprises a 3-acetyl-1,2-diacyl-sn-glycerol. In some embodiments, said oil has a lower caloric energy than oil isolated from a nontransformed host cell. In some embodiments, said lower caloric energy is a lower energy per gram. In some embodiments, said acetyltriacylglycerol range from 1%-99% (molar ratio by dry weight) of total triacylglycerols in said isolated oil. In some embodiments, said acetyltriacylglycerol is at least 44% (molar ratio) of total triacylglycerols in said oil. In some embodiments, said acetyltriacylglycerol is at least 46% (molar ratio) of total triacylglycerols in said oil. In some embodiments, said acetyltriacylglycerol is at least 60% (molar ratio) of total triacylglycerols in said oil. In some embodiments, said acetyltriacylglycerol is at least 90% (molar ratio) of total triacylglycerols in said oil. In some embodiments, said acetyltriacylglycerol is at least 98% (molar ratio) of total triacylglycerols in said oil. In some embodiments, said acetyltriacylglycerol is at least 80% (molar ratio) of total triacylglycerols in said oil. Accordingly, in other embodiments, said molar ratio of acetyltriacylglycerol is at least 20%, 30%, 35%, 40%, 45%, 46%, 47%, 48%, 49%, 50%, 55%, 60%, 65%, 70%, 75%, 80%, 85%, 90%, 95%, 98%, 99% (or more) of total triacylglycerols in said oil. In some embodiments, said isolated oil has a density at 24° C. ranging from 0.900-1.00 g/cc. In some embodiments, said isolated oil has a Kinematic viscosity at 24° C. ranging from 8-40 cSt. In some embodiments, said isolated oil has an intrinsic viscosity at 24° C. ranging from 8-36 cP.

Additionally, in some embodiments, the inventions provide a plant comprising a heterologous plant nucleic acid sequence encoding an acetyl-CoA diacylglycerol acyltransferase protein. The present inventions are not limited to a particular plant, Indeed a variety of plants are contemplated, including but not limited to a *Jatropha* plant, an oil crop plant, a palm oil plant, and an alga. In some embodiments, said plant has low long chain-triacylglycerol production. In some embodiments, said plant further comprises at least one silenced fatty acid elongase 1 gene, wherein said silenced gene has reduced expression of a functional FAE1 protein when compared to said gene in a wild-type plant. In some embodiments, said plant is a CB25 *Arabidopsis* plant. In some embodiments, said plant further comprises at least one silenced triacylglycerol synthesis gene, wherein said silenced gene has reduced expression when compared to said gene in a wild-type plant. It is not meant to limit the method of reduction in expression of said triacylglycerol synthesis gene. Indeed a variety of methods are contemplated including identifying a natural mutation in said gene, inducing a mutation in said gene, engineering the reduction in expression of said gene and the like. In some embodiments, said expression is reduced due to a mutation that results in lowered expression of said gene. In some embodiments, said expression is reduced due to expression of an RNAi molecule for silencing said gene. In some embodiments, said silenced triacylglycerol synthesis gene is selected from the group consisting of diacylglycerol acyltransferase 1, diacylglycerol acyltransferase 2, phospholipid:diacylglycerol acyltransferase, and the like. In some embodiments, said plant is a plant cell. In some embodiments, said plant cell includes but is not limited to a *Brassica* plant cell and Brassicaceae plant cell. In some embodiments, said plant cell includes but is not limited to an *Arabidopsis* plant cell, *Camelina* plant cell, *crambe* plant cells, etc.

The present invention is not limited to any particular ac-TAG producing plant, i.e. an ac-TAG plant producing a seed comprising ac-TAGs. Indeed, a variety of ac-TAG producing plants are contemplated, including but not limited to an ac-TAG producing plant, an ac-TAG producing plant comprising an agronomically desirable trait, a progeny plant of a transgenic ac-TAG producing plant, an ac-TAG producing plant that is an agronomically desirable plant, an ac-TAG producing plant that is a commercially desirable plant, and an ac-TAG producing plant that is a commercially desirable cultivar.

Additionally, in some embodiments, the inventions provide a seed comprising a plant nucleic acid sequence encoding an acetyl-CoA diacylglycerol acyltransferase protein. The present inventions are not limited to a particular seed. Indeed a variety of seeds are contemplated, including but not limited to a *Jatropha* plant seed, an oil crop plant seed, a palm oil plant seed, and an alga seed. In some embodiments, said seed includes but is not limited to a *Brassica* plant seed and Brassicaceae plant seed. In some embodiments, said seed includes but is not limited to an *Arabidopsis* plant seed, *Camelina* plant seed, *crambe* plant seed, etc.

Additionally, in some embodiments, the inventions provide a composition comprising a seed, wherein said seed comprising a heterologous plant nucleic acid sequence encoding an acetyl-CoA diacylglycerol acyltransferase protein capable of forming acetyltriacylglycerol molecules.

In addition the present invention provides methods, comprising, a) providing, i) an isolated nucleic acid sequence encoding an acetyl-CoA diacylglycerol acetyltransferase protein capable of forming an acetyltriacylglycerol, and ii) a host cell, b) transforming said host cell with said isolated nucleic acid sequence such that said nucleic acid expresses said protein, and c) isolating an acetyltriacylglycerol from said host cell. In some embodiments, said acetyltriacylglycerol is a 3-acetyl-1,2-diacyl-sn-glycerol. In some embodiments, said host cell is selected from a fungal cell, an alga cell and a plant cell. In some embodiments, said isolating comprises lipid extraction. In some embodiments, said methods further comprise incubating said transformed cell in a medium. In some embodiments, said host cell further comprises a heterologous gene and expresses said heterologous gene under conditions increasing a substrate for said acetyl-CoA diacylglycerol acyltransferase protein. The present inventions are not limited to a particular heterologous gene. Indeed a variety of heterologous genes are contemplated, including but not limited to genes for altering fatty acid synthesis, fatty acid synthesizing enzymes, and the like. In some embodiments, said heterologous gene reduces long chain fatty acid synthesis. In some embodiments, expression of said heterologous gene reduces long chain fatty acid synthesis. In some embodiments, said heterologous gene encodes an ATP-citrate lyase enzyme. In some embodiments, said heterologous gene encodes an acyl-ACP thioesterase (FatB) protein. In some embodiments, said heterologous gene encodes a FAE1 mutant protein. In some embodiments, said heterologous gene encodes a FAE1 truncation mutant protein. In some embodiments, said host cell further comprises an inhibitory heterologous nucleic acid capable of interfering with the production of a long-chain-triacylglycerol molecule for increasing amounts of isolated acetyltriacylglycerol. The present inventions are not limited to a particular inhibitory heterologous nucleic acid. Indeed a variety of inhibitory heterologous nucleic acids are contemplated, including but not limited to a diacylglycerol acyltransferase 1 gene, diacylglycerol acyltransferase 2 gene, and phospholipid:diacylglycerol acyltransferase gene. In some embodiments, said inhibitory nucleic acid is a siRNA. In some embodiments, said production of long chain-triacylglycerol molecules is reduced. In some embodiments, said host cell has lower long chain-triacylglycerol production. In some embodiments, said host cell has low long chain-triacylglycerol production. In some embodiments, said host cell expresses a mutant fatty acid elongase gene 1 gene resulting in lower long chain-triacylglycerol production. In some embodiments, said host cell expresses a mutant fatty acid elongase gene 1 gene resulting in low long chain-triacylglycerol production. In some embodiments, said acetyltriacylglycerol comprises a 3-acetyl-1,2-diacyl-sn-glycerol.

In addition the present invention provides methods, comprising, a) providing, a plant part comprising a heterologous nucleic acid sequence encoding an acetyl-CoA diacylglycerol acetyltransferase protein capable of forming acetyltriacylglycerol, and b) growing said plant part under conditions such that said nucleic acid expresses said protein wherein acetyltriacylglycerol production is increased, and c) isolating acetyltriacylglycerol from said plant part. In some embodiments, said acetyltriacylglycerol is 3-acetyl-1,2-diacyl-sn-glycerol. In some embodiments, said plant part is selected from a seed, aril, stem, leaf, tubers, mesocarp, pericarp, exocarp, cell wall, and frond. In some embodiments, said host cell further comprises an inhibitory heterologous nucleic acid capable of interfering with the production of a long-chain-triacylglycerol molecule for increasing amounts of isolated 3-acetyl-1,2-diacyl-sn-glycerol. In some embodiments, said inhibitory nucleic acid is selected from the group consisting of a diacylglycerol acyltransferase 1 gene, diacylglycerol acyltransferase 2 gene, and a phospholipid:diacylglycerol acyltransferase gene. In some embodiments, said inhibitory nucleic acid is a siRNA. In some embodiments, said production of long-chain-triacylglycerol molecules is reduced. In some embodiments, said plant part further comprises a heterologous nucleic acid sequence encoding a protein capable of increasing a substrate for said acetyl-CoA diacylglycerol acyltransferase protein. In some embodiments, said heterologous nucleic acid encodes a truncated FATTY ACID ELONGASE 1 mutant protein. In some embodiments, said heterologous nucleic acid is a mutant fatty acid elongase 1 gene. In some embodiments, said plant part further comprises a heterologous acyl nucleic acid sequence encoding a protein capable of increasing a substrate for said acetyl-CoA diacylglycerol acyltransferase protein. In some embodiments, said heterologous gene encodes an ATP-citrate lyase enzyme. In some embodiments, said heterologous gene encodes an acyl-ACP thioesterase protein. In some embodiments, said heterologous gene encodes a FATTY ACID ELONGASE 1 protein. In some embodiments, said substrate is selected from the group consisting of a short chain acyl-CoA and medium chain acyl-CoA. In some embodiments, said substrate is selected from the group consisting of an acetyl-CoA, butyryl-CoA, hexanoyl-CoA, octanoyl-CoA, and decanoyl-CoA.

In addition, the present invention provides methods, comprising, a) isolating oil from a host cell expressing a heterologous gene encoding a protein capable of making an acetyl-triacylglycerol, wherein said oil comprises a triacylglycerol consisting of two functionalized acyl groups and an acetyl group, and b) using said oil in an application selected from the group consisting of lubricant, biofuel, spray coating, food oil, in food processing, and thermoplastic polymer products.

In addition, the present invention provides methods, comprising, a) isolating oil from a host cell expressing a heterologous gene encoding a protein capable of making an acetyl-triacylglycerol, wherein said oil comprises a triacylglycerol consisting of two acyl groups and an acetyl group, and b) using said oil in an application selected from the group consisting of lubricant, biofuel, spray coating, food oil, in food processing, and thermoplastic polymer products.

In addition, the present invention provides methods, comprising, a) providing, a host plant capable of producing seeds, and b) treating said host plant so as to reduce long chain-triacylglycerol production in said seeds under conditions for increasing acetyltriacylglycerol production in said seeds. In some embodiments, said treating comprises transfecting said host plant with a mutant gene whose expression is capable of reducing long chain-triacylglycerol production. In some embodiments, said mutant gene is a fatty acid elongase 1 gene. In some embodiments, said mutant gene is a truncated fatty acid elongase 1 gene. In some embodiments, said host plant comprises a heterologous nucleic acid sequence encoding an acetyl-CoA diacylglycerol acetyltransferase protein capable of forming an acetyltriacylglycerol. In some embodiments, said method further comprises step c) isolating said acetyltriacylglycerols from said seed. In some embodiments, said method further comprises step d) using said isolated acetyltriacylglycerols in an application selected from the group consisting of lubricant, biofuel, spray coating, food oil, in food processing, and thermoplastic polymer products. Additionally, in some embodiments, the inventions provide a seed produced by the methods. In some embodiments, said seed has low long chain-triacylglycerols. Additionally, in some embodiments, the inventions provide a composition comprising a seed produced by the methods. Additionally, in some embodiments, the inventions provide an oil isolated from said a seed produced by the methods. In some embodiments, said oil has low long chain-triacylglycerols. Additionally, in some embodiments, the inventions provide a composition comprising said oil. In some embodiments, said host plant comprises a heterologous nucleic acid sequence encoding an acetyl-CoA diacylglycerol acetyltransferase protein capable of forming an acetyltriacylglycerol.

Definitions

To facilitate an understanding of the present invention, a number of terms and phrases as used herein are defined below:

The use of the article "a" or "an" is intended to include one or more.

The term "plant" is used in it broadest sense. It includes, but is not limited to, any species of woody, ornamental or decorative, crop or cereal, fruit or vegetable plant, and photosynthetic algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. and are also referred to as "plant parts."

The term "wild-type" in reference to a plant and cell and gene, etc. refers to a plant, cell, gene, etc., as found in its natural state, i.e. a plant, cell, gene, etc., that was not molecularly engineered, for example, a gene sequence whose codons were not molecularly altered by man.

The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture.

The term "plant part" as used herein refers to a plant structure or a plant tissue.

The term "seed" as used herein refers to a fertilized ovule of a plant, comprising an embryo, endosperm, and a seed coat. The term "seed" in reference to it's oil refers to lipid within the seed or oil isolated from the seed.

The term "aril" or "arillus" refers to a "fleshy" or "pulpy covering" or "appendage" or "covering" found on one end of certain seeds. An aril is formed at the attachment point of the seed and is often a bright colored envelope, such as found as red to orange arils (considered a fruit) enclosed by a four-lobed pink, yellow or orange capsule in Ea plants, a red berry-like aril in yew plants. Arils may produce specific compounds such as the spice mace isolated form arils of nutmeg seeds.

The terms "leaf" and "leaves" refer to a usually flat, green structure attached to a stern or branch of a plant wherein photosynthesis and transpiration take place.

The term "stem" refers to a main ascending axis of a plant.

The term "alga" refers to a singular organism while "algae" refers to plural organisms referring to any of various green, red, or brown organisms that grow mostly in water, ranging in size from single cells to large spreading seaweeds.

The term "algae" is used in it's broadest sense. The term "algae" includes microalgae, single-celled organisms, and macroalgae, multi-cellular organisms, both freshwater and saltwater strains. Microalgae include algal mixtures, algal strains, diatoms, and cyanobacteria. In some preferred embodiments, algal are green algae and diatoms. An alga comprises a photosynthetic pigment, such as chlorophyll (i.e. green, for example, *Chlorophyta*, including sea lettuce), a carotenoid (i.e. yellow, orange, or brown, for example, *Phaeophyta*; *Laminaria* species, such as kelp, including Rockweed (*Ascophyllum nodosum*)), and an anthocyanin (i.e. red, for example, Rhodophyta including nori). Algae include some eukaryotic and some prokaryotic organisms and any organism also called "Protist" or "Protista" and any organism called "Chromista." An alga encompasses microalgae, such as single cell organisms, for example, *Botryococcus* species, and macroalge, such as seaweed and kelp.

A "plant part" in reference to a multicellular alga, such as kelp, refers to parts including but not limited to a thallus: the algal body; lamina: a flattened structure that is somewhat leaf-like; sorus: spore cluster; air bladders: float-assist organ (on blade), such as on Fucus; floats: float-assist organ (between lamina and stipe); such as on kelp, stipe: a stem-like structure supporting the blade (analogous to a leaf); blade, consisting of both a laminar (flattened) photosynthetic tissue and a rachis, referring to a portion of the stem to which the laminar tissue is attached; holdfast: specialized basal structure providing attachment to a surface, often a rock or another alga; haptera: finger-like extensions of holdfast anchoring to benthic substrate. The stipe and blade are collectively known as the "frond."

The term "crop" or "crop plant" is used in its broadest sense. The term includes, but is not limited to, any species of edible plant, (e.g. rice, corn, beans, etc.), including edible algae, capable of being eaten by humans or used as a feed for animals, and any plant or algae consumed by and used by humans, including any plant or algae used in industry or commerce that is cultivated by man.

The term "oil crop plant" or "oil seed plant" or "crop oil plant" refers to a plant or algae cultivated by man for commercial oil production. As opposed to the term "oil plant" which is an oil producing plant or algae not currently an oil crop plant. An oil plant may be cultivated by man for non-oil producing purposes, for example, cultivated by man as a shrubbery plant.

The term "oleaginous" in reference to an organism, species or strain, generally refers to oil production, such as an organism, species or strain capable of producing at least 20% TAGs by dry weight. Examples of oleaginous organisms include "oleaginous fungus" such as *Mortierella alpina* 1S-4, *Mortierella ramanniana* var. *angulispora* (Pillai et al., J. Biochem, 2002, Vol, 132, No. 1 121-126, herein incorporated by reference), *Gliocladium roseum*, *Aspergillus niger*, etc.; "oleaginous yeast" such as *Lipomyces starkeyi*, *Rhodotorula glutinis*, *Candida* 107, etc.; "oleaginous mold" such as *Entomophthora exitalis*, etc.; and "oleaginous algae" such as *Botryococcus* sp., marine algae, and diatoms. In general, oil production may have strain specificity.

The term "oil-producing species" refers to plant species that produces and stores triacylglycerol in specific organs, primarily in seeds. Such species include but are not limited to soybean (*Glycine max*), rapeseed and canola (including *Brassica napes* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species (species not typically cultivated for oil production) which are useful in developing appropriate expression vectors for use in the present inventions, such as tobacco plants, rapid cycling *Brassica* plant species, and *Arabidopsis*

*thaliana*, in addition to wild species which may be a source of unique fatty acids in combination with ac-TAGs of the present inventions.

The term "*Euonymus*" refers to a plant or plants from the genus *Euonymus*. Non-limiting examples of *Euonymus* include plants from the species *E. alata*, The term also refers to *E. alata* plants from which nucleic acid sequence SEQ ID NO:10 was isolated.

The terms "diacylglycerol" and "DAG" and "diglyceride" refer to a molecule comprising a glycerol backbone to which two acyl groups are esterified. Typically, the acyl groups are esterified to the sn-1 and sn-2 positions, although the acyl groups may also be esterified to the sn-1 and sn-3 positions, or to the sn-2 and sn-3 positions; the remaining position is unesterified and contains a hydroxyl group. This term may be represented by the abbreviation DAG.

The terms "diacylglycerol" or "DAG" in reference to a substrate refers to molecules comprising a DAG group, such as 1,2-diacylglcerols with combinations of acyl chains including, but not limited to, hexanoate, laurate, palmitate, palmitoleate, stearate, oleate, linoleate, linolenate, arachidonate, eicosenoate, and eicosadienoate. For example, with the fatty acids palmitate and oleate, the following 1,2-diacylglycerol molecules can be formed: 1,2-dipalmitoyl-glycerol, 1-palmitoyl-2-oleoyl-glycerol, 2-palmitoyl-1-oleoyl-glycerol and 1,2-dioleoyl-glycerol."

The terms "triacylglycerol" and "triglyceride" and "TAG" refer to a molecule comprising a glycerol backbone to which three acyl groups are esterified.

The term "long chain-triacylglycerol" or "lc TAG" or "lc-TAG" or "LcTAG" refers to a triacylglycerol in which all three acyl groups are long chain fatty acids also called long-chain fatty acids, are typically at least 16 up to 18 carbons in length. Thus a long-chain-triacylglycerol will contain a total number of acyl carbon atoms ranging from 48-54 (in other words an acyl carbon number of at least C48 up to C54).

The term "medium-chain-triacylglycerol has least one C8-C14 fatty acid acyl group, and up to three C8-C14 fatty acyl groups. Thus a medium-chain-triacylglycerol may have an acyl carbon number of at least C24, (e.g. trioctinoin) up to C42 (e.g. trimyristin), for example the type of glycerides found in coconut oil.

The term "VLC" and "VLCFA" refers to "very long chain" and "very long chain fatty acid" respectively having at least 20 carbon atoms, including 20 carbon atom chains and higher.

The term "fatty acid elongase 1" or "fae1" gene refers to a wild-type gene encoding a FAE1 protein (enzyme) resulting in the elongation of primarily $C_{18}$ fatty acid moieties, and $C_{20}$ fatty acids, to produce VLCFAs, in other words, oil producing plants expressing a heterologous functional FAE1 protein has increased proportions of 22:1 in the seed oil. In contrast, a mutant fatty acid elongase 1 gene, such as a truncation mutant, of the present inventions results in lower amounts of fatty acids of at least $C_{20}$ and higher.

The term "canola-quality" in reference to an oil refers to Canadian standards of less than 2% erucic acid in oil and less than 30 moles of aliphatic glucosinolates per gram in canola meal (see, world.wide.web.hc-sc.gc.ca/fn-an/gmf-agm/appro/low_erucic-faible_erucique-eng.php, Health Canada 2003-03-27).

The term "acyl group" may also be referred to by the letter C followed by the number of carbons in the linear aliphatic chain, as, for example, $C_{16}$ refers to an acyl group of 16 carbons in length. An acyl group includes a functionalized acyl group as defined herein.

The term "functionalized acyl group" refers to an acyl group comprising a reactive group, i.e. a group that can undergo a chemical reaction, such as a double bond, a hydroxyl group, and the like, in addition to the carboxylate head group of the fatty acid.

The terms "acetyl glyceride" and "acetyl triacylglycerol" and "acetyltriacylglycerol" and "ac-TAG" and "AcTAG" and "acetyldioleoyl glycerol" and the like refer to a triglyceride to which at least one acetyl or related group is esterified to the glycerol backbone. A particular acetyl glyceride is denoted by the position(s) to which an acetyl or related group is esterified; thus, "sn-3-acetyl glyceride" or "1,2-diacyl-3-acetin" or "3-acetyl-1,2-diacyl-sn-glycerol" refer to triacylglycerol with long acyl chains at the sn-1 and sn-2 positions and an acetyl group at the sn-3 position.

The term "sn" in reference to a Carbon atom refers to a stereospecific numbering system used for naming glycerolipid molecules. Sn as a prefix, such as "sn glycerol" refers to the position number of the Carbon (C) atom in the glycerol backbone of a lipid molecule.

An "acetyl" or "related group," when used in reference to ac-TAG, refers to an acyl moiety other than a long-chain acyl group esterified to TAG. The acyl moiety is any linear aliphatic chain 10 or less carbon atoms in length; it may or may not have side group chains or substituents. Related group members include but are not limited to propionyl, butyryl, hexanoyl, octanoyl, and deconyl.

The term "diacylglycerol acyltransferase" or "DGAT" refers to a polypeptide (protein) with the capacity to transfer an acyl group to a diacylglycerol substrate. In particular, a diacylglycerol acyltransferase (enzyme) transfers an acyl group to the sn-3 position of the 1,2-diacyl-sn-glycerol (DAG). An acyl substrate for a DGAT is typically esterified to CoA; thus, the acyl substrate is typically an acyl-CoA. Thus, a DGAT enzyme is also referred to as an "diacylglycerol:acyl-CoA acyltransferase," and in some particular embodiments, as an "acyl-CoA: 1,2-diacyl-sn-glycerol acyltransferase," and the like. The term may be referred to by the abbreviation DGAT. At least four different types of DGAT enzymes capable of catalyzing such a reaction have been identified in various species.

The term "low long chain-triacylglycerol production" in general refers to a mol of long chain-triacylglycerol in total isolated lipid (from a plant part, seed or microorganism) ranging from negligible (less than 0.5 mole %) to approximately 10 mole %. For examples, a plant described as having low long chain-triacylglycerol production refers to a plant having low long chain-triacylglycerol in its seeds, wherein a seed having low long chain-triacylglycerol production refers to its lipids having low long chain-triacylglycerol content. Low long chain-triacylglycerol production in reference to an oil isolated from a microorganism generally refers to a 0.5 mol %-approximately 10 mole %.

The term "lower" or "lowered" or "lowering" or "reduce" or "reduced" "reducing" in reference to producing fatty acid molecules in an oil, i.e. long chain-triacylglycerol molecules, refers to altering the wild type long chain-triacylglycerol content of a plant, seed or oil by manipulation in order to isolate an oil from a plant or seed containing fewer long chain-triacylglycerol molecules. As one example, see Example XII, wherein expression of a truncation mutant fae1 gene results in seed oil with reduced long chain-triacylglycerol production.

The term "triacylglycerol synthesis gene" refers to any gene related to the synthesis of long chain-triacylglycerols, including but not limited to DGAT1, DGAT2, and PDAT genes.

The term "DGAT1" or "diacylglycerol acyltransferase 1" refers to a DGAT enzyme containing at least six predicted transmembrane domains and showing similarity to a group of proteins such as *Arabidopsis* AT2G19450 in the MBOAT protein superfamily.

The term "DGAT2" or "diacylglycerol acyltransferase 2" refers to a DGAT enzyme predicted to have two transmembrane domains and showing similarity to proteins such as *Arabidopsis* AT3G51520 but which is not a member of the MBOAT protein superfamily.

The term "DGAT3" or "diacylglycerol acyltransferase 3" refers to a DGAT/wax ester synthase transmembrane enzyme, such as ADP1 from *Acinetobacter* calcoaceticus, also considered as a member of the MBOAT protein superfamily (for example, see, Kalscheuer, et al., Vol. 278, 10(7):8075-8082, (2003), herein incorporated by reference).

The term "DGAT4" or "diacylglycerol acyltransferase 4" refers to a soluble DGAT enzyme rather than membrane bound, for example, showing similarity to a soluble DGAT present in peanut cotyledons (for example, see, Saha, et al., Plant Physiology, 141:1533-1543 (2006), herein incorporated by reference).

The terms "PDAT" or "phospholipid:diacylglycerol acyltransferase" refers to a "phospholipid diacylglycerol acyltransferase" (EC 2.3143) enzyme using phosphatidylcholine as the acyl donor for synthesizing lc-TAGS and showing similarity to proteins such as *Arabidopsis* AT5G13640.

The term "MBOAT protein superfamily" or "membrane bound O-acyl transferase protein superfamily" refers to proteins containing the conserved MBOAT domain as defined by the National Center for Biotechnology Information (NCBI) Conserved Domains Database accession number PFAM03062.

The term "diacylglycerol acetyltransferase" or "DAcT" or "AcDGAT" refers to a diacylglycerol acyltransferase nucleotide sequence and encoded polypeptide (enzyme) with a unique acyl group transfer specificity also referred to as a "short chain acyl-CoA diacylglycerol acyltransferase," such that the polypeptide is able to transfer an acetyl or a related group to a diacylglycerol substrate and the diacylglycerol acetyltransferase exhibits increased specificity for an acetyl or related group compared to a diacylglycerol acyltransferase obtained from a plant in which acetyl TAGs are not present, or are present in only trace amounts (in other words, in a wild-type host cell or plant the ac-TAGs are present at less than about 1% of total TAGs). The acetyl or related group substrate of the transferase of the present inventions is typically esterified to CoA; thus, typical short chain acyl-CoA substrates include but are not limited to acetyl-CoA, propionyl-CoA, butyryl-CoA, benzoyl-CoA, or cinnamoyl-CoA, etc., as described above. These CoA substrates are typically non-micellar acyl-CoAs, or possess high critical micelle concentrations (CMCs), in that they form micelles at relatively high concentrations when compared to the CMCs of long chain acyl-CoAs.

A diacylglycerol substrate of DAcT is typically a long chain diacylglycerol, although other chain length diacylglycerols, such as longer or shorter C numbers, and other acyl acceptors (other than diacylglycerides) are also contemplated. The acyl (or other) groups are esterified to the sn-1 and sn-2 positions, although the acyl groups may also be esterified to the sn-1 and sn-3 positions, or to the sn-2 and sn-3 positions. Thus, an enzyme of the present inventions is also referred to as an "diacylglycerol:acetyl-CoA acetyltransferase," or in particular embodiments, as an "acetyl-CoA:sn-1,2-diacylglycerol acetyltransferase" and the like. This term may be referred to by the abbreviation DAcT, indicating an activity of increased specificity for transfer of acetyl or related groups.

The term "enzyme" refers to a protein capable of catalyzing a chemical reaction. Enzymes are specific for one or more of a substrate and specific for a reaction. Such that an enzyme may catalyze the transformation of just one substrate or a family of substrates, such as described herein for DAcT enzymes that are structurally related. Further, enzymes are capable of catalyzing one or more of the possible reactions of the substrate(s). The specificity of an enzyme depends on the characteristics of the active site, a region where it binds to the substrate before the substrate transformation into a product.

The term "reactant molecule" refers to at least one of the starting materials in a chemical reaction.

The term "substrate" refers to a reactant molecule that is capable of binding to (or otherwise interacting with) the active site of an enzyme.

The term "product" refers to a reactant modified (transformed) by an enzyme.

The term "substrate specificity" or "specificity" in reference to an enzyme of the present inventions refers to the ability of the enzyme to bind to a substrate with a defined structure, typically a 3 dimensional structure, while having little or no interaction with other molecules. In general, substrate specificity refers to a range of substrates that an enzyme will act upon to produce a product. Substrate specificity also refers to the relative ratio of activity towards two or more different substrates, when the substrates are compared, they are assayed independently with the enzyme, such that each substrate has a measurement of activity, thus allowing a ranking of higher to lower specificity. "Specificity" may also refer to acyl donor specificity and acyl acceptor specificity and is determined by either in vivo or in vitro assays. As measured with an in vivo assay, specificity is determined by measuring the proportion of total TAGs products that are ac-TAGs, where the ac-TAGs are synthesized by the presence of a heterologous diacylglycerol acetyltransferase. As measured with an in vitro assay, acyl donor specificity refers to the activity of transfer of an acetyl or related group to a diacylglycerol, when the substrate is an acetyl-CoA or related group esterified to CoA. An increase in specificity of transferring an acetyl or related group by an *Euonymus alatus* diacylglycerol acetyltransferase (EaDAcT) of the present inventions is at least about 1.5 times, or about 2 times, or about 5 times, or about 10 times, or about 20 times, or about 50 times, or about 100 times, or up to about 2000 times, the specificity of a DGAT obtained from a plant in which acetyl TAGs are not present, or are present in only trace amounts. One standard DGAT to which an EaDAcT specificity is compared, for determining specificity of transfer of an acetyl or related group, is a DGAT obtained from *Arabidopsis* (AtDGAT1).

The term "substrate selectivity" refers to assays in which two or more substrates compete directly for reaction with the enzyme in the same assay, such that a substrate with a higher affinity to an enzyme will out compete a substrate with a lower affinity for the same enzyme.

The term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (for example, kinetics or thermodynamics) of binding by the first polypeptide may be the same as or greater than or less than the efficiency substrate binding by the second polypeptide. For example, the equilibrium binding constants (KD) for binding to the substrate may be different for the two polypeptides. A competitive binding assay may also be based on the competition between a labeled and an unlabelled substrate in the reaction with an enzyme.

The term "substrate competition for one binding site on an enzyme" refers to a relative difference in affinity between different substrates, such as shown in a competitive binding assay, i.e. two substrates for one binding site, an inhibitory competition such as a competitive inhibition, and the like.

The term "inhibitor" in reference to an enzyme refers to groups of competitive inhibitors and the noncompetitive inhibitors. The competitive inhibitors are molecules that chemically mimic the true substrate close enough to fit into the active site; it is like a key that fits into a lock but doesn't work. However, the enzyme does not act upon these mimics or analogues, but as long as they occupy the active site they compete with the natural substrates and prevent its modification.

The term "enzyme inhibitor" as used herein, refers to any compound that either directly or indirectly reduces the biological activity of an enzyme. Such reduction in activity may be a result of competitive or non-competitive inhibitor (i.e., for example, by using a small molecule inhibitor), or by using an enzyme's antisense nucleic acid.). The terms "*Euonymus*" and "*Euonymus*-like" and "Ea" when used in reference to a DAcT, for example, an EaDAcT refer to a DAcT obtained from *Euonymus alata* or with a substrate specificity that is similar to a DAcT obtained from *Euonymus alata*. The term may be referred to by the abbreviation, "EaDAcT," indicating an enzyme obtained from *Euonymus alata*, or from the genus *Euonymus*, or from the closely related plant family Celestraceae, or an enzyme which has an amino acid sequence with a high degree of similarity to or identity with a DGAT obtained from *Euonymus alata*. By "high degree of similarity" or "substantial identity" it is meant that it is more closely related to EaDAcT than to EaDGAT by BLAST scores (identity) or other amino acid sequence comparison/alignment software programs, such as align (NCBI) (identity).

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (in other words, identity), "Sequence identity" refers to a measure of relatedness between two or more proteins, and is given as a percentage with reference to the total comparison length.

The identity calculation takes into account those amino acid residues that are identical and in the same relative positions in their respective larger sequences. Calculations of identity may be performed by algorithms contained within computer programs.

The term "chimera" when used in reference to a polypeptide refers to the expression product of two or more coding sequences obtained from different genes, that have been cloned together and that, after translation, act as a single polypeptide sequence.

Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structures, or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a plant includes a plant with changes in gene function, such as changes in an activity, changes in an accumulated product, changes in gene expression, changes in protein expressed from a gene, and the like, for example, a change in ac-TAG production, lc-TAG production, etc., especially when compared to a population of wild-type plants of the same species.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (for example, replacement of leucine with isoleucine). More rarely, a variant may have "non-conservative" changes (for example, replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on) within a single polypeptide.

The term "knock-out" or "deletion mutant" in reference to a plant refers to completely inactivating a specific gene via any one of a variety of mechanisms that may affect gene transcription, translation, or the sequence of the protein product, removing the gene function from a cell type, target tissue or whole organism. Alternatively, a knock-out refers to significant but partial inactivation via any one of a variety of mechanisms that may affect gene transcription, translation, or the sequence of the protein product, removing the gene function from a cell type, target tissue or whole organism.

As used herein, the term "altered levels" or "natural variant" refers to the production of gene product(s) in transgenic organisms in amounts or proportions or sequence composition that differ from that of an untreated or a normal or a wild-type or a non-transformed organism or cell.

The term "wild-type" in reference to a gene refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

The term "gene" refers to a nucleic acid (for example, DNA or RNA) sequence that comprises coding sequences necessary for the production of RNA, or a polypeptide or its precursor (for example, proinsulin). A functional polypeptide can be encoded by a full length coding sequence or by any portion of the coding sequence as long as the desired activity or functional properties (for example, enzymatic activity, ligand binding, signal transduction, etc.) of the polypeptide are retained.

The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "heterologous gene" refers to a gene encoding a factor that is not in its natural environment (in other words, has been altered by or taken from its natural environment by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence that is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target. When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4 \bullet H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed. High stringency conditions when used in reference to nucleic acid hybridization comprise conditions equivalent to binding or hybridization at 42° C. in a solution consisting of 5X SSPE (43.8 g/l $NaCl_2$, 6.9 g/l $NaH_2PO_4 \bullet H_2O$ and 1.85 g/l EDTA, pH adjusted to 7.4 with NaOH), 0.5% SDS, 5X Denhardt's reagent and 100 µg/ml denatured salmon sperm DNA followed by washing in a solution comprising 0.1X SSPE, 1.0% SDS at 42° C. when a probe of about 500 nucleotides in length is employed. It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above. When used in reference to a single-stranded nucleic acid sequence, the term "substantially homologous" refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q βreplicase, MDV-1 RNA is the specific template for the replicase (Kacian et al. (1972) Proc. Natl. Acad. Sci. USA, 69:3038, herein incorporated by reference). Other nucleic acid will not be replicated by this amplification enzyme. Similarly, in the case of T7 RNA polymerase, this amplification enzyme has a stringent specificity for its own promoters (Chamberlin et al. (1970) Nature, 228:227, herein incorporated by reference). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560, herein incorporated by reference). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press, herein incorporated by reference).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the exemplary method of Mullis, U.S. Pat. Nos. 4,683,195, 4,683,202, and 4,965,188, all of which are herein incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "RACE" refers to Rapid Amplification of cDNA Ends.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987, herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987, herein incorporated by reference).

The terms "promoter element," "promoter," and "promoter sequence" as used herein, refer to a DNA sequence that is located at the 5' end (in other words precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue.

The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (for example, peroxidase conjugated) secondary antibody that is specific for the primary antibody is allowed to bind to the sectioned tissue and specific binding detected (for example, with avidin/biotin) by microscopy.

The term "compartments or organelles" in reference to a plant cell is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "host cell" refers to any cell capable of replicating and/or transcribing and/or translating a heterologous gene.

As used herein, the term "cell" refers to any small, usually microscopic, mass of protoplasm bounded externally by a semipermeable membrane, usually including one or more nuclei and various nonliving products, capable alone or interacting with other cells of performing all the fundamental functions of life, and forming the smallest structural unit of living matter capable of functioning independently. For example, a cell as contemplated herein includes, but is not limited to, an epithelial cell, vascular cell, a vegetative cell, a mesenchymal cell, a cell capable of photosynthesis, a pollen grain, i.e. male reproductive cell of a plant, germ cell of a plant, an ovule cell, i.e. female reproductive cell of a plant, egg cell of a plant, a tissue cell, a pod cell, an endosperm cell, mesenchymal cell, meristem cell, oil seed plant cell, a seed cell, an embryo cell, etc. The term "cell" also refers to a single cell that may be comprised in a population of cells in vitro and/or in vivo.

The term "agronomically viable plant" has an agronomic, horticultural, ornamental, economic, and/or commercial value. Agronomically important plants are grown for their seed oil (such as Canola, soybeans, etc.), seed products (such as fruits and vegetables as diverse as beans, peas, corn, and tomatoes), and leaf tissue (such as lettuce, spinach, and other greens).

As used herein, the term "agronomic trait" and "economically significant trait" and "agronomically desirable trait" refers to any selected trait that increases the commercial value of a plant part, for example, a preferred oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, seed yield, plant type, plant height, lodging, shatter, herbicide resistance, disease resistance, insect resistance, nematode resistance, drought tolerance, drought resistance, water tolerance, water resistance, temperature tolerance, such as cold weather resistance, hot weather resistance, and the like, growth habit, maturity group, field tolerance, and growth in a hardiness zone. As opposed to a non-agronomic plant species which refers to a plant that typically lacks one or more characteristics for large scale commercial use, such as lacking an economic use, having a trait that renders it unsuitable for commercial use, such as producing a seed containing a toxic compound, and the like.

As used herein, the term "commercially viable levels" in reference to seed oil composition in general refers to a level of a specific type of oil production, i.e. ac-TAG % mol composition in oils of the present inventions, in organisms or seeds which is economically sustainable to bring to market, i.e. a level (% mol or % composition) at which harvesting, isolating and purifying makes commercial sense. In one preferred embodiment, the level of oil comprises at least 50% ac-TAG % mol up to 100% TAG % mol.

As used herein, the term "commercial production level" in reference to seed oil composition in general refers to a level of a specific type of oil production, i.e. ac-TAG % mol composition in oils of the present inventions, in organisms or seeds which is at a level similar to other specialty oils under commercial production. For example, unusual fatty acids sold in specialty oils under commercial production range from 50%-55% 18:3 fatty acids in Linseed oil, 80-90% C6 to C4 fatty acids in Palm Kernel oil and Coconut oil, and 90% 18-OH fatty acids in Castor oil (from The Lipid Handbook, eds. Gunstone, Harwood and Padley, 1986, Chapman and Hall, London).

Promoters may be constitutive or regulatable. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, herein incorporated by reference), mannopine synthase, octopine synthase (ocs), superpromoter (see for example, WO 95/14098, herein incorporated by reference), and ubi3 (see for example, Garbarino and Belknap (1994) Plant Mol. Biol. 24:119-127, herein incorporated by reference) promoters. Such promoters have been used successfully to direct the expression of heterologous nucleic acid sequences in transformed plant tissue.

In contrast, a "regulatable" promoter is one that is capable of directing a level of transcription of an operably linked nuclei acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene for which it is not naturally associated, e.g. placed by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species). The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) Molecular Cloning: A Laboratory Manual, 2nd ed., Cold Spring Harbor Laboratory Press, New York, pp. 16.7-16.8, herein incorporate by reference). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7, herein incorporated by reference).

The term "selectable marker" refers to a gene which encodes an enzyme having an activity that confers resistance to an antibiotic or drug upon the cell in which the selectable marker is expressed, or which confers expression of a trait which can be detected (for example, luminescence, fluorescence, etc). Selectable markers may be "positive" or "negative." Examples of positive selectable markers include the neomycin phosphotransferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium (i.e. a medium with a selective marker added for growing cells expressing a particular trait, such as a heterologous nucleic acid sequence of the present inventions) to a medium, such as a growth medium, cell culture medium, and the like) containing gancyclovir or acyclovir selects against cells capable of expressing a functional HSV TK enzyme.

The term "medium" or "culture medium" refers to any substance containing nutrients used to cultivate (i.e. grow or maintain) living cells in vitro, such as medium for yeast cells, medium for plant cells, and the like. A medium may be a liquid or gelatinous substance.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium that causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus,

*Agrobacterium* strains which cause production of nopaline (for example, strain LBA4301, C58, A208, GV3101) are referred to as "nopaline-type"
Agrobacteria; *Agrobacterium* strains which cause production of octopine (for example, strain LBA4404, Achy, B6) are referred to as "octopine-type" Agrobacteria ; and
*Agrobacterium* strains which cause production of agropine (for example, strain EHA105,
EHA101, A281) are referred to as "agropine-type" Agrobacteria.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator
(PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (in other words, a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. A wild-type gene is that which is most frequently observed in a population and is thus arbitrarily designated the "normal" or "wild-type" form of the gene.

In contrast, the term "modified" or "mutant" when made in reference to a gene or to a gene product refers, respectively, to a gene or to a gene product (i.e. protein) which displays modifications in sequence and/or functional properties (in other words, altered characteristics) when compared to the wild-type gene or gene product. It is noted that naturally-occurring mutants can be isolated; these are identified by the fact that they have altered characteristics when compared to the wild-type gene or gene product. A modified or mutant gene may code for a protein with either increased or decreased activity. One example of a mutant is a "mutant fae1 gene" or "fae1 mutant gene", such that translation of a mutant fae1 gene into an "FAE1 mutant protein" described herein, results in reduced levels of functional FAE1 protein, for example, see, Kunst et al., 1992, Plant Physiol. Biochem. 30:425-434, herein incorporate by reference.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA," Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long;
often siRNAs contain from about two to four unpaired nucleotides at the 3' end of each
strand. At least one strand of the duplex or double-stranded region of a siRNA is substantially homologous to or substantially complementary to a target RNA molecule.
The strand complementary to a target RNA molecule is the "antisense strand;" the strand
homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "RNA interference" or "RNAi" or "siRNA" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

The term "overexpression" refers to the production of a gene product in transgenic organisms that exceeds levels of production in normal or non-transformed organisms.

The term "co-suppression" refers to the expression of a foreign gene that has substantial homology to an endogenous gene resulting in the suppression of expression of both the foreign and the endogenous gene. The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) Molecular Cloning: A Laboratory Manual, Cold Spring Harbor Press, NY, pp 9.31-9.58, herein incorporated by reference).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. (1989) supra, pp 7.39-7.52, herein incorporated by reference).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a plant DGAT includes, by way of example, such nucleic acid in cells ordinarily expressing a DGAT, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a seed, specimen or culture obtained from any source, as well as biological and environmental samples. Biological samples may be obtained from plants or animals (including humans) and encompass seeds, tissues, fluids, solids, and gases. These examples are not to be construed as limiting the sample types applicable to the present invention.

The term "biodiesel" in reference to a fuel in the United States refers to a domestic "renewable fuel" for diesel engines derived from natural oils, such as soybean oil, and meets the specifications of ASTM (American Society for Testing & Materials) D 6751. Biodiesel contains no petroleum and is biodegradable, nontoxic, and "clean burning" as essentially free of sulfur and aromatics. Biodiesel can be used in compression-ignition (diesel) engines with no major modifications. Biodiesel is simple to use, biodegradable, nontoxic, and essentially free of sulfur and aromatics. Technically, "biodiesel, n" refers to a fuel composed of mono-alkyl esters of long chain fatty acids derived from vegetable oils or animal fats, designated B 100, and meeting the requirements of ASTM (American Society for Testing & Materials) D 6751. Biodiesel is typically produced by a reaction of a vegetable oil or animal fat with an alcohol such as methanol or ethanol in the presence of a catalyst to yield mono-alkyl esters and glycerin, which is removed. Biodiesel, as defined in D 6751, is registered with the United States (U.S.) Environmental Protection Agency (EPA) as a fuel and a fuel additive under Section 211(b) of the Clean Air Act.

The term "blended diesel fuel" refers to a diesel fuel that contains some portion of biologic oils such as soybean or cottonseed oil. While biologic oils tend to have low sulfur content, they often have low cetane ratings and can support the growth of living organisms this fuel. Despite this, biologic blends can be used as long as the DF2 still meets total specifications for cetane, cloud point, pour point, lubricity, sulfur content and the biologic content is no more than 20 percent. Biodiesel may also be blended at any concentration with petroleum diesel to create a "biodiesel blend," for example, "B20" (a blend of 20 percent biodiesel with 80 percent petroleum diesel) has demonstrated significant environmental benefits with a minimum increase in cost for fleet operations and other consumers. "Biodiesel Blend, n" refers to a blend of biodiesel fuel meeting ASTM D 6751 with petroleum-based diesel fuel, designated BXX, where XX represents the volume percentage of biodiesel fuel in the blend.

The term "cetane" as in "cetane number" in reference to an ignition value of the fuel, for example, a measure of the ignition characteristics of diesel fuel oil in compression ignition engines. Most electronic diesel engines require a cetane rating of 45 or higher. Higher cetane values tend to improve the engine's cold-starting performance and reduce white smoke. Currently the on-highway DF2 has a value from 40 to 55.

The term "cloud point" in general refers to a temperature at which the first precipitation or crystal of solute forms in a petroleum product as it is cooled. A cloud point is related to a function of solute and solvent apparent molecular weights and their mole fractions, however the type of crystallization may further influence the cloud point. In general, as the apparent molecular weight of solution decreases, the cloud point temperature decreases, however there may be exceptions depending upon the materials present in the sample. A cloud point is typically measured at intervals of 2° F.

The term "melting point" refers to a temperature at which a pure substance liquefies.

The term "pour point" refers to the lowest temperature at which an oil or petroleum product will begin to flow. Pour point is typically measured at intervals of 5° F. This interval gives a range in which to account for error inherent in the measuring procedure. A sample with a pour point of 10.5° F. and a sample with a pour point of 14.5° F. would be labeled as having a pour point of 15° F. Even with the 4° difference they would be considered the same. However, a sample with a pour point of 15.5° F. would be labeled as having a pour point of 20° F. even though it is only 1° higher than the 14.5° F. sample mentioned before.

The term "lubricity" refers to an ability of a compound (lubricant) to reduce friction between moving parts in a machine or mechanism. In many cases, the lubricant is a heavy oil or grease that coats and acts as a cushion between parts. In some cases, thin oil is forced, under pressure, into precision-machined spaces (such as bearing journals), and acts as a support between parts. Still in other cases, the lubricating compound is suspended in a liquid (such as sulfur in diesel fuel), and momentarily reduces friction before it is whisked away. Reducing sulfur content in diesel fuel due to EPA mandates caused a reduction in diesel fuel lubricity. Thus alternative fuels need to demonstrate appropriate lubricity to maintain engine performance. One way of measuring an oil's ability to lubricate is to measure its viscosity.

The term "oil weight" or "viscosity" or "viscosity of a fluid" refers to a measure of the fluid's resistance to flow, i.e. fluid friction. Water is an example of a fluid with low viscosity, it pours easily and quickly. Cooking oil has a higher viscosity, it pours more slowly than water. An oil used as an engine lubricant should have a viscosity that does not change significantly as the temperature increases. Temperature requirements set for oil by the Society of Automotive Engineers (SAE) are 0 degrees F. (low) and 210 degrees F. (high).

The term "fuel density" or "density of a fuel" refers to a value commonly expressed in kilograms per cubic meter, or grams/cubic centimeter, as a measure of the amount of mass that occupies a given volume. The greater the fuel density, the greater the mass of fuel that can be stored in a given tank and the greater the mass of fuel than can be pumped for a given pump. Fuel density generally increases with increasing molecular weight of the fuel molecules. Fuel density also generally increases with increasing molecular weight of the component atoms of the fuel molecules. Fuel density is used to calculate fuel volume ratio, which is in turn used to calculate a tank mass.

The term "Newtonian fluids" refers to fluids and gases for which the shearing stress is linearly related to the rate of shearing strain. Newtonian materials, such as fluids, are referred to as true liquids since their viscosity or consistency is not affected by shear such as agitation or pumping at a constant temperature. Water and oils are examples of Newtonian liquids.

The term "trioctanoin" or "tricaprylin" or "glycerol trioctanoate" or "propane-1,2,3-triyl trioctanoate" in reference to a compound with a CAS Number of 538-23-8 and RN: 538-23-8 with a molecular formula $C_{27}H_{50}O_6$ and structural formula:

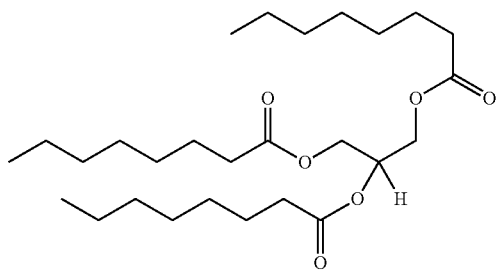 [SMILES: CCCCCCCC(=O)OCC(COC(=O)CCCCCCC)OC(=O)CCCCCCC]

refers to a medium-chain triglyceride (MCT) low viscosity polyol ester that is combustible. Trioctanoin is used medically as $^{13}$C-trioctanoin, a chemically synthesized product, used in human patient medical tests, such as a nonradioactive breath test to detect fat malabsorption, and is used as an emollient and thickening agent in cosmetics.

As used herein, the terms "F-generation" and "filial generation" refers to any of the consecutive generations of cells, tissues or organisms after a biparental cross. The generation resulting from a mating of the a biparental cross (i.e. parents) is the first filial generation (designated as "F1" and "$F_1$") in reference to a seed and it's plant, while that resulting from crossing of F1 individuals is the second filial generation (designated as "F2" or "$F_2$") in reference to a seed and it's plant. For example, an F2 seed and a resulting plant are produced by self-pollination of F1, while later F generations are produced from self-pollination of the immediate prior generation.

As used herein, the terms "T-generation" and "transformed generation" and "T" refers to any of the consecutive generations of cells, tissues or organisms after the insertion of transgenic DNA into the host genome. The generation resulting from a the transformation of the parent plant is the first transformed generation (designated as "T1" or "$T_1$") referring to both the seed and its plant, while that resulting from crossing of T1 individuals is the second filial generation (designated as "T2" or "$T_2$") in reference to a seed and its plant. For example, a T2 seed and a resulting plant are produced by the self-pollination of a T1 plant derived from a T1 seed, while later T generations are produced from self-pollination of the immediate prior generation.

As used herein, the term "line" refers to a plant nursery term to describe a group of individuals from similar parentage.

BRIEF DESCRIPTION OF THE DRAWINGS

FIG. 5 shows exemplary cDNA sequences identified as candidates for ac-TAG production. The candidate DNA sequence identified as an EaDAcT of the present inventions, is shown, SEQ ID NO:10, and Ea39113, SEQ ID NO:11, a candidate cDNA sequence, that failed to encode an ac-TAG producing enzyme of the present inventions. Forward 17392_F, SEQ ID NO:12, and reverse 17329_R2, SEQ ID NO:13 and reverse att_seq_3prime (AAA TTC GAG CTG GTC ACC TC, SEQ ID NO: 16), PCR primers for amplifying EaDAcT. Forward 39113_F, SEQ ID NO:14, and reverse 39113_R, SEQ ID NO:15, PCR primers for amplifying Ea39113, FIG. 6 shows EaDAcT SEQ ID NO:1 and Table 3 showing exemplary relationships of the EaDAcT [*Euonymus alatus*] SEQ ID NO:01 of the present inventions to sequences with the highest identity from a BLAST search in addition to a one on one comparison to an *Euonymus alatus* 1,2-diacyl-sn-glycerol:acyl-CoA acyltransferase (DGAT1), GenBank ACCESSION AAV31083 (SEQ ID NO:09).

Figure 13:
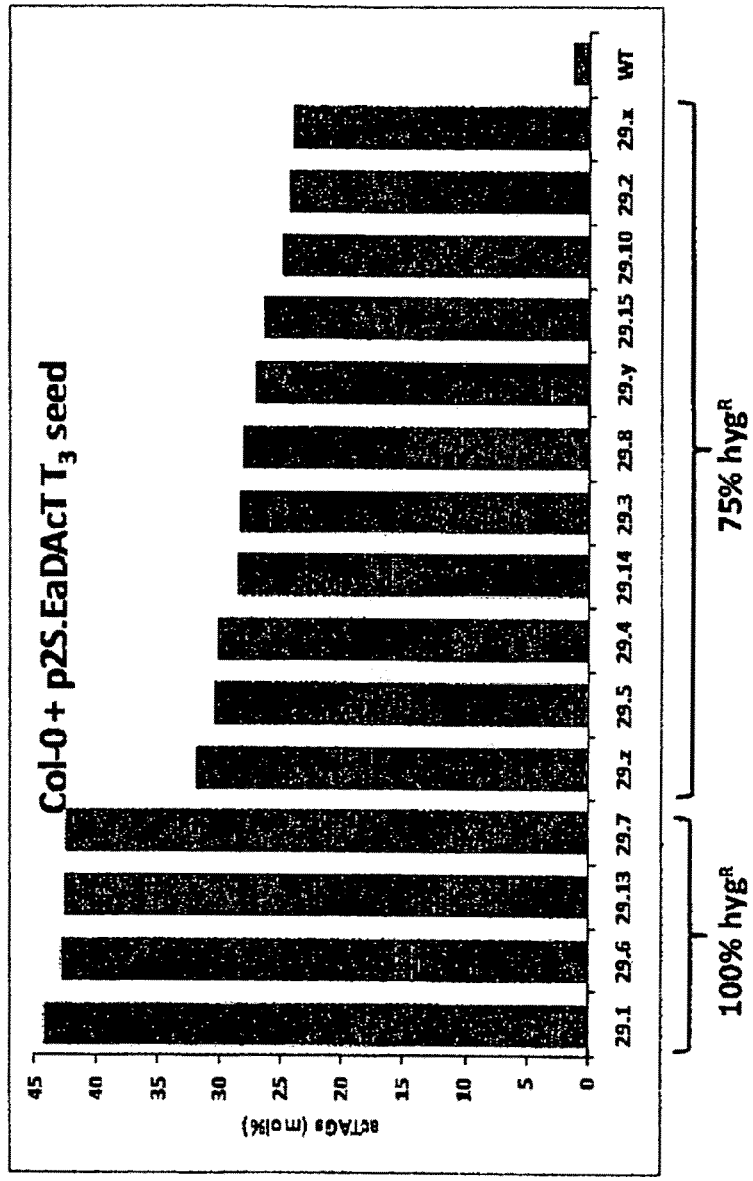

FIG. 13 shows exemplary accumulated ac-TAGs from a segregating population of transgenic *Arabidopsis* plants expressing EaDAcT. T3 seeds from Col-0 plants expressing EaDAcT were germinated in the presence of hygromycin. Neutral lipids were also extracted from these seeds and analyzed using ESI-MS to measure the accumulation of ac-TAGs.

Figure 14:
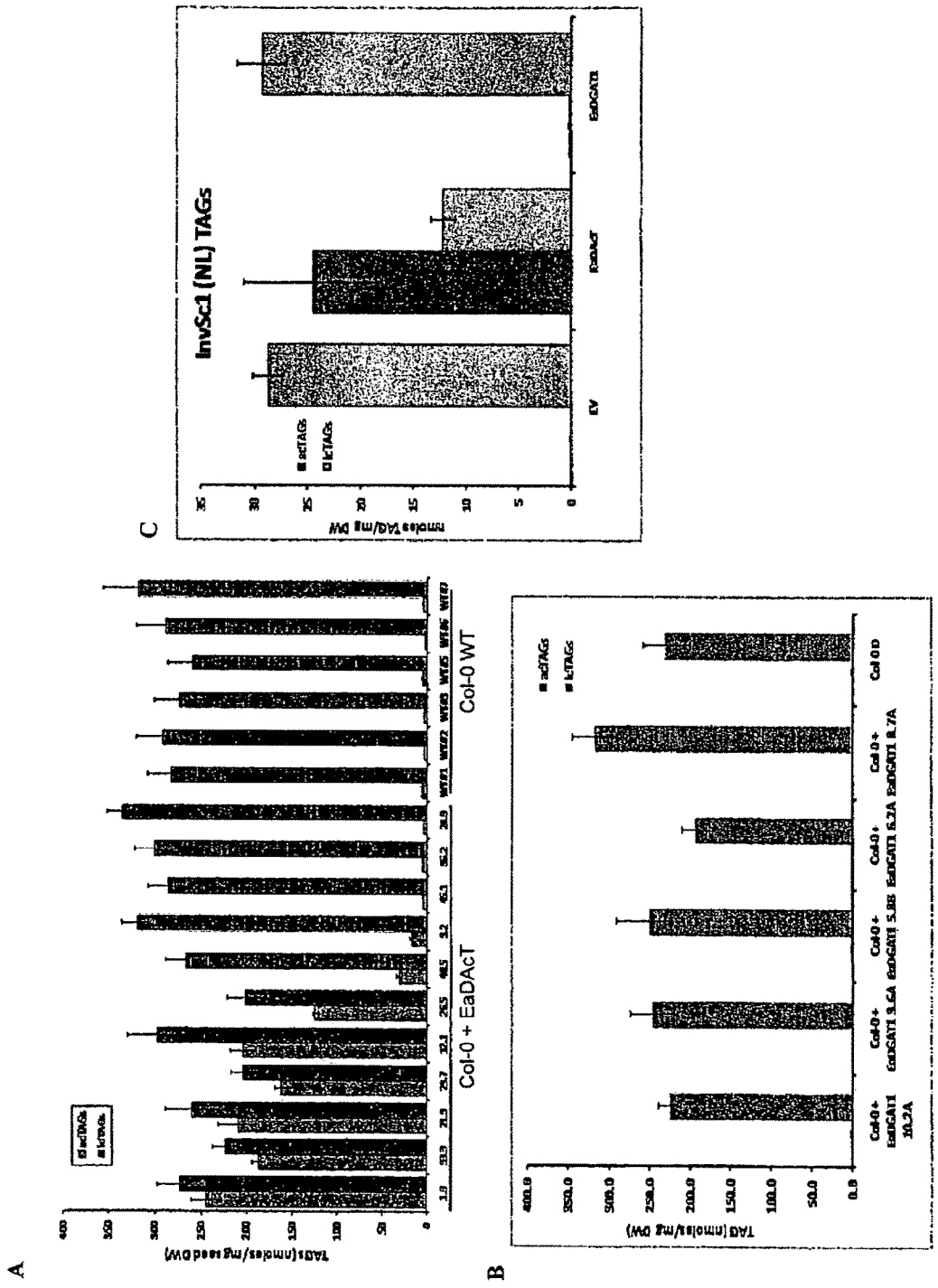

FIG. 14 shows exemplary comparisons of transgenic *Arabidopsis* plants and yeast cells expressing either heterologous EaDGAT1 or heterologous EaDAcT. (A) TAG composition of T3 pooled seed from heterologous EaDAcT expressing *Arabidopsis* plants showing varying levels of ac-TAG production in seeds. (B) TAG composition of T4 pooled seed from heterologous EaDGAT1 expressing *Arabidopsis* plants which lacked ac-TAG production as did the control Col-0 D *Arabidopsis* plant; and (C) Transgenic yeast cells (strain InvSc1) expressing heterologous EaDGAT1 vs. yeast cells heterologous EaDAcT showing ac-TAG production from the EaDAcT expressing yeast cells whereas the yeast cells that expressed EaDGAT1 and control yeast cells lacked ac-TAGs.

Figure 15:
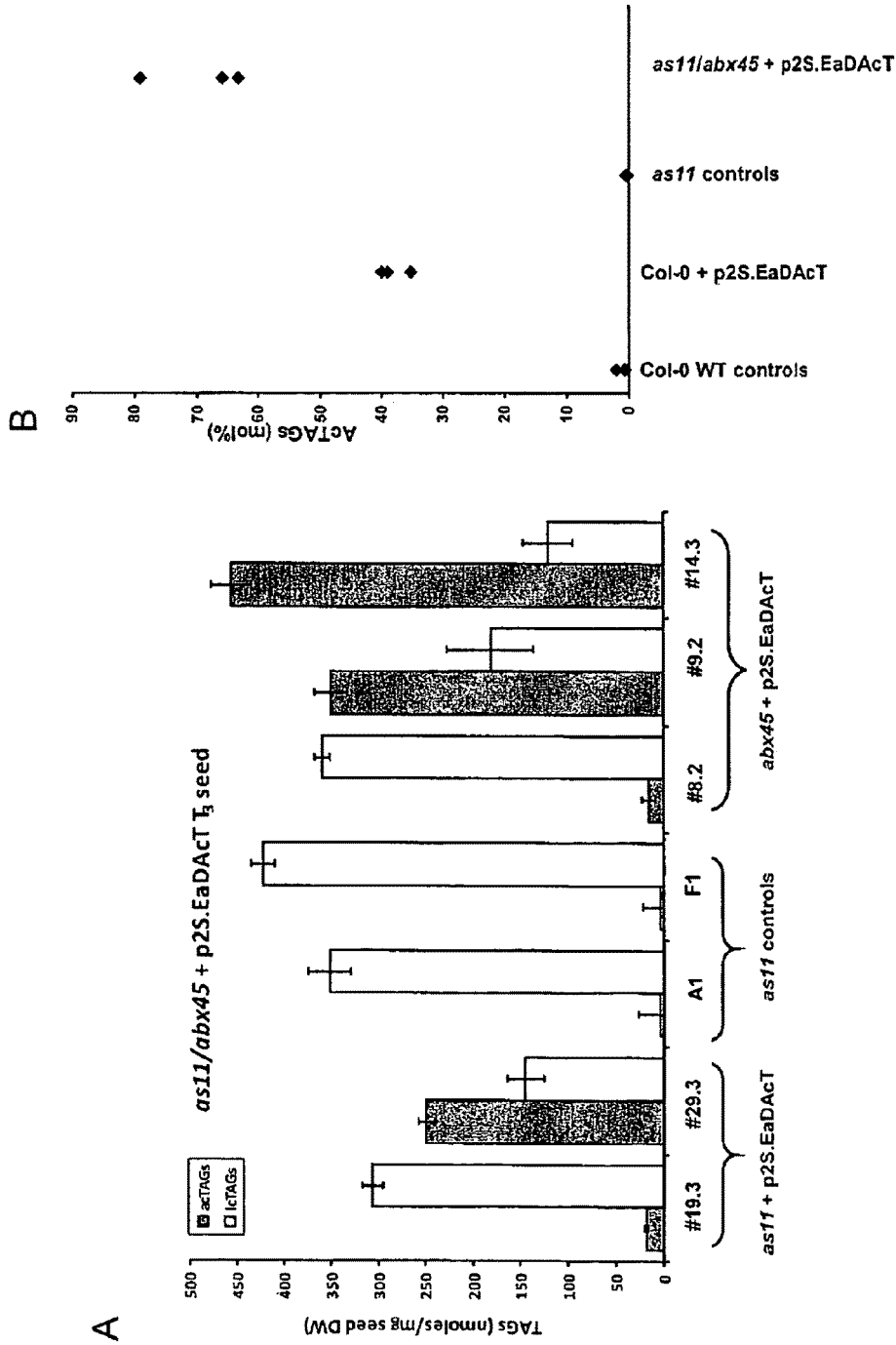

FIG. 15 shows exemplary *Arabidopsis* seeds from several different mutant backgrounds expressing EaDAcT and accumulating ac-TAGs. (A) TAG composition of T$_3$ seeds from *Arabidopsis* as11 or abx45 mutants (both containing mutations in AtDGAT1) expressing EaDAcT. Seeds were germinated on hygromycin to determine which seed lines were homozygous for the EaDAcT transgene; neutral lipids were then extracted from these seeds and analyzed using ESI-MS. Dark bars show ac-TAG amounts while clear bars show lcTAG amounts. (B) Scatter plot comparing the distribution of the ac-TAG composition of T$_3$ seed from Col-0 (WT) or as11 or abx45 mutant seeds expressing EaDAcT. Seed oil from Col-0 (WT) plants show an ac-TAG composition of approximately 35-44% when transfected with an EaDAcT gene of the present inventions. Surprisingly, seed oil from mutant as11 *Arabidopsis* plants showed a 60-80% ac-TAG composition, an increase to commercial production levels, when transfected with an EaDAcT gene of the present inventions. Also shown are ac-TAG compositions of control Col-0 WT and as11 seeds.

FIG. 16 shows exemplary *Arabidopsis* seeds with different mutant backgrounds expressing EaDAcT and accumulating ac-TAGs. (A) TAG composition of T$_3$ seeds from *Arabidopsis* fae1 mutants (containing a mutations in the fatty acid elongase gene 1) expressing EaDAcT. Neutral lipids were extracted from seeds of fae1 mutant plants homozygous for EaDAcT transgenes then analyzed using ESI-MS. Dark bars show ac-TAG amounts while light bars show lcTAG amounts. (B) Scatter plot comparing the distribution of the ac-TAG composition of T$_3$ seed from fae1 mutant seeds expressing EaDAcT or from fae1 control plants (plants not transfected with an EaDAcT construct of the present inventions). Surprisingly, seed oil from mutant fae1 *Arabidopsis* plants showed a 40-60% ac-TAG composition, when transfected with an EaDAcT gene of the present inventions.

FIG. 17 shows exemplary T2 *Camelina* seed expression of EaDAcT and accumulated ac-TAGs. A. Genotyping of *Camelina* plants expressing EaDAcT. Wildtype *Camelina* plants were transformed with the binary vector p2S.EaDAcT according to the method of (Lu and Kang (2008) Plant Cell Rep 27:273-278, herein incorporated by reference). T2 seed was selected on media containing 30 microM hygromycin. Hygromycin resistant plants were transferred to soil and allowed to grow to maturity. DNA was extracted from the leaves of these plants (lines #1, #19, #20), as well as from wildtype (WT) *Camelina* plants (plants WT e, WT f, and WT g). The presence of the EaDAcT transgene was confirmed using PCR with the gene specific primers 17392 (SEQ ID NO:12) and att_seq_3prime (aaattcgagctggtcacctc, SEQ ID NO: 16). PCR products were separated on a 1% agarose gel, stained with ethidium bromide and visualized under ultraviolet light. Lanes 1-3 show the presence of an approximately 1.4 kb PCR product, consistent with the size of the expected PCR product and identified plants containing the EaDAcT transgene. A band of approximately the same molecular weight was found in lane 7 (positive control), which contains the PCR product from a reaction using DNA from an *Arabidopsis* plant transformed with EaDAcT and shown to produce ac-TAGs of the present inventions. Lanes 4-6 showed a faint, non-specific band similar to a band found in the negative control that lacked an EaDAcT DNA-template (Lane 8). B. TAG composition of T2 pooled seed from heterologous EaDAcT expressing *Camelina* plants showing varying levels of ac-TAG production in seeds. C. Scatter plot showing the distribution of the ac-TAG composition of T2 seed from different transgenic *Camelina* lines expressing EaDAcT compared to *Camelina* wildtype (WT) seed. D. ESI-MS$^2$ analysis of neutral lipid extracts from the T2 seed of *Camelina* plants expressing EaDAcT. Shown are exemplary daughter fragment peaks from ac-TAGs with [M+NH4]$^+$ adducts with m/z values of 675 and 705. The daughter peaks with m/z values of 597.7 (Daughters of 675) and 627.9 (Daughters of 705) indicate loss of an ammonium acetate group from the [M+NH$_4$]$^+$ parent ion and which is consistent with a parent ac-TAG ion.

DETAILED DESCRIPTION OF THE INVENTION

The present invention relates to novel diacylglycerol acyltransferase genes and proteins, and methods of their use. In particular, the invention describes genes encoding proteins having diacylglycerol acetyltransferase activity, specifically for transferring an acetyl group to a diacylglycerol substrate to form acetyl-Triacylglycerols (ac-TAGs), for example, a 3-acetyl-1,2-diacyl-sn-glycerol. The present invention encompasses both native and recombinant wild-type forms of the transferase, as well as mutants and variant forms. The present invention also relates to methods of using novel diacylglycerol acyltransferase genes and proteins, including their expression in transgenic organisms at commercially viable levels, for increasing production of 3-acetyl-1,2-diacyl-sn-glycerols in plant oils and altering the composition of oils produced by microorganisms, such as yeast, by increasing ac-TAG production. Additionally, oils produced by methods of the present inventions comprising genes and proteins are contemplated for use as biodiesel fuel, in polymer production and as naturally produced food oils with reduced calories.

New types and sources of biofuels, predominantly biodiesel and bioethanol are actively sought as replacements for petroleum-based products and for use in conventional and emerging markets. Although several types of plant- and microbial-based feedstocks are under development to replace or blend with petroleum-based products, and while some feedstocks are now used for biodiesel and bioethanol production, these feedstocks have numerous undesirable physical characteristics. Further, these plant-based feedstocks have relatively high production costs, limitations in availability due to available acreage and agricultural resources necessary for cultivation, and compete with acreage necessary for growing food, 'Biodiesel' is registered as a fuel and fuel additive with the Environmental Protection Agency (EPA) in the United States (U.S.). Neat (100 percent) biodiesel was designated as an alternative fuel by the U.S. Department of Energy (DOE) and the U.S. Department of Transportation (DOT). Further in the U.S., each state may set standards, for example, in California, biodiesel must meet clean diesel standards established by the California Air Resources Board (CARB). Biodiesel may be blended according to specific set standards. For example, the Texas Commission on Environmental Quality (TCEQ) approved biodiesel blends comprised of 5 percent or less by volume biodiesel (B5) and 95 percent or more by volume diesel fuel. Biodiesel blends above B5 and up to B20 are also legal fuel in Texas, provided they are additive with TCEQ approved additives being sold or supplied for use in the Texas Low Emissions Diesel (TxLED) affected counties. Initially, vegetable oils were used directly as fuels for diesel engines but a number of problems were encountered during prolonged use, including coking, carbon deposits in the engines and gelling of lubricating oil as a result of contamination by the vegetable oils (Knothe et al., 1997, American Chemical Society Symposium Series 666, ACS, Washington, D.C., pp 172-208; Ma and Hanna, 1999, Bioresource Technol. 70:1-15, all of which are herein incorporated by reference).

Many of the problems encountered with the use of unprocessed natural vegetable oils were contemplated to arise from the high viscosity of vegetable oils (11-17 times that of diesel fuel), where poor atomization and volatility leads to incomplete combustion. Also, with increasing TAG unsaturation there was increasing TAG polymerization leading to gum formation. Specific functional properties of a vegetable oil are related to its acyl composition. For example, increasing unsaturation will give improved (i.e. lower) pour point, cloud point and kinematic viscosity. For instance, Knothe and Steidley (2005), herein incorporated by reference, report kinematic viscosity measurements for purified triolein, trilinolein and trilinolenin as 32.9, 24.9 and 17.3 cSt at 40° C. In contrast, increasing saturation (decreasing unsaturation) of these molecules improved (reduced) cetane number, lubricity and reduced tendency to form gums. Thus a balance must be obtained between opposing characteristics of fuel molecules in order to provide optimal fuel.

Medium chain-triacylglycerol oils were also considered for use as biodiesel (Goodrum and Eiteman, Bioresource Technology, 56(1):55-60 1996; Geller et al., 1999 Transactions of the ASAE 42(4): 859-862 and 2003 Transactions of the ASAE. 46(4):955-958, herein incorporated by reference). Although mc-TAGs have several desired properties over unsaturated lc-TAGs, a fundamental problem for both was the high melting point and pour points of such oils. For example, trioctanoin has a melting point of 8-10° C., while reported values for tridecanoin were 31-33° C.

Thus comparatively little further research was done on intact vegetable oils as substitutes for diesel fuel. However unlike vegetable oils, a large amount of information including specifications exist for traditional diesel fuels. For example, a typical diesel fuel (#2 grade) may have the following important properties, Table 1, as compared to the following properties of vegetable oils. For unsaturated vegetable oils an exemplary flash point is typically 240-290° C. Simple TAG species tripalmitin, triolein and trilinolein have CNs of 89, 45 and 32 respectively, while corresponding values for methyl palmitate, oleate and linoleate are 74-91, 53-80 and 38-46 (Murphy et al., 2004, herein incorporated by reference). For unsaturated vegetable oils CN is usually 38-42. For soybean oil the pour point was reported ranging from −12 to −25° C. and for canola oil the pour point is typically −21 to −31° C.

TABLE 1

A typical diesel fuel (# 2) may have these important properties.

| Property Name | Value |
| --- | --- |
| Flash point | >52° C., typically 60-80° C. |
| Cetane number (CN) | >40, typically 40-55 |
| Kinematic viscosity at 40° C. (KV) | 1.9-4.1 cSt |
| Pour point | −15 to −35° C. |
| Cloud point | −5 to −15° C. |

A specific functional property of a vegetable oil is, to a varying degree, dependent on its acyl composition. Increasing unsaturation will give improved (i.e. lower) pour point, cloud point and kinematic viscosity. For instance, Knothe and Steidley (2005) 84(9):1059-1065, herein incorporated by reference, report KV measurements for purified triolein, trilinolein and trilinolenin as 32.9, 24.9 and 17.3 cSt at 40° C. However, increasing saturation will give improved cetane number, lubricity and reduced tendency to form gums. Thus there is a balance between opposing trends. Medium chain-triacylglycerol oils have been considered for biodiesel (Goodrum and Eiteman, 1996; Geller et al., 1999 and 2003, herein incorporated by reference). Although they have several improved properties over unsaturated lc-TAG a fundamental problem is the high melting point of such oils. For example, trioctanoin has a melting point of 8-10° C., while tridecanoin the values are 31-33° C. Ac-TAG shows an exemplary viscosity in the same range as caprylic and capric acid rich vegetable oils (See, Tables 4 and 5), but since the long-chain fatty acids on these molecules are largely unsaturated, ac-TAG is contemplated to have more desirable, i.e. lower temperature properties. For example, trioctanoin has a melting point of 8-10° C., while for tridecanoin the values are 31-33° C. Although these measurements were merely contemplated for ac-TAG molecular species, when the inventors purified *Euonymus* ac-TAG seed oil, it was observed that the isolated oil remained liquid at and below freezing point (0° C.). In addition, the reduced number of unsaturated acyl groups in ac-TAG compared to a lc-TAG was contemplated to substantially reduce TAG polymerization and hence reduce coking and gum formation, problems caused by direct use of current vegetable oils.

Figure 1:
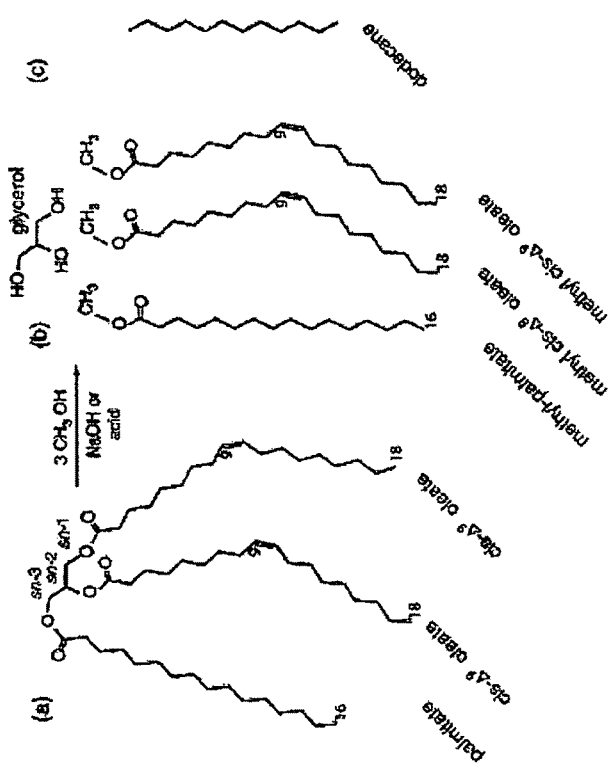
FIG. 1 shows exemplary triacylglycerol structures and biodiesel production via transesterification with methanol. Triacylglycerol (structure a) is converted to glycerol and fatty acid methyl esters (structures labeled b) by reaction with methanol in the presence of an acid or alkali catalyst (a to b). This figure also illustrates sn carbons (a), single chain fatty acids used in biofuel (structures labeled b) and the similarities in chemical structure to biofuel, for example, dodecane (c), a representative hydrocarbon found in conventional diesel.
Figure 3A:
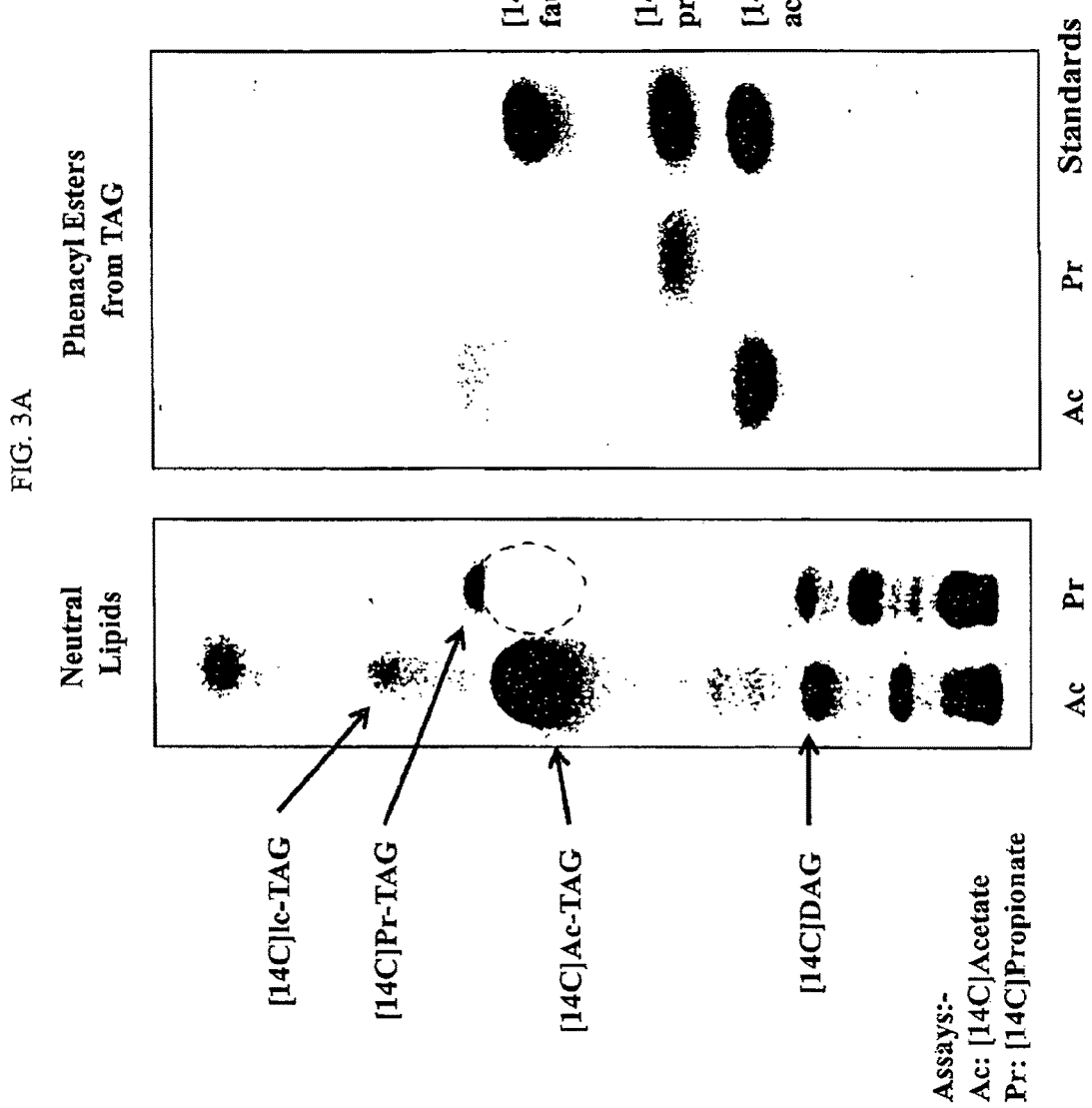
FIG. 3 shows exemplary [$^{14}$C] acetate and [$^{14}$C] propionate incorporation into lipid products from developing *Euonymus alatus* seeds. A: Left-hand panel shows examples of Thin layer chromatography (TLC) analyses of [$^{14}$C] neutral lipid products from incubation of developing *Euonymus alatus* seeds with labeled acetate ([$^{14}$C]acetate at 0.17 mM) and propionate ([$^{14}$C]propionate at 0.12 mM). Right-hand panel shows TLC analysis of phenacyl esters from products released by saponification of purified 3-acetyl-1,2-diacyl-sn-glycerol labeled from [$^{14}$C] acetate and purified 3-propionyl-1,2-diacyl-sn-glycerol labeled from [$^{14}$C] propionate. The right hand lane of this panel shows phenacyl ester standards. B: Concentration curves for acetate incorporation into [$^{14}$C acetyl] 3-acetyl-1,2-diacyl-sn-glycerol and propionate incorporation into [$^{14}$C propionyl] 3-propionyl-1,2-diacyl-sn-glycerol.

Despite the limitations of using vegetable oils directly for transportation fuel, several types of plants are grown specifically for harvesting (and isolating) their oils for subsequent modification prior to use as biofuels. Currently biodiesel is primarily manufactured from oils harvested from oil-seed crops such as Canola seed (a rapeseed), sunflower seed, and soybean seeds. Attempts to overcome these structural limitations primarily rely upon chemical modification that is primarily an in vitro transesterification of the acyl-groups to low MW monohydric alcohols such as methanol or ethanol so that they can be used directly as engine fuels. Thus unprocessed vegetable oils, seed derived oil, must be subjected to chemical modification (transesterification using alcohols such as methanol or ethanol) to make them suitable for use as biodiesel. Specifically, conventional oils from oil-crop species consist of greater than 95% and usually greater than 98% of long chain-triacylglycerols (TAGs). Despite certain similarities to petroleum products (see, FIG. 1), these TAGs are not used directly in engines as described herein. Further, use of current types of biodiesel fuels requires engine modification since biodiesel has different solvent properties and residual compounds (such as alcohol) that degrade natural rubber and seals that are not resistant to alcohol. Even with these drawbacks, use of biodiesel is increasing rapidly with an average annual growth rate of over 40% in recent years (For example, FIG. 3, in Renewables 2007 Global Status Report, Eric Martinot, REN21 (http://worldwideweb.worldwatch.org/node/5630, herein incorporated by reference).

Thus transesterified plant oils are substituted for conventional petroleum diesel for many types of engines. However for engine safety and optimal performance, this type of biodiesel is often blended with petroleum diesel prior to use. For example, when biodiesel has a viscosity level substantially higher than petroleum-based diesel it is blended with petroleum derived diesel, for lowering the viscosity to reduce engine damage. There were sources that suggested blending due to certain biodiesels (i.e. biodiesel fuels) that had much higher viscosity, or other traits. For another example, FarmandRanchGuide.com reports that ultra-low sulfur diesel affects lubrication in a different way than regular diesel. Therefore, some diesel fuel producers are blending biodiesel into regular diesel fuel in order to obtain superior lubricating characteristics. The National Biodiesel Board states that even a small blend of biodiesel will greatly enhance diesel fuel lubricity (worldwideweb.farmandranchguide.com/articles/2007/03/18/ag_news/production_ne
 ws/prod20.txt, worldwideweb.theautochannel.com/news/
  2008/06/20/090525.html, worldwideweb.biodiesel.org/
 pdf_files/fuelfactsheets/BDSpec.pdf).

In contrast to crop oil plants, a non-crop oil plant '*Euonymus alatus*,' named the 'burning bush' due to its distinctive red autumn foliage, was found growing in nature that produced atypical seed oils. In contrast to lc-TAG containing oils isolated from crop oil seed plants, seed oil from *Euonymus alatus* (Burning Bush) was found to contain almost exclusively ac-TAGs. Further, these oils contained acetyl-triacylglycerols in amounts orders of magnitude higher than found in oils isolated from any oil crop plant. Plant oils naturally rich in acetyl-TAGs are rare.

Further, the inventors' discovered that an ac-TAG having 2 long chain fatty acids instead of 3 (such as TAGS with 3 long chains produced in soybeans by soybean plants) has different physical properties than lc-TAGs. In particular, acetyl-TAGs were shown to have characteristics, such as viscosity, closer to trioctanoin, considered a medium-chain triglyceride, and transesterified lc-TAGs used as oil biodiesel. Thus, the inventors' contemplate using oils of the present inventions comprising ac-TAGs, including oils comprising ac-TAGs produced by nucleic acids and encoded proteins of the present inventions, for overcoming physical property limitations of using intact TAG feedstocks or transesterified feedstocks of TAGs.

The inventors contemplated that obtaining a gene encoding a protein for producing ac-TAGs would be useful for inducing ac-TAG production in host cells, host plants and host microorganisms. Further, they contemplated that the same gene would also be useful for inducing commercially viable amounts of ac-TAGs (substantially greater portions of ac-TAGs than found naturally in plant oils) in host cells, plants and microorganisms.

Although the occurrence and structural characterization of unusual sn-3-acetyl triacylglycerols in some seed oils was known for over forty years (Kleiman et al. (1967) Lipids 2:473-478, herein incorporated by reference), the biosynthesis of these novel glycerides was not investigated in depth until recently. These unusual triacylglycerols are found in varying amounts in a few plant species. Table II in the reference of Kleiman et al. (Lipids 2:473-478, 1967, herein incorporated by reference in its entirety) indicates a range of 13-98% ac-TAG across a range of plant species examined.

*Euonymus* species produce acetyl triacylglycerols, including sn-3-acetyl glycerides, making up to 98% of the total triacylglycerols in their seed oil. Thus, *Euonymus* was selected as a potential source of a diacylglycerol acyltransferase gene (DAcT) capable of inducing ac-TAG production in vivo.

In *Euonymus* sn-3-acetyl glycerides, the sn-1 and sn-2 positions are esterified with common long-chain fatty acids, predominantly palmitate, oleate and linoleate. Previous investigations included in vivo labeling of developing seeds with [$^{14}$C]acetate, and an assay of acetyltransferase activity in cell free extracts in *Euonymus alata* (Milcamps, et al., (2005) J. Biol. Chem. 280:5370-5377, herein incorporated by reference), which suggested a biosynthetic gene would encode an enzyme catalyzing a 1,2-diacyl-sn-glycerol:acetyl-CoA acetyltransferase. The first gene isolated from *Euonymus alatus*, i.e. from developing seeds, associated with forming TAGs, was identified as a member of the DGAT1 family, a sub-group of the MBOAT super-family of acyltransferases (Milcamps, 2005, U.S. Pat. Nos. 7,122,367 and 7,429,473, all of which are herein incorporated by reference). Named EaDAGAT1 and EaDGAT1, it was shown to have the potential to produce acetyl glycerides (Milcamps, et al., 2005, herein incorporated by reference). That is, EaDGAT1 had activity primarily directed towards long chain fatty acids (as acyl-CoAs) and also showed a significant activity with acetyl-CoA substrates. Thus it was established as a bona fide acyltransferase and was further contemplated to be responsible for high ac-TAG production. Surprisingly, subsequent experiments, including transfection experiments, showed that it did not induce large amounts of the desired short chain ac-TAGs production, in fact if any ac-TAG products were measurable; they were in mere trace amounts. Expression in host yeast cells further demonstrated that EaDGAT1 was not capable of inducing large amounts of ac-TAG production. As with previous attempts to modify TAGs, the heterologous expression of EaDGAT1 failed to yield the high levels of acetyl TAGs necessary for use in commercial products (Durrett, et al., The Plant Journal (2008) 54, 593-607, herein incorporated by reference in its entirety). Further discovery and development of compositions and methods comprising the second diacylglycerol acyltransferase candidate, EaDGAT2, a member of the DGAT2 family, were also found to lack ac-TAG production Durrett, et al., The Plant Journal (2008) 54, 593-607, herein incorporated by reference in its entirety).

Subsequently a third gene was found, i.e. EaDAcT as described herein, that in contrast to previously isolated gene candidates, actually demonstrated the capability to produce ac-TAGs in host cells, both in vitro and in vivo. Discovery, identification and cloning of this EaDAcT gene during the process of developing the present inventions involved the unexpected necessity of using gene transcript profiling. This process was largely contingent on the availability of large-scale parallel sequencing technology and the recognition that the synthesis of different types of oils, including ac-TAGs was different between tissues found in *Euonymus alatus* seed. Specifically, there were differences between the oils produced by different parts of the seed and plant, i.e. the seed embryo, the seed endosperm, and plant aril. The seed embryo produced a mixture of short and long-chain acyl-glycerols in the ratio of approximately 3:1, respectively. Conversely, the seed endosperm was found to produce exclusively acetyl-triacylglycerols (ac-TAGs). In contrast to the aril (a specialized outgrowth from the funiculus, the attachment point of the seed to the plant) produced exclusively conventional long-chain TAGs. These observations by the inventors led to using an mRNA profiling technique for obtaining genes encoding proteins (expressed genes) associated with ac-TAG production. Specifically, mRNA from the three different tissues, embryo, endosperm, and aril, was extracted, copied into cDNA, then sequenced and analyzed for differential expression (for example, genes expressed at levels much higher in endosperm but much less than in aril or embryo) for obtaining putative acyl transferase genes specifically expressed in each of the three tissues. As described herein, extensive analysis of genes highly expressed in endosperm resulted in the identification of an acyl transferase gene that was found to have a preference for diacylglycerol substrates, and subsequently named diacylglycerol acetyltransferase, (DAcT). An exemplary DAcT gene of the present invention was synthesized in vitro and used as a transgene for making transgenic plants whose seeds contained amounts of ac-TAGs (mol %) that were higher than plants not expressing a DAcT gene of the present inventions.

During the development of the present inventions, the inventors also discovered that despite the high levels of ac-TAGs in *E. alatus* seeds, in particular in the endosperm region, *E. alatus* is unsuitable for use in providing seeds and oils for use as biofuels or food oils. In particular, *E. alatus* is unsuitable for large-scale low cost production of seed oils unlike the seed oils of the present inventions. Specifically, *E. alatus* is undomesticated from a crop perspective, such that it lacks desired agronomic traits. Limitations that would need to be overcome for domestic use include cultivation as a perennial crop and shrub architecture. Even if these cultivation problems were overcome, then seed harvesting would require novel specialized mechanical harvesting techniques for harvesting its small seeds. Even further, if the seeds could be harvested on a large scale, then co-extraction products from *E. alatus* seeds contain undesirable extraction products in contrast to seeds of the present inventions. Undesirable extraction products from *E. alatus* seeds include toxic compounds and compounds that would be problematic for using the extracted oil as a fuel, such as bilyrubin, polymers that increase viscosity of an oil, etc.

Thus the inventors contemplated the use of DAcT genes and DAcT proteins of the present inventions in combination with plants whose seeds do not contain undesirable extraction products for use as biofuels. Further, the inventors contemplated the use of DAcT genes and proteins of the present inventions for use making oils in plants whose seeds and/or oils are edible (for example, seeds that do not contain human or animal toxins or compounds with an unpleasant taste, etc).

One member of the Brassicaceae family is *Arabidopsis thaliana*, an exemplary host plant that ordinarily does not produce ac-TAGs. Thus *Arabidopsis thaliana* plants were chosen as an exemplary member of the Brassicaceae family and oil-seed crop plants in general for determining whether an EaDAcT gene of the present inventions was capable of being transgenically expressed in Brassicaceae plants in a manner capable of providing a polypeptide for inducing ac-TAG production in plant seed oils. Further, *Arabidopsis thaliana* plants were further used as model plants for increasing the portion of oil containing ac-TAGs.

The inventors successfully demonstrated herein that an isolated and transfected DAcT protein (enzyme) of the present inventions induced large amounts of ac-TAG production in *Arabidopsis* plant seeds. *Arabidopsis* is an exemplary member of the Brassicea plant family, one group of plants contemplated for use with DAcT genes and proteins of the present inventions. Successful induction of ac-TAG production in this Brassicea family plant member supports the success of transfecting EaDAcT into other Brassicaceae plants. In particular, several cultivated oil-seed crop plants contemplated for use (as biofuels and/or edible oils) with the genes and proteins of the present inventions are members of Brassicaceae (Cruciferae), also known as the mustard family and cabbage plant family. Further, the inventors contemplate isolating plant oils, including those described herein, from seeds of mustard and cabbage plants such as rapeseed (for example, *Brassica* sp., such as *Brassica napus*), *Camelina* (for example, *Camelina* sp. such as *Camelina sativa*), mustard (for example, *Brassica* sp., such as *Brassica* alba, (for example, *Crambe* sp. such as *Crambe abyssinica*, also called sea cole, sea kale, Abyssinian mustard, Abyssinian kale, colewart, datran, etc.), field cabbage seed (*Brassica* sp. Such as campestris, var. *oleifera* (for obtaining Colaz oil), *Brassica* campestris, var. *chinensis*—Bok choi, pak choi, pak choy, pok choi, etc.) and the like.

Further, due to the success of inducing oils comprising ac-TAGs using an EaDAcT nucleic acid of the present inventions, the inventors contemplate the use of additional types of plants, including algae, for producing novel oils comprising ac-TAGs. Thus, the inventors contemplate inserting (transferring; transfecting) a DAcT gene of the present inventions into conventional oil-seed crop plants, including but not limited to an oil-seed crop of the Brassicea family.

Additionally, the inventors contemplate a system for large-scale production of oil comprising ac-TAGs for economically viable production. Thus, in some embodiments, plants currently grown for producing biofuel, oils, and food oil production are contemplated for use in combination with a heterologous ac-TAG producing gene of the present inventions, such as soybean plants, sunflower plants, rapeseed plants, flax plants, safflower plants, *Jatropha* plants, palm plants, *Camelina* plants, crambe plants, etc., and including plant families such as mustard family plants which include *Arabidopsis* plants (see, Examples), *Camelina* plants, and the like. Further, oil produced by transgenic plants and fungi, i.e. yeast, of the present inventions, was evaluated and determined that the polypeptide encoded by the DAcT of the present inventions was capable of inducing ac-TAGs at levels necessary for commercial use.

Initially, the inventors discovered that DAcT genes and DAcT proteins of the present inventions were capable of inducing increases of ac-TAG production in *Arabidopsis* plant seeds harvested from progeny of transgenic plants (wild-type background), at levels approximately 35-44% (mol %) over negligible levels in nontransgenic wild-type plants. Even more surprisingly, oil isolated from seeds produced by mutant as11 and abx45 *Arabidopsis* plants transfected with an EaDAcT gene of the present inventions showed ac-TAG levels of 60-80% (mol %), over negligible levels in control as11 plants, at commercial level ac-TAG production in seeds.

Specifically, EaDAcT was expressed under the control of a seed specific promoter, S2 (see above) in wild-type (Col-0) *Arabidopsis* plants and two *Arabidopsis* mutant lines: as11 and abx45. Both of the mutant plant lines contained a mutation in the *Arabidopsis* DGAT1 gene (At2g19450) responsible for the bulk of TAG synthesis in *Arabidopsis* seeds (Zhang et al. (2009) Plant Cell 21:3885, herein incorporated by reference). as11 plants contained a mutation that introduces an 81 base pair insertion into the AtDGAT1 transcript (Zou et al. (1999) Plant J. 19:645, herein incorporated by reference); while abx45 contained a base pair deletion leading to a shift in the reading frame of the AtDGAT1 transcripts (Routaboul, et al. (1999) Plant Physiol Biochem 37:831, herein incorporated by reference). An *Arabidopsis* plant containing either one of these mutations has an approximate 40% reduction in lc-TAG oil content in its seeds. Lipids were extracted from the seeds of transgenic plants and TAG content analyzed using ESI-MS, see Examples.

Figure 12:
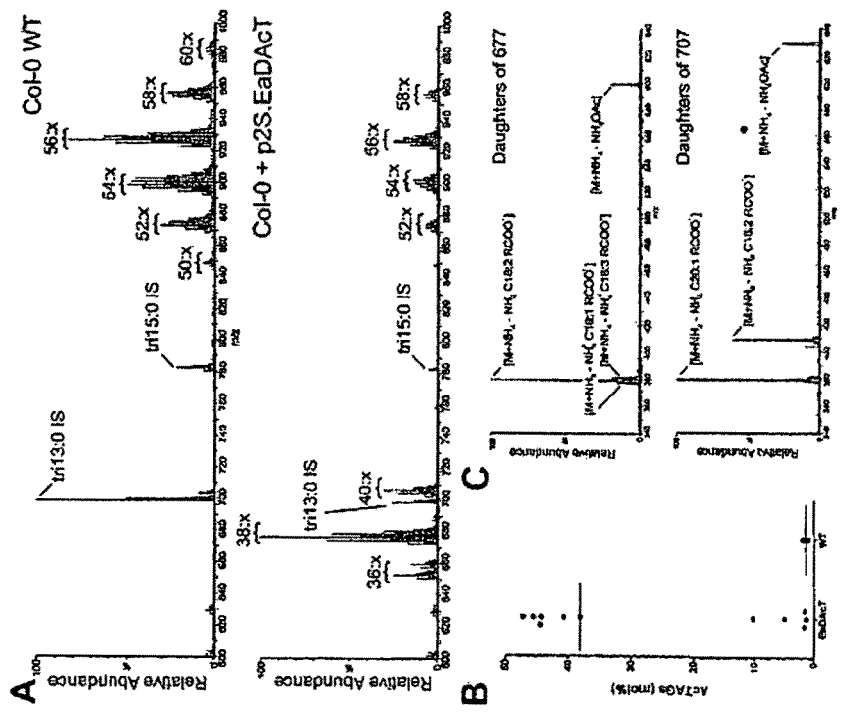
FIG. 12 shows exemplary *Arabidopsis* seeds expression of EaDAcT and accumulated ac-TAGs. (A) Positive-ion ESI mass spectra of neutral lipid extracts from Col-0 wildtype seed or T3 seed from Col-0 plants expressing EaDAcT. Peaks correspond to m/z values of the [M+NH4]$^+$ adduct. Tritridecanoin (tri13:0 IS) and tripentadecanoin (tri15:0 IS) were added as internal standards. The number of acyl carbons in each series of TAG molecules is indicated. (B) Scatter plot showing the distribution of the ac-TAG composition of T3 seed from different transgenic Col-0 plant lines expressing EaDAcT or of Col-0 wildtype seed. Horizontal lines represent the median value for each sample group. (C) ESI-MS2 analysis of neutral lipid extracts from the T3 seed of Col-0 plants expressing EaDAcT. Shown are exemplary daughter fragment peaks from ac-TAGs with [M+NH4]$^+$ adducts with m/z values of 677 and 707.

The molar percentage amounts of ac-TAGs in oils isolated from plants of the present inventions were even higher than the 44 mol % achieved when EaDAcT was expressed in a Col-0 wild type background (FIGS. 12B and 15B). This demonstrated that expressing EaDAcT in combination with reducing the activity of endogenous TAG producing enzymes (in this case through mutation of the *Arabidopsis* DGAT1 gene) was used to create transgenic plants where the majority of the seed oil comprised ac-TAGs. Thus, in one embodiment, a plant comprising an EaDAcT gene of the present inventions further comprises a mutant DGAT1 gene, wherein said mutation reduces lc-TAG production. In other embodiments, the inventors contemplate inserting a DAcT gene of the present inventions into an oil crop plant comprising at least mutation resulting in the reduction of lc-TAGs compared to the wild-type plant. In one embodiment, the inventions provide a plant comprising an EaDAcT gene of the present inventions whose seed contains Ac-TAGs greater than 35% (mol %) of total TAGs. In one embodiment, the inventions provide a plant comprising an EaDAcT gene of the present inventions whose seed contains ac-TAGs greater than 40% of total TAGs. In one embodiment, the inventions provide a plant comprising an EaDAcT gene of the present inventions whose seed contains ac-TAGs up to 44% of total TAGs. In one embodiment, the inventions provide a plant comprising an EaDAcT gene of the present inventions whose seed contains ac-TAGs greater than 50% of total TAGs. In one embodiment, the inventions provide a plant comprising an EaDAcT gene of the present inventions whose seed contains ac-TAGs greater than 60% of total TAGs. In one embodiment, the inventions provide a plant comprising an EaDAcT gene of the present inventions whose seed contains ac-TAGs greater than 70% of total TAGs. In one embodiment, the inventions provide a plant comprising an EaDAcT gene of the present inventions whose seed contains ac-TAGs greater than 80% of total TAGs. In one embodiment, the inventions provide a plant comprising an EaDAcT gene of the present inventions whose seed contains ac-TAGs up to 99% of total TAGs.

Figure 9:
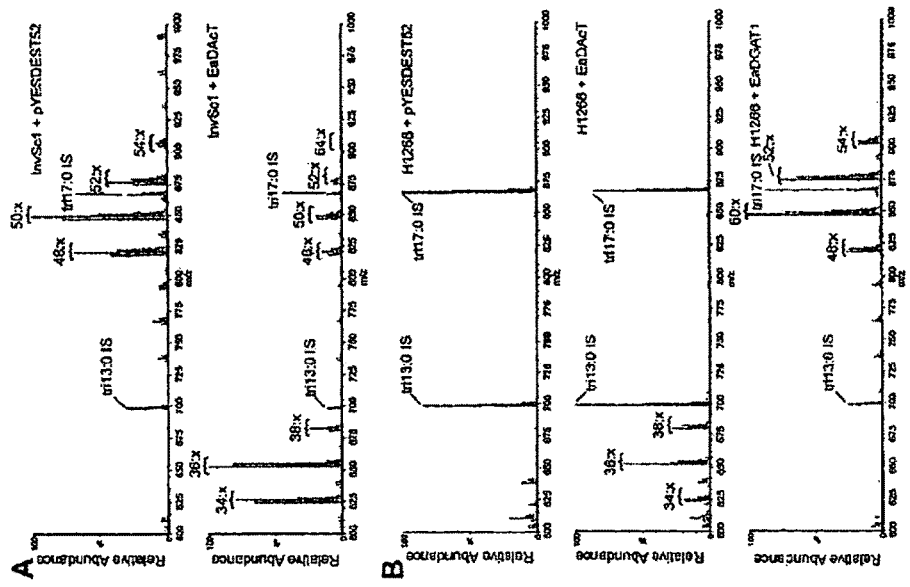
FIG. 9 shows exemplary yeast expression of EaDAcT associated with accumulated ac-TAGs but not lc-TAGs. Positive-ion ESI mass spectra of neutral lipid extracts from yeast strains InvSc1 (A) or H1266 (B) expressing the empty vector pYES-DEST52, EaDAcT, or EaDGAT1. Peaks correspond to m/z values of the [M+NH4]+ adduct. Tritridecanoin (tri13:0 IS) and triheptadecanoin (tri17:0 IS) were added as internal standards. The number of acyl carbons in each series of TAG molecules is indicated.

Additionally, recombinant expression of EaDAcT in host yeast cells demonstrated successful ac-TAG production that was not found in nontransfected wild-type yeast (normal yeast) (for example, see, FIG. 9). Further, recombinant expression of EaDAcT in host yeast cells demonstrated successful ac-TAG production at commercially viable levels that was not found in nontransfected wild-type yeast (normal yeast) (for example, see, FIG. 9). The ac-TAG composition of oil from a wild type yeast (InvSc1) expressing EaDAcT was 47.3% (FIG. 9A) whereas the ac-TAG composition of oil from the TAG deficient yeast H1266 expressing EaDAcT was 100% (FIG. 9B). In one embodiment, the inventions provide a microorganism containing oil which is at least 20% ac-TAG (mol %). In one embodiment, the inventions provide a microorganism containing oil which is at least 25% ac-TAG (mol %). In one embodiment, the inventions provide a microorganism containing oil which is at least 30% ac-TAG (mol %). In one embodiment, the inventions provide a microorganism containing oil which is at least 40% ac-TAG (mol %). In one embodiment, the inventions provide a microorganism containing oil which is at least 47% ac-TAG (mol %). In one embodiment, the inventions provide a microorganism containing oil which is at least 60% AcTAG (mol %). In one embodiment, the inventions provide microorganism-containing oil which is at least 70% ac-TAG (mol %). In one embodiment, the inventions provide a microorganism containing oil which is at least 80% ac-TAG (mol %). In one embodiment, the inventions provide a microorganism containing oil which is at least 90% ac-TAG (mol %). In one embodiment, the inventions provide a microorganism containing oil which is up to 100% ac-TAG (mol %).

Thus, in one embodiment, a microorganism comprising a EaDAcT gene of the present inventions further comprises a mutant with inactivated TAG-synthesis genes, such as DGAT2 or PDAT or DGAT1, wherein said mutation reduces lc-TAG production. In a preferred embodiment, said microorganism is a yeast. In one embodiment, said yeast has mutations in a TAG-synthesis gene selected from the group consisting DGAT1 (such as a yeast ACAT-like ARE1 or ARE2 gene), in a preferred embodiment, said yeast has mutations in a TAG-synthesis gene selected from the group consisting of a DGAT2 and PDAT.

Even further, embodiments comprising compositions and methods of the present invention further relates to increasing the portion of ac-TAGS, such as 3-acetyl-1,2-diacyl-sn-glycerols, in plant oils isolated from plant parts, such as seeds, mesocarp, pericarp, stems, leaves, cells, including parts of algae, such as blades, intralamellar areas, surface areas, and oils released into culture media or enclosed systems, such as algal growth chambers and the like.

The present invention also relates to the efficient production of acetyl-Triacylglyeerols (ac-TAGs) by biological organisms (bio-production). In one embodiment, the ac-TAGs are for use in biofuels, in particular biodiesel as a fuel for engines. One exemplary use for a heterologous ac-TAG producing gene and encoded protein of the present inventions includes transforming a *Jatropha* plant for producing ac-TAGs for use in combination with traditional jet fuels and other types of biofuels. *Jatropha* plants encompass a large grouping of mainly nonedible succulent plants, shrubs and trees that grow in nutrient poor soil. Specifically, *Jatropha curcas* (in addition to palm plants) are cultivated in plantations as feedstocks for transesterification to produce biodiesel. In addition to bio-diesel production, by-products of '*Jatropha Curcas*' trans-esterification process are used to make a wide range of products including paper, energy pellets, soap, cosmetics, toothpaste, embalming fluid, pipe joint cement, cough medicine and as a moistening agent in tobacco. Recently, transesterified *Jatropha* oil was successfully used in jet engine airplane flight tests. These tests used a 50/50 mixture of algae/modified *Jatropha* oil and Jet A fuel.

One exemplary use for a heterologous ac-TAG producing gene and encoded protein of the present inventions includes transforming a *Camelina* plant for producing ac-TAGs for use in combination with traditional jet fuels and other types of biofuels, (see, http://livingclean.com/alternativeenergy/bio-fuel-substitute-jet-fuel/). For example, a jet fuel may be a combination of an ac-TAG oil of the present inventions isolated from a seed or plant part expressing a heterologous DAcT gene encoding a polypeptide for inducing ac-TAG production of the present inventions in combination with other types of biofuels, an ac-TAG oil of the present inventions in combination with traditional fuels and combinations thereof.

An exemplary method for *Camelina* seed expression of EaDAcT for producing novel *Camelina* seed oils is described as follows. Briefly, EaDAcT was ligated into the plant binary expression vector p2S. GATEWAY, which was constructed by ligating 1 kb of genomic sequence upstream of the *Arabidopsis* 2S seed storage protein gene (At4g27160) and the GATEWAY att recombination cassette from pMDC32 (Curtis and Grossniklaus (2003) Plant Physiol 133:462-469, herein incorporated by reference) into the multiple cloning site of pCAMBIA1390 (world.wide.web.cambia.org) Sequence at GenBank ACCESSION AF234307, herein incorporated by reference). This construct, p2S, EaDAcT, was then introduced into *Agrobacterium tumefaciens* strain C58C1 and transformed into wild type *Camelina* plants using a floral dip method with a vacuum infiltration step as described by Lu and Kang (2008) Plant Cell Rep 27:273-278, herein incorporated by reference.

*Agrobacterium tumefaciens* strain C58C1 was grown at 28° C. in YEP medium, supplemented with the appropriate antibiotics: rifampicine 50 mg/ml, streptomycin 25 mg/ml or gentamycin at a few mg/ml. The constructs (p2S.EaDAcT), i.e. vectors comprising a EaDAcT gene (such as SEQ ID NO. 01), were used when transferred into *A. tumefasciens* strain C58C1 via electroporation. The presence or absence of the EaDAcT sequence was verified with whole cell PCR, using EaDAcT specific primers.

Six-week old *Camelina* plants were transformed via the floral dip method with the *A. tumefasciens* strains, comprising (carrying) a promoter sequence p2S and EaDAcT. The plants were grown to maturity. Seeds (T1) were collected and transgenic plants (T1) were selected by germination on MS media containing 30-μg/ml hygromycin. The surviving hygromycin resistant plants were allowed to grow to maturity, set seed and desiccate. Mature *Camelina* plant T2 seeds were collected from the siliques of 8-12 week old plants, grown in the growth chambers (16 h light period, 22° C., 80 to 100 μE light intensity). Neutral lipids were quantitatively extracted and analyzed using ESI-MS as described in Example I.

FIG. 17 shows exemplary T2 *Camelina* seed expression of EaDAcT and percentage and analysis of accumulated ac-TAGs. T2 seedlings were selected by growing on media containing 30 microM hygromycin which did not support the germination of nontransgenic seeds. Hygromycin resistant plants grown from hygromycin medium were transferred to soil and allowed to grow to maturity. DNA was extracted from the leaves of some of these plants (lines #1, #19, #20), as well as from some wildtype *Camelina* plants (plants WT e, WT f, and WT g) shown in FIG. 17A. The presence of the EaDAcT transgene was confirmed using PCR DNA amplification from genomic DNA with the gene specific primers 17392_F (SEQ ID NO:12) and att_seq_3prime (aaattcgagctggtcacctc, SEQ ID NO: 16), shown in FIG. 17A. PCR DNA products were separated on a 1% agarose gel, stained with ethidium bromide and visualized under ultraviolet light. Lanes 1-3, shown in FIG. 17A, showed the presence of an approximately 1.4 kb PCR product, consistent with the size of the expected PCR product which identified plants containing the EaDAcT transgene. A band of approximately the same molecular weight was found in lane 7 (positive control), which contained the PCR product from a reaction using DNA from an *Arabidopsis* plant transformed with EaDAcT and shown to produce ac-TAGs of the present inventions. Lanes 4-6, of FIG. 17A, showed a faint, non-specific band similar to a band found in the negative control that lacked a EaDAcT DNA-template (Lane 8, FIG. 17A).

Lipids were extracted from the seeds of transgenic plants and TAG content analyzed using ESI-MS. Isolated seed oils provided novel oils comprising ac-TAGs produced by transgenic plants that were not present in oils isolated from non-transgenic plants. FIG. 17B shows an exemplary TAG composition of T2 pooled seed from heterologous EaDAcT expressing *Camelina* plants showing varying levels of ac-TAG production in seeds. FIG. 17C shows an exemplary scatter plot which demonstrated the distribution of the ac-TAG composition of T2 seed between different transgenic *Camelina* plant lines that expressed EaDAcT as compared to *Camelina* plant wildtype seed. FIG. 17D shows an exemplary ESI-MS$^2$ analysis of neutral lipid extracts from the T2 seed of *Camelina* plants that expressed EaDAcT. Shown are exemplary analyses of fragment ions derived from the molecular ion that indicate the presence of ac-TAGs in the isolated seed oils. Specifically, a parent molecular ion peak (the $[M+NH_4]^+$ adduct) at m/z=675 was fragmented to produce a daughter ion at m/z value of 597.7; FIG. 17D, upper spectrum. The loss of 78 atomic mass units corresponds to the loss of ammonium acetate. By contrast, the loss of ammonium linoleate (18:2) or ammonium linolenate (18:3) from this molecular ion produces the peaks at m/z=377.7 and 379.5 respectively. Thus the molecular ion at m/z=675 corresponds to the ammonium adduct of acetyl-linoleoyl-linolenoyl-glycerol. In a second example the parent molecular ion peak (the $[M+NH_4]^+$ adduct) at m/z=705 was fragmented and this produced a daughter ion at m/z value of 627.9; FIG. 17D, lower spectrum. Again, the loss of 78 atomic mass units corresponds to the loss of ammonium acetate from the $[M+NH_4]^+$ parent ion, which is consistent with a parent ac-TAG ion.

Therefore, *Camelina* plants that expressed an EaDAcT gene of the present inventions gained the capability to make ac-TAGs in their seeds. *Camelina* plants with exemplary heterozygous gene expression ranges from 1-20% ac-TAGs in seed oil, see, FIG. 17C. The inventors contemplated increasing levels to commercial levels in a variety of ways, including but not limited to plants comprising homozygous alleles, additional promoters, i.e. a promoter from a *Camelina* species, etc.

Thus in one embodiment, the inventors contemplate silencing (i.e. lowering) expression of lc-TAGs in host plants, by identifying plants with natural mutations, plants with induced mutations, and using plants or engineered mutant plants with lowered lc-TAG production as host cells for transfection or introgression of an EaDAcT gene of the present inventions. The inventors further contemplated the use of such plants and plant cells for producing seeds with high amounts of ac-TAGs, either total yield per plant, i.e. total yield for acre or fraction of ac-TAG in the oil. Even further, the inventors contemplate the isolation of ac-TAGs from these seeds for use in biofuel or as novel oils for commercial uses. Additionally, the inventors contemplate the use of parental, T1, transgenic plants expressing EaDAcT of the present inventions for use in breeding in order to develop commercially and/or agronomically viable cultivars and lines.

In particular, the present invention provides systems and methods for producing ac-TAGs with transgenic organisms expressing the diacylglycerol acyltransferase (DAcT) gene derived from *Euonymus alatus* (EaDAcT). In one embodiment a heterologous DAcT gene is expressed in transgenic yeast cells, transgenic oil-seed crop plants and transgenic algae for providing novel oil. In a further embodiment, the oil is for use in providing biofuels. In other embodiments, DAcT is expressed in transgenic yeast cells, transgenic oil-seed crop plants, transgenic algae, and transgenic fungi, where the oil recovered is used for providing novel TAG monomers for use in polymerization reactions, and even further embodiments for providing new types of polymers with commercial properties.

In another embodiment, the inventors contemplate a new polymer substrate. In particular, substitution of acetyl-TAGs for conventional TAGs in polymer production methods comprising polymer substrates will yield novel polymers with properties of conventional polymers. In another contemplated embodiment, ac-TAGs would provide relatively more linear polymers than conventional TAGs which would provide benefits to economic considerations of commercial polymer production. In a further embodiment, these novel TAG monomers would yield novel polymers with novel properties for commercial uses.

In yet another embodiments, organisms such as fungus, (for example, yeast) and plants producing the ac-TAGs of the present inventions are contemplated for use in methods for both edible oils and industrial oils, such that methods of ac-TAG oil production comprising one type of engineered organism expressing a nucleotide, protein, and oil of the present inventions would be used in the food industry and oleochemical industry and biofuels industry, as needed. Thus, for example, plant acreage designated for ac-TAG oil production using methods and compositions of the present inventions would produce am oil comprising ac-TAGs whose use would be designated after production for use in specific industries, such as the food industry, oleochemical industry, biofuels industry, etc. This contemplated post-production designation of use is in contrast to current practices of pre-production designated use currently necessary since each type of crop plant produces a limited type of oil for a narrow range of use. Thus, pre-production designation of acreage is necessary for meeting a particular type of oil need prior to seeding (planting) plants. Thus, unlike this current agriculture practice of designating acreage use, and thus the type of plants to cultivate, prior to planting, the use of plants of the present inventions would provide flexibility in oil production by eliminating pre planting acreage designation. Plants of the present inventions provide this flexibility since the oils comprising ac-TAGs of the present inventions would provide an oil feedstock capable of being used in a larger range of industries.

Additional contemplated benefits of using genes and proteins of novel diacylglycerol acyltransferase (DAcT) from *E. alatus* and other plants for producing novel oils includes but is not limited to the following examples. Novel plants oils with large amounts of ac-TAGs would provide new biofuels, such that acetyl-triacylglycerols in a new oil-type would be directly extractable from oil-seed crops and provide improved properties for use in fuels. In preferred embodiments, these new oils would need substantially less processing than current biodiesel feedstock oils. For example, since these molecules have two instead of three long chain fatty acids, in one embodiment, esterification reaction times in methods comprising these oils for producing biodiesel would be significantly less than for TAG transesterification of three long chains. In a preferred embodiment, these new oils comprising ac-TAGs would be used directly as fuel without esterification. In a further embodiment, oils comprising ac-TAGS of the present invention would be cold pressed (extracted) out of host cells (i.e. seeds, etc.) filtered than used directly as fuel by pouring the filtrate directly into a gas tank, oven fuel tank, fuel tank, or for direct use as a lubricant. In another embodiment, oils of the present inventions are blended with conventional biodiesel, such that methyl or ethyl esters would be blended with acetyl-TAGs produced by nucleic acids of the present inventions.

In another embodiment, the inventors contemplate a higher production capacity of total oil per seed weight and thus a greater production capacity per hectacre over currently available plant or algal oils comprising ac-TAGs.

In particular, the inventors contemplate that transgenic expression of enzymes of the present inventions in oil-seed crops, such as soybean, sunflower, rapeseed (Canola), etc., ac-TAGs will be produced in relative abundance over levels of ac-TAGs in wild-type oils of these crops.

In another embodiment, the inventors contemplate lower production cost of biodiesel. Specifically, production of ac-TAGs in oils of plants for direct consumption would substantially lower costs associated with converting conventional TAGs to biofuels. In a preferred embodiment, the use of these new oils would eliminate the necessity of chemical transesterification steps.

Current methods of bioethanol production using starch from corn as a fermentation feedstock (used either as a gasoline replacement or oxygenate) are moderately efficient. However, production capacity is limited by the availability of corn. Acreage devoted to corn for bioethanol production competes directly with areable land area for growing corn as animal, fowl and fish feed, human food, and other industrial uses. Alternative sources of fermentation sugars from cellulosic biomass (whether crop residues such as corn stover or dedicated fuel crops such as switch grass) are commonly discussed and highly touted. However, technical difficulties with biomass hydrolysis, and economic issues with harvest, transport, and supply, in addition to increasing demands on fertilizer production capabilities are slowing the commercial development of bioethanol from cellulosic sources.

Similar technical difficulties are encountered with biodiesel production. Like bioethanol, biodiesel is dependent on agricultural production and hence available farm acreage. As in the case with corn, capacity is limited by the availability of the amount of oil-seed crop grown, dedicated transesterification capacity, economic issues with growth, harvest, transport, supply, and further limited by technical capabilities of engines to efficiently use biodiesel, such as jet engines, car engines, truck engines, tractor engines, et cetera. As an example, soybean acreage devoted for biodiesel production also competes directly with arable land area for growing soybeans for oil for food and other industrial uses and oil seed crop plants that require specific growing requirements found in arable land, such as soybean plants, sunflower plants and the like. Thus, alternative biofuel oil supplies from plants, such as *Jatropha*, and the like, which are capable of growing on land that is unable to support traditional oil seed crops, such as unarable land, where farming for traditional food crops is not economically feasible. For example, unarable land typically has no source of fresh water, and is often too hot (desert), too cold (arctic), too rocky, too mountainous, too salty, too rainy, too snowy, or too cloudy, including land with steep hills, rocky outcrops, located in dry climates, located in wet climates, etc. Alternative plants capable of growing on unarable land are needed for providing additional cultivated land areas needed to accommodate the growing demand for biodiesel and other vegetable oils.

The present invention relates to compositions comprising diacylglycerol acyltransferase genes and polypeptides, and in particular *Euonymus* and *Euonymus*-like diacylglycerol acyltransferase genes and polypeptides, where the enzyme exhibits primary specificity for diacylglycerol (DAG) and acyl-CoA substrates (described herein). These polypeptides are referred to as diacylglycerol acetyltransferases, designated 'DAcT,' indicating an activity of increased specificity for transfer of acetyl or related groups to DAG substrates, and/or 'EaDAcT,' indicating an enzyme polypeptide obtained from or derived from *Euonymus* alata plants.

The present invention encompasses compositions comprising both native and recombinant forms of the enzyme, as well as mutant and variant forms, some of which possess altered characteristics relative to the wild-type. The present invention also comprises isolated lipids and isolated fatty acids from host cells expressing EaDAcT genes and polypeptides. The present invention also comprises novel triacylglycerols synthesized by DAcT. The present invention also provides methods for using DAcT genes and polypeptides. The present invention also provides methods for isolating novel triacylglycerols synthesized by EaDAcT.

In some embodiments, the present invention provides novel isolated nucleic acid sequences encoding an EaDAcT and DAcT polypeptides. In other embodiments, the invention provides isolated nucleic acid sequences encoding mutants, variants, homologs, chimeras, and fusions of an EaDAcT and DAcT polypeptides. In other embodiments, the present invention provides methods of generating such sequences. In other embodiments, the present invention provides methods of cloning and expressing such sequences, as well as methods of purifying and assaying the expression product of such sequences.

In additional embodiments, the present invention provides purified EaDAcT genes and EaDAcT polypeptides. In some embodiments, the present invention provides purified EaDAcT-like genes and EaDAcT like polypeptides (i.e. DAcT genes and DAcT polypeptides) from plants that have the capability to make ac-TAGs. Exemplary plants for providing DAcT genes and DAcT polypeptides for use in the present inventions include Celastraceae, exemplary plants include: *Euonymus* sp., (such as *Euonymus europaeus, Euonymus latifolius*, etc.), *Celastrus* sp., (such as *Celastrus orbiculatus* (Asiatic bittersweet), *Celastrus scandens* (American bittersweet)); Lardizabalaceae, exemplary plants include: *Akebia quinata, Decaisnea fargesii, Lardizabala, biternata; Maytenus* sp., (such as *Maytenus ilicifolia*, etc.)); *Gymnosporia* sp., (such as *Gymnosporia harveyana, Gymnosporia Montana, Gymnosporia royleana*, etc.); Ranunculaceae, exemplary plants include *Adonis aestivalis*, etc.), Rosaceae, exemplary plants include: *Sorbus aucuparia, Sorbus mougeotii*, other types of Mountain ashes, apple trees, peach trees, plum trees, strawberry plants; and the like. In other embodiments, the present invention provides mutants, variants, homologs, chimeras, and fusion proteins of EaDAcT, EaDAcT-like (i.e. homologs and paralogs, etc.), DAcT and DAcT-like (i.e. homologs and paralogs, etc.). In some embodiments, the present invention provides methods of purifying, and assaying the biochemical activity of wild type as well as mutants, variants, homologs, chimeras, and fusions of EaDAcT and DAcT, as well as methods of generating antibodies to such proteins.

In other embodiments, the present invention provides compositions comprising novel triacylglycerols synthesized by EaDAcT polypeptides and/or DAcT polypeptides and/or DAcT-like polypeptides from plant of the present invention. Such syntheses may be accomplished by any of the methods described below.

In some embodiments, the present invention provides methods of using novel isolated nucleic acid sequences encoding EaDAcT polypeptides and/or DAcT polypeptides and/or DAcT-like polypeptides from plants to produce products of the acetyltransferase activity. In some embodiments, the methods involve adding the DAcT sequences to in vitro transcription and translation systems that include the substrates of the EaDAcT polypeptides and/or DAcT polypeptides from other plants, such that the products of the acetyltransferase (oils) may be recovered (isolated). In other embodiments, the methods involve transforming organisms with DAcT sequences such that the sequences are expressed as products, such as EaDAcT polypeptides and/or DAcT polypeptides from other plants. In particular embodiments, the products are recovered. In particular embodiments, the products are isolated. In other embodiments, the products remain in situ.

In some embodiments, the present invention provides methods of using recombinant EaDAcT polypeptides and/or DAcT polypeptides from other plants (i.e. homologs, paralogs, etc.) to produce lipids containing acetyl or short-chain acyl groups as a result of the acetyltransferase and acyltransferase activity. In some embodiments, the methods involve adding the polypeptides to an in vitro system that includes the substrates of the DAcT (DAGs), such that the products of the DAcT may be recovered (isolated).

In other embodiments, the methods involve transforming a plant with a novel isolated nucleic acid sequence encoding EaDAcT polypeptides and/or DAcT polypeptides from other plants, such that products of the DAcT are produced.

In some embodiments, the present invention provides an organism transformed with heterologous gene encoding an EaDAcT polypeptide and/or DAcT polypeptides from other plants. In some embodiments, the organism is a microorganism. In some embodiments, the organism is a yeast cell. In some embodiments, the organism is an algal cell. In other embodiments, the organism is a nonalgal plant. In other embodiments, the organism is a plant part. In some embodiments, the present invention also provides a cell transformed with a heterologous gene encoding EaDAcT polypeptides and/or DAcT polypeptides and/or DAcT-like polypeptides from plants. In some embodiments, the cell is a microorganism. In other embodiments, the cell is a plant cell.

In other embodiments, the present invention provides a plant seed transformed with a nucleic acid sequence encoding EaDAcT polypeptides and/or DAcT polypeptides and/or DAcT-like polypeptides from plants. In yet other embodiments, the present invention provides an oil from a plant, a plant seed, or a microorganism transformed with a heterologous gene encoding an EaDAcT polypeptides and/or DAcT polypeptides and/or DAcT-like polypeptides from plants.

The inventions described herein, contemplate one embodiment wherein the production of reduced carbon number TAGs without recourse to alterations in fatty acid synthesis to produce acetyltriacylglycerols which are directly used in commercial products. In further embodiments, the inventors' contemplate altering fatty acid synthesis to increase production of ac-TAGs in seeds and tissues. The description below provides specific, but not limiting, illustrative examples of embodiments of the present invention. This description includes a discovery of a novel class of DGATs, namely DAcT from *Euonymus*, a member of the MBOAT superfamily of acyltransferases. This description also includes a discovery of DAcT polypeptides of the present invention, DAcT coding sequences of the present invention, methods of identifying DAcT proteins and coding sequences, methods of expressing DAcT coding sequences, methods of producing acetyl glycerides, and methods of manipulating diacylglycerol acetyltransferase activity in plants and microorganisms, such as yeast.

Further discoveries included the surprise that unlike the known DGAT1, the EaDAcT of the present inventions induces significant production of ac-TAGs in yeast and *Arabidopsis* seeds. Even further discoveries include EaDAcT-like (homologous) genes in other plants, such as grapes (*Vitis vinifera*), castor beans (*Ricinus communis*) and poplar trees (*Populus trichocarpa*). Further, contemplated uses of novel oils and increased production of oils comprising acetyl-TAGs of the present inventions are described herein.

I. Discovery of an Additional Diacylglycerol Acetyltransferase Gene and Polypeptide in *Euonymus*.

The biochemistry and genetics describing the biosynthesis of TAG (consisting of 3 long- or medium-chain fatty acids) was described, for example, in Durrett et al. (2008) Plant J. 54:593-607, herein incorporated by reference. Furthermore, an enzyme activity responsible for ac-TAG synthesis was demonstrated in cell free extracts from developing *Euonymus* seeds (Milcamps et al., 2005, herein incorporated by reference), and shown to be a 1,2-diacyl-sn-glycerol:acetyl-CoA 3-O-acetyltransferase.

However the specific genes responsible for ac-TAG production were not known. In fact, during the discovery of a gene of the present inventions, the inventors first discovered several other diacylglycerol acyltransferase genes and proteins thought to be responsible for or associated with ac-TAG production prior to their discovery of the diacylglycerol acyltransferase genes and proteins of the present inventions. Moreover, EaDAcT genes and proteins of the present inventions were at least the third major candidate acyl transferase gene found while looking for a specific enzyme responsible for ac-TAG production. Furthermore, a DAcT gene of the present inventions was not a gene that was or would have been discovered by a homology based search using known DGAT gene sequences. Even further, the use of traditional enzyme activity fractionation, protein purification and subsequent protein sequencing was contemplated by the inventors as an unlikely method of isolation in part due to the contemplated transmembrane location of ac-TAG producing enzyme. Solubilization and separation of membrane bound proteins while retaining enzyme activity is usually problematic. This was confirmed by actual experimentation by the inventors who found that although the enzyme was partially isolated, the majority of enzyme activity was lost during isolation, in particular during fractionation. Any remaining activity was unstable and rapidly lost over time. In particular, activity levels of endogenous 1,2-diacyl-sn-glycerohacetyl-CoA 3-O-acetyltransferase protein isolated from developing *Euonymus* seeds were low in cell free extracts, lost substantially activity (i.e. was unstable) over time while membrane fractionation yielded almost no protein, even before attempting any activity determination. Thus another experimental approach had to be devised by the inventors, and is described below as methods using trasnscriptomics.

A. Strategy for Identifying a DAcT Coding Sequence.

Based upon the evidence obtained from the investigations of the biosynthesis of sn-3-acetyl glycerides in *Euonymus* described above, including the failure of previous strategies to identify a gene for making sn-3-acetyl glycerides, a new strategy for identifying a DGAT coding sequence was developed. This strategy begins with the observation of the presence of sn-3-acetyl glycerides in specific plant tissues (endosperm) and the observation of the absence of sn-3-acetyl glycerides in other plant tissues (arils) that also synthesize oils (FIG. 5).

The next step was labeling studies of intact tissues and tissue homogenates, to confirm that the ability to synthesize sn-3-acetyl glycerides is in fact present in the endosperm tissue and absent from the aril tissue, and to determine the exact structure of the reaction substrates and particularly the acetyl donor. The next step is obtaining the correct cDNA from total RNA prepared from tissue (which for *Euonymus* is the developing seeds), which synthesizes sn-3-acetyl glycerides, preferably to a relatively high level. For *Euonymus*, the lipid profiles of developing seeds were analyzed, to determine the developmental stage when sn-3-acetyl glycerides accumulated at the highest rate; seeds obtained at this developmental stage are then used to prepare a cDNA library.

To obtain the correct cDNA, cDNA libraries from both endosperm and aril tissues were sequenced using 454 pyrosequencing to obtain a transcript profile of the different tissues. As the endosperm tissue produces ac-TAGs whereas the aril does not, and as the endosperm and the aril synthesize TAG at approximately the same rate (moles glycerol/day/g fresh weight tissue), the inventors hypothesized that cDNAs required for ac-TAG production would be present at much higher levels in the endosperm compared to the aril. In this manner a cDNA for a candidate DAcT was identified and then cloned using gene specific primers designed based on the sequence information obtained from the 454 pyrosequencing (Described in more detail in the Examples).

Confirmation that the cloned sequence encodes a DAcT was obtained by expression of the candidate clone in vivo or in vitro, such that sn-3-acetyl glycerides were produced upon expression of the candidate clone or increased acetyl-transferase activity was present in microsomes from cells expressing the candidate clone. The 3-acetyl glycerides may be produced in cells of an organism, or in an enzyme assay conducted with extracts obtained from an organism. Preferably, the system is in vivo, and the candidate clone transfected into and expressed in a host organism. More preferably, the system in one in which sn-3-acetyl glycerides are not normally produced; a non-limiting example is a system in which the host organism is a yeast strain. Even more preferably, the system possesses or is able to synthesize ac-TAGs using a suitable DAG substrate. A non-limiting example is a system in which the host organisms are yeast cells. However since eukaryotic cells need a diacylglycerol pool and acetyl-CoA for routine energy and biosynthesis related processes it was contemplated that any cell transformed with an EaDAcT gene capable of making sn-3-acetyl glyceride should be able to synthesize ac-TAGs.

B. Identification of DAcT Coding Sequence.

This strategy was utilized for developing *Euonymus alata* seeds, as described above and in the Examples, and resulted in the identification and isolation of a full-length cDNA coding sequence for a DGAT. A deduced amino acid sequence is shown in FIG. 6.

Confirmation of the identity of the *Euonymus alata* DAcT (EaDAcT), and the ability of EaDAcT to synthesize sn-3-acetyl glycerides (ac-TAGs), was obtained by expression of EaDAcT in yeast cells, and observing TAGs synthesized both in vivo in intact yeast cells, and in vitro with transgenic yeast membrane fractions (i.e. microsomes) and in seeds from transgenic *Arabidopsis* plants. Expression of *Euonymus* DAcT (EaDAcT) in yeast cells resulted in the greatly increased accumulation of ac-TAGs when compared to the controls (yeast transformed with an empty vector). Moreover, expression of EaDAcT in yeast cells also resulted in the synthesis of sn-3-acetyl glycerides (ac-TAG to about 60% of the total amount of ac-TAG and lc-TAG synthesized. Molecular species of ac-TAG were identified by ESI-MS analysis of the lipids extracted from the yeast cells expressing EaDAcT; these species are C16:1C16:1, C16:1C16:0, C16:0C16:0, C16:1C18:1, C16:0C18:1, C16:1C18:0, C16:0C18:0, C18:1C18:1, C18:1C18:0, C18:0C18:0 (where the molecular species is identified by using the convention Cx:y to indicate the fatty acyl residues at the sn-1 and sn-2 positions, with x referring to the number of acyl carbons and y the number of double-bonds).

In comparison to EaDAcT, expression of *Euonymus* DGAT1 in yeast cells only resulted in synthesis of ac-TAGs to about 0.9% of total ac-TAG and lc-TAGs. Thus, EaDAcT exhibits an increased capability to synthesize ac-TAG when compared to EaDGAT1 in vivo in yeast cells.

In vitro assays showed that when assayed in the presence of an acyl donor, such as oleoyl-CoA, EaDGAT1 possessed oleoyl-transferase activity much greater than that of EaDAcT, about 52 pmoles/min/mg protein compared to about 1 mole/min/mg, respectively (FIG. 11B, 11C). When assayed in the presence of acetyl-CoA, both enzymes were able to synthesize ac-TAG; the EaDGAT1 enzyme possessed acetyltransferase activity of about 60 pmoles/min/mg compared to about 20 pmoles/min/mg for EaDAcT (FIG. 11A, C). The absolute specific activities cannot be compared between enzymes, as the protein is the total microsomal protein and not the specific recombinant enzyme protein. However, EaDAcT demonstrates a much greater capacity to synthesize ac-TAG in vivo (FIGS. 9 and 14). Clearly the capacity of EaDGAT1 to synthesize ac-TAG is suppressed in vivo, by an as yet unidentified mechanism. This highlights the importance of defining function through in vivo experiments rather than by merely in vitro assays.

Therefore, these data clearly confirm that the candidate *Euonymus* gene encodes a protein which functions as a diacylglycerol acetyltransferase (EaDAcT) with enhanced ability to synthesize sn-3-acetyl glycerides.

In summary, sequence similarity alone was not sufficient to identify or demonstrate protein function, as demonstrated by the similarities of EaDAcT amino acid sequences to other acyl transferases while having different activities in vivo and in vitro.

Confirmation of the identity and activity of EaDAcT was obtained by expression of the isolated coding sequence and determination of the activity of the encoded protein. The EaDAcT amino acid sequence was contemplated for use to discover other DAcT genes and proteins, as described herein.

II. Diacylglycerol Acetyltransferase Polypeptides.

The present invention provides compositions comprising purified diacylglycerol acetyltransferase (DAcT) polypeptides as well as compositions comprising variants of DAcT, including homologs, mutants, fragments, and fusion proteins thereof (as described further below).

In some embodiments of the present invention, the polypeptide is a purified product, obtained from expression of a native gene in a cell, while in other embodiments it may be a product of chemical synthetic procedures, and in still other embodiments it may be produced by recombinant techniques using a prokaryotic or eukaryotic host (for example, by bacterial, yeast, higher plant, insect and mammalian cells in culture). In some embodiments, depending upon the host employed in a recombinant production procedure, the polypeptide of the present invention may be glycosylated or may be non-glycosylated, or exhibit other post-translational amino acid modifications such as phosphorylation. In other embodiments, the polypeptides of the invention may also include an initial methionine amino acid residue.

A. Reaction Catalyzed.

A DAcT is a diacylglycerol acyltransferase polypeptide with a unique acyl group transfer specificity, such that the polypeptide is able to transfer an acetyl or related group from an acyl-CoA to a diacylglycerol substrate (FIG. 2C), and such that the diacylglycerol acetyltransferase exhibits increased specificity for an acetyl or related group compared to a diacylglycerol acyltransferase obtained from a plant in which acetyl TAGs are not present, or are present in only trace amounts (in other words, less than about 1% of the total TAGs), and which will generally exhibit a specificity preference for long-chain acyl-CoA.

Figure 2:
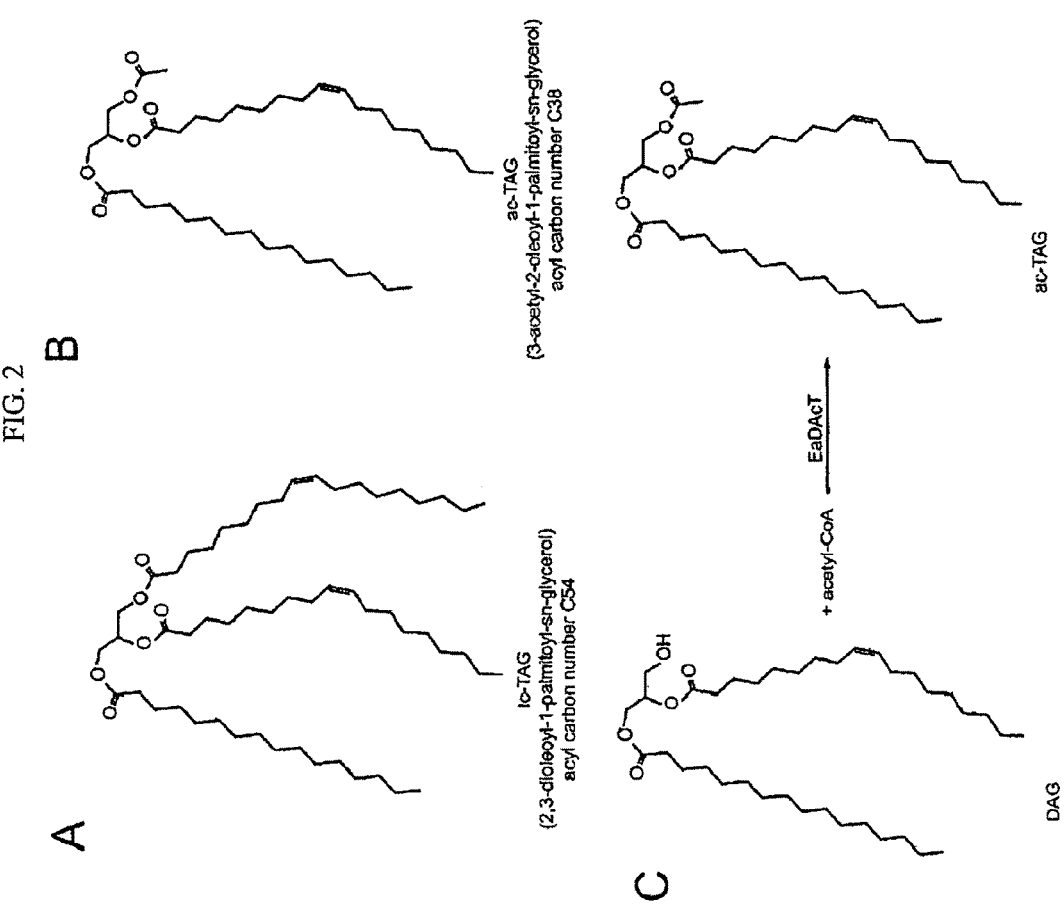
FIG. 2 shows exemplary triacylglycerol structures and an exemplary enzymatic reaction catalyzed by EaDAcT of the present inventions. (A) Structure of a representative lc-TAG with 54 acyl carbons (C54): 2,3-dioleoyl-1-palmitoyl-sn-glycerol. (B) Structure of a representative ac-TAG with a 38 acyl carbons (C38): 3-acetyl-2-oleoyl-1-palmitoyl-sn-glycerol. (C) EaDAcT catalyzes the acetylation of DAG, using acetyl-CoA as the acyl donor, to form ac-TAGs.

Thus, a DAcT polypeptide catalyzes the transfer of an acetyl or related group to diacylglycerol (DAG), as exemplified by the following general reaction: DAG+acyl group->TAG, where the acyl group is acetyl or a related group, and where the preferred embodiment may be acetyl transferred to diacylglycerol (DAG) to form acetyl triacylglycerol (ac-TAG) (FIG. 2C). Typically, the acetyl or related group is transferred to the sn-3 position of DAG, although other positions are also contemplated, such as the sn-1 and sn-2 positions of DAG. The enzyme in situ most likely acts on an acetyl group of acetyl-CoA, and most likely transfers the acetyl group to the sn-3 position of DAG. However, the enzyme may utilize different substrates under different conditions to differing degrees of activity, and may produce other products as well. Thus, other substrates may include DAG where the sn-1 or the sn-2 position is available to accept the acetyl group, monoacylglycerols, etc. Other groups transferred include groups related to acetyl, such as propionyl, butyryl, hexanoyl, benzoyl, cinnamyl, and ferulyl; typically, these groups are esterified to Co-A, such that the substrate of the transferase are propionyl-CoA, butyryl-CoA, hexanoyl-CoA, benzoyl-CoA, cinnamyl-CoA, or ferulyl-CoA.

The specificity of DAcT may be determined by either in vivo or in vitro assays. From an in vivo assay, the specificity is the proportion of total TAGs that are ac-TAGs, where the ac-TAGs are synthesized by the presence of a heterologous diacylglycerol acetyltransferase. An in vivo experiment can use a labeled or unlabeled short-chain substrate. As demonstrated in FIG. 3A, a propionyltriacylglycerol can be synthesized by developing *Euonymus* seeds from the added C3 precursor, propionic acid. The exogenous propionic acid must be activated to propionyl-CoA to compete with the endogenous acetyl-CoA for reaction with EaDAcT. Comparing the concentration curves for acetic and propionic acids (FIG. 3B) shows that a maximum rate of triacylglycerol synthesis is about 5-fold greater for acetate than propionate, but whether this is a limitation imposed by EaDAcT specificity or by the rate of exogenous carboxylic acid transport into the seed tissue and into the cell, and by the acyl-CoA synthetase enzyme(s) is uncertain. From an in vitro assay, the specificity is the activity of transfer of an acetyl or related group to a diacylglycerol, when the substrate is an acetyl-CoA or related group esterified to CoA. The increase in specificity of transferring an acetyl or related group for a DAcT is at least about 1.5 times, or about 2 times, or about 5 times, or about 10 times, or about 20 times, or about 50 times, or about 100 times, or up to about 2000 times, the specificity of a DGAT obtained from a plant in which acetyl TAGs are not present, or are present in only trace amounts. One standard DGAT to which a DAcT is compared, in order to determine specificity of transfer of an acetyl or related group, is a DGAT obtained from *Arabidopsis*. The *Arabidopsis* DGAT1 has over a 100-fold greater activity towards a long-chain acyl-CoA than towards acetyl-CoA when expressed in yeast (H1226 background) (Milcamps, 2005, J. Biol. Chem. 280:5370-5377, herein incorporated by reference).

A DAcT gene and polypeptide of the present inventions is different from other known acyltransferase enzymes. Specifically, previous work demonstrated that formation of ac-TAGs in developing *Euonymus* seed was the result of an sn-1,2-diacylglycerol:acyl CoA acyltransferase (DGAT; E.C. 2.3.1.20) reaction (Milcamps, 2005, J Biol. Chem. 280:5370-5377, herein incorporated by reference). At least four different types of DGAT enzymes were found capable of catalyzing such a reaction in various species. Two of these enzymes, DGAT1 and DGAT2 were found responsible for the bulk of TAG synthesis in most organisms. DGAT1 proteins are members of the MBOAT protein superfamily and are very different structurally from DGAT2 proteins. For example, DGAT1 proteins are larger than DGAT2, and possess six transmembrane domains compared to the two predicted in DGAT2 (Yen, 2008, J. Lipid Res., 49:2283-2301, herein incorporated by reference). It was found that these two enzymes play non-redundant roles in TAG synthesis. For example in animals, whereas DGAT2 knockout mice die shortly after birth due to extremely reduced TAG levels (Stone, 2004, J. Biol.

Chem. 279:11767-11776, herein incorporated by reference), mice lacking DGAT1 are viable with only modest reductions in tissue TAG content (Smith, 2000, Nat Genet 25:87-90, herein incorporated by reference). In the model plant *Arabidopsis thaliana*, mutations in DGAT1 but not DGAT2, were reported that affected seed oil levels (Katavic, 1995, Plant Physiology 108:399-409; Routaboul, 1999, Plant Physiol. Bioch. 37:831-840; Zou, 1997, Plant Cell 9:909-923, herein incorporated by reference). Instead, in some plants DGAT2 orthologs appear to incorporate unusual fatty acids in the seed storage oils (Burgal, 2008, Plant Biotechnology Journal 6:819-831; Kroon, 2006, Phytochemistry 67:2541-2549; Shockey, 2006, Plant Cell 18:2294-2313, herein incorporated by reference). Further, tang tree (*Vernicia fordii*) DGAT1 and DGAT2 localize to different sub-domains of the endoplasmic reticulum (Shockey, 2006, Plant Cell 18:2294-2313, herein incorporated by reference). The bifunctional DGAT/wax ester synthase ADP1 from *Acinetobacter calcoaceticus*, another member of the MBOAT superfamily, represents a third class of DGAT enzyme (Kalscheuer, 2003, J. Biol. Chem. 278:8075-8082, herein incorporated by reference). Homologues of ADP1 have been characterized in petunia and *Arabidopsis* but for these proteins the DGAT activity is either absent or much lower compared to the wax synthase activity (King, 2007, Planta 226:381-394; Li, 2008, Plant Physiol. 148:97-107, herein incorporated by reference). Lastly, a soluble DGAT enzyme has been identified in peanut cotyledons (Saha, 2006, Plant Physiol 141:1533-1543, herein incorporated by reference), but functional orthologs have yet to be identified in other species. In addition to the DGATs, phospholipid:diacylglycerol acyltransferases (PDAT, EC 2.3.1.43) also synthesize TAG, using phosphatidylcholine as the acyl donor (Dahlqvist, 2000, Proceedings of the National Academy of Sciences of the United States of America 97:6487-6492; Stahl, 2004, Plant Physiol 135:1324, herein incorporated by reference). Of these DGATs, it was discovered during the development of the present inventions that DGAT1 protein sequences showed the closest homology to DAcT putative protein sequences, see, FIG. 6.

B. *Euonymus* Diacylglycerol Acetyltransferase Polypeptide.

In some embodiments, the polypeptide comprises a *Euonymus* DGAT; in other embodiments, the polypeptide comprises a *Euonymus alata* DGAT. In one embodiment, the polypeptide FIG. 6 (SEQ ID NO:1) is encoded by an exemplary nucleic acid sequence shown in FIG. 5 (SEQ ID NO:10). In other embodiments, a nucleic acid encodes a polypeptide comprising the amino acid sequence shown in FIG. 6 (SEQ ID NO:2-8).

As described above under the reaction catalyzed by a DAcT, a crucial feature of a DAcT from *Euonymus* is its ability to use acetyl-CoA (or a related group-CoA) instead of a long-chain acyl-CoA as a substrate. These latter substrates presumably bind to acyl-CoA binding proteins and to membranes, and form micelles by themselves, whereas acetyl-CoA is primarily water-soluble. Thus the capability of a DAcT to utilize a water-soluble acyl-CoA (or related group-CoA) substrate is an important feature.

C. Variant Diacylglycerol Acetyltransferase Polypeptides.

In other embodiments, the present invention provides isolated variants of the disclosed DAcT polypeptides; these variants include mutants, fragments, fusion proteins or functional equivalents of DAcT.

In some embodiments, isolated variants include post-translational variants. Exemplary variants are described further below.

D. Assay of Diacylglycerol Acetyltransferase Polypeptides.

The activity of diacylglycerol acetyltransferase (DAcT) may be assayed in a number of ways. These include, but are not limited to, in vivo assays and in vitro assays, as described further below.

In some embodiments, enzyme activity is determined in vivo by expressing a nucleic acid sequence encoding the acetyltransferase in a transgenic organism and then analyzing the content and composition of the TAG fraction present in the transgenic organism. Thus, the activity is measured as the presence of or increase in the amount of endogenous TAG and acetylated TAG (ac-TAG) in a transgenic organism which comprises an exogenous nucleic acid sequence having a coding sequence of the present invention (for example, encoding a DAcT, as, for example, SEQ ID NO:10 encoding a polypeptide, SEQ ID NO:01), and nucleic acid sequences encoding a DAcT related sequence, as, for example, SEQ ID NOs: 2-8); such transgenic organisms are obtained as described below. The amount of TAG and ac-TAG in a transgenic organism was compared to that present in a non-transgenic organism. TAG production is typically analyzed from lipids extracted from samples of a transgenic organism; the samples are homogenized in methanol/chloroform (1:2, v/v) with the lipids extracted as described by Bligh and Dyer (1959) Can. J. Biochem. Physiol. 37:911-917, and in hexane:isopropanol as described by Hara and Radin, Anal. Biochem. 90:420-426 (1978), herein incorporated by reference.

In other embodiments, enzyme activity is determined in vivo by adding exogenous substrates to tissue samples obtained from an organism that may or may not be transgenic (transgenic organisms are described below). For example, in plants, tissue samples include but are not limited to leaf samples (such as discs), stem and root samples, and developing and mature seed embryonic or endosperm tissue. Typically, tissue samples are incubated with [$^{14}$C]acetate substrate, which can be taken up and incorporated into tissue lipids. Other potential short-chain carboxylic acid substrates, such as propionate, described above in Section IIA and in FIG. 3, are contemplated for use by a DAcT enzyme of the present inventions. Incubations generally proceed at room temperature in a buffered solution, such as 0.1M potassium MES at pH 5.5-6.5, for a suitable period of time. The samples are then washed in buffer, and the tissue samples homogenized in methanol/chloroform (1:2, v/v) and the lipids extracted as described by Bligh and Dyer (1959), herein incorporated by reference, and in hexane:isopropanol as described by Hara and Radin, Anal. Biochem. 90:420-426 (1978), herein incorporated by reference.

In yet other embodiments, enzyme activity is determined in vitro in a cell-free homogenate or subcellular fraction obtained from an organism which may or may not be transgenic (transgenic organisms are described below), where the tissue is disrupted and filtered or centrifuged to result in cell-free fractions. For example, in plants, subcellular fractions may be obtained from any of the types of tissues described above, and include whole cell and microsomal membranes, plastids and plastid membrane fractions, or other isolated and purified organelles and membranes such as mitochondria and peroxisomes and plasmalemma. The preparation of such fractions is well-known in the art. The subcellular fraction is then incubated with an acetyl- or related group-CoA substrate, such as $^{14}$C-acetyl-CoA, which can be taken up and incorporated into lipids. Additional co-factors for lipid synthesis, as required, may be present during the incubation; such co-factors include but are not limited to DAG. Other reagents which may enhance lipid synthesis may also be added; such reagents include phospholipid liposomes (for example, containing DAG) and lipid transfer proteins. The samples are incubated and the lipids extracted as described above.

In yet other embodiments, enzyme activity is determined from an in-vitro nucleic acid expression system, to which a nucleic acid sequence having a coding sequence of the present invention (for example, encoding a DAcT, as, for example, SEQ ID NO:10 or comprising a DAcT coding sequence, as, for example, SEQ ID NO: 10) is added and the encoded enzyme expressed, and the activity of the expressed enzyme determined. Such expression systems are well known in the art, and include, for example reticulocyte lysate or wheat germ. The enzyme may be stabilized by the presence of TAGs and/or other glycerolipids, by phosphoglycerolipids that produce membrane structures, or by mixtures of lipids and detergents that produce micellar structures; these structures may be included in the mixture and may include the substrate upon which the enzyme might act, and might include the product produced by the enzyme. It is preferable that such micellar structures are obtained from sources such as from plant tissues where the plant does not contain endogenous diacylglycerol acetyltransferase activity, but which does possess DAG, or other lipids which can be used to produce DAG (such as a glycerolipid), or which can incorporate DAG. Direct and quantitative measurements may require the incorporation of labeled lipids into the micellar or membrane structures and the assurance that the utilization of a DAG substrate is not limiting. The activity of newly expressed enzyme is then analyzed as described above for subcellular fractions.

The extracted lipid products of DAcT are analyzed by methods well known in the art. For example, the extracted TAG products can be analyzed by normal-phase silica thin layer chromatography (TLC), reversed-phase or silver nitrate TLC (used, for example, for analysis of products first separated by normal-phase silica TLC), high temperature GC (in some cases with odd-chain internal standards), by GC/MS, by ESI-MS, and by HPLC.

E. Purification of Diacylglycerol Acetyltransferase Polypeptides.

In some embodiments of the present invention, a diacylglycerol acetyltransferase (DAcT) polypeptide purified from organisms is provided; such organisms include transgenic organisms, comprising a heterologous DAcT gene, as well as organisms in which DAcT occurs naturally. In other embodiments, a DAcT polypeptide is purified from an in vitro nucleic acid expression system, which comprises a nucleic acid sequence having a coding sequence of the present invention (for example, encoding a DAcT, as, for example, SEQ ID NO:1, or comprising a DAcT coding sequence, as, for example, any one of SEQ ID NO: 2-8 and genes encoding proteins at least 43% identical to SEQ ID NO:1) and from which the expressed DAcT molecule can be purified. The present invention provides a purified DAcT polypeptide as well as variants, including homologs, mutants, fragments, and fusion proteins thereof (as described further below).

The present invention also provides methods for recovering and purifying plant DAcT from an organism or from an in vitro nucleic acid expression system; exemplary organisms include single and multi-cellular organisms. When isolated from an organism, the cells are typically first disrupted and then fractionated before subsequent enzyme purification.

Purification methods are also well-known, and include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, and isoelectric focusing. It is contemplated that DAcT purified in an active or inactive form will require the presence of detergents to maintain its solubility in aqueous media during fractionation. It is further contemplated that assay of the enzyme activity will require removal of the detergent and reconstitution in liposomes to recover full activity. For exemplary methods, see Hjehneland and Chrambach, Furth et al., and van Renswoude and Kempf (1984) Methods in Enzymology 104, p305, 318 and 329 respectively, and Lardizabal et al. (2000) Plant Physiology 122:645-655, all of which are herein incorporated by reference, where the jojoba wax synthase, a plant acyltransferase and MBOAT member, was solubilized and purified.

The present invention further provides nucleic acid sequences having a coding sequence of the present invention (for example, SEQ ID NO: 1) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of a DAcT and which results in expression of the polypeptide in the case of a bacterial host, and in other embodiments vector PT-23B, which adds a hexahistidine tag to the C terminal of a DAcT and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell 37:767, herein incorporated by reference).

F. Chemical Synthesis of Diacylglycerol Acetyltransferase Polypeptides.

In some embodiments of the present invention, a DAcT protein is produced using chemical methods to synthesize either an entire DAcT amino acid sequence or a portion thereof. For example, peptides are synthesized by solid phase techniques, cleaved from the resin, and purified by preparative high performance liquid chromatography (See for example, Creighton (1983) *Proteins Structures And Molecular Principles*, W H Freeman and Co, New York N.Y., herein incorporated by reference). In other embodiments of the present invention, the composition of the synthetic peptides is confirmed by amino acid analysis or sequencing (See for example, Creighton, supra, herein incorporated by reference).

Direct peptide synthesis can be performed using various solid-phase techniques (Roberge et al. (1995) Science, 269: 202-204, herein incorporated by reference) and automated synthesis may be achieved, for example, using Applied Biosystems (ABI) 431A Peptide Synthesizer (Perkins Elmer) in accordance with the instructions provided by the manufacturer. Additionally, an amino acid sequence of a DAcT, or any part thereof, may be altered during direct synthesis and/or combined using chemical methods with other sequences to produce a variant polypeptide.

G. Generation of Diacylglycerol Acetyltransferase Antibodies.

In some embodiments of the present invention, antibodies are generated to allow for the detection and characterization of a DAcT protein. The antibodies may be prepared using various immunogens. In one embodiment, the immunogen is a *Euonymus* DAcT polypeptide (for example, an amino acid sequence as depicted in SEQ ID NO:1 or peptide fragments thereof or synthetic peptide fragment thereof, to generate antibodies that recognize *Euonymus* DAcT. Such antibodies include, but are not limited to polyclonal, monoclonal, chimeric, single chain, $F_{ab}$ fragments, and $F_{ab}$ expression libraries.

Various procedures known in the art may be used for the production of polyclonal antibodies directed against a DAcT protein. For the production of antibody, various host animals can be immunized by injection with the peptide corresponding to a DAcT epitope including but not limited to rabbits, mice, rats, sheep, goats, etc. In a preferred embodiment, the peptide is conjugated to an immunogenic carrier (for example, diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (for example, aluminum hydroxide), surface-active substances (for example, lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward a DAcT, it is contemplated that any technique that provides for the production of antibody molecules by continuous cell lines in culture finds use with the present invention (See for example, Harlow and Lane, Antibodies: A Laboratory Manual, Cold Spring Harbor Laboratory Press, Cold Spring Harbor, N.Y., herein incorporated by reference). These include but are not limited to the hybridoma technique originally developed by Köhler and Milstein (Köhler and Milstein (1975) Nature, 256:495-497, herein incorporated by reference), as well as the trioma technique, the human B-cell hybridoma technique (See for example, Kozbor et al. (1983) Immunol. Today 4:72, herein incorporated by reference), and the EBV-hybridoma technique to produce human monoclonal antibodies (Cole et al. (1985) in *Monoclonal Antibodies and Cancer Therapy*, Alan R. Liss, Inc., pp. 77-96, herein incorporated by reference).

In addition, it is contemplated that techniques described for the production of single chain antibodies (U.S. Pat. No. 4,946,778, herein incorporated by reference) find use in producing a DAcT-specific single chain antibodies. An additional embodiment of the invention utilizes the techniques described for the construction of $F_{ab}$ expression libraries (Huse, et. al. Science, 246:1275-1281 (1989), herein incorporated by reference) to allow rapid and easy identification of monoclonal $F_{ab}$ fragments with the desired specificity for a DAcT.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and $F_{ab}$ fragments that can be generated by treating the antibody molecule with papain and a reducing agent.

In the production of antibodies, it is contemplated that screening for the desired antibody is accomplished by techniques known in the art (for example, radioimmunoassay, ELISA (enzyme-linked immunosorbant assay), "sandwich" immunoassays, immunoradiometric assays, gel diffusion precipitin reactions, immunodiffusion assays, in situ immunoassays (for example, using colloidal gold, enzyme or radioisotope labels, for example), Western blots, precipitation reactions, agglutination assays (for example, gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of a DAcT (for example, for Western blotting), measuring levels thereof in appropriate biological samples, etc. The antibodies can be used to detect DAcT in a biological sample from a plant. The biological sample can be an extract of a tissue, or a sample fixed for microscopic examination.

The biological samples are then tested directly for the presence of DAcT using an appropriate strategy (for example, ELISA or radioimmunoassay) and format (for example, microwells, dipstick (for example, as described in International Patent Publication WO 93/03367, herein incorporate by reference), etc. Alternatively, proteins in the sample can be size separated (for example, by polyacrylamide gel electrophoresis (PAGE), in the presence or not of sodium dodecyl sulfate (SDS), and the presence of DAcT detected by immunoblotting (Western blotting). Immunoblotting techniques are generally more effective with antibodies generated against a peptide corresponding to an epitope of a protein, and hence, are particularly suited to the present invention.

III. Diacylglycerol Acetyltransferase Coding Sequences.

The present invention provides compositions comprising purified nucleic acid sequences encoding any of the diacylglycerol acetyltransferases described above or below. Coding sequences include but are not limited to genes, cDNA, and RNA.

Thus, the present invention provides compositions comprising purified nucleic acid sequences encoding a DAcT, as well as nucleic acid sequences encoding variants of DAcT, including homologs, mutants, or fragments, or fusion proteins thereof, as described above and below. In yet other embodiments, the nucleic acid sequences encode a portion of a DAcT that retains some functional characteristic of a DGAT. Examples of functional characteristics include the ability to act as an immunogen to produce an antibody that recognizes a DGAT.

Coding sequences for DAcT include sequences isolated from an organism, which either comprises the coding sequence naturally or is transgenic and comprises a heterologous DAcT coding sequence, sequences which are chemically synthesized and which may be codon-optimized, as well as sequences which represent a combination of isolated and synthesized (as, for example, where isolated sequences are mutagenized, or where a sequence comprises parts of sequences isolated from different sources and/or synthesized from different sources).

Thus, in some embodiments of the invention, the coding sequence of a diacylglycerol acetyltransferase (DAcT) is synthesized, whole or in part, using chemical methods well known in the art (See, for example, Caruthers, et. al. (1980) Nucl. Acids Res. Symp. Ser. 7:215-233; Crea and Horn (1980) Nucl. Acids Res. 9:2331; Matteucci and Caruthers (1980) Tetrahedron Lett. 21:719; and Chow and Kempe (1981) Nucl. Acids Res. 9:2807-2817, all of which are herein incorporate by reference.

A. *Euonymus* Diacylglycerol Acetyltransferase Coding Sequence.

In some embodiments, the sequences encode a *Euonymus* diacylglycerol acetyltransferase (DAcT); in other embodiments, the sequences encode a *Euonymus alata* DAcT. In some embodiments, the sequences comprise the sequence shown in FIG. 6 (SEQ ID NO:1); in other embodiments, the sequences encode any of the amino acid sequence shown in FIG. 6 (SEQ ID NOs:2-8).

B. Variant Diacylglycerol Acetyltransferase Coding Sequences.

In other embodiments, the sequences encode a variant of the disclosed diacylglycerol acetyltransferase (DAcT) polypeptides; these variants include mutants, fragments, fusion proteins or functional equivalents of DAcT. Exemplary sequences encoding variants are described further below.

C. Additional Diacylglycerol Acetyltransferase Coding Sequences and Genes.

The present invention provides isolated nucleic acid sequences encoding DAcT in addition to those described above. For example, some embodiments of the present invention provide isolated polynucleotide sequences that are capable of hybridizing to SEQ ID NO: 10 under conditions of low to high stringency as long as the polynucleotide sequence capable of hybridizing encodes a protein that retains a desired biological activity of DAcT as described above. In preferred embodiments, hybridization conditions are based on the melting temperature (Tm) of the nucleic acid binding complex and confer a defined "stringency" as explained above (See for example, Wahl, et. al. (1987) Meth. Enzymol., 152: 399-407, incorporated herein by reference).

In other embodiments of the present invention, alleles of a DAcT are provided. In preferred embodiments, alleles result from a mutation, (in other words, a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

These additional DAcT genes are discovered by the methods such as are described below.

IV. Methods of Identifying Diacylglycerol Acetyltransferase Coding Sequences and Genes.

Other embodiments of the present invention provide methods to isolate nucleic acid sequences encoding DAcT. In some embodiments, the methods include the step of providing plant tissue in which ac-TAGs are present; this step is based upon the hypothesis that the presence of ac-TAGs in plant tissue, preferably seed tissue, is indicative of the presence of DGAT with diacylglycerol acetyltransferase activity, or a DAcT. Ac-TAG is present in a tissue if it is present at greater than about 1% of the total TAGs in that tissue; in preferred embodiments, ac-TAGs are present at greater than about 5% of the total TAGs in that tissue, or present at greater than about 10% of the total TAGs in that tissue.

In some embodiments, method involve obtaining a cDNA for DAcT by using RT-PCR with degenerate primers to give a partial length clone, and subsequently using 3' and 5' RACE to define the 3' and 5' cDNA ends. A full length cDNA clone is then obtained via RT-PCR using primers based on the sequence of the 3' and 5' RACE products; this clone is then used to confirm the identity of the encoded polypeptide as a DAcT. Confirmation of the identity of the encoded polypeptide includes expressing the polypeptide of the sequence encoding a putative DAcT (for example the full length cDNA clone), and characterizing the polypeptide of the putative DAcT coding sequence.

Characterization includes but is not limited to detecting the presence of the expressed polypeptide by antibody-binding (where, for example, the antibody is specific for DAcT, such as by binding to *Euonymus* DAcT) or by detecting the reaction products of the expressed polypeptide as in any of the DAcT assays described above. In further embodiments, ac-TAGs are present in the tissue from which the cDNA is prepared.

In some other embodiments, methods involve the preparation of a cDNA library from tissue; in further embodiments, ac-TAGs are present in the tissue from which the cDNA library is prepared. In some preferred embodiments, ac-TAGs are present in relatively high levels, at greater than about 25% of the total TAGs in the tissue, or at greater than about 50% of the total TAGs in the tissue. The cDNA library may be screened by hybridization with a DGAT probe, or with a DAcT probe (obtained, for example, from SEQ ID NO:1). cDNA clones are identified which appear to encode a DGAT or a DAcT; in other embodiments, cDNA clones are identified which appear to code for a portion of a DGAT or DAcT, and which can be assembled into or utilized to create a complete coding sequence. Further embodiments include confirmation of a coding sequence as a DAcT, as described above.

In yet other embodiments, methods involve first an examination of a plant expressed sequence tag (EST) database, in order to discover novel potential DGAT encoding sequences. Preferably, the plant source of the EST database comprises tissue in which ac-TAGs are present, such as its seed tissue. In some embodiments, examination of a plant EST database involves blasting the database with the amino acid sequence of the *Euonymus* DAcT (for example, SEQ ID NO:1) in order to discover ESTs encoding amino acid sequences with homology to the *Euonymus* DAcT protein. In some further embodiments, the methods involve next assembling a clone encoding a complete putative DAcT, and characterizing the expression products of such sequences so discovered as described above. In other further embodiments, these methods next involve sequencing likely candidate sequences, and characterizing the expression products of such sequences so discovered as described above. In some embodiments, DAcT coding sequences, discovered by the methods of the present invention, can also be used to identify and isolate other plant genes. To isolate a gene, a $^{32}$P-radiolabeled DAcT coding sequence (or cDNA) is used to screen, by DNA-DNA hybridization, a genomic library constructed from a plant genomic DNA. In further embodiments, ac-TAGs are present in the tissue from which the cDNA is prepared. Single isolated clones that test positive for hybridization are proposed to contain part or all of a DAcT gene, and are sequenced. The sequence of the positive cloned plant genomic DNA is used to confirm the identity of the gene as a DAcT. If a particular clone encodes only part of the gene, additional clones that test positive for hybridization to the DAcT coding sequence (or cDNA) are isolated and sequenced. Comparison of the full-length sequence of a putative DAcT gene to a cDNA is used to determine the location of introns, if they are present.

In other embodiments of the present invention, upstream sequences such as promoters and regulatory elements of a gene encoding a DAcT are detected by extending the gene by utilizing a nucleotide sequence encoding DAcT (for example, SEQ ID NO:10) in various methods known in the art. In some embodiments, it is contemplated that polymerase chain reaction (PCR) finds use in the present invention. This is a direct method that uses universal primers to retrieve unknown sequence adjacent to a known locus (Gobinda, et. al. (1993) PCR Methods Applic., 2:318-322, herein incorporated by reference). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia, et. al. (1988) Nucleic Acids Res., 16:8186, herein incorporated by reference). The primers may be designed using Oligo 4.0 (National Biosciences Inc, Plymouth Minn.), or another appropriate program, to be, for example, 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In yet other embodiments of the present invention, capture PCR (Lagerstrom, et. al. (1991) PCR Methods Applic., 1:111-119, herein incorporated by reference) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker, et. al. (1991) Nucleic Acids Res., 19:3055-60, herein incorporated by reference). The PROMOTERFINDER kit (Clontech) uses PCR, nested primers and special libraries to "walk in" genomic DNA.

This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, (1995); Lui, et. al. (1995), each of which are herein incorporated by reference).

Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic libraries are useful for obtaining introns and extending 5' sequence.

It is contemplated that the methods described above are used to discover other DAcT gene coding sequences and genes from plants that are known to possess ac-TAGs. Exemplary plants include those from families Celastraceae, Lardizabalaceae, Rosaceae and Ranunculaceae.

V. Variants of Diacylglycerol Acetyltransferase.

In some embodiments, the present invention provides isolated variants of the disclosed nucleic acid sequence encoding DAcT, and the polypeptides encoded thereby; these variants include mutants, fragments, fusion proteins, or functional equivalents of DAcT. Thus, nucleotide sequences of the present invention are engineered in order to alter a DAcT coding sequence for a variety of reasons, including but not limited to alterations that modify the cloning, processing and/or expression of the gene product (such alterations include inserting new restriction sites, altering glycosylation patterns, and changing codon preference) as well as varying the enzymatic activity (such changes include but are not limited to differing substrate affinities, differing substrate preferences and utilization, differing inhibitor affinities or effectiveness, differing reaction kinetics, varying subcellular localization, and varying protein processing and/or stability). For example, mutations are introduced which alter the substrate specificity, such that the preferred substrate is changed.

A. Mutants and Homologs of a Plant Diacylglycerol Acetyltransferase.

Some embodiments of the present invention provide mutant forms of a DAcT (in other words, muteins). In preferred embodiments, variants result from mutation, (in other words, a change in the nucleic acid sequence) and generally produce altered mRNAs or polypeptides whose structure or function may or may not be altered. Any given gene may have none, one, or many mutant forms. Common mutational changes that give rise to variants are generally ascribed to deletions, additions or substitutions of nucleic acids.

Each of these types of changes may occur alone, or in combination with the others, and at the rate of one or more times in a given sequence. Still other embodiments of the present invention provide isolated nucleic acid sequence encoding DAcT homologs, and the polypeptides encoded thereby.

It is contemplated that is possible to modify the structure of a peptide having an activity (for example, a diacylglycerol acetyltransferase activity) for such purposes as increasing synthetic activity or altering the affinity of the DAcT for a substrate, or for increasing stability or turnover or subcellular location of the polypeptide. Such modified peptides are considered functional equivalents of peptides having an activity of a DAcT as defined herein. A modified peptide can be produced in which the nucleotide sequence encoding the polypeptide has been altered, such as by substitution, deletion, or addition.

In some preferred embodiments of the present invention, the alteration increases synthetic activity or alters the affinity of the DAcT for a particular acetyl- or related group-CoA or acetyl or related group acceptor substrate. In particularly preferred embodiments, these modifications do not significantly reduce the synthetic activity of the modified enzyme. In other words, construct "X" can be evaluated in order to determine whether it is a member of the genus of modified or variant DAcT of the present invention as defined functionally, rather than structurally. In preferred embodiments, the activity of variant DAcT is evaluated by the methods described in the Examples. Accordingly, in some embodiments the present invention provides nucleic acids encoding a DAcT that complement the coding region of SEQ ID NO:1. In other embodiments, the present invention provides nucleic acids encoding a DAcT that compete for the binding of diacylglycerol or acetyl substrates with the protein encoded by SEQ ID NO:1.

In other preferred embodiments of the alteration, the alteration results in intracellular half-lives dramatically different from that of the corresponding wild-type protein. For example, an altered protein is rendered either more stable or less stable to proteolytic degradation or other cellular process that result in destruction of, or otherwise inactivate DAcT. Such homologs, and the genes that encode them, can be utilized to alter the activity of DAcT by modulating the half-life of the protein. For instance, a short half-life can give rise to more transient DAcT biological effects. Other variants have characteristics which are either similar to wild-type DAcT, or which differ in one or more respects from wild-type DAcT.

As described above, mutant forms of a DAcT are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (in other words, conservative mutations) will not have a major effect on the biological activity of the resulting molecule. Accordingly, some embodiments of the present invention provide variants of a DAcT disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (for example, Stryer, ed. (1981) Biochemistry, pg. 17-21, 2nd ed, WH Freeman and Co., herein incorporated by reference). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (for example, replacement of a glycine with a tryptophan). Analogous minor variations can also include amino acid deletions or insertions, or both. Guidance in determining which amino acid residues can be substituted, inserted, or deleted without abolishing biological activity can be found using computer programs (for example, LASERGENE software, DNASTAR Inc., Madison, Wis.).

Mutants of a DAcT can be generated by any suitable method well known in the art, including but not limited to site-directed mutagenesis, randomized "point" mutagenesis, and domain-swap mutagenesis in which portions of the Euonymus DGAT cDNA are "swapped" with the analogous portion of other plant or bacterial DGAT-encoding cDNAs (Back and Chappell (1996) PNAS 93: 6841-6845, herein incorporated by reference).

Variants may be produced by methods such as directed evolution or other techniques for producing combinatorial libraries of variants. Thus, the present invention further contemplates a method of generating sets of combinatorial mutants of the present DAcT proteins, as well as truncation mutants, and is especially useful for identifying potential variant sequences (in other words, homologs) that possess the biological activity of a DAcT of the present invention (for example, transfer of an acetyl or related group to diacylglycerol). In addition, screening such combinatorial libraries is used to generate, for example, novel DAcT homologs that possess novel substrate specificities or other biological activities; examples of substrate specificities are described above.

It is contemplated that the DAcT nucleic acids (for example, SEQ ID NO:1 and fragments and variants thereof) can be utilized as starting nucleic acids for directed evolution. These techniques can be utilized to develop DAcT variants having desirable properties such as increased synthetic activity or altered affinity for a particular acyl-CoA or acyl acceptor substrate.

In some embodiments, artificial evolution is performed by random mutagenesis (for example, by utilizing error-prone PCR to introduce random mutations into a given coding sequence). This method requires that the frequency of mutation be finely tuned.

As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458-67; Leung et al. (1989) Technique, 1:11-15; Eckert and Kunkel (1991) PCR Methods Appl., 1:17-24; Caldwell and Joyce (1992) PCR Methods Appl., 2:28-33; and Zhao and Arnold (1997) Nuc. Acids. Res., 25:1307-08, all of which are herein incorporated by reference). After mutagenesis, the resulting clones are selected for desirable activity (for example, screened for diacylglycerol acetyltransferase activity as described subsequently). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (for example, Smith (1994) Nature, 370:324-25; U.S. Pat. Nos. 5,837,458; 5,830,721; 5,811,238; 5,733,731, all of which are herein incorporated by reference). Gene shuffling involves random fragmentation of several mutant DNAs followed by their reassembly by PCR into full-length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398-91; Stemmer (1994) Proc. Natl. Acad. Sci. USA, 91, 10747-10751; Crameri et al. (1996) Nat. Biotech., 14:315-319; Zhang, et. al. (1997) Proc. Natl. Acad. Sci. USA, 94:4504-09; and Crameri, et. al. (1997) Nat. Biotech., 15:436-38, all of which are herein incorporated by reference). Variants produced by directed evolution can be screened for DGAT activity by the methods described subsequently (see, for example, Example II).

In some embodiments of a combinatorial mutagenesis approach of the present invention, the amino acid sequences of a population of DAcT coding sequences are aligned, preferably to promote the highest homology possible. Such a population of variants can include, for example, DAcT homologs from one or more species, or DAcT homologs from the same species but which differ due to mutation. Amino acids that appear at each position of the aligned sequences are selected to create a degenerate set of combinatorial sequences.

In preferred embodiments of the present invention, the combinatorial DAcT library is produced by way of a degenerate library of genes encoding a library of polypeptides that each includes at least a portion of candidate DAcT-protein sequences. For example, a mixture of synthetic oligonucleotides is enzymatically ligated into gene sequences such that the degenerate set of candidate DAcT sequences are expressible as individual polypeptides, or alternatively, as a set of larger fusion proteins (for example, for phage display) containing the set of DAcT sequences therein.

There are many ways by which the library of potential DAcT homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential DAcT sequences. The synthesis of degenerate oligonucleotides is well known in the art (see, for example, Narang, Tetrahedron Lett., 39:3-9 (1983); Itakura, et. al. Recombinant DNA, in Walton (ed.), Proceedings of the 3rd Cleveland Symposium on Macromolecules, Elsevier, Amsterdam, pp 273-289 (1981); Itakura, et. al. Annu. Rev. Biochem., 53:323 (1984); Itakura, et. al. Science 198:1056 (1984); Ike, et. al, Nucl. Acid Res., 11:477 (1983), all of which are herein incorporated by reference). Such techniques have been employed in the directed evolution of other proteins (See for example, Scott, et. al. Science, 249:386-390 (1980); Roberts, et. al. Proc. Natl. Acad. Sci. USA, 89:2429-2433 (1992); Devlin, et. al. Science, 249:404-406 (1990); Cwirla, et. al. Proc. Natl. Acad. Sci. USA, 87:6378-6382 (1990); as well as U.S. Pat. Nos. 5,223,409, 5,198,346, and 5,096,815; all of which are herein incorporated by reference).

B. Truncation Mutants of Plant Diacylglycerol Acetyltransferase.

In addition, the present invention provides isolated nucleic acid sequences encoding fragments of DAcT (in other words, truncation mutants), and the polypeptides encoded by such nucleic acid sequences. In preferred embodiments, the DAcT fragment is biologically active.

In some embodiments of the present invention, when expression of a portion of a DAcT protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat, et. al. (1987) J. Bacteriol., 169:751-757, herein incorporated by reference) and *Salmonella typhimurium* and its in vitro activity has been demonstrated on recombinant proteins (Miller, et. al. (1990) Proc. Natl. Acad, Sci. USA, 84:2718-1722, herein incorporated by reference). Therefore, removal of an N-terminal methionine, if desired, can be achieved either in vivo by expressing such recombinant polypeptides in a host that produces MAP (for example, *E. coli* or CM89 or *S. cerevisiae*), or in vitro by use of purified MAP.

C. Fusion Proteins Containing Plant Diacylglycerol Acetyltransferase.

The present invention also provides nucleic acid sequences encoding fusion proteins incorporating all or part of DAcT, and the polypeptides encoded by such nucleic acid sequences. In some embodiments, the fusion proteins have a DAcT functional domain with a fusion partner. Accordingly, in some embodiments of the present invention, the coding sequences for the polypeptide (for example, a DAcT functional domain) is incorporated as a part of a fusion gene including a nucleotide sequence encoding a different polypeptide. In one embodiment, a single fusion product polypeptide transfers an acetyl group to diacylglycerol (one fusion partner possesses the ability to synthesize ac-TAG).

In some embodiments of the present invention, chimeric constructs code for fusion proteins containing a portion of a DAcT and a portion of another gene. In some embodiments, the fusion proteins have biological activity similar to the wild type DAcT (for example, have at least one desired biological activity of DAcT). In other embodiments, the fusion proteins have altered biological activity.

In other embodiments of the present invention, chimeric constructs code for fusion proteins containing a DAcT gene or portion thereof and a leader or other signal sequences which direct the protein to targeted subcellular locations. Such sequences are well known in the art and direct proteins to locations such as the chloroplast, the mitochondria, the endoplasmic reticulum, the tonoplast, the Golgi network, and the plasmalemma.

In addition to utilizing fusion proteins to alter biological activity, it is widely appreciated that fusion proteins can also facilitate the expression and/or purification of proteins, such as a DAcT protein of the present invention. Accordingly, in some embodiments of the present invention, a DAcT is generated as a glutathione-S-transferase (in other words, GST fusion protein). It is contemplated that such GST fusion proteins enables easy purification of a DAcT, such as by the use of glutathione-derivatized matrices (see, for example, Ausubel, et. al. (eds.) (1991) Current Protocols in Molecular Biology, John Wiley & Sons, New York, herein incorporated by reference).

In another embodiment of the present invention, a fusion gene coding for a purification leader sequence, such as a poly-(His)/enterokinase cleavage site sequence at the N-terminus of the desired portion of a DAcT allows purification of the expressed DAcT fusion protein by affinity chromatography using a $Ni^{2+}$ metal resin. In still another embodiment of the present invention, the purification leader sequence is then subsequently removed by treatment with enterokinase (see, for example, Hochuli, et. al. (1987) J. Chroniatogr., 411:177; and Janknecht, et. al. Proc. Natl. Acad. Sci. USA, 88:8972, herein incorporated by reference). In yet other embodiments of the present invention, a fusion gene coding for a purification sequence appended to either the N (amino) or the C (carboxy) terminus allows for affinity purification; one example is addition of a hexahistidine tag to the carboxy terminus of a DAcT, which is contemplated to be useful for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See for example, Current Protocols in Molecular Biology, supra). In yet other embodiments of the present invention, epitope tags of DAcT are prepared. Epitope tags are prepared as described by Lin et al., who epitope tagged a human ACAT (AcylCoA:cholesterol acyltransferase) a gene in the same gene family as DGAT. The epitope tags were single HA tags placed internally at 12 well distributed sites along the polypeptide and a C-terminal HIS tag, where the protein retained full or partial activity with these tags.

D. Screening Gene Products.

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of DAcT homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate DAcT gene products are displayed on the surface of a cell or viral particle, and the ability of particular cells or viral particles to synthesize ac-TAGs is assayed using the techniques described in the Examples. In other embodiments of the present invention, the gene library is cloned into the gene for a surface membrane protein of a bacterial cell, and the resulting fusion protein detected by panning (WO 88/06630; Fuchs, et. al. (1991) BioTechnol., 9:1370-1371; and Goward, et. al. (1992) TIBS 18:136-140, each of which is herein incorporated by reference). In other embodiments of the present invention, fluorescently labeled molecules that bind DAcT can be used to score for potentially functional DAcT homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phages can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (See, for example, WO 90/02909; WO 92/09690; Marks, et. al. (1992) J. Biol. Chem., 267:16007-16010; Griffths et al. (1993) EMBO J., 12:725-734; Clackson, et. al. (1991) Nature, 352:624-628; and Barbas, et. al. (1992) Proc. Natl. Acad. Sci., 89:4457-4461, all of which are herein incorporated by reference).

In another embodiment of the present invention, the recombinant phage antibody system (for example, RPAS, Pharmacia Catalog number 27-9400-01) is modified for use in expressing and screening of DAcT combinatorial libraries. The pCANTAB phagemid of the RPAS kit contains the gene that encodes the phage gIII coat protein. In some embodiments of the present invention, the DAcT combinatorial gene library is cloned into the phagemid adjacent to the gIII signal sequence such that it is expressed as a gIII fusion protein. In other embodiments of the present invention, the phagemid is used to transform competent E. colt TG1 cells after ligation. In still other embodiments of the present invention, transformed cells are subsequently infected with M13KO7 helper phage to rescue the phagemid and its candidate DAcT gene insert. The resulting recombinant phage contains phagemid DNA encoding a specific candidate DAcT-protein and display one or more copies of the corresponding fusion coat protein. In some embodiments of the present invention, the phage-displayed candidate proteins that are capable of, for example, metabolizing a hydroperoxide, are selected or enriched by panning. The bound phage is then isolated, and if the recombinant phage expresses at least one copy of the wild type gIII coat protein, they will retain their ability to infect E. coli. Thus, successive rounds of reinfection of E. coli and panning will greatly enrich for DAcT homologs, which can then be screened for further biological activities in order to differentiate agonists and antagonists.

In another embodiment of the present invention, the gene library is expressed in the TAG deficient mutant H1246 and transformants selected on medium containing high levels of a particular fatty acid. Growth on high levels of fatty acids in the absence of TAG synthesis genes is lethal (see, for example, Siloto, et. al. (2009). Plant Physiol. Biochem. 47:456-461, herein incorporated by reference). Thus colonies possessing functional DGAT enzymes capable of using the selective fatty acid as a substrate will survive, permitting selection of different enzymes with different fatty acid specificities.

In light of the present disclosure, other forms of mutagenesis generally applicable will be apparent to those skilled in the art in addition to the aforementioned rational mutagenesis based on conserved versus non-conserved residues. For example, DAcT homologs can be generated and screened using, for example, alanine scanning mutagenesis and the like (Ruf, et. al. (1994) Biochem., 33:1565-1572; Wang, et. al. (1994) J. Biol. Chem., 269:3095-3099; Balint (1993) Gene 137:109-118; Grodberg, et. al. (1993) Eur. J. Biochem., 218: 597-601; Nagashima, et. al. (1993) J. Biol. Chem., 268:2888-2892; Lowman, et. al. (1991) Biochem., 30:10832-10838; and Cunningham, et. al. (1989) Science, 244:1081-1085), by linker scanning mutagenesis (Gustin, et. al. (1993) Virol., 193:653-660; Brown, et. al. (1992) Mol. Cell. Biol., 12:2644-2652; McKnight, et. al. Science, 232:316); or by saturation mutagenesis (Meyers, et. al. (1986) Science, 232:613, all of which are herein incorporated by reference).

VI. Expression of Cloned Diacylglycerol Acetyltransferase.

In other embodiment of the present invention, nucleic acid sequences corresponding to the DAcT genes, homologs and mutants as described above may be used to generate recombinant DNA molecules that direct the expression of the encoded protein product in appropriate host cells.

DAcT-encoding nucleotide sequences possessing non-naturally occurring codons may also find use for producing novel oils. Therefore, in some preferred embodiments, codons preferred by a particular prokaryotic or eukaryotic host (Murray, et. al. (1989) Nucl. Acids Res., 17:477-498, herein incorporated by reference) can be selected, for example, to increase the rate of DAcT expression or to produce recombinant RNA transcripts having desirable properties, such as a longer half-life, than transcripts produced from naturally occurring sequence.

A. Vectors for Production of Plant Diacylglycerol Acetyltransferase.

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic acid sequences as broadly described above (for example, SEQ ID NO: 1). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial constructs, such as pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector, including vectors for use with *Agrobacterium* expression systems, plant cell, plant seed expression, algal expression, fungal, i.e. yeast expression, may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, a nucleic acid sequence of the present invention within an expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (for example, dihydrofolate reductase or neomycin resistance for eukaryotic cell culture, or tetracycline or ampicillin resistance in *E. coli*).

In some embodiments of the present invention, transcription of the DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Plant Diacylglycerol Acetyltransferase.

In a further embodiment, the present invention provides host cells containing any of the above-described constructs. In some embodiments of the present invention, the host cell is a higher eukaryotic cell (for example, a plant cell). In other embodiments of the present invention, the host cell is a lower eukaryotic cell (for example, a yeast cell). In still other embodiments of the present invention, the host cell can be a prokaryotic cell (for example, a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman (1981) Cell 23:175, herein incorporated by reference), 293T, C127, 3T3, HeLa and BHK cell lines, NT-1 (tobacco cell culture line), root cell and cultured roots in rhizosecretion (Gleba, et. al. (1999) Proc Natl Acad Sci USA 96:5973-5977, herein incorporated by reference).

Other examples include microspore-derived cultures of oilseed rape (Weselake and Taylor (1999) Prog. Lipid Res. 38:401, herein incorporated by reference), and transformation of pollen and microspore culture systems. Further examples are described in the Examples.

The constructs in host cells can be used in a conventional manner to produce the gene product encoded by any of the recombinant sequences of the present invention described above. In some embodiments, introduction of the construct into the host cell can be accomplished by calcium phosphate transfection, DEAE-Dextran mediated transfection, or electroporation (See for example, Davis et al. (1986) Basic Methods in Molecular Biology, herein incorporated by reference). Alternatively, in some embodiments of the present invention, a polypeptide of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from a DNA construct of the present invention. Appropriate cloning and expression vectors for use with prokaryotic and eukaryotic hosts are described by Sambrook, et. al. (1989), Molecular Cloning: A Laboratory Manual, Second Edition, Cold Spring Harbor, N.Y., herein incorporated by reference.

In some embodiments of the present invention, following transformation of a suitable host strain and growth of the host strain to an appropriate cell density, the selected promoter is induced by appropriate means (for example, temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

VII. Production of Acetyl-TAGs.

In one aspect of the present invention, methods are provided for producing acetyl glycerides (ac-TAGs). Although the following methods are described in terms of production of ac-TAGs, it is understood that these methods are also applicable to a DAcT that transfers a related group, resulting in production of TAGs to which the group related to acetate is transferred. In some embodiments, ac-TAGs are produced in vivo, in organisms transformed with a heterologous gene encoding a polypeptide exhibiting diacylglycerol acetyltransferase activity and grown under conditions sufficient to effect production of ac-TAGs. In other embodiments, ac-TAGs are produced in vitro, from either nucleic acid sequences encoding a DAcT of the present invention or from polypeptides exhibiting diacylglycerol acetyltransferase activity.

A. Novel TAGs.

By controlling the type of substrate, it is possible to produce novel TAGs. For example, the results from expression of *Euonymus* DAcT (EaDAcT) in yeast cells (as described in Example V) demonstrate that a triacylglycerol species acetyldipahnitolein was produced; this triacylglycerol species has not been previously reported in yeast cells, and is therefore novel. It is further contemplated that the use of the EaDAcT can be used to produce structures such as acetyldiricinolein; acetyldivemolin, or acetyldicaprin; these structures also have not been previously reported, and are therefore novel.

In some embodiments, novel compounds are produced by incubating a EaDAcT enzyme with acetyl-CoA and the appropriate DAG substrate (for example, diricinolein or divernolin) under suitable conditions such that the ac-TAG products are synthesized. In other embodiments, novel compounds are produced by incubating a EaDAcT enzyme with a DAG substrate and an appropriate related group-CoA (for example, cinnamoyl) under suitable conditions such that novel TAG products (for example, cinnamoyl-TAG, etc.) are synthesized. It is contemplated that cinnamoyl-TAG will absorb UV and can be used in sunscreens. Exemplary suitable conditions for incubations are described below and in the Examples for DGAT assays.

Such compounds can be produced in vivo by transforming a plant in which the appropriate DAG substrate is present with a gene encoding EaDAcT under control of a suitable promoter (see, for example, Example V), such that EaDAcT is expressed when and where the appropriate DAG and acyl-CoA substrates are synthesized, resulting in the synthesis of a novel TAG. The DAG and acyl-CoA substrates may be endogenous substrates, or may be the products of expression of additional genes, including genes for biosynthetic enzymes or for up-regulating pathways. As one example, a host plant cell may express mutant fae1 genes for lowering lc-TAG production and increasing ac-TAG production, Example XII.

B. In Vivo Production in Transgenic Organism.

In some embodiments of the present invention, ac-TAGs are produced in vivo, by providing an organism transformed with a heterologous gene encoding a DAcT of the present invention and growing the transgenic organism under conditions sufficient to effect production of ac-TAGs. In other embodiments of the present invention, ac-TAGs are produced in vivo by transforming an organism with a heterologous gene encoding a DAcT of the present invention and growing the transgenic organism under conditions sufficient to effect production of ac-TAGs. Illustrative examples of transgenic organisms are described below and provided in the Examples.

Organisms which are transformed with a heterologous gene encoding a DAcT of the present invention include preferably those which naturally synthesize and store in some manner triacylglycerols (TAGs), and those which are commercially feasible to grow and suitable for harvesting large amounts of the TAG products. Such organisms include but are not limited to, oleaginous yeast and algae, and plants and animals. Examples of yeasts include oleaginous yeast, which include but are not limited to the genera *Lipomyces, Candida, Rhodotorula, Rhodosporidium* and *Cryptococcus*, which can be grown in commercial-scale fermenters. Examples of plants include preferably oil-producing plants, such as soybean, rapeseed and canola, sunflower, cotton, corn, cocoa, safflower, oil palm, coconut palm, flax, castor, and peanut. Many commercial cultivars can be transformed with heterologous genes. In cases where that is not possible, non-commercial cultivars of plants can be transformed, and the trait for expression of DAcT of the present invention moved to commercial cultivars by breeding techniques well known in the art.

A heterologous gene encoding a DAcT of the present invention, which includes variants of a DAcT, includes any suitable sequence of the invention as described above. Preferably, the heterologous gene is provided within an expression vector such that transformation with the vector results in expression of the polypeptide; suitable vectors are described above and following.

A transgenic organism is grown under conditions sufficient to effect production of ac-TAGs. In some embodiments of the present invention, a transgenic organism is supplied with exogenous substrates of the DAcT (for example, in a fermentor). Such substrates can comprise sugars as carbon sources for TAG synthesis, fatty acids and glycerol used directly for the production of DAG and TAG, DAG itself, and acetic acid which will both provide a general carbon source and be used for the production of acetyl-CoA and/or diacylglycerols (DAGs). When related groups are transferred to DAG, such substrates may instead or in addition be provided to the transgenic organism; exemplary related group include but are not limited to butyrate, propionate, and cinnamate. Substrates may be supplied in various forms as are well known in the art; such forms include aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters.

In yet other embodiments of the present invention, a transgenic organism comprises a heterologous gene encoding a DAcT of the present invention operably linked to an inducible promoter, and is grown either in the presence of the an inducing agent, or is grown and then exposed to an inducing agent. In still other embodiments of the present invention, a transgenic organism comprises a heterologous gene encoding a DAcT of the present invention operably linked to a promoter which is either tissue specific or developmentally specific, and is grown to the point at which the tissue is developed or the developmental stage at which the developmentally specific promoter is activated. Such promoters include seed specific promoters.

In alternative embodiments, a transgenic organism as described above is engineered to produce greater amounts of the diacylglycerol substrate. Thus, it is contemplated that a transgenic organism may include further modifications such that fatty acid synthesis is increased, and may in addition or instead include exogenous acyltransferases, phosphatidylcholine:diacylglycerol cholinephosphotransferase and/or phosphatidic acid phosphatases. In one exemplary embodiment, fatty acid synthesis is altered by producing nonfunctional FAE1 protein, i.e. truncated mutant FAE1 protein. In one exemplary embodiment, fatty acid synthesis is altered by reducing FAE1 protein production. In other embodiments of the present invention, a host organism produces large amounts of a desired substrate, such as acetyl-CoA or DAG; non-limiting examples include organisms transformed with genes encoding acetyl-CoA synthetases and/or ATP citrate lyase.

In some embodiments, it is contemplated that certain DAGs will result in the synthesis of novel ac-TAGs with desirable properties. Thus, a particularly suitable host is one that produces a high proportion of such a DAG. Such hosts may include organisms with high levels of oleic, ricinoleic or vernolic acids, or of short- and medium-chain fatty acids. These hosts may include plants such as *Cuphea, Vemonia* or *Euphorbia* species, which are undergoing domestication; plants such as *Ricinus communis*, which is a specialty oil crop; plants such as *Brassica* and soybean, for which high oleic lines have been developed; and transgenic plants where the endogenous fatty acid composition of the seed oil has been altered by seed-specific expression of biosynthetic genes.

In other embodiments, a host organism produces low amounts of endogenous TAGs but retain the capacity to up-regulate the synthesis of DAG when there is a draw on the DAG pool. It is contemplated that in such hosts, novel TAGs produced from an exogenous DAcT are a higher proportion of the total TAGs; advantages include less expensive purification of the novel TAGs. Non-limiting exemplary hosts include those with low endogenous DGAT activity (either or both DGAT1 or DGAT2), PDAT activity or other acyltransferase activity resulting in the synthesis of TAGs. Such hosts may occur naturally or via genetic engineering techniques. Non-limiting exemplary techniques include knock-out produced by EMS and transposon tagging.

In other embodiments of the present invention, the methods for producing ac-TAGs further comprise collecting the ac-TAGs produced. Such methods are known generally in the art, and include harvesting the transgenic organisms and extracting the ac-TAGs (see, for example, Christie, (1982) Lipid Analysis, 2nd Edition (Pergamon Press, Oxford); and Kates, (1986) Techniques of Lipidology (Elsevier, Amsterdam), all of which are herein incorporated by reference). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37:911-917, herein incorporated by reference). In another embodiment lipids are extracted by pressing of the seed or other plant parts and by hexane extraction, the solvent evaporated, and the oil refined by degumming, neutralization, bleaching, filtration, deodorization and other processes commonly practiced in the vegetable oil industry. In yet other embodiments of the present invention, the AcTAGs are further purified, for example by thin layer liquid chromatography, gas-liquid chromatography, counter current chromatography, high performance liquid chromatography, high-temperature, reduced pressure distillation, and the like.

1. Transgenic Plants, Seeds, and Plant Parts.

Plants are transformed with at least a heterologous gene encoding a DAcT of the present invention according to procedures well known in the art. It is contemplated that the heterologous gene is utilized to increase the level of the enzyme activities encoded by the heterologous gene.

a. Plants.

The methods of the present invention are not limited to any particular plant. Indeed, a variety of plants are contemplated, including but not limited to tomato, potato, tobacco, pepper, rice, corn, barley, wheat, *Brassica, Arabidopsis*, sunflower, soybean, poplar, and pine. Preferred plants include oil-producing species, which are plant species that produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species undergoing domestication, such as *Vernonia* and *Cuphea*, which may be a source of unique fatty acids. In addition plant lines where the endogenous DGAT gene(s) has been inactivated by any method, but including mutagenesis (Katavic et al, 1995 and Zou et al., 1999, herein incorporated by reference), transposon tagging (Routaboul et al., 1999, herein incorporated by reference), hairpin RNA (Stoutjesdijk et al. (2002) Plant Physiol. 129: 1723; Liu et al. (2002) Plant Physiol. 129:1732) and chimeraplasty (Beetham et al. (1999) Proc. Natl. Acad. Sci. USA 96:8774; Zhu et al. (2000) Nat. Biotechnol. 18:555, all of which are herein incorporated by reference) are considered ideal for optimum when used in conjunction with expression of the *Euonymus* DAcT gene. In addition lines where DGAT genes from other gene families and other routes to TAG such as PDAT have been down regulated are contemplated. In addition plants engineered to make increased amounts of medium chain fatty acids (which are consequently incorporated into DAG and then into TAG) are contemplate for transformation with DAcT to produce oil with further reductions in kinematic viscosity. Such plant engineering would be accomplished by methods comprising altering fatty acid synthesizing enzymes, such as acyl-ACP thioesterases, i.e. FATB enzymes and a FATB genetic engineering strategy (see, for examples, Dehesh, et. al. (1996) Plant. Physiol. 110:203-210; Dehesh, et. al. (1996) Plant J. 9:167-172, herein incorporated by reference). Different plant lines may have different seed oil fatty acid compositions, which may be generated by selection, mutagenesis or a genetic engineering strategy, and thus may furnish different products when transformed with DAcT of this invention. For example, low and high saturated fatty acid, high oleic and high linoleic lines of sunflower are available (Gunstone and Pollard, 2001, chapter 6, in "Structured and Modified Lipids (ed. Gunstone), Marcel Dekker, New York, herein incorporated by reference), and each will give a distinctive ac-TAG composition in DAcT-transformed sunflower.

Additional types of natural and engineered plants are contemplated for use in the present inventions, such plants produce low levels of TAGs comprising short chain TAGs, medium chain TAGs and combinations thereof. These results shown in the Examples provide support for the use of such plants for enriching ac-TAG products in these plants. In some embodiments, the oils produced by such plants expressing a nucleic acid of the present inventions would be novel oils. Further, the utility of EaDAcT contemplated for providing engineered oilseeds (including *Cuphea* sp., FATB co-transformed plants, etc.) is provided herein.

b. Vectors.

The methods of the present invention contemplate the use of at least a heterologous gene encoding a DAcT of the present invention, as described above. Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F, M. et al. (1989) Current Protocols in Molecular Biology, John Wiley & Sons, New York, N.Y., all of which are herein incorporated by reference).

In general, these vectors comprise a nucleic acid sequence of the invention encoding a DAcT of the present invention (as described above) operably linked to a promoter and other regulatory sequences (for example, enhancers, polyadenylation signals, etc.) required for expression in a plant.

Promoters include but are not limited to constitutive promoters, tissue-, organ-, and developmentally specific promoters, and inducible promoters. Examples of promoters include but are not limited to: constitutive promoter 35S of cauliflower mosaic virus; a wound-inducible promoter from tomato, leucine amino peptidase ("LAP," Chao, et. al. (1999) Plant Physiol 120: 979-992, herein incorporated by reference); a chemically-inducible promoter from tobacco, Pathogenesis-Related 1 (PR1) (induced by salicylic acid and BTH (benzothiadiazole-7-carbothioic acid 5-methyl ester)); a tomato proteinase inhibitor II promoter (PIN2) or LAP promoter (both inducible with methyl jasmonate); a heat shock promoter (U.S. Pat. No. 5,187,267, herein incorporated by reference); a tetracycline-inducible promoter (U.S. Pat. No. 5,057,422, herein incorporated by reference); seed-specific promoters, such as those for seed storage proteins (for example, phaseolin, napin, oleosin, and a promoter for soybean beta conglycin (Beachy et al. (1985) EMBO J. 4: 3047-3053, herein incorporated by reference), and 25 promoter sequences, such as an *Arabidopsis* seed specific promoter used as an exemplary promoter in the Examples, found on BAC T24A18, nucleotides 31032 to 32179, and promoters for lipid biosynthetic genes such as DGAT1 and FAE1 (Lu et al. (2003) Plant Mol. Biol. 52:31-41; Rossak et al. (2001) Plant Mol. Biol. 46:717-725, herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its optimal polyadenylation. Appropriate transcriptional terminators and those which are known to function in plants include, but are not limited to, the CaMV 355 terminator, the tml terminator, the pea rbcS E9 terminator, and the nopaline and oetopine synthase terminator (See for example, Odell, et. al. (1985) Nature 313:810; Rosenberg, et. al. (1987) Gene, 56:125; Guerineau, et. al. (1991) Mol. Gen. Genet., 262:141; Proudfoot (1991) Cell, 64:671; Sanfacon, et. al. Genes Dev., 5:141; Mogen, et. al. (1990) Plant Cell, 2:1261; Munroe, et. al. (1990) Gene, 91:151; Ballad, et. al. (1989) Nucleic Acids Res. 17:7891; Joshi et al. (1987) Nucleic Acid Res., 15:9627, all of which are herein incorporated by reference).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Calais et al. (1987) Genes Develop. 1: 1183, herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone, et. al. (1984) Cell 39:499; Lassoer, et. al. (1991) Plant Molecular Biology 17:229, each of which is herein incorporated by reference), a plant translational consensus sequence (Joshi (1987) Nucleic Acids Research 15:6643), an intron (Luehrsen and Walbot (1991) Mol. Gen. Genet. 225: 81, herein incorporated by reference), and the like, operably linked to the nucleic acid sequence encoding DAcT.

In preparing a construct comprising a nucleic acid sequence encoding DAcT of the present invention, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan, et. al. (1983) Nature 304:184, herein incorporated by reference), the bar gene which confers resistance to the herbicide phosphinothricin (White, et. al. (1990) Nucl Acids Res. 18:1062; Spencer, et. al. (1990) Theor. Appl. Genet. 79:625, herein incorporated by reference), the hph gene which confers resistance to the antibiotic hygromycin (Blochlinger and Diggelmann (1984) Mol. Cell. Biol. 4:2929), and the dhfr gene, which confers resistance to methotrexate (Bourouis, et. al. (1983) EMBO J., 2:1099, herein incorporated by reference).

In some preferred embodiments, the vector is adapted for use in an *Agrobacterium* mediated transfection process (See for example, U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967, herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted DAcT polynucleotide of the present invention can be expressed from these vectors as a fusion protein (for example, coat protein fusion protein) or from its own subgenomic promoter or other promoter. Exemplary methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the E. coli GUS gene and the CaMV 35S transcriptional terminator (for example, WO 93/07278, herein incorporated by reference).

c. Transformation Techniques.

Once a nucleic acid sequence encoding a DAcT of the present invention is operatively linked to an appropriate promoter and inserted into a suitable vector for the particular transformation technique utilized (for example, one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See for example, U.S. Pat. Nos. 5,451,513; 5,545,817; 5,545,818; PCT application WO 95/16783, all of which are herein incorporated by reference). The basic technique for chloroplast transformation involves introducing regions of cloned plastid DNA flanking a selectable marker together with the nucleic acid encoding the RNA sequences of interest into a suitable target tissue (for example, using biolistic techniques or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, et. al. (1990) PNAS, 87:8526; Staub and Maliga, (1992) Plant Cell, 4:39, all of which are herein incorporated by reference). The presence of cloning sites between these markers allowed creation of a plastid targeting vector introduction of foreign DNA molecules (Staub and Maliga (1993) EMBO J., 12:601, herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913, herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet., 202:179, herein incorporated by reference). In still other embodiments, the vector is transferred into the plant cell by using polyethylene glycol (Krens, et. al. (1982) Nature, 296:72; Crossway, et. al. (1986) BioTechniques, 4:320, herein incorporated by reference); fusion of protoplasts with other entities, either minicells, cells, lysosomes or other fusible lipid-surfaced bodies (Fraley, et. al. (1982) Proc. Natl. Acad. Sci., USA, 79:1859, herein incorporated by reference); protoplast transformation (EP 0292435, herein incorporated by reference); direct gene transfer (Paszkowski, et. al. (1984) EMBO J., 3:2717; Hayashimoto, et. al. (1990) Plant Physiol. 93:857, herein incorporated by reference).

In still further embodiments, the vector may also be introduced into the plant cells by electroporation (Fromm, et. al. (1985) Proc. Natl Acad. Sci. USA 82:5824; Riggs, et. al. (1986) Proc. Natl. Acad. Sci. USA 83:5602, herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; and McCabe, et. al. (1988) Biotechnology 6:923, each of which is herein incorporated by reference). See also, Weissinger, et. al. (1988) Annual Rev. Genet. 22:421; Sanford, et. al. (1987) Particulate Science and Technology, 5:27 (onion); Svab, et. al. (1990) Proc. Natl. Acad. Sci. USA, 87:8526 (tobacco chloroplast); Christou, et. al. (1988) Plant Physiol., 107 87:671 (soybean); McCabe, et. al. (1988) Bio/Technology 6:923 (soybean); Klein, et. al. (1988) Proc. Natl. Acad. Sci. USA, 85:4305 (maize); Klein, et. al. (1988) Bio/Technology, 6:559 (maize); Klein, et. al. (1988) Plant Physiol., 91:4404 (maize); Fromm, et. al. (1990) Bio/Technology, 8:833; and Gordon-Kamm, et. al. (1990) Plant Cell, 2:603 (maize); Koziel, et. al. (1993) Biotechnology, 11:194 (maize); Hill, et. al. (1995) Euphytica, 85:119 and Koziel, et, al. (1996) Annals of the New York Academy of Sciences 792:164; Shimamoto, et. al. (1989) Nature 338:274 (rice); Christou, et. al. (1991) Biotechnology, 9:957 (rice); Datta, et. al. (1990) Bio/Technology 8:736 (rice); European Patent Application EP 0332581 (orchardgrass and other Pooideae); Vasil, et. al. (1993) Biotechnology, 11:1553 (wheat); Weeks, et. al. (1993) Plant Physiol., 102:1077 (wheat); Wan, et. al. (1994) Plant Physiol. 104:37 (barley); Jahne, et. al. (1994) Theor. Appl. Genet. 89:525 (barley); Knudsen and Muller (1991) Planta, 185:330 (barley); Umbeck, et. al. (1987) Bio/Technology 5:263 (cotton); Casas, et. al. (1993) Proc. Natl. Acad. Sci. USA 90:11212 (sorghum); Somers, et, al. (1992) Bio/Technology 10:1589 (oat); Torbert, et. al. (1995) Plant Cell Reports, 14:635 (oat); Weeks, et. al. (1993) Plant Physiol., 102:107715 (wheat); Chang, et. al., WO 94/13822 (wheat) and Nehra, et. al. (1994) The Plant Journal, 5:285 (wheat), all of these references are herein incorporated by reference.

In addition to direct transformation, in some embodiments, the vectors comprising a nucleic acid sequence encoding a DAcT of the present invention are transferred using *Agrobacterium*-mediated transformation (Hinchee, et. al. (1988) Biotechnology, 6:915; Ishida et al. (1996) Nature Biotechnology 14:745, herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237:1176, herein incorporated by reference). Species that are susceptible infection by *Agrobacterium* may be transformed in vitro. Alternatively, plants may be transformed in vivo, such as by transformation of a whole plant by *Agrobacterium* infiltration of adult plants, as in a "floral dip" method (Bechtold, et. al. (1993) Cr. Acad. Sci. III—Vie 316:1194-1199, herein incorporated by reference).

d. Regeneration of Whole Plants from Transformed Cells and Tissues.

After selecting for transformed plant material that can express the heterologous gene encoding a DAcT of the present invention, whole plants are regenerated. Plant regeneration from cultured protoplasts is described in Evans et al. (1983) Handbook of Plant Cell Cultures, Vol. 1: (MacMillan Publishing Co. New York); and Vasil (ed.), Cell Culture and Somatic Cell Genetics of Plants, Acad. Press, Orlando, Vol. I (1984), and Vol, III (1986), herein incorporated by reference. It is known that many plants can be regenerated from cultured cells or tissues, including but not limited to all major species of sugarcane, sugar beet, cotton, fruit and other trees, legumes and vegetables, and monocots (for example, the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins, Shoots and roots normally develop simultaneously. Efficient regeneration will depend on the medium, on the genotype, and on the history of the culture. The reproducibility of regeneration depends on the control of these variables.

e. Generation of Transgenic Plant Lines.

In one embodiment, transgenic plant lines will be established from transgenic plants of the present inventions by tissue culture propagation. In some embodiments, progeny transgenic plants and progeny plant lines will be established using founder transgenic plants in plant breeding programs. In some embodiments, said DAcT transgenic plants of the present inventions are heterologous for DAcT genes. In other embodiments, said DAcT transgenic plants of the present inventions are homozygous for DAcT genes. In other embodiments, the presence of nucleic acid sequences encoding a heterologous DAcT of the present invention (including mutants or variants thereof) may be transferred from founder or progeny plants to related plant varieties by traditional plant breeding techniques.

Transgenic plant lines of the present inventions are then utilized for evaluation of oil production and other agronomic traits. In some embodiments, these evaluated plant lines will be used in plant breeding programs for developing commercial varieties and commercial plant lines.

C. In vitro Systems.

In other embodiments of the present invention, ac-TAGs are produced in vitro, from nucleic acid sequences encoding a DAcT of the present inventions. In other embodiments of the present invention, ac-TAGs are produced in vitro, from polypeptides exhibiting a DAcT-like diacylglycerol acetyltransferase activity.

1. Using Nucleic Acid Sequences Encoding a Diacylglycerol Acetyltransferase.

In some embodiments of the present invention, methods for producing ac-TAGs comprise adding an isolated nucleic acid sequence encoding a DAcT of the present invention to in vitro expression systems under conditions sufficient to cause production of ac-TAGs. The isolated nucleic acid sequence encoding a plant acetyltransferase is any suitable sequence of the invention as described above, and preferably is provided within an expression vector such that addition of the vector to an in vitro transcription and translation system results in expression of the polypeptide. Furthermore, the system contemplated is specific for the translation and function of eukaryotic membrane proteins, that is, it is a microsomal system. The system further comprises the substrates for DAcT, as previously described. Alternatively, the system further comprises the means for generating the substrates for a DAcT of the present invention. Such means include but are not limited to those previously described.

In other embodiments of the present invention, the methods for producing large quantities of ac-TAGs further comprise collecting the ac-TAGs produced. Such methods are known generally in the art, and described briefly above. In yet other embodiments of the present invention, the ac-TAGs are further purified, as for example by thin layer liquid chromatography, gas-liquid chromatography, high-pressure liquid chromatography, crystallization and/or vacuum distillation.

2. Using a Diacylglycerol Acetyltransferase Polypeptide.

In some embodiments of the present invention, methods for producing large quantities of ac-TAGs comprise incubating a DAcT of the present invention under conditions sufficient to result in the synthesis of ac-TAGs; generally, such incubation is carried out in a mixture that comprises the DAcT.

A DAcT of the present invention, as described above, is obtained by purification of either naturally occurring DAcT or recombinant DAcT from an organism transformed with heterologous gene encoding a DAcT, as described above. A source of naturally occurring DAcT is contemplated to include but not limited to plants, as for example *Euonymus*, or other members of the plant family Celastraceae, and in addition in the families Lardizabalaceae, Ranunculaceae and Rosaceae. A source of recombinant DAcT is either plant, bacterial or other transgenic organisms, transformed with heterologous gene encoding DAcT of the present invention, as described above. The recombinant DAcT may include a means for improving purification, as for example a 6x-His tag added to the C-terminus of the protein as described above. Alternatively, DAcT is chemically synthesized.

The incubation mixture is further comprises substrates for DAcT, as described above. Alternatively, the inventors contemplate that the mixture further comprises a means for generating substrates for DAcT, such as expressing a gene encoding a protein for making more ac-TAG substrate available for making more ac-TAGs, i.e. increasing the amount of ac-TAG substrate for increasing the amount of ac-TAGs. Ac-TAG substrate is contemplated to be increased by using enzymes, such as using ATP-citrate lyase (EC: 4.1.3.8) to generate acetyl-CoA molecules from a precursor molecule, such as generating acetyl-CoA from citrate. Examples of ATP-citrate lyase are described in Fatland, et. al., Plant Physiology, 130: 740-756 (2002), herein incorporated by reference in its entirety). Alternatively, acetyl-CoA synthetase would be used to generate acetyl-CoA from a precursor molecule, such as acetyl-CoA from acetate. As another alternative, phosphatidic acid phosphatase would be used to generate diacylglycerol from phosphatidic acid. As another alternative, phospholipase C would be used to generate diacylglycerol from phospholipids. In other embodiments of the present invention, the methods for producing ac-TAGs further comprise collecting the ac-TAGs produced; such methods are described above.

VIII. Manipulation of Diacylglycerol Acetyltransferase Activity in Plants.

Further contemplated is that nucleic acids encoding a DAcT of the present invention may be utilized to either increase or decrease the level of DAcT mRNA and/or protein in transfected cells as compared to the levels in wild-type cells. Such transgenic cells have great utility, including but not limited to further research as to the effects of the overexpression of DAcT, and as to the effects as to the underexpression (lower than average of wild-type levels) or a complete lack of DAcT.

A. Increased Diacylglycerol Acetyltransferase Activity.

Accordingly, in some embodiments, expression in plants of nucleic acid sequences encoding a DAcT of the present invention by the methods described above leads to the induced expression and overexpression of DAcT in transgenic plants, plant tissues, or plant cells.

Accordingly, in further embodiments, an increase in DAcT expression corresponds to increased production of ac-TAGs, for example, isolated oils comprise increased amounts of ac-TAGs when compared to isolated oils from unmanipulated plants.

B. Increased Diacylglycerol Acetyltransferase Activity Through Reduced Expression of Other Genes.

In other embodiments of the present invention, nucleic acids encoding lc-TAG synthesizing proteins are utilized to decrease the level of lc-TAG production as compared to wild-type plants, plant tissues, plant cells, or seeds, thus increasing the ac-TAG composition of oil. For example, by altering mRNA and/or protein in transgenic plants, plant tissues, plant cells, or seeds lipid synthesizing proteins are altered by increasing or decreasing overall activity. One method of reducing TAG production utilizes expression of antisense transcripts. Antisense RNA has been used to inhibit plant target genes in a tissue-specific manner (e.g., van der Krol, et. al. (1988) Biotechniques 6:958-976, herein incorporated by reference). Antisense inhibition has been shown using the entire cDNA sequence as well as a partial cDNA sequence (e.g., Sheehy, et, al. (1988) Proc. Natl. Acad. Sci. USA 85:8805-8809; Cannon et al. (1990) Plant Mol. Biol. 15:39-47, herein incorporated by reference). There is also evidence that 3' non-coding sequence fragment and 5' coding sequence fragments, containing as few as 41 base-pairs of a 1.87 kb cDNA, can play important roles in antisense inhibition (Ch'ng, et. al. (1989) Proc. Natl. Acad. Sci. USA 86:10006-10010, herein incorporated by reference).

Accordingly, in some embodiments, nucleic acid sequences encoding lipid-synthesizing proteins for use in reducing TAG production are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA.

Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full-length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al. (1988) Nature 334:585-591, herein incorporated by reference. Ribozymes targeted to the mRNA of a lipid biosynthetic gene, resulting in a heritable increase of the target enzyme substrate, have also been described (Merlo, et. al. (1998) Plant Cell 10:1603-1621, herein incorporated by reference).

Another method comprising nucleic acid sequences encoding lipid synthesizing proteins for use in reducing TAG production utilizes the phenomenon of co-suppression or gene silencing (see, e.g., U.S. Pat. No. 6,063,947, herein incorporated by reference). The phenomenon of co-suppression has also been used to inhibit plant target genes in a tissue-specific manner. Co-suppression of an endogenous gene using a full-length cDNA sequence as well as a partial cDNA sequence (730 bp of a 1770 bp cDNA) is known (e.g., Napoli, et. al. (1990) Plant Cell 2:279-289; van der Krol, et. al. (1990) Plant Cell 2:291-299; and Smith et al. (1990) Mol. Gen. Genetics 224:477-48, all of which are herein incorporated by reference). Accordingly, in some embodiments the nucleic acid sequences encoding a DGAT1, DGAT2, PDAT, etc. polypeptide of the present invention and fragments and variants thereof are expressed in another species of plant to effect co-suppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For co-suppression, the introduced sequence in the expression cassette, needing less than absolute identity, also need not be full-length, relative to either the primary transcription product or fully processed mRNA. This may be preferred to avoid concurrent production in some plants that are overexpressers of the co-suppression cassette. A higher identity in a shorter than full-length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley, et. al. (2001) Plant J. 27: 581-590, herein incorporated by reference).

The inventors contemplate expression of a heterologous DAcT gene and encoded protein of the present inventions in additional host plants (different plant backgrounds) that would be useful for increasing the proportion of ac-TAGs in the seed oil. In one embodiment, a host plant would have low or reduced lc-TAG production. Multiple methods are available for reducing lc-TAG production in plants for use as host plants for inserting DAcT genes of the present inventions for producing oil with a high ac-TAG content. In some embodiments, cultivars of oil crop plants are identified with naturally low production of lc-TAGs in comparison to wild-type plants for use as a host plant. In other embodiments, plants are mutagenized for reducing lc-TAG production for use as a host plant. In yet further embodiments, plants are engineered for reducing lc-TAG production, for example, using RNAi for inhibiting gene expression of proteins providing substrates or inhibiting gene expression of proteins with direct lc-TAG production for use as a host plant. Indeed, it is contemplated that multiple methods of reducing 1 lc-TAG production may be employed together to produce the host plant for DAcT expression. Thus, the inventors contemplate using certain plants with alterations in their genetic capability to synthesize lc-TAGs as hosts for heterologous DAcT expression. In other embodiments, homologous DAcT expression is contemplated. In yet further embodiments, inducible DAcT expression is contemplated.

In some embodiments, alterations in lc-TAG production may be found naturally in plants, for example, a natural variation in lc-Tag production found within and between variants, cultivars and populations of plants (i.e. species and varieties or variations found within species and varieties), such as Arabidopsis plants, Camelina plants, soybean plants, Brassica species, including B. napsus plants. In other embodiments, alterations in seed oil fatty acids were or are induced by mutation. In yet further embodiments, alteration in lc-TAG production may be induced by genetic engineering. In additional embodiments, alterations in lc-TAG production are contemplated to result from a combination of alterations, for example, in one embodiment, identifying a naturally low lc-TAG producing plant for use in mutational and/or genetic engineering for producing oil with a high ac-TAG content.

The strategy for genetic engineering contemplated by the present invention for any particular plant is on a species by species basis, i.e. some plant species will require different compositions and/or method for increasing ac-TAG production for use in the present invention, such different compositions and methods being described herein. For example, a plant of the Brassicea family, where in general Brassicea plants depend on DGAT1 for lc-TAG synthesis, would require genetic manipulation associated with DGAT1 activity. In contrast, in an oilseed plant that is not a member of the Brassicaceae family it may be more important to silence activity associated with the DGAT2 gene. For example, in castor (Ricinus communis L.) the most strongly expressed TAG-synthesis gene in seeds is the DGAT2 gene. DGAT2 expression was induced 18-fold during seed maturation, whereas DGAT1 was barely induced (Kroon, et. al., 2006, Phytochemistry 67:2541-2549, herein incorporated by reference).

One specific example of such a host plant contemplated for use in the present inventions, as a plant affected in its ability to synthesize endogenous lc-TAGs is an *Arabidopsis* plant line having a mutation in a gene associated with lowering lc-TAG production. Such a mutation is contemplated in any one or more of a DGAT1 gene, a PDAT gene, and combinations of mutations in more than one gene within the same plant. Examples of combination mutations in plants that may find use in the present inventions are host plants with double mutations comprising a mutation in at least one mutation in it's DGAT1 gene in combination with a mutation in it's PDAT gene. In some embodiments, mutations include deletion mutants. In yet other embodiments, other genetic combinations in plants include complete null plants, such that plants have low or undetectable DGAT1 activity and low or undetectable PDAT expression.

In another embodiment, a plant with low lc-TAG production will be engineered or bred to increase the level of substrates for ac-TAG production. For example, embodiments are contemplated to comprise altered expression, i.e. increased or decreased expression of a gene for the goal of increasing substrate levels for further increasing ac-TAG production.

An exemplary method for one embodiment of increasing (i.e. enhancing) levels of ac-TAGs in transgenic *Arabidopsis* plants by expression of EaDAcT in mutant plants (plants with a mutant, nonwild-type background) comprises using host plants expressing mutant genes which reduce levels of lc-TAGs in seeds. Expression of an EaDAcT gene was contemplated to have one of two effects in plants containing lowered yields of lc-TAGs (with little to no expression of ac-TAGs), either there would be no effect in ac-TAG production or there would be a slight increase of ac-TAG production/yield, either by increasing % mol of ac-TAGs in seed oil.

Specifically, in this example, the exemplary mutant *Arabidopsis* plant used was a fatty acid elongation-1 gene, fae1, mutant already having greatly reduced expression of very long chain fatty acids in its seed. The FAE1 gene encodes a cytosolic 3-ketoacyl-CoA synthase that is responsible for the biosynthesis of very long chain fatty acids in plant seeds (Kunst et al., 1992, Plant Physiol. Biochem, 30:425-434; Millar and Kunst, 1997, Plant J. 12:121-131, herein incorporated by reference). This cytosolic 3-ketoacyl-CoA synthase (elongatase) utilizes a cytosolic source of malonyl-CoA, which is in turn derived from the cytosolic pool of acetyl-CoA. In particular, the fae1 gene mutations or molecular genetic strategies that eliminate the elongase function of this gene greatly reduced long-chain (C20, C22) fatty acid in seed oils. fae1 mutant plants were transformed with an EaDAcT gene of the present inventions. Because experiments on overexpression of *Arabidopsis* FAE1 gene (Millar and Kunst, Plant J. 12:121-131 (1997), herein incorporated by reference) and a heterologous FAE1 gene (Mietiewska et al., Plant Physiol. 136:2665-2675 (2004), herein incorporated by reference) in *Arabidopsis* seeds increased the levels of VLCFA, there is not a limitation of the cytosolic acetyl-CoA pool in wild type seeds. Thus it is not at all expected that the transformation of fae1 *arabidopsis* with EaDAcT gene would cause higher levels of ac-TAG production than in a wild type line, because there is no evidence to suggest that the cytosolic acetyl-CoA supply to drive the EADAcT acetyl transferase reaction is at all limiting. Thus the enhancement discovered in ac-TAG levels in fae1 background when compared to wild-type in EaDAcT-transformed *Arabidopsis*, found in the experiments of the present inventions, described herein, was unexpected.

In particular, EaDAcT was expressed under the control of a seed specific promoter, 2S (see above) in an *Arabidopsis* mutant line fae1 plants. An exemplary mutant, such as a mutant comprising a stop codon in a fae1 gene, any mutant that reduces approximately 90%-100% of long chain fatty acids. The fae1 mutant chosen for the study was the CB25 *Arabidopsis* plant line comprising a fae1 mutant gene resulting in a 90% reduction in VLCFAs compared to WT plants. CB25 was isolated from an ethyl methanesulphonate mutagenized population and contains a truncated FAE1 protein due to a mutation resulting in a stop codon at amino acid 465. It is a homozygous, backcrossed, bulked seed line. Plants containing these mutations have a 90-95% reduction in very long chain fatty acids in the seeds while overall oil production similar to that of wild type seeds. However, any of the several fae1 mutants published would have been appropriate for the experiment as CB25 has a similar reduction in VLCFA to these other published mutants.

In order to determine if a plant with a fae1 mutation would cause an increase in ac-TAG production in combination with an EaDAcT gene of the present inventions, EaDAcT was expressed in a CB25 host plant. In particular, an EaDAcT gene of the present inventions was cloned into a plant transformation vector under the control of the *Arabidopsis* 25 seed storage promoter as described in Example VIII. This construct, p2S.EaDAcT, was then introduced into *Agrobacterium tumefaciens* strain C58C1 and transformed into *Arabidopsis* mutant line fae1 plants using the floral dip method (Clough and Bent (1998) Plant J. 16:735-743, herein incorporated by reference). Plants were grown as described previously in Example VIII. Seeds from transformed plants were germinated on hygromycin in order to determine which seed lines were homozygous for the EaDAcT transgene. Once identified by healthy germination into seedlings, seeds were grown into plants whose seed was harvested from these homozygous transgenic EaDAcT lines for extraction of neutral lipids. Neutral lipids were analyzed using ESI-MS. Spectra from lipids extracted from the seeds of transgenic plants were compared as TAG content and TAG composition of $T_3$ seeds from *Arabidopsis* fae1 mutants expressing EaDAcT. Comparative analysis was made to neutral lipids isolated from wild-type *Arabidopsis* seeds and shown in FIG. 16. FIG. 16 (A) shows an exemplary TAG composition of $T_3$ seeds from *Arabidopsis* fae1 mutants (plants containing mutations in the fatty acid elongase gene 1) expressing EaDAcT. Dark bars showed ac-TAG amounts while light bars showed lc-TAG amounts. FIG. 16 (B) shows an exemplary scatter plot comparing the distribution of the ac-TAG composition of $T_3$ seed from fae1 mutant seeds expressing EaDAcT to fae1 control plants (not transfected with an EaDAcT construct of the present inventions). Surprisingly, seed oil from mutant fae1 *Arabidopsis* plants showed a 40-60% ac-TAG composition, when transfected with an EaDAcT gene of the present inventions.

Unexpectedly, four of the seven transgenic lines expressing a homozygous EaDAcT transgene of the present inventions (FIG. 16) showed a higher proportion of ac-TAGs, of 40-60% ac-TAG composition, see, FIG. 16B compared to nontransgenic *Arabidopsis* fae1 mutant plants. For comparison, 3 other EaDAcT transgenic fae lines showed approximately less than 10% ac-TAG T3 seed oil composition.

About half of *Arabidopsis* fae1 mutant plant lines that expressed an EaDAcT transgene of the present inventions showed a high range of 40-60% ac-TAG composition. In comparison, *Arabidopsis* plants on a wild-type background that expressed an EaDAcT transgene of the present inventions showed a high range of up to approximately 40%. Therefore, in one embodiment, the inventors contemplated the construction of oil seed plants, and other types of plants, for expression of an EaDAcT transgene of the present inventions in combination with genetic backgrounds that result in reduced levels of fae1 expression for making plants where high levels of the seed oil comprises ac-TAGs, i.e. approximately 40% and higher.

In one contemplated embodiment, host plants comprising lowered FAE1 expression, naturally or induced, would have a higher percentage and/or amount of ac-TAG containing oil in their seeds. The comparison would be to oil isolated from the same amount (by weight) of seeds from wild-type plants or from other plants with wild-type backgrounds consisting of expression of an EaDAcT of the present inventions on a background of wild-type expression of FAE1.

In one contemplated embodiment, a host plant comprising lowered VLCFAs are Canola producing rapeseed plants are contemplated for use in combination with expression of an EaDAcT gene of the present inventions for producing oil with high amounts of ac-TAGs. As one example, fae1 gene mutations or molecular genetic strategies that eliminate the elongase function of this gene result in greatly reduced long-chain (C20, C22) fatty acid in seed oils. One example of the use of seed oils from plants bred for reduced long-chain fatty acids was the development of Canola oil (low erucic acid rape seed, LEAR) producing varieties of rapeseed plants. Edible oil extracted from LEAR plants is Canola oil essentially devoid of VLCFAs. LEAR containing Canola oil is viewed as the preferred edible seed oil over wild type rapeseed (HEAR) oil with high amounts of VLCFAs. Rapeseed plants with LEAR were analyzed and found to comprise deletion mutant fae1 genes associated with low VLCFAs (Wang, et al., BMC Plant Biology, 10:137 (2010), herein incorporated by reference. Thus in one embodiment, a host plant is a Canola oil producing plant. In another embodiment, the hose cell is a cell obtained from a Canola oil producing plant.

IX. Advantages of Using Ac-TAGs Genes and Polypeptides for Producing Novel Oils.

Euonymus genes and encoded polypeptides find use in the present inventions for producing oils comprising ac-TAGs contemplated for use as a biofuel. For example, current and future cultivation of oil-seed crops producing ac-TAGs by compositions and methods of the present inventions (either transgenic introduction or through plant breeding) are contemplated to provide a new biofuel with improved properties and production compared with existing biodiesel products and oils used in engines (such as jet engines, etc.). Primary advantages of using genes and polypeptides of the present inventions for providing novel oils include increasing economic viability for using natural oils by eliminating (or reducing) processing (transesterification) time and costs. In other words, reducing or eliminating alcohol modification of plant oils prior to use. In some embodiments, oils comprising ac-TAGs of the present inventions are contemplated for use combined with conventional fuel or in combination with other types of biofuels.

Thus the inventors contemplated that ac-TAGs produced by Euonymus genes and encoded polypeptides expressed in plants and cells other than Euonymus alatus would also be useful for producing novel oils. These novel oils comprising ac-TAGs would contain ac-TAGs in amounts higher than found in plants and cells not expressing Euonymus genes and encoded polypeptides. Thus genes and polypeptides for producing ac-TAGs are contemplated to provide oils for commercial use in bioenergy, machine oil, oleochemical, and nutritional fields. Ac-TAGs produced by Euonymus genes and encoded polypeptides in novel oils, are contemplated to have utility for use, either as components of isolated oils or as isolated lipids, as biofuels and biolubricants and for use as oleochemicals and in food products.

In some embodiments, oils produced by cells and whole organisms (such as transgenic cells and organisms) expressing heterologous ac-TAGs genes and encoded polypeptides of the present inventions are contemplated for use as additives in diesel and gasoline fuels in automotive or airplane industries. Fuel additives are usually used in automotive fuels, such as gasoline and diesel, to help meet the fuel specifications and improve fuel and engine performance. In some embodiments, oils produced by cells and whole organisms (such as transgenic cells and organisms) expressing heterologous ac-TAGs genes and encoded polypeptides of the present inventions are contemplated for use as diesel additives, for example, as cetane improvers, lubricity improvers, wax modifiers, and the like. In some embodiments, oils produced by cells and whole organisms (such as transgenic cells and organisms) expressing heterologous ac-TAGs genes and encoded polypeptides of the present inventions are contemplated as gasoline additives, for example as deposit control additives, anticorrosion additives, antioxidant additives, and the like.

Oils comprising ac-TAGs produced by genes and polypeptides (amino acid sequences) of the present inventions are contemplated for use as polymer feedstock. For example, oils comprising ac-TAGs are contemplated to provide novel feedstock for polymers to replace conventional. TAGs. Further, ac-TAG comprising oils of the present inventions are contemplated to provide new polymers with new properties.

A. Ac-TAGs of the Present Inventions for Use as Biofuels and Biolubricants.

Despite the fact that esterified TAGs and petroleum fuels are chemically similar (see, for example, FIG. 1), seed oil from plants are an unsuitable fuel for unmodified diesel engines. The high viscosity of TAGs results in poor atomization in engines, leading to incomplete combustion and subsequent problems such as carbon deposition and coking. Additionally, during the high temperatures of combustion, the acyl chains in TAGs can polymerize, leading to gum formation. To overcome these problems, TAGs are currently converted to fatty acid methyl or ethyl esters via reaction with an alcohol, adding a processing cost to this biofuel. The inventors contemplate that the unusual structure of ac-TAGs would greatly reduce problems that limit the direct use of traditional seed oils as a fuel. First, ac-TAGs are contemplated to possess lower viscosity than regular TAGs (Example X and Table 8). Second, the absence of a third unsaturated acyl chain is contemplated to substantially reduce the polymerization that occurs between TAG molecules when combusted in engines or under high heat. In particular, it is contemplated that the ac-TAG oils would be replacements oils used for fuel in machinery that uses heavy-duty diesel engines, such as in shipping, railroad locomotive and heavy earth-moving machinery, which can more readily tolerate higher viscosity fuels. Thus, isolated oils comprising ac-TAGs produced by heterologous DAcT genes and proteins, including homologous of genes encoding proteins at least 43% identical to SEQ ID NO:01, of the present inventions are contemplated for use directly in diesel engines.

Vegetable oils, comprising primarily long chain acyl groups provide excellent lubricity and were used as base fluids for a variety of lubricant applications (Horner, 2002, J. Synthetic Lubricants 18:327-347, herein incorporated by reference). In these applications the vegetable oil was formulated with an additive package to bring its performance up to the specification required for a particular application. Additive packages include dispersants, detergents, antiwear and anticorrosion inhibitors, friction modifiers, antioxidants, viscosity enhancers, antifoaming agents and pour point depressants.

The inventors contemplated that oils comprising primarily ac-TAGs should provide a lower viscosity base fluid to blend into or completely replace current vegetable oil formulations based on lc-TAG. Thus it is anticipated that oils comprising primarily ac-TAGs, will show enhanced lubricity when compared to a medium chain TAG-based vegetable oil such as coconut or palm kernel oil, which contains predominantly medium-chain saturated fatty acids. Thus in one embodiment, the inventors contemplate vegetable oils produced by host cells and plants of the present inventions having performance measurements closer than wild-type vegetable oils to values required for use as lubricants.

One advantage of using TAGs in general as a lubricant feedstock or as a base stock for mixing with other types of oils is their complete biodegradability. Thus in another embodiment, the ac-TAGs of the present inventions are contemplated for use as base fluids in lubricants, and in particular a lubricant for use on or in engines. In one embodiment, where lubricants are immediately lost to the environment (for example, chainsaw engines, marine engines, and the like) the inventors contemplate the use of a lubricant comprising an ac-TAG, oil, etc., of the present inventions that would undergo rapid biodegradation without residual toxic products. In another embodiment, the inventors contemplate the use of an ac-TAG, oil, etc., where the oxidative load during use is relatively mild (for examples, hydraulic fluids, textile or food processing machinery).

Further, an ac-TAG oil of the present inventions is contemplated to contain monounsaturated fatty acids at the sn-1 and sn-2 position, and thus the ac-TAG base fluid will have a much better lower temperature performance than a base fluid based on currently available medium-chain TAGs, and at least equivalent to existing unsaturated lc-TAG vegetable oils. And finally, because current unsaturated lc-TAG vegetable oils contain a large fraction of molecules with three unsaturated fatty acids, whereas ac-TAG contains only molecules with two unsaturated fatty acids, the thickening and formation of residues from the base fluid by thermal and oxidative polymerization processes is likely to be significantly reduced.

B. Polymer Feedstock.

TAGs are polymerized for use in a variety of industries. For example, triolein or trilinolein form cross-linked thermosetting polymers via metathesis. In contrast, ac-TAGs lacking a third long acyl chain are contemplated to form linear thermoplastic polymers. Likewise, consider oils rich in hydroxy fatty acids, such as castor oil, which can be used for the synthesis of polyurethanes. Castor oil is rich in triricinolein (Propane-1,2,3-triyl tris(12-hydroxyoctadec-9-enoate), stereoisomer; CAS #2540-54-7). When triricinolein was reacted with a diisocyanate it produced a cross-linked polyurethane of a certain level of thermoplastic properties. However, when a polyurethane with additional thermoplastic properties was desired, then an acyldiricinolein feedstock was necessary for the reaction. It is extremely unlikely that a vegetable oil enriched in triricinolein could be engineered to produce just diricinoleoyl TAG species, because even if the balance of hydroxylation to oleic fatty acid production could be controlled to give a 2:3 molar ratio, the oleic acid moiety being the precursor to ricinoleic acid, the product TAGs would almost certainly be a mix of mono-, di- and tri-ricinoleoyl species. However, using DAcT, a seed producing predominantly triricinolein could be converted to produce acetyldiricinolein with a simple gene engineering strategy of knocking out the endogenous TAG synthesizing genes and replacing them with DAcT induced lipids. Thus another contemplated use for oils comprising ac-TAGs produced by heterologous DAcT genes and proteins, including homologous of genes encoding proteins at least 43% identical to SEQ ID NO. 01, of the present inventions are as oleochemical feed stocks for the modulation of polymer properties in the production of such polymers.

C. Reduced Calorie Oil Substitutes.

Modified triacylglycerols were developed commercially and used as reduced calorie oils. For example, SALATRIM consists of saturated fatty acids and short-chain fatty acids esterified to glycerol whereas ECONA/ENOVA is a mixture of acylglycerols dominated by 1,3 diacylglycerols. These reduced calorie oils are currently synthesized using chemical and enzyme catalysts. With a similar chemical structure, from the viewpoint that ac-TAGs contain at least one short-chain fatty acid in place of a medium or long chain, ac-TAGs alone or in mixtures with longer chain fatty acids, are contemplated to represent an alternative form of these existing reduced calorie oils. However, in contrast to currently used oils, oils comprising ac-TAGs are contemplated to have numerous advantages over known reduced calorie oil substitutes. Thus in one embodiment, plant oils produced by heterologous DAcT genes and proteins in plants, including homologous of genes encoding DAcT and DAcT-like proteins at least 43% identical to SEQ ID NO:01, of the present inventions are contemplated for use as edible oils. In another embodiment, plant oils of the present inventions are directly extracted from seed oil crops capable of producing these molecules. Isolation methods include but are not limited to cold pressing, by hand or machine, and the like. Thus isolation of oils of the present inventions is contemplated to be more economical to produce than currently produced commercial oils. In yet a further embodiment, direct isolation of oils of the present inventions are contemplated to reduce or eliminate the cost of processing. In an additional embodiment, oils of the present inventions are potentially more attractive from a consumer standpoint, i.e. fewer unpleasant or unwanted health side effects induced by current reduced calorie oils.

Oils comprising ac-TAGs produced by genes and polypeptides (amino acid sequences) of the present inventions are further contemplated for use as a food ingredient. For example, oils comprising ac-TAGs are contemplated to provide lower calorie content compared to conventional TAG oils in addition to a niche use in producing reduced calorie foods or as novel cooking oil. In some embodiments, the oils of the present inventions are contemplated for use in food processing applications such as baking, sprays, and food machinery lubricants. Another advantage of using ac-TAG to reduce calorie intake from fat arises from the reduced viscosity of ac-TAGs, allowing fat to more effectively drain from deep-fried foods after the frying step.

In another embodiment, the inventors contemplate a new low calorie food ingredient with lower cost. In particular, the lower calorie content of ac-TAGs when compared to equivalent conventional TAGs (due to one less long chain fatty acid) provides an opportunity to produce natural plant oils for use in the food industry. In a preferred embodiment, foods comprising ac-TAGs produced by compositions and methods of the present inventions would have lower calorie content without the need for chemical modification. In one embodiment, a DAcT gene and polypeptide of the present inventions is contemplated for expression in a transgenic oil-seed crop plant, for example, in a food-approved species such as soybeans, canola etc., to provide a commercial source of oil from which ac-TAGs would be extracted (isolated).

Table 2 shows an exemplary calculated calorific value for a variety of triacylglycerols based on their molecular formulae. Ac-TAG has a reduction in calorific value of about 6.5% when compared to lc-TAG. However, when assessing the potential of candidate reduced calorie fats and oils it is important to consider not just the total calorific value of the oil and the extent of digestion and absorption, but also the metabolic fates of the absorbed products, as well as the potential for any adverse side effects. The inventors contemplate that ac-TAG would be digested and totally absorbed and with no toxicologically adverse effects. The use of ac-TAG oil of the present inventions as a safer oil alternative is supported by the observation that acetic acid esters of mono- and diglycerides, which belong to the group of α-tending emulsifier are used as coatings and foam stabilizers in food products (Lauridsen, (1976) "Food emulsifiers: surface activity, edibility, manufacture, composition, and application" J. Amer. Oil Chem. Soc. 53:400-408, herein incorporated by reference). Ingestion of these acetic acid esters are not limited as supported by "Acceptable Daily Intake for Man for Selected Food Emulsifiers" (15th and 17th Reports of the Joint FAO/WHO Expert Committee on Food Additives).

TABLE 2

Energy Content of Triacylglycerols of Various Acyl Compositions.

| Triacylglycerol | CarbonNumber | Calorific Value Kcal/g | (%) |
|---|---|---|---|
| Tristearin | 57 | 9.36 | 100 |
| Acetyl-distearin | 41 | 8.75 | 93.5 |
| Tricaprin | 33 | 8.24 | 88 |
| Diacetyl-stearin | 25 | 7.5 | 80 |
| Acetyl-dicaprin | 25 | 7.5 | 80 |
| Diacetyl-caprin | 17 | 6.27 | 67 |
| Triacetin | 12 | 3.76 | 40 |

It is important to note that medium- and long-chain fatty acids (>C10) are metabolized differently than short-chain fatty acids. The former are used for resynthesis of TAG in the intestinal mucosa, which are then assembled as chylomicrons and transported to the adipose tissues via the lymphatic system. By contrast, short-chain fatty acids are transported directly via the portal vein to the liver for use as energy supplies. Thus acetyl groups should probably not be counted as calories available for direct deposition as fat. Tristearin has a calorific content of 9.4 kcal/g, all of which is available for deposition in the adipose tissue, whereas the calorific content of acetyl-distearin that is correspondingly available is 8.2 kcal/g, a reduction of 13%. Another example of a reduced calorie oil food product is diacylglycerol (DAG) oil, which contains 26% 1,2-DAG and 61% 1,3-DAG, the latter giving the low calorie function to the oil. Kao Corporation has successfully introduced DAG oil (brand name-Econa) in Japan as cooking oil in 1999 and it is being test-marketed in the U.S. (brand name—Enova). It has only 2% less food energy value than regular TAG but reduces body fat accumulation and lower serum TAG. Triglycerides are converted to 2-monoacylglycerol (MAG) and fatty acids mainly by intestinal lipases. The free fatty acids and the 2-MAG can then pass into epithelial cells where TAG is resynthesized. Much of these TAGs are then packaged into chylomicrons and passed into the lymph and bloodstream for storage as fat. In contrast, 1,3-DAG, the primary component of DAG oil, is converted into 1-MAG or completely hydrolyzed by the lipases in the small intestine. Inside the epithelial cells, resynthesis of TAG from the MAG is difficult since the middle position on the glycerol backbone is vacant. So fatty acids are not efficiently repackaged into TAG and chylomicrons but instead get diverted into the portal vein to the liver. In the liver, lipid oxidation of fatty acids occurs. This reduces fat deposition. Thus DAG oil is a good example of the importance of considering subsequent metabolism, not just its calorific content.

Ingestion of ac-TAG used as in food oil is contemplated to release free acetic acid by the gastrointestinal lipases which may further suppress body fat accumulation (Kondo, et. al., 2009, Biosci. Biotechnol. Biochem., 73:1837-1843, herein incorporated by reference). The mechanism of this effect of vinegar has been established as an upregulation of PPAR-alpha and fatty acid oxidation related proteins in the tissues (Kondo, et. al., 2009, J. Agr. Food Chem. 57:5982-5986, herein incorporated by reference). As obesity causes approximately 300,000 deaths in the United States annually the US Surgeon General has recommended that the US consumption of fats and oils be reduced from 40% to 30% of total calories in the diet. If this lc-TAG consumption was substituted in whole or in part by weight with ac-TAG the reduced calorific content of 6.5% would go a significant way towards the 25% reduction in consumption of calories recommended by the United States Surgeon General. However, as described above, there may be significant additional weight loss benefits if more of the absorbed calories are directed towards metabolism in the liver rather than to TAG re-synthesis and deposition in the adipose tissues.

In another embodiment, oils for use in food preparation and as a part of a food product are contemplated for use after isolation from plant parts expressing heterologous DAcT proteins. Thus, the inventors contemplated that expression of a heterologous DAcT gene and encoded protein of the present inventions would be useful for producing novel oils in plant parts such as leaves. Because ac-TAGs are not usually produced in *Arabidopsis* plants, *Arabidopsis* leaves as models for *Brassica* plants will be chosen for testing ectopic transfection and expression of a heterologous DAcT gene and encoded protein for producing ac-TAGS in leaves of plants.

GATEWAY technology is contemplated to be used for transferring a EaDAcT gene from an entry vector to a plant binary vector where the gene will be expressed under the control of a constitutive promoter, such as a CMV 355 promoter. This construct will be transformed into *Arabidopsis* leaves using *Agrobacterium* mediated transformation.

In other embodiments, expression of a DAcT gene of the present inventions will be used for making transgenic plants of the present inventions where the DAcT gene is under control of plant part specific promoter, such as a leaf promoter.

Lipids will be extracted from the leaves of transgenic plants from either ectopic transfection or from leaves harvested from whole transgenic plants. TAG content will be determined using ESI-MS as described herein.

In a preferred embodiment, a plant for use in making an ac-TAG oil for human consumption is a plant currently used for providing edible oils from seeds and plant parts, include but are not limited to a *Brassica* napsus plant (providing Canola oil), a soybean plant (providing soybeans and soybean oil), and the like.

X. Summary.

Unlike typical oil-seed crops, *Euonymus* is not a suitable plant to develop as an oilseed crop. Therefore the genes for enzyme or enzymes necessary for ac-TAG production needed to be isolated and then used as a heterologous gene expressed in a host cell using genetic engineering (for example, using the isolated gene as a transgene contemplated for increasing ac-TAG production in vivo to produce a transgenic cell or whole organism). A primary characteristic of the ac-TAG producing enzyme would be a protein capable of transferring an acetyl group to a diacylglycerol (DAG) molecule to form ac-TAG.

Previous work isolating an ac-TAG producing gene/protein resulted in the cloning of the *Euonymus alatus* enzyme diacylglycerol acyltransferase 1 (EaDGAT1) initially as a candidate for producing ac-TAGS. However, transgenic EaDGAT1 expression alone was subsequently found to be incapable of synthesizing significant amounts of ac-TAGs in vivo (FIG. 14C and Table 7). Surprisingly, yeast and *Arabidopsis* lines expressing an EaDGAT1 transgene accumulated very low levels of ac-TAGs (FIG. 14C and Table 7). In contrast, the diacylglycerol acetyltransferase (DAcT) genes encoding a protein enzyme described herein, was found capable of producing ac-TAGs both in vitro and in vivo when expressed in yeast and in plants (FIG. 14 and Tables 5-7. For example, analysis of lipids produced by yeast and seeds from plants transformed with the EaDAcT gene showed that EaDAcT expression was capable and sufficient for the production of ac-TAGs both in vivo and in vitro, see Examples.

EXPERIMENTAL

The following examples serve to illustrate certain embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); gfw (gram fresh weight); l or L (liters); ml (milliliters); µl (microliters); cm (centimeters); mm (millimeters); µm (micrometers); nm (nanometers); ° C. (degree Centigrade); MW (molecular weight in kd); k (kilo); dal and d (daltons); parts per million (ppm); atomic mass units (amu); cP centipoises where cP=-2 poise, 1 p=100 cP, and the like: Stoke (St) where 1 St=10-4 m2/s, and the like; Centistokes (cSt) where 1 St=100 cSt and 1 cSt=10-6 m2/s, and the like; grams/cubic centimeter (g/cc); SI-system (International System of Units, SI units); The American National Institute of Standards and Technology (NIST); American Society for Testing and Materials (ASTM, ASTM International); PCR (polymerase chain reaction); RT-PCR (reverse-transcriptase-PCR); TAIL-PCR (thermal asymmetric interlaced-PCR); RACE (Rapid Amplification of cDNA Ends); EST, expressed sequence tag; BLAST (Basic Local Alignment Search Tool); C16, C18, etc (fatty acyl group designation by number of carbon atoms in acyl chain); DAG (diacylglycerol); TAG (triacylglycerol); Ac-TAG (1,2-diacyl-3-acetins); LeTAG (long chain-triacylglycerols); PC (phosphatidylcholine); DGAT (diacylglycerol acyltransferase); diacylglycerol acetyltransferase (DAcT); FAME (fatty acid methyl ester); GC/MS (gas chromatography/mass spectrometry); TLC (thin layer chromatography); FID (flame ionization detection/detector); ESI-MS (electrospray ionization mass spectrometry); SC medium (synthetic complete medium); NT medium (*Nicotiana tabaccum* medium); MES (2-(N-morpholino)ethanesulphonic acid); hepes (N-2-hydroxyethylpiperazine-N'-2-ethanesulphonic acid); 2,4-D (2,4-dichlorophenoxyacetic acid); CFH (cell free homogenate); DW (dry weight); and MSU (Michigan State University).

Example I

Exemplary Materials and Methods Resulting in the Discovery of an EaDAcT (*Euonymus alatus* Diacylglycerol Acyltransferase)

This Example describes exemplary Materials and Methods used during the discovery of an exemplary novel enzyme of the present inventions, including an exemplary diacylglycerol acyltransferase (DAcT) gene and DAcT protein, from *Euonymus alatus* for use in producing ac-TAGs in host cells and plant parts, including seeds.

A. Experimental Plant Materials.

*Euonymus alata* bushes flower in late May (Michigan, United States) while the onset of the seed maturation phase delayed until August. During maturation the seed coat arils become colored intensely orange. Seed fresh weight, dry weight and lipid accumulation over time (see, FIG. 1., and U.S. Pat. No. 7,429,473, herein incorporated by reference). These weight and lipid accumulations follow a pattern typical for developing oilseeds. Exemplary oil content of *Euonymus alata* seed at maturity was measured at approximately 43%. A related exemplary developmental assay showed that the majority of lipid deposition occurred in September and during this period approximately 0.24 mg lipid/day/seed was deposited. This lipid was mainly 3-acetyl-1,2-diacyl-sn-glycerol (as determined by molecular weight (MW) of 1,2-dioleoyl-3-acetyl-sn-glycerol of 662 Daltons). Thus an exemplary rate of deposition was calculated in order to determine a relative (yardstick) measurement of an estimated in vitro enzymatic activity rate for an enzyme or enzymes contemplated for contributing to ac-TAG production. At mid-maturation the average seed fresh weight was about 30 mg of which the inventors' contemplated an average rate of 3-acetyl-1,2-diacyl-sn-glycerol deposition of approximately 500 nmoles/hr/gfw (grain fresh weight). This rate of deposition was also a useful specific activity against which to judge the degree of contribution of exogenous acetate to the biosynthesis of 3-acetyl-1,2-diacyl-sn-glycerols in vivo, for making pool size estimates, and to judge in vitro enzymatic activity.

Therefore for use in the development of the present inventions, developing *Euonymus alatus* fruit (seeds) were collected from bushes over time during the fall, August to October as collections 1-4 (1 the earliest to 4 the latest) on the grounds of Michigan State University. Seeds were removed from the capsule and separated from their yellowish-orange aril. Some whole seed tissue was frozen for analysis while plant parts were removed from the remainder.

Plant parts were also collected, specifically aril, endosperm and embryo tissues dissected out of seeds, frozen in aliquots and stored at −80° Celsius, Separate aliquots of these tissues were subsequently used in RNA extraction or dried at 85° C. for lipid extraction and analysis.

B. Biochemistry Procedures Including Lipid Analysis.

1. Lipid Extractions and Analyses of Plant Tissue (Parts).

After drying, separate aliquots of *Euonymus* tissues were ground into a course powder then extracted twice with volumes of 3:2 (v/v) hexane:isopropanol. Procedures were carried out on ice or at 4° C. Frozen embryo, aril, or and endosperm tissue was added to two volumes of chilled buffer containing 0.3 M sucrose, 10 mM NaF, 5 mM MgCl$_2$, 2 mM dithiothreitol, 1 mM EDTA and 40 mM Hepes-NaOH (pH 7.4), homogenized, and filtered through two layers of Miracloth. The residue was re-homogenized in two more volumes of buffer and filtered. The filtrates were combined and constitute the cell free homogenate (CFH). The CFH was frozen and stored at −70° C. until used and typically contained 12-17 mg protein/ml. Protein concentrations were estimated using the Bio-Rad protein assay, which is based on the Bradford method Anal. Biochem. 72:248-254 (1976), herein incorporated by reference, using bovine serum albumin as the standard. The protocol of Hara and Raclin, Anal. Biochem. 90:420-426 (1978), herein incorporated by reference, was then followed to recover the lipids. Lipids were assayed gravimetrically and by analysis of fatty acid methyl esters released by transmethylation.

2. Isolation of Oils from Yeast Cells.

Cell pellets from 30 ml yeast cultures grown to stationary phase were made by pelleting cells via centrifugation. Pellets were washed once with 20 mM Tris-HCl pH 7.9, frozen, then lyophilized to determine a dry weight, and resuspended in distilled water to a volume of 500 µl. Cells were lysed in a vibration mill (Retsch Inc. Newtown, Pa., United States) with 0.5 mm glass beads for 5 minutes and extracted four times with 0.935 ml 2:1 (v/v) chloroform:methanol. 1.25 ml chloroform and 1.3 ml 0.15M acetic acid were added to the pooled extracts, which were then vortexed thoroughly. The organic phase was removed and the aqueous phase re-extracted with 2 ml chloroform. The combined organic phases were dried under nitrogen and dissolved in 300 µl toluene. To isolate neutral lipids, total lipid extracts were applied to a 6 cm column of 60 Å silica gel in a Pasteur pipette pre-equilibrated with 10 ml of eluent (99:1 (v/v) chloroform:methanol). Neutral lipids were recovered with 4 ml of eluent, dried under nitrogen and dissolved in 300 µl toluene.

3. Isolation of Oils from Plant Seeds.

*Euonymus* seed oil was isolated from dried seeds for lipid analysis. Total *Euonymus* seed lipid was analyzed by extraction of dried seeds with hexane-isopropanol according to Hara and Radin, Anal, Biochem. 90:420-426 (1978), herein incorporated by reference. After extraction the organic solvent was evaporated away and the remaining oil was weighed for providing a total oil amount. The isolated oil was then used to determine the amount of ac-TAGS.

*Arabidopsis* seed oil was isolated and extracted as total lipids from *Arabidopsis* seeds according to Li et al. Phytochemistry 67:904-915 (2006), herein incorporated by reference. Neutral lipids were purified using the technique described for yeast, see number 2 above. Neutral lipid extracts were analyzed using ESI-MS.

C. $^{14}C$ DGAT Assays.

A standard (Ac)DGAT assay contained [1-$^{14}C$]acetyl-CoA (18 µM, 100 nCi) plus reaction buffer (50 mM HEPES pH 7.4, 10% glycerol, 5 mM MgCl$_2$ and 1 mM DTT) in a total volume of 100 µl. 1,2-dioleoyl-sn-glycerol (230 µM) or 1,2-dihexanoyl-sn-glycerol (230 µM) was added as 1 µl of ethanol solution. The assay was initiated by adding 20 µg of microsomal protein. The reaction was run at 30° C. for 30 min and terminated by the addition of hot isopropanol (2 ml). Lipids were extracted with hexane and isopropanol as described by Hara and Radin, Anal. Biochem. 90:420-426 (1978). The [$^{14}C$]lipid residue was dissolved in hexane and an aliquot assayed for radioactivity by liquid scintillation counting. The standard long-chain DGAT assay contained 8 µM [1-$^{14}C$] oleoyl-CoA (50 nCi); remaining methods were done as in acetyl DGAT assays.

D. Exemplary Lipid Analysis.

The isolation and determination of the presence and relative amount of individual lipid classes are described herein. Internal standards, for example, triheptadecanoin and dipentadecanoyl phosphatidylcholine, were added to an aliquot of total lipids. The lipid classes were isolated by preparative TLC. Transmethylation of the total lipids and of the lipid classes was accomplished by heating in sulphuric acid-methanol-toluene (5:95:25 v/v/v) for one hour at 80° C. The lipid classes recovered after preparative TLC were transmethylated directly on the silica, with methyl nonadecanoate added to each fraction for relative quantifications. GLC analysis of fatty acid methyl esters was accomplished using a 50 m×0.25 mm CP-Sil88 column temperature programmed from 150° C. to 220° C., with a FID.

For analysis of triacylglycerols in different tissues of *Euonymus*, internal standards of triheptadecanoin and acetyl-dipentadecanoin were added to tissue lipid extracts. Long-chain-triacylglycerols and acetylglycerides were then isolated by preparative TLC and analyzed by high temperature GC using a 30 m×0.25 mm DB-5ht column, temperature programmed from 250° to 360° C., with a FID. Aliquots of the sample were also transmethylated for quantification of total fatty acids.

Thin layer chromatography analysis of unlabeled and labeled lipid classes was conducted using K6 silica plates (Whatman). 80/20/1 (v/v/v) Hexane/diethyl ether/acetic acid was used for analysis of triacylglycerols; 80/10/10/0.4 (v/v/v/v) toluene/ethyl ether/ethyl acetate/acetic acid was used for analysis of diacylglycerols; and 65/25/4 chloroform/methanol/water (v/v/v), 65/25/4 (v/v/v) chloroform/methanol/28% aqueous ammonium hydroxide and/or 85/15/5/2 (v/v/v/v) chloroform/methanol/acetic acid/water were used for analysis of polar lipids. Reverse phase analysis of triacylglycerols was carrier out using KC18F TLC plates developed with 3:1 (v/v) acetone:acetonitrile or 100% methanol. Silver nitrate TLC used silica TLC plates impregnated with 15% (w/v) silver nitrate in acetonitrile and developed three times with toluene at −15° C. After development of the TLC plates in the above solvent systems, radioactivity in bands was quantitated with a Packard Instant Imager. Lipid classes recovered from TLC plates after in vivo labeling experiments were analyzed as follows. The transmethylation method of Ichihara, et. al. (1996) was employed. This derivatization, run at room temperature with sodium hydroxide/methanol/heptane, can be performed with quantitative recovery of [$^{14}C$] long-chain fatty acid methyl esters and complete loss of [$^{14}C$] acetyl groups (primarily as methyl acetate). When the [$^{14}C$] heptane-soluble material recovered from the transmethylation is analyzed by TLC, the contribution from [$^{14}C$] long-chain fatty acid methyl esters can be measured, and hence the amount of [$^{14}C$] long-chain fatty acids in the original [$^{14}C$] lipid determined. The use of transmethylation with complete loss of labeled methyl acetate and recovery of long-chain fatty acid methyl esters was also used to quantify the distribution of label between acetyl and long-chain acyl groups in isolated [$^{14}C$]3-acetyl-1,2-long-chain diacyl-sn-glycerols.

Lipid extracts were analyzed using ESI-MS as described previously by Bates, et. al. (2009) Plant Physiol. 150:55-72, in brief, ESI-MS in positive ion mode was performed by direct infusion with a Shimadzu (Columbia, Md.) SIL-5000 autosampler into a Waters (Milford, Mass.) Quattro micro mass spectrometer. Ten µl of sample in toluene was infused to the electrospray source in a 65:32:3 chloroform:methanol: 100 mM ammonium acetate solution at a flow rate of 0.1 ml/minute. The capillary and extractor voltages were 3.2 kV and 2.0 V, respectively. The source and desolvation temperatures were 110 and 350° C., respectively. The desolvation gas flow rate was 400 l/hr. Mass spectra were collected for 2 min; the m/z range scanned in the MS measurements was from 500 to 1000 (1 sec/scan) and in the MS2 measurements from 20 to the mass of the parent ion. Collision-induced dissociation used argon as the collision gas (2×10-3 mbar) with the collision energy set at 22 eV. Mass spectra data was acquired with MassLynx 4.0; TAG ion peaks were smoothed and integrated using QuanLynx software.

In order to correct for the effect of the number of acyl chain carbons and double bonds on the signal strength [Han and Gross, 2001, Anal. Biochem 295:88-100], TAG standards with varying acyl chain length and number of double bonds were analyzed at different concentrations. After correcting for natural isotope abundance effects, the ion peak intensities for each TAG species were normalized to the internal standard (10 µM triheptadecanoin). The normalized peak intensity was plotted against TAG concentration. The slope of this standard curve was determined for each TAG species. Multiple linear regressions were then used to create a correction function relating the slope of the standard curve to the number of acyl chain carbons and double bonds. To determine the concentration of TAG molecular species, the ion peak intensities were deisotoped and corrected for natural isotope abundance and then normalized to the 10 µM triheptadecanoin internal standard. The correction function for acyl chain carbons and double bonds was then applied to determine the absolute concentration of each TAG species.

E. In Vivo *Euonymus* Seed Assays.

Incubations contained 7-10 halved *Euonymus alata* seeds at early to mid-maturation, but no more than 200 mg fresh weight of tissue. Unless stipulated otherwise, assays contained 5 µCi of [1-$^{14}$C] acetic acid or propionic acid (specific activity 57 Ci/mol), diluted with cold sodium acetate or propionate, pH adjusted to 6.0, to give the required concentration. Assays were run in 25 mM NaMES buffer, pH 6.0, with 400 mM sorbitol and 25 mM sucrose osmoticum in a total volume of 1.0 ml. Assays were run for 2 hours at 28° C., with vigorous agitation to assist oxygenation of the medium. Assays were terminated by rapidly washing the tissue twice with distilled water to remove labeled substrate and then immediately heating at 90° C. in isopropanol for 5 minutes to inactivate enzymes (and particularly an endogenous phospholipase D activity) prior to lipid extraction. Lipids were extracted from the inactivated, homogenized seed tissue with hexane-isopropanol, as described by Hara and Radin, Anal. Biochem. 90: 420-426 (1978). An aliquot of the heptane-soluble [$^{14}$C]lipids was assayed for radioactivity by liquid scintillation counting. TLC analysis of labeled lipid classes was conducted using K6 silica plates (Whatman). 80/20/1 (v/v/v) hexane/diethyl ether/acetic acid was used for analysis of triacylglycerols. For analysis of phenacyl esters K6F silica plates (Whatman) were developed with 70/30/1 (v/v/v) hexane/diethyl ether/acetic acid. After development of the TLC plates in the above solvent systems quantification of radioactivity in bands was by Packard Instant Imager.

For identification of [$^{14}$C]acetyl, [$^{14}$C]propionyl and [$^{14}$C] long-chain acyl groups within a lipid class phenacyl esters were used. The lipid sample (about 20 µmoles) was saponified by heating at 60° C. for one hour in 0.2 ml of 1M KOH in aqueous ethanol (200 µmoles KOH). The reaction mixture was then partially neutralized with 0.16 ml of 1M HCl in aqueous ethanol (160 moles HCl), and the resulting suspension evaporated to dryness. The residue was heated with 0.5 ml of acetonitrile containing 0.2M phenacyl bromide (100 µmoles), 10 mM 18-crown-6 (5 µmoles) and 0.1M triethylamine (50 mmoles) at 90° C. for one hour. The acetonitrile was evaporated, the residue resuspended in acetone, and an aliquot analyzed by TLC. Using this protocol about 85% of the radioactivity could be recovered, independent of C2-C18 chain length, with complete conversion to the non-volatile phenacyl ester. Transmethylation of [$^{14}$C]lipid residues utilized the sodium hydroxide-methanol-heptane method of Ichihara, et. al. (1996) Lipids 31:535-539, herein incorporated by reference. This derivatization can be performed with quantitative recovery of [$^{14}$C] long-chain fatty acid methyl esters and complete loss of [$^{14}$C] acetyl or propionyl groups (primarily as methyl acetate or propionate). When the [$^{14}$C] heptane-soluble material recovered from the transmethylation is analyzed by TLC the contribution from [$^{14}$C] long-chain fatty acid methyl esters can be measured, and hence the amount of [$^{14}$C] long-chain fatty acids in the original [$^{14}$C] lipid determined. The use of transmethylation with complete loss of labeled methyl acetate and recovery of long-chain fatty acid methyl esters was also used to quantitate the distribution of label between acetyl and long-chain acyl groups in isolated [$^{14}$C]3-acetyl-1,2-long-chain diacyl-sn-glycerols.

F. Molecular Biology and Related Procedures.

PCR reactions described herein included appropriate controls consisting of the PCR reaction with primer and without a cDNA template.

*Escherichia coli* strains DH5α and TOP10 (Invitrogen) were grown at 37° C. in Luria Broth media (Silhavy, et. al, Experiments with Gene Fusions (Cold Spring Harbor Lab. Press, Plainview, N.Y. (1984)), supplemented with the appropriate antibiotics for selection of the constructs: ampicillin 100 mg/ml (pYES2CT and pYES-DEST52), kanamycin 50 mg/ml (pENTR-D/TOPO, p2S.GATEWAY and p2S.EaDAcT), rifampicine 50 mg/ml (p2S.GATEWAY and p2S.EaDAcT).

Database searches were done using the BLAST algorithm DNA sequences and the deduced amino acid sequence were analyzed with the Vector NTI Suite of Invitrogen, Corporation, Carlsbad, Calif. Polymerase chain reaction (PR) primers use for cloning a 2S promoter sequence that was used (ligation and expression) in the following examples were forward primer p2S-H$_{13}$ F catAaGCtTCAAGAGTGTAAAACG-TACCGATCA (SEQ ID NO:17) and reverse primer p2S-P$_{13}$R GTTctgCAgGTTTTTGCTATTTGTGTATGTTTTC (SEQ ID NO:18) for obtaining sequence:

(SEQ ID NO: 19)

```
caagagtgtaaaacgtaccgatcaaatgtctttataaaaaaacgtgttgatgttgttctgtgaatacaattagttctggttaaca gctggtcgaccattttctgatgagaatttatgtaaggccattgctctggtgttgagaaggtttagtttggttcaagctaaccgtgg ttagaaagttagaatataatgtgtttcttgatcagtgatatcgatcggatttgtattattcatattgtttactctttgagtaattcatagt ggtaactcttttttttttttttttttttttcatattggtaactctttgaaatgaaaaacatagctaagaattgctagctttgatttagtcgag acgtacgaactctcgattttggtttttgatttgttggtgtaaaactctcgatattcataactcgtaagattttgtacgtatcatcttctt attctcttcatcgctctgttttcaattttatgtcaaaacatggttttggtaatttcttttactcctacttcacggtttgagttataatttttt ggtaaacccttaaccacgagttttgatgtattttgacacctctaattatgtgtgtatacgtacacatataattcggtattttcttaaca
```

```
tatatatccctcataaaaatttcttacatgcattgttcgtgagtgacccgttaatatatatattgatagatactcttataaaattatatt ctaaatttcagattaagctggcacaactatatttccaacatcactagctaccatcaaaagattgacttctcatcttactcgattga aaccaaattaacatagggtttttatttaaataaaagtttaaccttcttttaaaaaattgttcatagtgtcatgtcagaacaagagct acaaatcacacatagcatgcataagcggagctatgatgagtggtattgttttgttcgtcacttgtcactcttttccaacacataat cccgacaacaacgtaagagcatctctctctctccacacacactcatgcatgcatgcattcttacacgtgattgccatgcaaatc tcctttctcacctataaatacaaaccaaccttcactacactcttcactcaaaccaaaacaagaaaacatacacaaatagcaaa ac.
```

Example II

Figure 4:
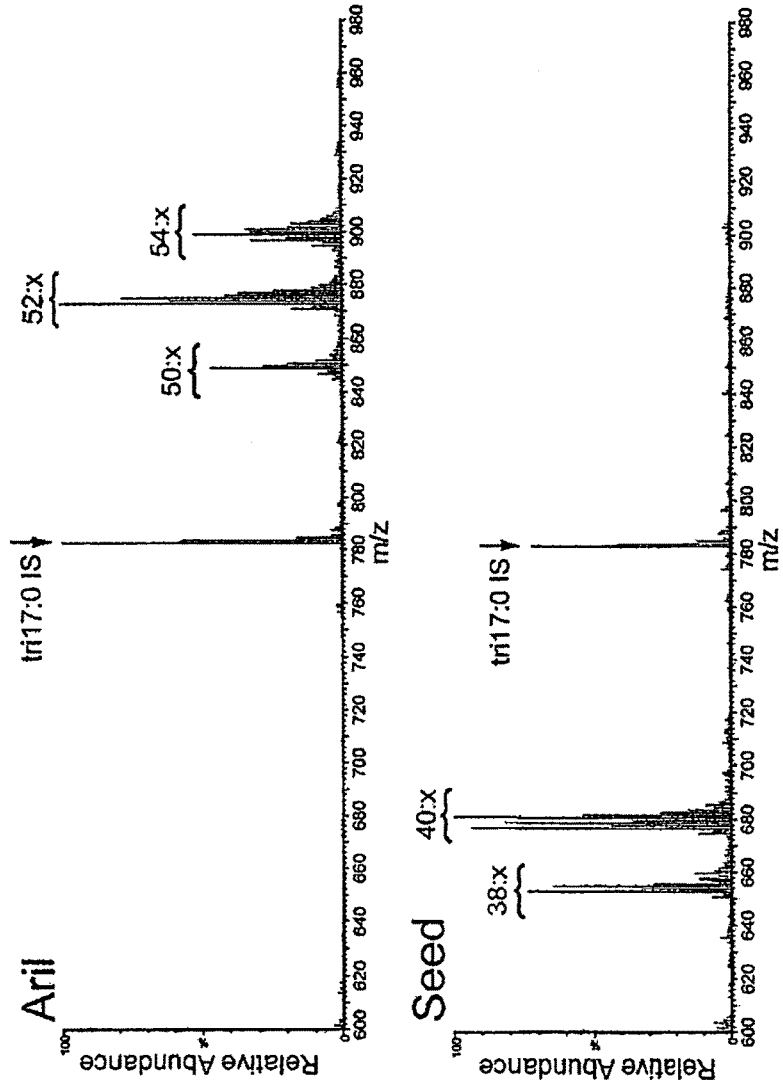
FIG. 4 shows exemplary lipid extracts from *Euonymus alatus* fruit that synthesize different types of TAGs in a tissue specific manner. Positive-ion ESI mass spectra of lipid extracts from *Euonymus alatus* aril and endosperm (seed) tissues, demonstrated the accumulation of lc-TAGs in the aril and ac-TAGs in the endosperm. Tripentadecanoin (tri15:0) was added as an internal standard. The number of acyl carbons in each series of TAG molecules is indicated.

Exemplary *Euonymus Alatus* Tissues that Synthesize Short Chain (Acetyl)-Tags or Long Chain-Tags in a Tissue Specific Manner The inventors tested specific *Euonymus* tissues for identifying a specific tissue with high levels ac-TAGs and a different tissue with low or lack of ac-TAG production for use in molecular isolation techniques described herein for another attempt in isolating a gene for use in inducing ac-TAG production in plants. Endosperm and the aril tissues of developing *Euonymus* seeds were chosen for comparison, as described above, lipids were extracted and analyzed (see, FIG. 4, Table 3 below). Analysis of triacylglycerol (TAG) content revealed different TAG compositions between the two tissues: the endosperm synthesized >98% ac-TAGs whereas the aril tissue synthesized >98% long chain TAGs. Furthermore, the difference between aril and endosperm could not be accounted for by low total lipid mass in aril, since both are oil rich tissues.

While the type of storage lipids found in *Euonymus* endosperm are primarily ac-TAGs (FIG. 4, Table 3), other tissues in the *Euonymus* fruit (seed) accumulate lc-TAGs. For example, up to 30% of the TAG in the embryo was found to be lc-TAG. Significantly, the aril tissue surrounding the seed was found to exclusively synthesize lc-TAGs (FIG. 4, Table 3),

TABLE 3

Exemplary Lipid Compositions of Seed, Embryo and Endosperm Tissues at Mid-Maturation.*

| Lipid Class | Percent distribution** | | | |
|---|---|---|---|---|
| | Embryo | Endosperm | Whole Seed | Aril |
| Triacylglycerol | 26.1 | 1.6 | 3.3 | 92.2 |
| 3-Acetyl-1,2-diacylglycerol | 65.6 | 94.5 | 91.7 | 0.5 |
| 1,2-Diacylglycerol | 1.7 | 1.3 | 1.9 | 2 |
| 1,2-Diacylglycerol | 6.6 | 2.6 | 3.1 | 4.9 |

*Values are for total lipids extracted from a 60 seed sample
**Measured as a percentage of total acyl groups.

Example III

Discovery and Isolation of an Exemplary EaDAcT (*Euonymus Alatus* Diacylglycerol Acyltransferase) Gene With the discovery of tissue specific synthesis of ac-TAGs in *Euonymus* endosperm in contrast to lc-TAGS in the aril, deep transcriptional profiling was used to compare these two different tissues in order to identify candidate enzyme genes necessary for the production of ac-TAGS. Thus, RNA was extracted from endosperm tissue at different time points during seed development, as well as from aril and embryo tissue at a point during maximal TAG production.

At least two cDNA libraries were constructed from the RNA extracted from aril tissue and endosperm tissue. These libraries were sequenced using 454 pyrosequencing methods, see details below. When the results were compared and analyzed following sequence analysis of the cDNA, the inventors discovered an exemplary novel membrane-bound O-acyltransferase (MBOAT) gene family member abundantly expressed in the endosperm while absent from aril tissue. This gene was isolated and initially cloned into a GATEWAY entry vector for further testing of ac-TAG production capability as described below.

A. RNA Isolation Methods, Library Construction, and 454 Pyrosequencing.

Approximately 5 g of frozen tissue was ground to a fine powder in liquid nitrogen RNA was extracted using the method of López-Gómez and Gómez-Lim, (1992) Hort. Science 27:440-442, with the following modifications: after addition of the homogenization buffer the samples were incubated at 65° C. for 10 minutes and the final ethanol precipitation of the RNA was omitted. mRNA was purified from 1 mg of total RNA using the Illustra mRNA purification kit (GE Healthcare).

cDNA was synthesized using the SMART PCR cDNA synthesis kit (Clontech). First-strand cDNA synthesis was performed with 2-µg of mRNA in a volume of 10 µl using the provided SMART IV primer, a modified CDS III/3' cDNA Synthesis Primer (5'-TAGAGGCCGAGGCGGCCGACAT-GTTTTGTTTTTTTTTCTTTTTTTTTTVN-3'; SEQ ID NO:20) and SuperScriptll Reverse Transcriptase (Invitrogen Corporation, Carlsbad, Calif.). Double stranded cDNA was prepared by PCR (14 cycles) using 1-µl of the first-strand reaction in a 50-µl reaction volume. Following Proteinase K treatment, 8 PCR reactions were pooled prior to SfiI digestion and size fractionated on the provided CHROMA SPIN-400 column. Up to 40% of the ESTs in the endosperm libraries were found to correspond to seed storage proteins or oleosins. In order to increase the possibility of finding rare transcripts (i.e. transcripts specific for expression in endosperm), mRNA levels for one endosperm library were also normalized by the removal of abundant transcripts found in the aril libraries. This normalized 8/29-endosperm cDNA library was constructed at the Joint Genome Institute using the Trimmer-Direct cDNA normalization kit (Evrogen, Moscow, Russia) prior to additional rounds of PCR amplification.

DNA sequencing was performed at the Michigan State University Research Technology Support Facility and at the Joint Genome Institute using the GS20 sequencer (Roche Applied Science, Basel, Switzerland). Reads were trimmed to remove low quality and primer sequences using SeqClean (Pertea, et. al. (2003) Bioinformatics 19:651-652, herein incorporated by reference). Due to the high abundance of certain transcripts, initially 5% of the data was assembled with CAP3 (Huang (1999) Genome Res. 9:868-877) to identify these contigs, which were then removed from the full dataset using BLAT (Kent (2002) Genome Res. 12:656-664, herein incorporated by reference) The reduced dataset then underwent two rounds of assembly with CAP3. First-round CAP3 parameter settings for percent match, overlap length, maximum overhang percent, gap penalty, and base quality cutoff for clipping were-p 90 -o 50 -h 15 -g 2 -c 17, respectively. For the second-round-o was changed to 100. The resultant contigs were then annotated with a translated BLAST against the *Arabidopsis* Information Resource (TAIR) [TAIR8 released in April 2008] Carnegie Institution for Science Department of Plant Biology, and Universal Protein Resource (UniProt) (previously Swiss-prot) databases (The UniProt Consortium. The Universal Protein Resource (UniProt). *Nucleic Acids Res.* 37:D169-D174 (2009), herein incorporated by reference).

At least 338 thousand sequences were obtained for each library, with some libraries containing over 500 thousand sequences (Table 4). Contigs were assembled and then annotated based on their homology to *Arabidopsis* proteins. The transcript levels of genes encoding enzymes important for TAG synthesis in other species were of obvious interest (Table 4). Surprisingly, no EaDGAT1 transcripts were present in any of the endosperm libraries, including the normalized library enriched for less abundant sequences, further confirming that EaDGAT1 does not have a primary role in the formation of ac-TAGs. Further, endosperm expression levels of other TAG synthetic genes such as DGAT2 and phospholipid: diacylglycerol transferase (PDAT) were also low. In contrast, transcripts from all these genes were present in aril tissue, consistent with a role in the formation of the lc-TAGs in that tissue. Taken together, these results suggest that *Euonymus* endosperm contains a novel enzyme necessary for the production of ac-TAGs.

Figure 8:
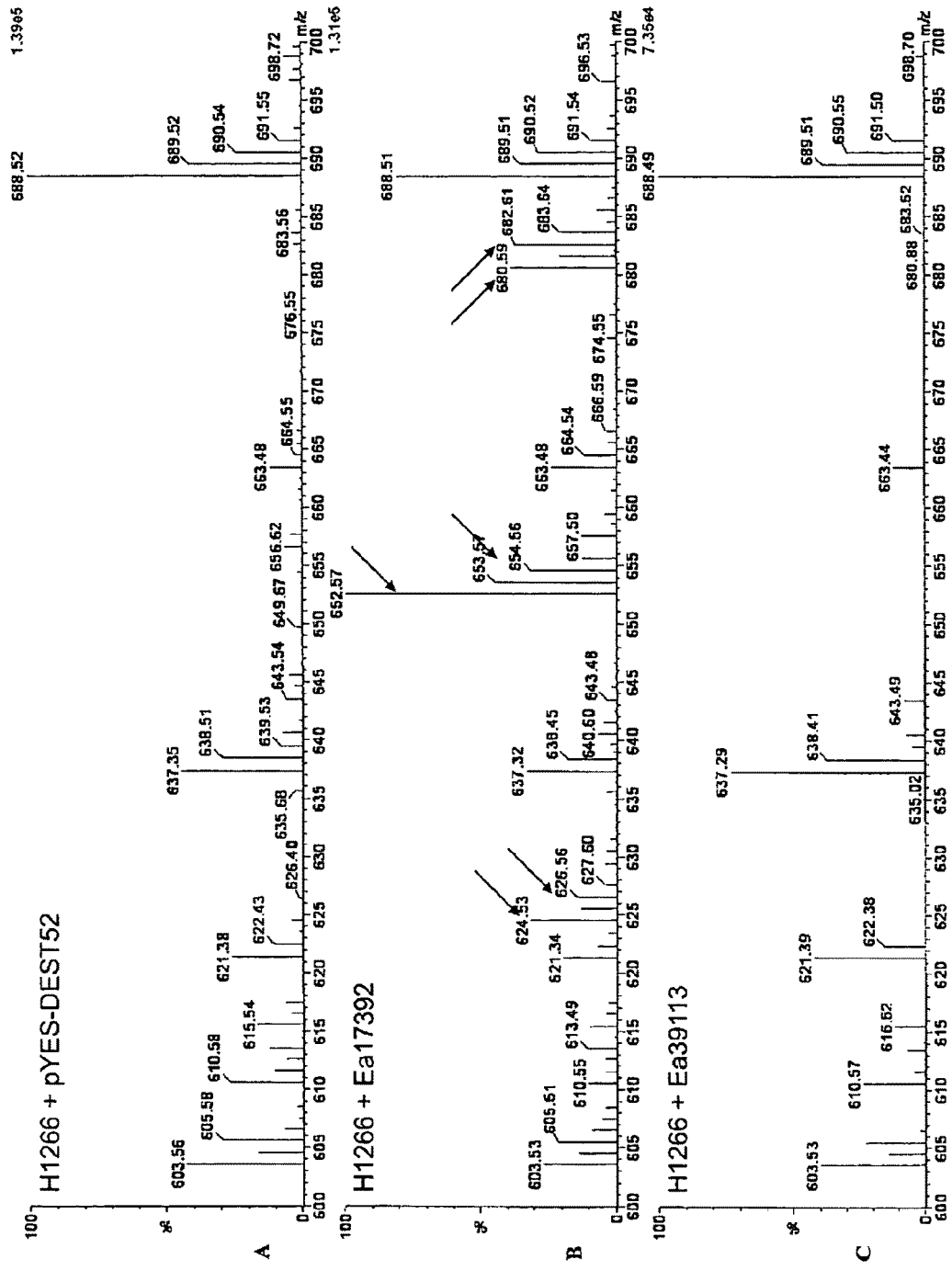
FIG. 8 shows exemplary expression of EaDAcT in yeast that resulted in production of ac-TAGs in vivo. Positive-ion ESI mass spectra of lipid extracts from H1266 yeast (TAG deficient) expressing A) the empty vector pYES-DEST52, and yeast expressing two candidate acyltransferases, B) Ea17392 (later renamed EaDAcT), and C) Ea39113. Peaks correspond to m/z values of the [M+NH4]+ adduct. Note: arrows point to novel peaks corresponding to ac-TAGs.

Ea17392 (subsequently named EaDAcT), Ea39113 and Ea27403. The full-length cDNAs for each candidate was cloned into pENTR-D/TOPO using gene specific primers designed to amplify the open reading frame revealed by the assembled contig. Then using GATEWAY technology, the cDNA was transferred to the yeast expression vector pYES-DEST52. The three different acyltransferase genes were then expressed in H1266 yeast (TAG deficient) and lipid extracts prepared from yeast cell cultures. Analysis of the lipid extracts using ESI-MS revealed that only yeast expressing Ea17392 accumulated ac-TAGs (FIG. 8).

One exemplary gene, a member of the Membrane Bound O-Acyltransferase (MBOAT) gene family, initially designated Ea17392 was subsequently named EaDAcT (*Euonymus alatus* diacyl-glycerol Acetyl transferase), is highly expressed in the endosperm and absent from the aril, consistent with a role in the synthesis of ac TAGs but not lc-TAGs (Table 3).

B. Isolation and Expression of cDNA Encoding EaDAcT.

An additional cDNA library was also constructed at the Joint Genome Initiative by pooling the mRNA extracted from aril, endosperm and embryo as described above. This mRNA was normalized and copied to cDNA using the methods described above. This pooled, normalized cDNA library was then ligated into the pDNR-LIB vector provided in the Clontech Creator™ SMART™ kit (Clontech Laboratories, Inc. Mountain View, Calif., United States) 10,000 clones were picked, grown and sequenced from both ends at the Joint Genome Initiative. In this manner a library consisting of cloned and sequenced *Euonymus* cDNA was created. Clones of interest were then identified after BLASTing (i.e. comparing isolated DNA sequences with selected DNA sequences) the desired sequence against the sequences obtained by sequencing both ends of the clones. For example, a clone named CCXA10733 containing the candidate Ea17392 (later designated EaDAcT) was identified when a BLAST search was done using the sequence of contig Eal 7392 (obtained from the 454 pyrosequencing) against the sequences corresponding to the cloned cDNA library.

TABLE 4

EST Counts and Transcript Levels of Genes Involved in TAG Synthesis in Different Euonymus cDNA Libraries.

| | Aril | Embryo | Endosperm | | | | Normalized |
|---|---|---|---|---|---|---|---|
| | 1 | 2 | 3 | 4 | 5 | 6 | Genes* |
| No. ESTs | 342,813 | 338,868 | 342,232 | 430,701 | 522,242 | 423,690 | 705,875 |
| DGAT1 | 3.6 | 0 | 0 | 0 | 0 | 0 | 0 |
| DGAT2 | 0.9 | 0.3 | 0.9 | 0.4 | 0.4 | 1.2 | 2.8 |
| PDAT | 3.6 | 1.8 | 0.3 | 0 | 0 | 0.2 | 0.5 |
| PDAT-like | 10.3 | 3.0 | 0.6 | 0 | 0.4 | 0.5 | 0 |
| EaDAcT | 0 | 22.2 | 62.2 | 30.7 | 48.7 | 42.4 | 39.7 |

*Gene expression levels are represented as the number of transcripts per 100,000 transcripts.

Up to 40% of the ESTs in the endosperm libraries were found to correspond to seed storage proteins or oleosins. In order to increase the possibility of finding rare transcripts (i.e. transcripts specific for expression in endosperm), mRNA levels for one endosperm library were also normalized by the removal of abundant transcripts found in the aril libraries. In order to identify a candidate enzyme(s), genes annotated as acyl-transferases with high transcript levels in the endosperm relative to the aril were selected for further evaluation as candidate ac-TAG producing genes. In this manner, three candidate acyltransferases were chosen for further study:

A full-length cDNA clone was obtained via PCR using primers designed to amplify the open reading frame in the candidate gene contigs assembled from the 454 pyrosequencing. Specifically, cDNA encoding the candidate (i.e. EaDAcT) was amplified with the gene specific primers 5'-CACCATGATGGATGCTCATCAAGAG-3' (SEQ ID NO:11) and 5'-ATTTATTTCATCGTCATCATCAATTTCC-3' (SEQ ID NO:12) using DNA extracted from the clone CCXA10733 as a template and then cloned into pENTR-D/TOPO (Invitrogen) following the manufacturer's general protocol.

Colonies carrying the vector with the correct insert were selected via colony PCR, using the same gene specific primers indicated above. Sequence analysis of these positive clones revealed that EaDAcT sequences had been isolated.

C. Full Length *Euonymus* Candidate EaDAcT cDNA.

Exemplary comparisons of a candidate EaDAcT amino acid sequence to known genes in GenBank are shown in Table 7 of FIG. 6. These genes include an *Euonymus alatus* DGAT1 sequence from Milcamps, et al., J. Biol. Chem. 280 (7), 5370-5377 (2005), U.S. Pat. Nos. 7,122,367 and 7,429,473, all of which are herein incorporated by reference in their entirety. This EaDGAT1 protein sequence (SEQ ID NO:09) shows an exemplary merely 28% identity to the EaDAcT amino acid sequence (SEQ ID NO:01).

Example IV

Phylogenetic Comparison of Candidate DAcT Sequence to Known Sequences and Creating an Unrooted Phylogenetic Tree of EaDAcT and Similar Proteins This Example describes identifying membrane bound O-acyl transferase (MBOAT) family of membrane proteins and assembly of an unrooted phylogenetic tree of EaDAcT with similar proteins.

Figure 7:
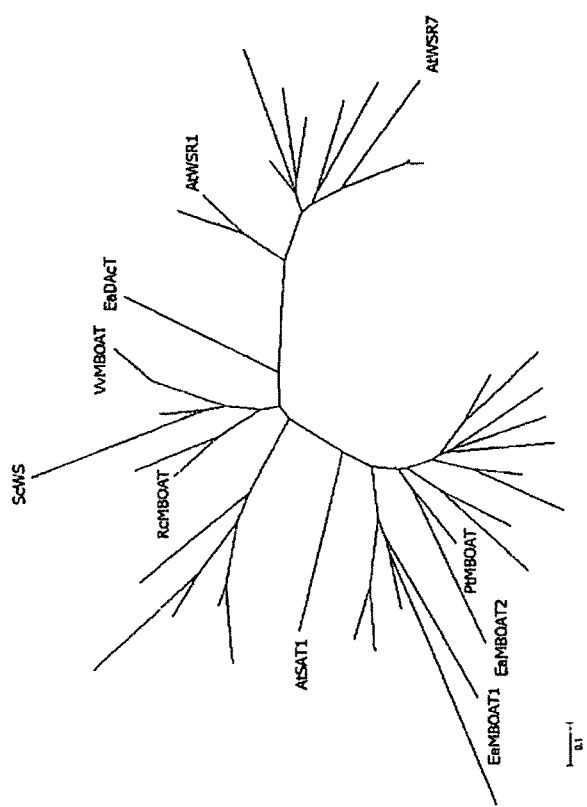
FIG. 7 shows an exemplary unrooted phylogenetic tree of EaDAcT and similar proteins. Fifty proteins with the highest similarity to EaDAcT in GenBank were queried using the NCBI BLAST server. Of these, the two top *Euonymus* EST database hits were queried with a local database BLAST algorithm. Amino acid sequences were aligned with MUSCLE. Redundant sequences differing by less than two amino acid residues were removed; the remaining sequences were further curated by GBLOCKS. Montpellier bioinformatics platform's PhyML server (with default settings) calculated the maximum likelihood tree. Select sequences labeled above correspond to the following GenBank or *Euonymus* EST database accession numbers: AtSAT1, *Arabidopsis thaliana* sterol O-acyltransferase 1, 145339386; AtWSR1, *A. thaliana* wax synthase related, 19699363; AtWSR7, *A. thaliana* wax synthase related, 18423734; EaMBOAT1, *E. alatus*, Ea63572; EaMBOAT2, *E. alatus*, Ea18619; PtMBOAT, *Populus trichocarpa*, 224106161; RcMBOAT, *Ricinus communis*, 255576260; ScWS, *Simmondsia chinensis* wax synthase, 5020218; VvMBOAT, *Vitis vinifera*, 225453317.

When the candidate DAcT sequences was phylogenetically compared to other plant genes, the candidate clustered MBOAT proteins clusters with a group of mostly uncharacterized proteins annotated as putative wax synthases based on their similarity to the Jojoba wax synthase (Lardizabal, et. al. (2000) Plant Physiol 122:645-656) (FIG. 7). Also included in this group was the *Arabidopsis* sterol transferase, AtSAT1 (Chen, et. al. (2007) Plant Physiol. 145:974-984). Therefore based upon sequence comparisons and annotations an ac-TAG capability for the candidate DAcT gene and encoded protein was unexpected.

Fifty proteins most similar to EaDAcT in GenBank were queried using the NCBI BLAST server. The two most similar *Euonymus* EST database hits were queried with a local database BLAST algorithm. Amino acid sequences were aligned with MUSCLE. Redundant sequences differing by less than two amino acid residues were removed; the remaining sequences were further curated by GBLOCKS. Montpellier bioinformatics platform's PhyML server (with default settings) calculated the maximum likelihood tree. Select sequences labeled above correspond to the following GenBank or *Euonymus* EST database accession numbers: AtSAT1, *Arabidopsis thaliana* sterol O-acyltransferase 1, 145339386; AtWSR1, *A. thaliana* wax synthase related, 19699363; AtWSR7, *A. thaliana* wax synthase related, 18423734; EaMBOAT1, *E. alatus*, Ea63572; EaMBOAT2, *E. alatus*, Ea18619; PtMBOAT, *Populus trichocarpa*, 224106161; RcMBOAT, *Ricinus communis*, 255576260; ScWS, *Simmondsia chinensis* wax synthase, 5020218; VvMBOAT, and *Vitis vinifera*, 225453317.

Example V

Yeast Cells Transformed with a Full-Length *Euonymus* Candidate DAcT Gene cDNA Produced ac-TAGs In Vivo This Example describes an exemplary expression experiment where the candidate DAcT gene (*Euonymus* MBOAT gene) was expressed in yeast cells to determine whether it was capable of inducing ac-TAG production in vivo. Further, the following describes exemplary methods of heterologous DGAT yeast expression and lipid analysis.

Despite the phylogenic comparison results that indicated a candidate DAcT protein function that was not annotated as capable of a diacylglycerol acyl transferase (DGAT) activity, the isolated and cloned *Euonymus* candidate DAcT cDNA was tested for ac-TAG production capability. The isolated and cloned *Euonymus* candidate DAcT cDNA was recombined into the yeast expression vector pYES-DEST52 (Invitrogen) using GATEWAY technology and then transformed into *Saccharomyces cerevisiae* strains InvSc1 (Invitrogen) and the triple mutant H1266 (Δdga1::kanM Δlro1::TRP1 Δare2::LEU2) provided by Dr. Sten Styrone (Swedish University of Agricultural 138 Sciences). Transformed yeast cells were grown to stationary phase when total lipids were extracted. Analysis of the lipids using ESI-MS revealed the surprising accumulation of ac-TAGs in the transformed cell lines.

The following describes exemplary methods of heterologous DGAT yeast expression and lipid analysis. Two controls were used in subsequent expression analysis. One was the yeast transformed with the empty vector pYES2-DEST52. The second was yeast transformed with the *Euonymus* DGAT1 cDNA cloned into pYES2CT. Yeast cells for each construct were grown in liquid medium and analyzed for lipid content. For growth-phase dependent analysis, a small 3 ml culture of each colony was started in SC-medium with 2% galactose and grown overnight. This culture was diluted to an OD of 0.125 in a volume of 30 ml and grown for 48 hours in SC-medium lacking uracil with 2% galactose, lipids extracted and then analyzed using ESI-MS as described in the lipid analysis methods (Example I).

Figure 10:
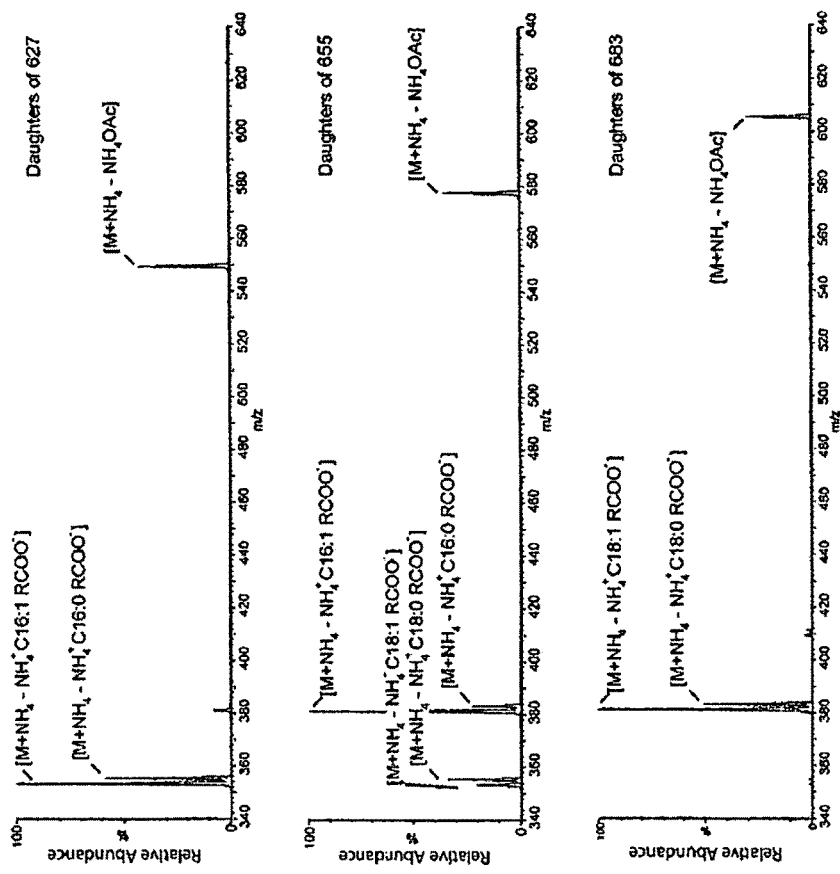
FIG. 10 shows exemplary novel oils produced by transgenic yeast cells of the present inventions for use as biofuels and novel oils as described herein. ESI-MS/MSspectra of ac-TAGs synthesized by yeast expressing EaDAcT. The spectra and corresponding daughter fragments for pseudomolecular ions with m/z 627, 655, and 683, are shown.

EaDAcT was expressed in wild type yeast cells (strain InvSc1) and neutral lipid extracts analyzed using ESI-MS. The resultant mass spectrum from EaDAcT lipid extract revealed a number of novel peaks with masses corresponding to the $[M+NH_4]+$ adduct of different ac-TAG molecular species (FIG. 9A). When subjected to ESI-$MS^2$, these novel peaks produced daughter fragments consistent with ac-TAGs (FIG. 10). Interestingly, ESI-$MS^2$ analysis indicated that in contrast to the fatty acid profile of ac-TAGs produced by *Euonymus*, the ac-TAGs synthesized in yeast contained high levels of the fatty acids palmitate, palmitoleate, stearate and oleate that dominated (i.e, were the majority of) other yeast lipids. Quantification of the ESI-MS analyses revealed that InvSc1 yeast expressing EaDAcT produced 17.5 nmol ac-TAG/mg DW and 12.3 nmol lc-TAG/mg DW, compared to no detectable ac-TAGs and 32.9 µmol lc-TAG/mg DW produced when yeasts were transfected by the empty vector control. These results demonstrate that EaDAcT is sufficient to produce ac-TAGs when expressed in yeast, suggesting it is the enzyme necessary for ac-TAG production in *Euonymus* endosperm. To determine whether EaDAcT was also capable of synthesizing lc-TAGs, the gene was expressed in the yeast strain H1266 (FIGS. 8 and 9B). Three genes important for TAG synthesis have been ablated in H1266, rendering this strain unable to accumulate TAG (Sandager et al. (2002) J Biol. Chem. 277:6478-6482, herein incorporated by reference). As expected, H1266 containing the empty vector (pYES-DEST52) did not possess any peaks corresponding to TAGs when neutral lipid extracts were analyzed using ESI-MS (FIG. 9B). When expressing EaDGAT1, H1266 yeast accumulated up to 13.6 nmol lc-TAG/mg DW, but no ac-TAGs (FIG. 9B). In contrast, H1266 yeast expressing EaDAcT accumulated 0.5 nmol ac-TAG/mg DW but no lc-TAGs (FIG. 9B), demonstrating that EaDAcT cannot synthesize lc-TAGs when expressed in yeast.

These results proved that the novel MBOAT candidate DGAT gene functioned as an acetyltransferase enzyme in vivo; thus the enzyme was named diacylglycerol acetyltransferase (DAcT).

Example VI

Microsomes Isolated from Yeast Transformed with a Full Length *Euonymus* DGAT (EaDAcT) cDNA Demonstrated Acetyl-transferase Activity In Vitro This example describes microsomes isolated from yeast transformed with EaDAcT that possess acetyltransferase activity in vitro when incubated with diacylglycerol and [$^{14}$C] acetyl-CoA. Microsome isolation and assays for DGAT activity are briefly described herein. Microsomes from cultures of InvSc1 and H1266 containing pYES-DEST52 (empty vector), pEaDAcT or pEaDGAT1 were isolated as described in Example I. DGAT assays with either [$^{14}$C]-acetyl CoA or [$^{14}$C]-oleoyl CoA were performed as described in Example I.

Figure 11:
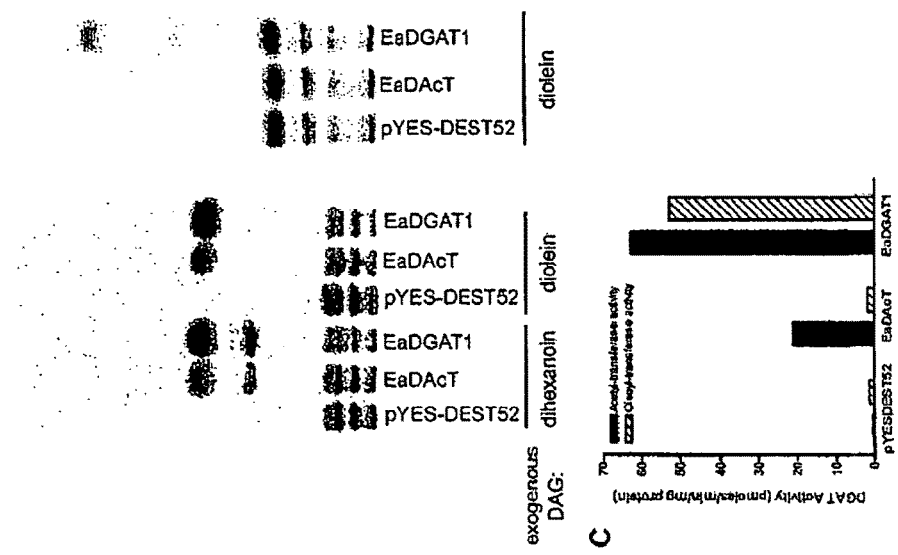
FIG. 11 shows exemplary EaDAcT proteins that demonstrated acetyltransferase but not oleolyltransferase activity in vitro. (A) Thin layer chromatography (TLC) separation of lipid extracts from yeast microsomes (InvSc1 background) expressing EaDAcT, EaDGAT1 and empty vector (pYES-DEST52) incubated with 15 µM [$^{14}$C] acetyl-CoA in the presence of exogenous 230 µM dihexanoin. In samples that did not contain dihexanoin, exogenous 230 µM of diolein was added. (B) TLC separation of lipid extracts from yeast microsomes (H1266 background) expressing vectors encoding EaDAcT and EaDGAT1 compared to an empty vector (pYES-DEST52) incubated with 8 µM [$^{14}$C] oleoyl-CoA. (C) Quantification of the in vitro acetyltransferase and oleoyltransferase activities depicted in (A) and (B), respectively.

Previous work demonstrated that ac-TAGs are synthesized in *Euonymus* endosperm by an 1,2-diacyl-sn-glycerol:acyl CoA acyltransferase reaction (Milcamps et al. (2005) J. Biol. Chem. 280:5370-5377). To determine whether the EaDAcT gene discovered during the development of the present inventions possesses this activity in vitro, microsomes were isolated from InvSc1 yeast samples expressing one of the following: EaDAcT expression vector, EaDGAT1 expression vector and the empty vector. These microsomes were incubated with [$^{14}$C]acetyl-CoA, resultant lipids extracted and then separated with TLC. Unlike in whole organisms, both EaDAcT and EaDGAT1 microsomes produced a labeled product that co-migrates with the ac-TAG fraction of *Euonymus* oil (FIG. 11). The observation that expression of EaDGAT1 in yeast microsomes produced ac-TAGs originally led the inventors to believe that EaDGAT1 was responsible for ac-TAG production, in contrast to experiments in whole organisms where transgenic EaDGAT1 expression failed to induce ac-TAG production, see, further information, supra. Additionally, this product from EaDGAT1 has previously been shown to be [$^{14}$C]ac-TAG (Milcamps et al. (2005) J. Biol. Chem. 280:5370-5377). Thus EaDAcT possesses the necessary acetyltransferase activity in vitro for the production of ac-TAGs. To prove that EaDAcT was acetylating DAG to form ac-TAGs, similar in vitro acetyltransferase reactions were performed with the addition of dihexanoin. The presence of this exogenous, short acyl-chain length DAG resulted in an additional labeled band from both the EaDAcT and EaDGAT1 microsomes. These results demonstrated that EaDAcT functions as 1,2-diacylglyeerol:acyl-CoA acyltransferase.

Microsomes were also isolated from H1266 yeast expressing EaDAcT, EaDGAT1 and the empty vector and then incubated with [$^{14}$C]oleoyl-CoA to determine whether EaDAcT possesses long chain acyltransferase activity. Under these conditions, only EaDGAT1 produced a labeled product that co-migrates with the lc-TAG fraction of *Euonymus* oil (FIG. 11). These results suggest that EaDAcT does not possess long chain acyltransferase activity and are consistent with the in vivo accumulation of ac-TAGs, but not lc-TAGs, by H1266 expressing EaDAcT (FIGS. 9 and 10).

Example VII

Novel Acyl Lipid Products from DGAT (EaDAcT) Proteins

DAcT proteins, whether present in their native plants and plant tissues, such as *Euonymus* seeds, or in a transgenic host organism, or in an in vitro assay, can be used to synthesize novel acyl lipids and in particular novel triacylglycerols. The novel products may arise from the acyl-CoA or acyl acceptor specificity of the native enzyme, whether in a native plant such as *Euonymus*, or in a host organism transformed with DAcT. The native plant or the transformed host organism may also be genetically manipulated to better provide required novel substrate, or if the transformed organism is grown in culture, the novel substrate(s) can be supplied directly. Alternatively, the DAcT amino acid sequence may be modified to provide altered and thus improved substrate specificity. Thus means for screening for native and altered substrate specificities are important. The function of product, and more specifically the triacylglycerol product, will depend on the molecular structure of the diacylglycerol or other acyl acceptor and on the acetyl or related-CoA group. In this section three different types of assay are used to demonstrate methods to screen for altered substrate specificity, and to define novel and functionally useful types of triacylglycerols. These novel triacylglycerols are altered in either 1,2-diacylglycerol or sn-3 acyl group specificity. Extensions and combinations of these novel specificities can be sought by those skilled in the art.

For the first example, in the yeast expression experiment described in Example V, a triacylglycerol species acetyldipalmitolein was produced; this triacylglycerol species has not been previously reported, and is therefore novel. It is synthesized because yeast can supply a dipalmitoleoylglycerol (C16:1/C16:1-DAG). Such a triacylglycerol will have improved functional properties over, for example, acetyldioleoylglycerol, in that the loss of four methylene groups will lower both its pour point and viscosity, making it a preferred ac-TAG for lubrication and biofuel applications. It is contemplated that the use of the EaDAcT can be used to produce structures such as acetyldiricinolein; acetyldivernolin, or acetyldicaprin; these structures also have not been previously reported, and are therefore novel.

In the second example novel compounds can be produced in vitro by incubating an EaDAcT enzyme with acetyl-CoA and the appropriate DAG substrate. In Example VI, the provision of a dihexanoin (C6:0/C6:0-DAG) produces a novel product, the triacylglycerol acetyldihexanoin, which is a C14 acyl carbon number triacylglycerol. This molecule is also expected to have optimum physical properties for biofuel. Furthermore, the fact that much shorter chain length DAGs are accepted by DAcT suggests that this enzyme will utilize other novel DAGs, for example, diricinolein or divernolin, under suitable conditions such that the corresponding ac-TAG products are synthesized. Such compounds can be produced in vivo by transforming a plant in which the appropriate DAG substrate is present with a gene encoding EaDGAT under control of a suitable promoter (as for example is described in Example 5), such that EaDGAT is expressed when and where the appropriate DAG substrate is synthesized, resulting in the synthesis of novel ac-TAG.

In addition, transformed or native organisms are contemplated to produce other novel glycerides when the organism contains an acetyltransferase gene and a substrate related to acetyl-CoA is present endogenously or can be generated from a exogenous substrate. In a third example, the synthesis of propionyl glycerides by seeds of *Euonymus* when provided with a novel related substrate, propionate, is demonstrated. Labeled acetate or propionate is readily incorporated into lipid products by developing seeds of *Euonymus alata*. Labeled lipid products from incubation of either [$^{14}$C]acetate or [$^{14}$C]propionate were analyzed by normal phase silica TLC, as shown in the left hand panel of the FIG. 3A. Normal phase TLC for neutral lipid separations shows the predominant mass band, 3-acetyl-1,2-diacyl-sn-glycerol (ac-TAG) to be highly labeled (35%) from acetate. DAG is labeled to 5%, lc-TAG to 2%, through [$^{14}$C]fatty acid labeling from acetate. Polar lipids, and especially phosphatidylcholine, are also highly labeled through fatty acid labeling. When the [$^{14}$C]3-acetyl-1,2-diacyl-sn-glycerol fraction was purified by preparative normal phase TLC and the distribution of label between the acetyl and long-chain acyl groups analyzed by saponification and phenacyl ester derivatization the major labeled band (89%) corresponded to the phenacyl acetate standard, whereas the minor labeled band (11%) corresponded to the phenacyl oleate standard. Thus [$^{14}$C]3-acetyl-1,2-diacyl-sn-glycerol is highly labeled in the acetyl group relative to the fatty acyl groups.

Labeled products from incubation of [$^{14}$C] propionate were analyzed by TLC. A small band (4.5%) was observed running just ahead of the major mass of 3-acetyl-1,2-diacyl-sn-glycerol and was putatively identified as 3-propionyl glyceride (Pr-TAG). The slight reduction in polarity of the 3-propionyl glyceride relative to the 3-acetyl-glyceride is expected. When the [$^{14}$C] 3-propionyl-1,2-diacyl-sn-glycerol fraction was purified by preparative normal phase TLC and the distribution of label between the propionyl and long-chain acyl groups analyzed by saponification and phenacyl ester derivatization the only labeled band corresponded to the phenacyl propionate standard.

Figure 3B:
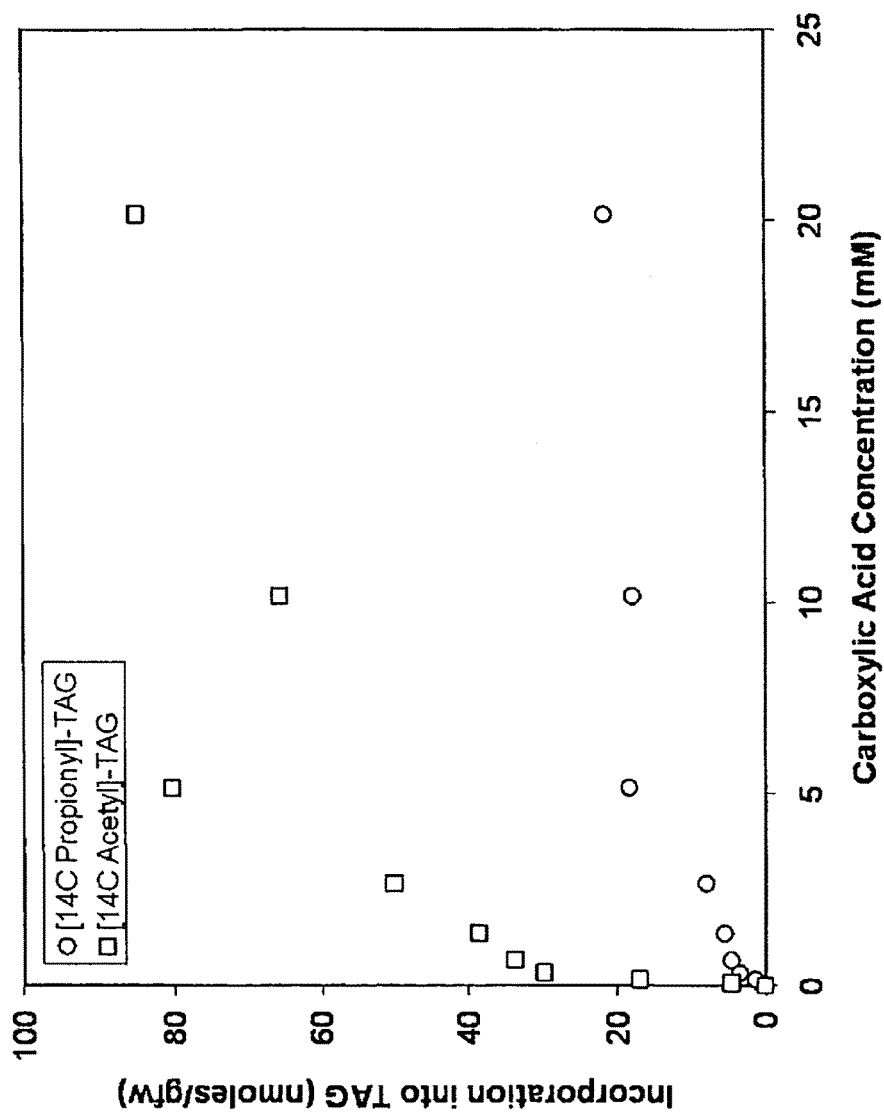

Acetate concentration curves are shown in FIG. 3B. Incorporation into [$^{14}$C acetyl]3-acetyl-1,2-diacyl-sn-glycerol reaches a maximum rate of about 40 nmoles/hr/g. fresh wt. at 5 mM acetate, with a half maximal velocity at about 1.3 mM acetate. The propionate concentration curve for incorporation into [$^{14}$C propionyl]3-propionyl-1,2-diacyl-sn-glycerol reaches a maximum rate of about 10 nmoles/hr/g. fresh wt. at 10 mM propionate, with a half maximal velocity at about 2.5 mM propionate.

Thus the maximal rate of propionate incorporation into the sn-3 position of the glycerides is about 25% of that for acetate. It is unclear whether this difference is a result of different rates of uptake and activation of acetate and propionate, or different rates of utilization by the sn-3 acyltransferase. However, the important point is that the in vivo experiment suggests there is substantial activity towards propionyl-CoA for EaDAcT.

Example VIII

Analysis of Seed from Transgenic Plant Lines Revealed High Levels of Acetyl-TAGs Present in the Seed EaDAcT was cloned into a plant transformation vector under the control of the *Arabidopsis* 2S seed storage promoter (BAC:T24A18, see, Example 1) and transformed into *Arabidopsis* Col-0 wild type plants. Briefly, EaDAcT was ligated into the plant binary expression vector p2S.GATEWAY, which was constructed by ligating 1 kb of genomic sequence upstream of the *Arabidopsis* 2S seed storage protein gene (At4g27160) and the att cassette from pMDC32 (Curtis and Grossniklaus (2003) Plant Physiol 133:462-469) into the multiple cloning site of pCAMBIA1390 (www.cambia.org). This construct, p2S, EaDAcT, was then introduced into *Agrobacterium tumefaciens* strain C58C1 and transformed into wild type Col-0 *Arabidopsis* plants using the floral dip method (a simplified method for *Agrobacterium*-mediated transformation of *Arabidopsis thaliana*) Clough and Bent (1998) Plant J. 16:735-743). Lipids were extracted from the seeds of transgenic plants and TAG content analyzed using ESI-MS. Isolated seed oils provided novel oils comprising ac-TAGs produced by transgenic plants there were not present in oils isolated from nontransgenic plants (FIG. 12A).

In over half of the transgenic lines, the proportion of ac-TAGS was high, with some lines accumulating up to 44 mol % ac-TAGs (FIGS. 12B, 13 and 14A). The identity of these heterologously produced ac-TAGs was confirmed using ESI-MS2, which produced the expected daughter fragments (FIG. 12C).

To determine the effect of EaDAcT insertion number, seed from all the T3 progeny of one high ac-TAG producing T2 plant (#13) had their lipids analyzed using ESI-MS. Seed that was 100% resistant to hygromycin and thus were deemed homozygous for the EaDAcT insertion event possessed higher levels (44 mol %) of ac-TAGs compared to the seed that was 75% resistant to hygromycin (and thus deemed hemizygous for the EaDAcT insertion event) and possessed 25 to 33 mol % ac-TAGs (FIG. 13). This demonstrates that homozygous lines possess higher levels of ac-TAGs.

A. Vectors and Transfection Methods for Providing Seeds.

*Agrobacterium tumefaciens* strain C58C1 was grown at 28° C. in YEP medium, supplemented with the appropriate antibiotics: rifampicine 50 mg/ml, streptomycin 25 mg/ml or gentamycin at a few mg/ml. The constructs (p2S.EaDAcT), i.e. vectors comprising a EaDAcT gene (such as SEQ ID NO. 01), were used when transferred into *A. tumefasciens* strain C58C1 via electroporation. The presence or absence of the EaDAcT sequence was verified with whole cell PCR, using EaDAcT specific primers.

Six-week old *Arabidopsis* plants (ecotype Colombia-0) were transformed via the floral dip method with the *A. tumefasciens* strains, comprising (carrying) a promoter sequence p25 and EaDAcT. The plants were grown to maturity. Seeds (T1, F1 generation) were collected and transgenic plants (T1) were selected by germination on MS media containing 30-μg/ml hygromycin. The surviving hygromycin resistant plants were allowed to grow to maturity, set seed and desiccate. Seed (T2) from a number of these single plant lines were harvested. T2 seedlings from these lines were germinated on hygromycin and lines that demonstrated a 75% survival rate were deemed to possess a single T-DNA insertion event and chosen for further study. Twelve surviving T2 plants from each chosen line were grown to maturity and seed (T3) collected. T3 seeds from individual T2 plants were germinated on hygromycin and lines that possessed a 100% survival rate were deemed to be homozygous for the T-DNA insertion; these seeds were analyzed for lipid content. Control seeds for seed analysis, such as T3 seeds, T4 seeds, etc. were collected from untransformed *Arabidopsis* plants (ecotype Colombia-0). EaDGAT1 expressing plants were provided as described for EaDAcT with the exception of using an EaDGAT1 gene in place of an EaDAcT gene. T4 seeds were harvested and T4 plants were grown as described for T1-T3 plants.

B. Plant Growth Methods for Providing T2, T3 and T4 Seeds for Analysis.

Mature *Arabidopsis thaliana* plant T3 (F3 generation) and T4 (F4 generation) seeds were collected from the siliques of 6-8 week old plants, grown in the growth chambers (16 h light period, 22° C., 80 to 100 μE light intensity). Neutral lipids were quantitatively extracted and analyzed using ESI-MS as described in Example I.

Example IX

Comparison Analysis of Oil Produced by Seeds of Arabidopsis Plants Transformed With a Full Length Euonymus DGAT1 cDNA vs. Seeds of Arabidopsis Plants Transformed with a Full Length Euonymus DAcT of the Present Inventions An additional comparison was made between seed oils produced by *Arabidopsis* plants expressing a heterologous EaDAcT nucleic acid sequence vs, *Arabidopsis* plants expressing a the original candidate nucleic acid sequence for ac-TAG production, EaDGAT1. The *Euonymus* DGAT cDNA was cloned into a plant expression vector under the control of the promoter of the *Arabidopsis* 2S seed storage protein gene (At4g27160). The *Euonymus* DGAT1 gene under control of this promoter was expressed in *Arabidopsis thaliana* (var. Columbia-0) to gauge its comparative capability to alter oil content. FIGS. 14 A and B show a comparison of accumulation of oil between transgenic *Arabidopsis* expressing EaDAcT vs. EaDGAT1. Exemplary FIG. 14A shows exemplary ac-TAG production in the darker (grey), left-hand bar pairs compared to lc-TAG production in the lighter (red) right-hand bar pair for plant seeds expressing EaDAcT vs. a lack of ac-TAG production in wild-type *Arabidopsis* plant seeds. FIG. 14B shows an exemplary lack of ac-TAG production compared to measurable levels of lc-TAG production in seeds from EaDGAT1 transformed plants.

A. Analysis of T3 Pooled Seed from Plants Expressing a Heterologous EaDAcT Sequence.

EaDAcT transformed lines possessed a range of ac-TAGs from 1.0% to 47% molar ratio of the total TAG content of the seeds (by dry weight) (FIGS. 13, 14A and Table 5). The ac-TAG analysis by ESI-MS showed a statistically valid increase in ac-TAGs (blue, lighter left bars of each data set), ranging approximately 3- to 30-fold over wild type (WT) ac-TAG production. Lc-TAG production is shown by red (dark, right bars of each data set) in FIG. 14A for comparison, B. Analysis of T4 Pooled Seed from Plants Expressing a Heterologous EaDGAT1 Sequence.

DGAT1 transformed *Arabidopsis* plant lines demonstrated ac-TAG production (blue, lighter left bars of data sets) ranging from 0.6 to 1.1% molar ratio of the total TAG content of the seeds (dry weight). Wildtype seeds (from wildtype *Arabidopsis* plants, i.e. plants not expressing a heterologous gene) showed approximately 1.2% ac-TAG production (FIG. 14B and Table 6). Thus, the ac-TAG content analysis by ESI-MS did not show a statistically valid increase in ac-TAGS over wild type plants. Lc-TAG production is shown by red (dark right side bars for each plant) in FIG. 14B for comparison.

The overall oil content of the seeds was not increased by expression of the *Euonymus* DGAT1 gene, indicating that under these experimental conditions and with this particular plant line, the expression of DGAT1 genes was not limiting to oil content.

TABLE 5

The following results show an exemplary analysis of T3 pooled seed from transgenic *A. thaliana* plants expressing EaDAcT (see also FIG. 14A).

| | Av (nmoles TAG/mg Seed DW) | | Total TAGs | | Std Dev | |
| --- | --- | --- | --- | --- | --- | --- |
| | acTAGs | lcTAGs | (nmoles/mg) | % acTAGs | acTAGs | lcTAGs |
| Col-0 + p2S.EaDAcT #1.3 | 244.029375 | 272.974861 | 517.004237 | 47.200653 | 16.96467 | 24.94505 |
| Col-0 + p2S.EaDAcT #3.2 | 16.9656846 | 318.813848 | 335.779533 | 5.0526262 | 1.732065 | 16.97331 |
| Col-0 + p2S.EaDAcT #12.1 | 203.875926 | 297.087613 | 500.963539 | 40.696759 | 13.74431 | 33.09176 |
| Col-0 + p2S.EaDAcT #21.3 | 208.63139 | 260.449136 | 469.080526 | 44.476668 | 21.98739 | 29.61942 |
| Col-0 + p2S.EaDAcT #26.5 | 123.975629 | 201.506758 | 325.482387 | 38.089812 | 2.830822 | 20.43366 |
| Col-0 + p2S.EaDAcT #28.3 | 4.5285228 | 334.37215 | 338.900673 | 1.336239 | 0.338601 | 16.76924 |
| Col-0 + p2S.EaDAcT #29.7 | 161.927951 | 203.922245 | 365.850196 | 44.260726 | 7.17758 | 13.5403 |
| Col-0 + p2S.EaDAcT #33.3 | 187.332968 | 223.808356 | 411.141324 | 45.56413 | 6.806338 | 13.70089 |
| Col-0 + p2S.EaDAcT #36.2 | 4.71344465 | 300.221519 | 304.934964 | 1.5457213 | 0.38946 | 21.43602 |
| Col-0 + p2S.EaDAcT #40.5 | 30.307236 | 266.535551 | 296.842787 | 10.209861 | 3.556838 | 22.40212 |
| Col-0 + p2S.EaDAcT #45.1 | 4.70832646 | 286.02553 | 290.733856 | 1.6194627 | 0.488389 | 22.10524 |
| Col-0 WT #1 | 4.89083064 | 281.99399 | 286.88482 | 1.7048064 | 0.52911 | 26.10846 |
| Col-0 WT #2 | 3.43053452 | 291.399593 | 294.830128 | 1.1635631 | 0.484424 | 29.21996 |
| Col-0 WT #3/#4 | 3.47576235 | 273.935897 | 277.41166 | 1.2529258 | 0.41893 | 26.21045 |
| Col-0 WT #5 | 5.20790939 | 259.233123 | 264.441033 | 1.9694029 | 0.548219 | 27.39953 |
| Col-0 WT #6 | 2.83047725 | 288.218806 | 291.049283 | 0.9725079 | 0.655338 | 31.72772 |
| Col-0 WT #7 | 4.49914431 | 317.602125 | 322.101269 | 1.3968105 | 0.657023 | 38.5133 |

TABLE 6

The following results show an exemplary analysis of T4 pooled seed from transgenic *A. thaliana* plants expressing EaDGAT1 (see also FIG. 14B).

| | Average (nmoles TAG/mg Seed DW) | | Total TAGS | | Std Dev | |
| --- | --- | --- | --- | --- | --- | --- |
| | acTAGs | lcTAGs | (nmoles/mg) | % acTAGs | acTAGs | lcTAGs |
| Col-0 + EaDGAT1 10.2A | 2.6 | 225.6 | 228.2 | 1.1 | 0.3 | 14.2 |
| Col-0 + EaDGAT1 3.6A | 1.9 | 246.0 | 248.0 | 0.8 | 0.2 | 28.8 |
| Col-0 + EaDGAT1 5.8B | 2.5 | 250.2 | 252.6 | 1.0 | 0.1 | 42.4 |

TABLE 6-continued

The following results show an exemplary analysis of T4 pooled seed from transgenic *A. thaliana* plants expressing EaDGAT1 (see also FIG. 14B).

| | Average (nmoles TAG/mg Seed DW) | | Total TAGS | | Std Dev | |
|---|---|---|---|---|---|---|
| | acTAGs | lcTAGs | (nmoles/mg) | % acTAGs | acTAGs | lcTAGs |
| Col-0 + EaDGAT1 6.2A | 2.0 | 193.4 | 195.4 | 1.0 | 0.2 | 16.9 |
| Col-0 + EaDGAT1 8.7A | 1.9 | 318.3 | 320.2 | 0.6 | 0.2 | 25.7 |
| Col-0 D | 2.8 | 229.8 | 232.6 | 1.2 | 0.3 | 29.0 |

TABLE 7

The following results show an exemplary analysis of TAGS isolated from Yeast (InvSc1) Expressing EaDGAT1 vs. EaDAcT genes (see also FIG. 14C).

| nmoles | Averages | | Std Dev | |
|---|---|---|---|---|
| TAG/mg DW | acTAGs | lcTAGs | acTAGs | lcTAGs |
| EV | 0.061 | 28.672 | 0.010 | 1.388 |
| EaDAcT | 24.450 | 12.165 | 6.502 | 1.158 |
| EaDGAT1 | 0.269 | 29.238 | 0.024 | 2.256 |

Example X

Ac-TAGS have Lower Kinematic Viscosities than lc-TAGs for Use in a Variety of Applications This example shows exemplary oil viscosity and density measurements made on purified acetyl-TAG and long-chain-TAG fractions from silica chromatography of isolated *Euonymus alatus* seed oil. For comparison, standards were soybean oil (100% lc-TAGS and 0% ac-TAGs) and trioctanoin (100% medium chain TAGs).

Oil was extracted from mature, dried and ground *Euonymus alatus* seeds (seed plus aril) by Soxhlet extraction with hexane. In a typical large scale purification of triacylglycerols winterized *Euonymus alatus* seed oil (100 g) was adsorbed in 400 g of 60-120 silica gel and packed on a silica column (12×70 cm). The column was washed with petroleum ether for 1-2 hrs, and then run with 0.1% ethyl acetate in petroleum ether up to complete elution of the upper color impurity. The column was again washed with hexane for 30 min to remove traces of ethyl acetate, and the TAGs eluted with a gradient of 2 to 4% isopropyl ether in petroleum ether. This protocol yielded a purified long-chain TAG fraction (17.0 g), a purified acetyl TAG fraction (51.5 g), and a mixed TAG fraction (15.1 g). ESI-MS analyses indicated the long-chain TAG purity to be 98.5% and the acetyl-TAG purity to also be 98.5% in the purified TAG fractions.

Intrinsic viscosity measurements were made using a TA instruments (New Castle, Del.) ARES parallel plate rheometer at ambient temperature (24° C.). Oil samples were placed between two-inch diameter plates set 0.9 mm apart, and shear rates increased incrementally from 0.1 to 100 sec$^{-1}$. Viscosity measurements reported are averages over the 10 to 100 sec$^{-1}$ range (6 data points), when the viscosity was independent of shear, in accordance with the expectation that the fluids would exhibit Newtonian behavior. Density measurements were made at ambient temperature using a 25 ml graduated flask.

The inventors' discovered that purified acetyl-TAG fractions, consisting of two long-chain acyl groups, showed a combination of significantly different characteristics when compared to standard triacylglycerols consisting of three long-chain acyl groups, see, Tables 8 and 9.

In order to compare their experimental values with known values additional information was obtained and Tables 8 and 9 were constructed for comparison. For example, Kinematic viscosity (KV) is primarily a function of molecular weight rather than molecular shape. In fact, KV=IV(intrinsic velocity)/density. Niedzielski (1976) *Ind. Eng. Chem. Prod. Res. Dev.*, 15 (1):54-58, herein incorporated by reference, showed that a plot of KV (at 38° C.) versus MW for neopentylglycol diesters, trimethylolpropane triesters and pentaerythritol tetraesters gave a straight line, with a slope of 0.078 cSt/amu.

The inventors used this as a calibration tool for reducing an exemplary amount of methylene groups (210 amu) for comparing an ac-TAG to lc-TAG, the inventors calculated a reduction in KV of 16.4 cSt. Thus, the actual measured reduction of 18 cSt in KV (at 24° C.) from purified lc-TAGs (a 39% reduction) exceeded a calculated estimate. The value of 28.5 cSt for ac-TAG was above the published biodiesel specification (ASTM D6751, 1.9-6 cSt at 40° C.). When the inventors' converted the 28.5 cSt measured value of ac-TAGs at 24° C. to an cSt at 40° C., a value of about 18 cSt at 40° C. was obtained. This value was within the specification for heating/fuel oil #4 (ASTM D975, 5.5-24 cSt at 40° C.). Thus an additional use of oils comprising ac-TAGS of the present inventions is for use as heating/fuel oil. Further, ac-TAGs of the present inventions are contemplated for biodiesel blending purposes and for use an intermediate marine fuel oil.

TABLE 8

Oil viscosity and density measurements of purified acetyl-TAG and long-chain-TAG fractions isolated from *Euonymus alatus* seed oil.*

| Sample | Acyl Carbon Number | Intrinsic Viscosity (cP) | Density (g/cc) | Kinematic Viscosity (cSt) |
|---|---|---|---|---|
| Soybean oil | 54 | 49.2 ± 2.4 | 0.921 | 53.5 |
| Trioctanoin | 24 | 23.3 ± 3.5 | 0.948 | 24.5 |
| Lc-TAG | approximately 52 | 42.6 ± 2.9 | 0.916 | 46.5 |
| Ac-TAG | approximately 37 | 26.3 ± 0.9 | 0.924 | 28.5 |

*Data obtained at ambient temperature (24° C.)

For comparison, an exemplary Table 9 is provided showing published measurements of other plant seed oils.

TABLE 9

Exemplary published viscosity measurements of plant seed oils and synthetic trioctanoin.

| | Intrinsic Viscosity (cP) (at 25° C.) | Density (g/cc) | Kinematic Viscosity (KV) (cSt at 40° C.) |
|---|---|---|---|
| sunflower oil | 49 (Abramovic and Klofutar (1998) Acta Chim. Slov. 45: 69-77) | 0.95 (Eitman and Goodrum (1993) Transact. ASAE 36: 503-507) | 33.9 |
| trioctanoin | 24.5 (Eitman and Goodrum (1993) Transact. ASAE 36: 503-507) | | |
| soybean oil | | 0.917 (Rice and Hamm, (1988) Amer. Oil Chem. Soc. 65: 1177-1179) | 32.6 |

The inventors observed that their purified *Euonymus* ac-TAG remained liquid at and below freezing point (0° C.). In addition, the reduced number of unsaturated acyl groups in ac-TAG compared to lc-TAG are contemplated to reduce TAG polymerization and thus having reduced coking and gum formation problems than those caused by direct use of vegetable oils.

The inventors' contemplate reducing Kinematic viscosity of ac-TAGs of the present inventions by combining with additional TAG MW reduction strategies. These strategies include but are not limited to blending ac-TAGs of the present inventions with other types of fatty acids and oils, such as manufactured oils, methanol treated oils, petroleum derived oils, and the like. In preferred embodiments, Kinematic viscosity of ac-TAGS of the present inventions would be lowered through a combination of plant breeding and methods of plant engineering, such as engineering methods described herein.

For one example of lowering Kinematic viscosity, such as a contemplated 10 cSt reduction, using an oil seed crop plant engineering method a plant making a large amount of C18 fatty acids incorporated in TAGs will be engineered to make a C8 fatty acid at the sn-1 or sn-2 position instead. Such plant engineering would be accomplished by methods comprising altering fatty acid synthesizing enzymes, such as FATB enzymes and a FATB genetic engineering strategy (see, for example, Dehesh, et. al. (1996) Plant Physiol 110:203-210; Dehesh, et, al. (1996) Plant J. 9:167-172, herein incorporated by reference).

Example XI

Comparison of Oil Produced by Col-0 Wild Type *Arabidopsis* Seeds Transformed with *Euonymus* DAcT of the Present Invention vs. *Arabidopsis* Seeds Containing Mutations in AtDGAT1 Transformed with an *Euonymus* DAcT Gene of the Present Inventions For the goal of enhancing (increasing) levels of ac-TAGs in transgenic *Arabidopsis* plants, this experiment was designed to determine whether expressing EaDAcT in mutant plants, already having greatly reduced expression of DGAT1, would result in higher levels of ac-TAG production or would require additional alterations in expression of other genes/proteins related to TAG expression. Specifically, EaDAcT was expressed under the control of a seed specific promoter, S2 (see above) in two *Arabidopsis* mutant lines: as11 and abx45. Both of these lines contain mutations in the *Arabidopsis* DGAT1 gene (At2g19450) responsible for the bulk of TAG synthesis in *Arabidopsis* seeds (Zhang, et. al. (2009) Plant Cell 21:3885, herein incorporated by reference). as11 contains mutation that introduces an 81 base pair insertion into the AtDGAT1 transcript (Zou, et. al. (1999) Plant J. 19:645, herein incorporated by reference); abx45 contains a base pair deletion leading to a shift in the reading frame of the AtDGAT1 transcripts (Routaboul, et. al. (1999) Plant Physiol Biochem 37:831, herein incorporated by reference). Plants containing either of these mutations have an approximate 40% reduction in oil content in the seeds.

EaDAcT was cloned into a plant transformation vector under the control of the *Arabidopsis* 2S seed storage promoter as described in Example VIII. This construct, p2S.EaDAcT was then introduced into *Agrobacterium tumefaciens* strain C58C1 and transformed into wild type Col-0 *Arabidopsis* plants using the floral dip method (Clough and Bent (1998) Plant J. 16:735-743, herein incorporated by reference). Lipids were extracted from the seeds of transgenic plants and TAG content analyzed using ESI-MS.

Non-transgenic plants failed to produce ac-TAGS (FIG. 15). In three of the transgenic lines (two in the abx45 background, one in the as11 background) comprising an EaDAcT gene of the present inventions the proportion of ac-TAGS was unexpectedly higher than in transgenic wild-type plants comprising an EaDAcT gene of the present inventions. One of the higher expressing lines accumulated up to 80 mol % ac-TAGs (FIG. 15). These values were much higher than the 44 mol % achieved when EaDAcT was expressed in a Col-0 wild type background (FIGS. 12B and 15B) which demonstrated that expressing EaDAcT in combination with reducing the activity of endogenous TAG producing enzymes (in this case through mutation of the *Arabidopsis* DGAT1 gene) can be used to create transgenic plants where the majority of the seed oil is comprised of ac-TAGs.

A. Vectors and Transfection Methods for Producing Seeds.

Methods were described previously in Example VIII, *Arabidopsis* as11 and abx45 mutant plant tissue was transformed using the floral dip method.

B. Plant Growth Methods for Providing T2, T3 and T4 Seeds for Analysis.

Methods were described previously in Example VIII.

Example XII

This is an exemplary method for one embodiment of increasing (i.e. enhancing) levels of ac-TAGs in transgenic *Arabidopsis* plants by expression of EaDAcT in mutant plants (plants with a mutant, nonwild-type, background).

Specifically, in this example, the exemplary mutant *Arabidopsis* plant used was a fatty acid elongation-1 gene, fae1, mutant already having greatly reduced expression of very long chain fatty acids in its seed. The FAE1 gene encodes a cytosolic 3-ketoacyl-CoA synthase that is responsible for the biosynthesis of very long chain fatty acids in plant seeds (Kunst et al., 1992, Plant Physiol. Biochem. 30:425-434; Millar and Kunst, 1997, Plant J. 12:121-131, herein incorporated by reference). This cytosolic 3-ketoacyl-CoA synthase (elongatase) utilizes a cytosolic source of malonyl-CoA, which is in turn derived from the cytosolic pool of acetyl-CoA. In particular, the fae1 gene mutations or molecular genetic strategies that eliminate the elongase function of this gene result in greatly reduced long-chain (C20, C22) fatty acid in seed oils.

fae1 mutant plants were transformed with an EaDAcT gene of the present inventions. Because experiments on overexpression of *Arabidopsis* FAE1 gene (Millar and Kunst, 1997, Plant J. 12:121-131, herein incorporated by reference) and a heterologous FAE1 gene (Mietiewska et al., 2004, Plant Physiol. 136:2665-2675, herein incorporated by reference) in *Arabidopsis* seeds increases the levels of VLCFA, there is not a limitation of the cytosolic acetyl-CoA pool in wild type seeds. Thus it is not at all expected that the transformation of fae1 *arabidopsis* with EaDAcT gene would cause higher levels of ac-TAG production than in a wild type line, because there is no evidence to suggest that the cytosolic acetyl-CoA supply to drive the EADAcT acetyl transferase reaction is at all limiting. Thus the enhancement discovered in ac-TAG levels in fae1 background when compared to wild-type in EaDAcT-transformed *Arabidopsis* was unexpected.

In particular, EaDAcT was expressed under the control of a seed specific promoter, 2S (see above) in an *Arabidopsis* mutant line fae1 plants. An exemplary mutant, such as a mutant comprising a stop codon in a fae1 gene, any mutant that reduces approximately 90%-100% of long chain fatty acids. The fae1 mutant chosen for the study was the CB25 *Arabidopsis* plant line comprising a fae1 mutant gene resulting in a 90% reduction in VLCFAs compared to WT plants. CB25 was isolated from an ethyl methanesulphonate mutagenized population and contains a truncated FAE1 protein due to a mutation resulting in a stop codon at amino acid 465. It is a homozygous, back-crossed, bulked seed line. Plants containing these mutations have a 90-95% reduction in very long chain fatty acids in the seeds while overall oil production similar to that of wild type seeds. However, any of the several fae1 mutants published would have been appropriate for the experiment as CB25 has a similar reduction in VLCFA to these other published mutants.

In order to determine if a plant with an fae1 mutation would cause an increase in ac-TAG production in combination with an EaDAcT gene of the present inventions, EaDAcT was expressed in a CB25 host plant. In particular, an EaDAcT gene of the present inventions was cloned into a plant transformation vector under the control of the *Arabidopsis* 2S seed storage promoter as described in Example VIII. This construct, p2S.EaDAcT, was then introduced into *Agrobacterium tumefaciens* strain C58C1 and transformed into *Arabidopsis* mutant line fae1 plants using the floral dip method (Clough and Bent (1998) Plant J. 16:735-743, herein incorporated by reference). Plants were grown as described previously in Example VIII. Seeds from transformed plants were germinated on hygromycin in order to determine which seed lines were homozygous for the EaDAcT transgene. Once identified by healthy germination into seedlings, seeds were grown into plants whose seed was harvested from these homozygous transgenic EaDAcT lines for extraction of neutral lipids. Neutral lipids were analyzed using ESI-MS. Spectra from lipids extracted from the seeds of transgenic plants were compared as TAG content and TAG composition of $T_3$ seeds from *Arabidopsis* fae1 mutants expressing EaDAcT. Comparative analysis was made to neutral lipids isolated from wild-type *Arabidopsis* seeds and shown in FIG. 16. FIG. 16 (A) shows an exemplary TAG composition of $T_3$ seeds from *Arabidopsis* fae1 mutants (plants containing mutations in the fatty acid elongase gene 1) expressing EaDAcT. Dark bars showed ac-TAG amounts while light bars showed lcTAG amounts. FIG. 16 (B) shows an exemplary scatter plot comparing the distribution of the ac-TAG composition of $T_3$ seed from fae1 mutant seeds expressing EaDAcT to fae1 control plants (not transfected with an EaDAcT construct of the present inventions). Surprisingly, seed oil from mutant fae1 *Arabidopsis* plants showed a 40-60% ac-TAG composition, when transfected with an EaDAcT gene of the present inventions.

Unexpectedly, four of the seven transgenic lines expressing a homozygous EaDAcT transgene of the present inventions (FIG. 16) showed a higher proportion of ac-TAGs, of 40-60% ac-TAG composition, see, FIG. 16B compared to nontransgenic *Arabidopsis* fae1 mutant plants. For comparison, 3 other EaDAcT transgenic fae lines showed approximately less than 10% ac-TAG T3 seed oil composition.

About half of *Arabidopsis* fae1 mutant plant lines that expressed an EaDAcT transgene of the present inventions showed a high range of 40-60% ac-TAG composition. In comparison, *Arabidopsis* plants on a wild-type background that expressed an EaDAcT transgene of the present inventions showed a high range of up to approximately 40%. Therefore, in one embodiment, the inventors contemplated the construction of oil seed plants, and other types of plants, for expression of an EaDAcT transgene of the present inventions in combination with genetic backgrounds that result in reduced levels of fae1 expression for making plants where high levels of the seed oil comprises ac-TAGs, i.e. approximately 40% and higher.

In one contemplated embodiment, host plants comprising lowered FAE1 expression, naturally or induced, would have a higher percentage and/or amount of ac-TAG containing oil in their seeds. The comparison would be to oil isolated from the same amount (by weight) of seeds from wild-type plants or from other plants with wild-type backgrounds consisting of expression of an EaDAcT of the present inventions on a background of wild-type expression of FAE1.

Example XIII

This is an Exemplary Method for *Camelina* Seed Expression of EaDAcT for Producing Novel *Camelina* Seed Oils Genotyping of wildtype *Camelina* plants which expressed an EaDAcT gene of the present inventions are described herein.

A. Vectors and Transfection Methods for Providing Seeds.

An exemplary method for *Camelina* seed expression of EaDAcT for producing novel *Camelina* seed oils is described as follows. Briefly, EaDAcT was ligated into the plant binary expression vector p2S. GATEWAY, which was constructed by ligating 1 kb of genomic sequence upstream of the *Arabidopsis* 2S seed storage protein gene (At4g27160) and the GATEWAY att recombination cassette from pMDC32 (Curtis and Grossniklaus (2003) Plant Physiol 133:462-469, herein incorporated by reference) into the multiple cloning site of pCAMBIA1390 (www.cambia.org) whose sequence was published at GenBank® (NIH genetic sequence database, an annotated collection of all publicly available DNA sequences (Nucleic Acids Research, 2008 January; 36(Database issue): D25-30)) ACCESSION AF234307, herein incorporated by reference). This binary vector construct, p2S.EaDAcT, was then introduced into *Agrobacterium tumefaciens* strain C58C1 and transformed into wild type *Camelina* plants using a floral dip method with a vacuum infiltration step as described by Lu and Kang (2008) Plant Cell Rep 27:273-278, herein incorporated by reference.

*Agrobacterium tumefaciens* strain C58C1 was grown at 28° C. in YEP medium, supplemented with the appropriate antibiotics: rifampicine 50 mg/ml, streptomycin 25 mg/ml or gentamycin at a few mg/ml. The constructs (p2S.EaDAcT), i.e. vectors comprising a EaDAcT gene (such as SEQ ID NO. 01), were used when transferred into *A. tumefasciens* strain C58C1 via electroporation. The presence or absence of the EaDAcT sequence was verified with whole cell PCR, using EaDAcT specific primers.

Six-week old *Camelina* plants were transformed via the floral dip method with the *A. tumefasciens* strains, comprising (carrying) a promoter sequence p2S and EaDAcT. The plants were grown to maturity. Seeds (T1) were collected and transgenic plants (T1) were selected by germination on MS media containing 30 hygromycin. The surviving hygromycin resistant plants were allowed to grow to maturity, set seed and desiccate. Mature *Camelina* plant T2 seeds were collected from the siliques of 8-12 week old plants, grown in the growth chambers (16 h light period, 22° C., 80 to 100 µE light intensity). Neutral lipids were quantitatively extracted and analyzed using ESI-MS as described in Example I. T2 seedlings from these lines were germinated on hygromycin and lines that demonstrated a 75% survival rate were deemed to possess a single T-DNA insertion event and chosen for further study. Twelve surviving T2 plants from each chosen line were grown to maturity and seed (T3) collected. T3 seeds from individual T2 plants were germinated on hygromycin and lines that possessed a 100% survival rate were deemed to be homozygous for the T-DNA insertion; these seeds were analyzed for lipid content. Control seeds for seed analysis, such as T3 seeds, T4 seeds, etc. were collected from untransformed *Camelina* plants.

B. Plant Growth Methods for Providing T2, T3 and T4 Seeds for Analysis.

Mature *Camelina* plant T3 and T4 seeds were collected from the siliques of 6-8 week old plants, grown in the growth chambers (16 h light period, 22° C., 80 to 100 µE light intensity). Neutral lipids were quantitatively extracted and analyzed using ESI-MS as described in Example I.

C. Analysis of *Camelina* Seed Oil.

FIG. 17 shows exemplary T2 *Camelina* seed expression of EaDAcT and percentage and analysis of accumulated ac-TAGs. T2 seedlings were selected by growing on media containing 30 microM hygromycin which did not support the germination of nontransgenic seeds. Hygromycin resistant plants grown from hygromycin medium were transferred to soil and allowed to grow to maturity. DNA was extracted from the leaves of some of these plants (lines #1, #19, #20), as well as from some wildtype *Camelina* plants (plants WT e, WT f, and WT g) shown in FIG. 17A. The presence of the EaDAcT transgene was confirmed using PCR DNA amplification from genomic DNA with the gene specific primers 17392_F (SEQ ID NO:12) and att_seq_3prime (aaattcgagctggtcacctc, SEQ ID NO: 16), shown in FIG. 17A. PCR DNA products were separated on a 1% agarose gel, stained with ethidium bromide and visualized under ultraviolet light. Lanes 1-3, shown in FIG. 17A, showed the presence of an approximately 1.4 kb PCR product, consistent with the size of the expected PCR product which identified plants containing the EaDAcT transgene. A band of approximately the same molecular weight was found in lane 7 (positive control), which contained the PCR product from a reaction using DNA from an *Arabidopsis* plant transformed with EaDAcT and shown to produce ac-TAGs of the present inventions. Lanes 4-6, of FIG. 17A, showed a faint, non-specific band similar to a band found in the negative control that lacked a EaDAcT DNA-template (Lane 8, FIG. 17A).

Lipids were extracted from the seeds of transgenic plants and TAG content analyzed using ESI-MS. Isolated seed oils provided novel oils comprising ac-TAGs produced by transgenic plants that were not present in oils isolated from non-transgenic plants. FIG. 17B shows an exemplary TAG composition of T1 pooled seed from heterologous EaDAcT expressing *Camelina* plants showing varying levels of ac-TAG production in seeds. FIG. 17C shows an exemplary scatter plot which demonstrated the distribution of the ac-TAG composition of T2 seed between different transgenic *Camelina* plant lines that expressed EaDAcT as compared to *Camelina* plant wildtype seed. FIG. 17D shows an exemplary ESI-MS$^2$ analysis of neutral lipid extracts from the T2 seed of *Camelina* plants that expressed EaDAcT. Shown are exemplary analyses of fragment ions derived from the molecular ion that indicated the presence of ac-TAGs in the isolated seed oils. Specifically, a parent molecular ion peak (the $[M+NH_4]^+$ adduct) at m/z=675 was fragmented to produce a daughter ion at m/z value of 597.7; FIG. 17D, upper spectrum. The loss of 78 atomic mass units corresponds to the loss of ammonium acetate. By contrast, the loss of ammonium linoleate (18:2) or ammonium linolenate (18:3) from this molecular ion produces the peaks at m/z=377.7 and 379.5 respectively. Thus the molecular ion at m/z=675 corresponds to the ammonium adduct of acetyl-linoleoyl-linolenoyl-glycerol. In a second example the parent molecular ion peak (the $[M+NH_4]^+$ adduct) at m/z=705 was fragmented and this produced a daughter ion at m/z value of 627.9; FIG. 17D, lower spectrum. Again, the loss of 78 atomic mass units corresponds to the loss of ammonium acetate from the $[M+NH_4]^+$ parent ion, which is consistent with a parent ac-TAG.

Therefore, *Camelina* plants that expressed an EaDAcT gene of the present inventions gained the capability to make ac-TAGs in their seeds. *Camelina* plants with exemplary heterozygous gene expression ranges from 1-20% ac-TAGs in seed oil, see, FIG. 17C. The inventors contemplating increasing levels to commercial levels in a variety of ways, including but not limited to plants comprising homozygous alleles, additional promoters, i.e. a promoter from a *Camelina* species, etc.

Thus in one embodiment, the inventors contemplate silencing (i.e. lowering) expression of lc-TAGs in host plants, by identifying plants with natural mutations, plants with induced mutations, and using plants or engineered mutant plants with lowered lc-TAG production as host cells for transfection or introgression of an EaDAcT gene of the present inventions. The inventors further contemplate the use of such plants and plant cells for producing seeds with high amounts of ac-TAGs, either total yield per plant, i.e. total yield for acre or fraction of ac-TAG in the oil. Even further, the inventors contemplate the isolation of ac-TAGs from these seeds for use in biofuel or as novel oils for commercial uses. Additionally, the inventors contemplate the use of parental, T1, transgenic plants expressing EaDAcT of the present inventions for use in breeding in order to develop commercially and/or agronomically viable cultivars and lines.

Example XIV

Contemplated Expression of a Heterologous DAcT Gene in Plant Backgrounds Affected in their Ability to Synthesize Endogenous TAGs The inventors contemplate expression of a heterologous DAcT gene and encoded protein of the present inventions in a host plant (plant background) that would be useful for increasing the proportion of ac-TAGs in its seed oil. Thus, the inventors contemplate using certain plants with alterations in their genetic capability to synthesize lc-TAGs as hosts for heterologous DAcT expression. In other embodiments, homologous DAcT expression is contemplated. In yet further embodiments, inducible DAcT expression is contemplated. In some embodiments, alterations in lc-TAG production may be found naturally in plants, for example, a natural variation in lc-TAG production found within and between variants, cultivars and populations of plants (i.e. species and varieties or variations found within species and varieties), such as *Arabidopsis* plants, *Camelina* plants, soybean plants, *Brassica* species, including *B. napsus* plants. In other embodiments, alterations were or are induced by mutation. In yet further embodiments, alteration in lc-TAG production may be induced by genetic engineering. In additional embodiments, greater reductions in lc-TAG production are contemplated to result from a combination of alterations, for example, identifying a naturally low lc-TAG producing plant for use in mutational and/or genetic engineering for producing oil with a high ac-TAG content.

The compositions and methods of genetic engineering contemplated for a plant are on a species by species basis, i.e. each plant species is likely to require a uniquely designed composition and/or method for increasing ac-TAG production for use in the present inventions. For example, a plant of the Brassicea family, where in general Brassicea plants depend on DGAT1 for lc-TAG synthesis, would require genetic manipulation associated with DGAT1 activity. In contrast, in an oilseed plant that is not a member of the Brassicaceae family it may be more important to silence activity associated with the DGAT2 gene. For example, in castor (*Ricinus communis* L.) the most strongly expressed TAG-synthesis gene in seeds is the DGAT2 gene. DGAT2 expression was induced 18-fold during seed maturation, whereas DGAT1 was barely induced at all (Kroon et al., 2006, Phytochemistry 67:2541-2549, herein incorporated by reference).

One specific example of such a host plant contemplated for use in the present inventions as a plant affected in its ability to synthesize endogenous lc-TAGs is an *Arabidopsis* plant line having a mutation in a gene associated with lowering lc-TAG production. Such a mutation is contemplated in any one or more of a DGAT1 gene, a PDAT gene, and combinations of mutations in more than one gene within the same plant. Examples of combination mutations in plants that may find use in the present inventions are host plants with double mutations comprising a mutation in at least one mutation in it's DGAT1 gene in combination with a mutation in it's PDAT gene. In some embodiments, mutations include deletion mutants. In yet other embodiments, other genetic combinations in plants include complete null plants, such that plants have low or undetectable DGAT1 activity and low or undetectable PDAT expression.

Example XV

Contemplated Plant Part Expression of a Heterologous DAcT Gene and Encoded DAcT Protein The inventors contemplated that expression of a heterologous DAcT gene and encoded protein of the present inventions would be useful for producing novel oils in plant parts such as leaves. Because ac-TAGs are not usually produced in *Arabidopsis* plants, *Arabidopsis* leaves will be chosen for ectopic transfection and expression of a heterologous DAcT gene and encoded protein for producing ac-TAGs in leaves of transgenic plants.

GATEWAY technology will be used to transfer an EaDAcT gene from an entry vector to a plant binary vector where the gene will be expressed under the control of a constitutive promoter, such as a CMV 35S promoter. This construct will be transformed into *Arabidopsis* leaves using *Agrobacterium* mediated transformation.

Lipids will be extracted from the leaves of transgenic plants. TAG content will be determined using ESI-MS as described herein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in fatty-acid chemistry, molecular biology, biochemistry, chemistry, organic synthesis, paint and varnish manufacturing, botany, human and veterinary nutrition and medicine, or related fields are intended to be within the scope of the following claims.

We claim:

1. An isolated nucleic acid encoding a protein operably linked to a heterologous promoter, wherein said protein is at least 95% identical to SEQ ID NO:01.

2. The nucleic acid of claim 1, wherein said protein is capable of acetylating a diacylglycerol substrate comprising a fatty acid to form an acetyltriacylglycerol.

3. The nucleic acid claim 2, wherein said fatty acid is Oleate.

4. The nucleic acid of claim 2, wherein said diacylglycerol substrate is 1,2-dioleoyl-glycerol.

5. The nucleic acid of claim 2, wherein said protein is capable of acylating said diacylglycerol substrate with an acyl-coenzyme A substrate.

6. The nucleic acid of claim 5, wherein said acyl-coenzyme A substrate is a short chain acyl-coenzyme A.

7. The nucleic acid of claim 5, wherein said acyl-coenzyme A substrate is propionyl-coenzyme A.

8. The nucleic acid claim 1, wherein said protein is SEQ ID NO:01.

9. The nucleic acid of claim 1, wherein said protein is from a plant selected from the group of Celastraceae, Lardizabalaceae, Ranunculaceae, Rosaceae, and Vitaceae.

10. The nucleic acid of claim 1, wherein said protein is from a plant selected from the group of *Euonymus*, *Maytenus*, *Akebia*, *Adonis*, *Sorbus* and *Vitis* species.

11. The nucleic acid of claim 1, wherein said protein is from an *Euonymus alata* plant.

12. The nucleic acid sequence of claim 1, wherein said heterologous promoter is a seed specific promoter.

13. A vector comprising the nucleic acid of claim 1.

14. A host cell comprising the vector of claim 13.

15. The host cell of claim 14, wherein said host cell is selected from the group consisting of a plant cell and a microorganism.

16. The host cell of claim 15, wherein said plant cell is selected from the group consisting of an edible crop plant cell, an oil seed crop plant cell, a seed cell, a pollen cell, an ovule cell, mesenchymal cell, meristem cell, an endosperm cell, a male reproductive cell, a female reproductive cell, and an embryo cell.

17. The host cell of claim 15, wherein said plant cell is selected from the group consisting of a *Jatropha* plant, an oil crop plant, a palm oil plant, and an alga.

18. The host cell of claim 15, wherein said plant cell is selected from the group consisting of *Brassica* plants and *Brassicaceae* plants.

19. The host cell of claim 15, wherein said plant cell is selected from the group consisting of *Arabidopsis* plants, *Camelina* plants, and *crambe* plants.

20. The host cell of claim 15, wherein said microorganism is a fungus cell.

21. The host cell of claim 20, wherein said fungus cell is a yeast cell.

22. The host cell of claim 14, wherein said host cell has lower long chain-triacylglycerol production.

23. The host cell of claim 22, wherein said host cell further comprises at least one mutant fatty acid elongase I gene, wherein said mutation results in lowered long chain-triacylglycerol production in host cell.

24. The host cell of claim 22, wherein said host cell further comprises at least one silenced triacylglycerol synthesis gene, wherein said gene is silenced due to a mutation which results in lowered expression of said gene.

25. The host cell of claim 24, wherein said silenced triacylglycerol synthesis gene is diacylglycerol acyltransferase 1.

26. A seed, wherein said seed comprises a heterologous plant nucleic acid encoding a protein that is at least 95% identical to SEQ ID NO:01.

27. A composition comprising a host cell, wherein said host cell comprises a heterologous plant nucleic acid sequence encoding a protein that is at least 95% identical to SEQ ID NO:01.

28. The composition of claim 27, wherein said host cell is an oil seed plant cell, a mesenchymal cell, meristem cell, an endosperm cell, a pollen cell, a male reproductive cell, a female reproductive cell, and an embryo cell.

29. The composition of claim 27, further comprising acetyltriacylglycerol.

30. The composition of claim 29, wherein said acetyltriacylglycerol comprises a 3-acetyl-1, 2-diacyl-sn-glycerol.

\* \* \* \* \*